US012767664B2

(12) United States Patent
Chen et al.

(10) Patent No.: US 12,767,664 B2
(45) Date of Patent: Oct. 20, 2026

(54) SPIROCYCLIC COMPOUND AS KRAS-G12C INHIBITOR

(71) Applicants: Shanghai Euregen Biopharma Co., Ltd., Shanghai (CN); Shanghai Youli Biopharma Co., Ltd., Shanghai (CN)

(72) Inventors: Xuxing Chen, Shanghai (CN); Jing Li, Shanghai (CN); Yanhong Chen, Shanghai (CN); Zhao Zhao, Shanghai (CN)

(73) Assignees: Shanghai Euregen Biopharma Co., Ltd., Shanghai (CN); Shanghai Youll Biopharma Co., Ltd., Shanghai (CN)

( * ) Notice: Subject to any disclaimer, the term of this patent is extended or adjusted under 35 U.S.C. 154(b) by 686 days.

(21) Appl. No.: 18/259,221

(22) PCT Filed: Dec. 23, 2021

(86) PCT No.: PCT/CN2021/140991

§ 371 (c)(1),
(2) Date: Jan. 8, 2024

(87) PCT Pub. No.: WO2022/135546

PCT Pub. Date: Jun. 30, 2022

(65) Prior Publication Data

US 2025/0034161 A1 Jan. 30, 2025

(30) Foreign Application Priority Data

Dec. 25, 2020 (CN) ......................... 202011556213.4
Jun. 3, 2021 (CN) ......................... 202110619679.2

(51) Int. Cl.

*A61P 35/00* (2006.01)
*A61K 31/519* (2006.01)
*A61K 31/527* (2006.01)
*C07D 471/04* (2006.01)
*C07D 471/20* (2006.01)
*C07D 491/20* (2006.01)
*C07D 519/00* (2006.01)

(52) U.S. Cl.

CPC .......... *C07D 491/20* (2013.01); *A61K 31/519* (2013.01); *A61K 31/527* (2013.01); *A61P 35/00* (2018.01); *C07D 471/04* (2013.01); *C07D 471/20* (2013.01); *C07D 519/00* (2013.01)

(58) Field of Classification Search

CPC .. C07D 491/20; C07D 471/04; C07D 471/20; C07D 519/00; C07D 471/10; C07D 513/04; C07D 487/04; A61K 31/519; A61K 31/527; A61P 35/00
USPC .......................................................... 514/257
See application file for complete search history.

(56) References Cited

FOREIGN PATENT DOCUMENTS

| | | | | | |
|---|---|---|---|---|---|
| JP | 2020111571 | A | | 7/2020 | |
| WO | 2019013311 | A1 | | 1/2019 | |
| WO | WO-2020236940 | A1 | * | 11/2020 | C07D 403/14 |
| WO | 2021093758 | A1 | | 5/2021 | |
| WO | 2021139748 | A1 | | 7/2021 | |

OTHER PUBLICATIONS

International Search Report issued Mar. 14, 2022 in PCT/CN2021/140991.

* cited by examiner

*Primary Examiner* — Yevgeny Valenrod
(74) *Attorney, Agent, or Firm* — ICE MILLER LLP

(57) ABSTRACT

The present invention relates to a spirocyclic compound, represented by formula (I), as a KRAS-G12C inhibitor, which can be used in the preparation of a drug for treating KRAS G12C-mediated tumors.

I

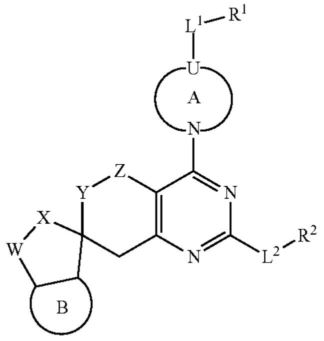

13 Claims, 1 Drawing Sheet

SPIROCYCLIC COMPOUND AS KRAS-G12C INHIBITOR

CROSS-REFERENCE TO RELATED APPLICATION

This application is a Section 371 of International Application No. PCT/CN2021/140991 filed Dec. 23, 2021, which was published in the Chinese language Jun. 30, 2022, under International Publication No. WO 2022/135546 A1, which claims priority to Chinese Patent Application No. 202011556213.4 filed Dec. 25, 2020, and Chinese Patent Application No. 202110619679.2 filed Jun. 3, 2021, the disclosures of which are incorporated herein by reference in their entireties.

TECHNICAL FIELD

The invention relates to the field of pharmaceutical chemistry. In particular, the present invention relates to a class of spirocyclic compound, which can be used as KRAS-G12C inhibitors to prepare drugs for the treatment of KRAS G12C-mediated tumors.

BACKGROUND

The Kirsten rat sarcoma 2 viral oncogene homolog ("KRAS") is a GTPase enzyme and is a member of the RAS oncogene family. KRAS acts as a molecular switch of cycles between inactive (guanosine diphosphate (GDP)-binding) and active (GTP-binding) states to transduce upstream cellular signals received from a variety of tyrosine kinases to downstream effectors to regulate a variety of processes, including cell proliferation (Current Opin Pharmcol. 2013 (13): 394-401).

KRAS is one of the most frequently mutated oncogene in cancers. About 22% of cancer patients have KRAS mutations, especially in pancreatic cancer (68%), cholangiocarcinoma (27%) and lung cancer (17%). Wherein, the incidence of KRAS G12C in non-small cell lung cancer, colorectal cancer and pancreatic cancer is 48%, 10% and 1%, respectively. The lack of ideal small molecule binding pockets for KRAS proteins and high affinity of the KRAS protein for the abundant GTP make it challenging to design specific small molecule drugs.

Among various known KRAS mutations, KRAS G12C mutation is considered to be the most potent drug target. Several covalent inhibitors targeting KRAS G12C are currently in clinical trials, such as AMG 510 of Amgen and MRTX849 from Mirati Therapeutics. All of these compounds covalently bind to KRAS G12C at cysteine residue 12, keeping KRAS G12C in an inactive state of GDP-binding and inhibiting KRAS-dependent signal transduction.

After more than thirty years of research, the development of KRAS inhibitors have made certain progress, but there is still no KRAS inhibitor that has shown sufficient safety and efficacy to gain regulatory approval. Therefore, pharmaceutical companies need to make continuous efforts to develop novel KRAS inhibitors so as to treat various diseases, such as cancers.

WO2020/236940 discloses a compound 819, the binding affinity between compound 819 and KRAS G12C was predicted using software based on two methods: MMGBSA and CovDock, but does not provide the synthetic method, the characterization results or any biological test results of the compound.

819

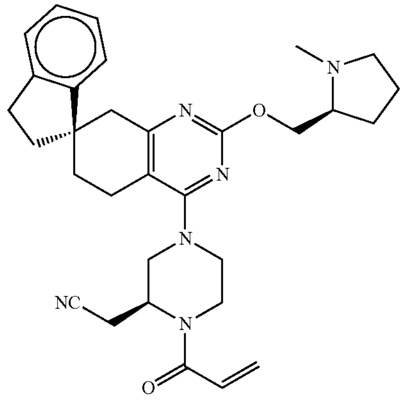

SUMMARY

The purpose of the present invention is to provide a class of spirocyclic compounds or pharmaceutically acceptable salts thereof.

Another purpose of the present invention is to provide a pharmaceutical composition comprising the spirocyclic compounds or the pharmaceutically acceptable salts thereof.

A further purpose of the present invention is to provide the use of the spirocyclic compounds or the pharmaceutically acceptable salts thereof or the compositions comprising the spirocyclic compounds or the pharmaceutically acceptable salts thereof in the preparation of anti-tumor drugs.

In the first aspect of the present invention, provided is a compound of formula I, or pharmaceutically acceptable salts thereof, enantiomers, diastereomers, tautomers, cis-trans isomers, solvates, polymorphs, deuterated compounds, or combinations thereof,

I

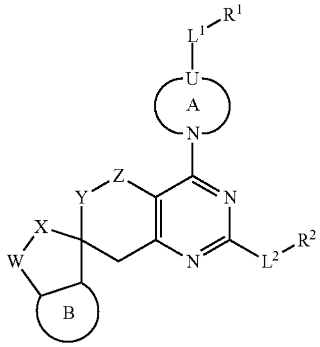

wherein,

A is a 4-12 membered saturated or partially saturated monocyclic ring, fused ring, bridged ring or spiro ring, wherein the saturated or partially saturated monocyclic ring, fused ring, bridged ring, or spiro ring is optionally substituted by one or more $R^3$;

each $R^3$ is independently oxo, $C_{1-3}$ alkyl, $C_{2-4}$ alkenyl, $C_{2-4}$ alkynyl, cyano, —C(O)O$R^4$, —CON$(R^4)_2$, or —N$(R^4)_2$, wherein the $C_{1-3}$ alkyl is optionally substituted by cyano, halogen, —O$R^4$, or —N$(R^4)_2$;

each $R^4$ is independently hydrogen or $C_{1-3}$ alkyl;

U is N or CH;

$L^1$ is absent or $NR^N$, and when U is N, $L^1$ is absent, and when U is CH, $L^1$ is $NR^N$;

$R^N$ is hydrogen or $C_{1-3}$ alkyl;

$R^1$ is

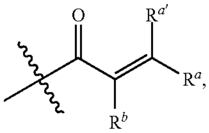
,
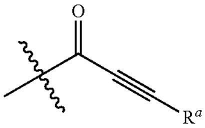
,
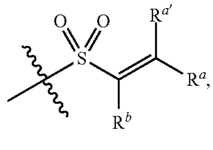
,
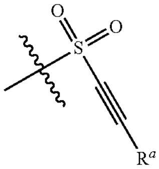
,
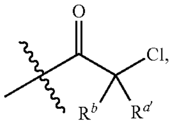
or
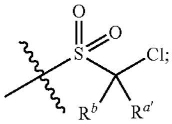
;

wherein, $R^a$ is hydrogen, halogen, optionally substituted $C_{1-3}$ alkyl, —$N(R^5)_2$, optionally substituted 4-6 membered saturated heterocyclyl, $C_{1-3}$ alkoxy, $C_{1-3}$ alkylthio or acetyl, wherein the substituents for optionally substituted described in $R^a$ is selected from the group consisting of: methyl, ethyl, —$N(R^5)_2$, halogen, $C_{1-3}$ alkoxy, and 4-6 membered saturated heterocyclyl;

each $R^5$ is independently hydrogen or $C_{1-3}$ alkyl;

$R^{a'}$ and $R^b$ are independently hydrogen, halogen or $C_{1-3}$ alkyl;

$L^2$ is absent, —O—, —S—, —$NR^6$—, —SO—, —$SO_2$— or —CO—, wherein, $R^6$ is hydrogen or $C_{1-4}$ alkyl;

$R^2$ is hydrogen, optionally substituted $C_{1-4}$ alkyl, optionally substituted saturated or unsaturated 3-8 membered carbocyclyl, optionally substituted saturated or unsaturated 4-12 membered heterocyclyl, optionally substituted saturated or unsaturated 3-8 membered carbocyclyl fused 6-10 membered aryl, optionally substituted saturated or unsaturated 3-8 membered carbocyclyl fused 5-10 membered heteroaryl, optionally substituted saturated or unsaturated 3-8 membered heterocyclyl fused 6-10 membered aryl, optionally substituted saturated or unsaturated 3-8 membered heterocyclyl fused 5-10 membered heteroaryl, optionally substituted 6-10 membered aryl or optionally substituted 5-10 membered heteroaryl; wherein the substituents for optionally substituted described in $R^2$ is selected from the group consisting of: deuterium, halogen, hydroxy, cyano, oxo, $C_{1-3}$ alkoxy, —$NR^cR^d$, —$CO_2R^7$, —$CONR^eR^f$, $C_{1-4}$ alkyl sulfoxide, $C_{1-4}$ alkyl sulfonyl, —$SO_2NR^gR^h$, optionally substituted 3-8 membered saturated or unsaturated carbocyclyl, and optionally substituted 4-8 membered saturated and unsaturated heterocyclyl;

$R^c$ and $R^d$ are each independently selected from hydrogen, optionally substituted $C_{1-6}$ alkyl, optionally substituted 3-8 membered carbocyclyl and optionally substituted 4-8 membered heterocyclyl, or $R^c$ and $R^d$ together with N to which they are connected form an optionally substituted 4-8 membered heterocycle;

$R^e$ and $R^f$ are each independently selected from hydrogen, optionally substituted $C_{1-6}$ alkyl, optionally substituted 3-8 membered carbocyclyl and optionally substituted 4-8 membered heterocyclyl, or $R^e$ and $R^f$ together with N to which they are connected form an optionally substituted 4-8 membered heterocycle;

$R^g$ and $R^h$ are each independently selected from hydrogen, optionally substituted $C_{1-6}$ alkyl, optionally substituted 3-8 membered carbocyclyl and optionally substituted 4-8 membered heterocyclyl, or $R^g$ and $R^h$ together with N to which they are connected form an optionally substituted 4-8 membered heterocycle;

$R^7$ is hydrogen or optionally substituted $C_{1-4}$ alkyl;

W is —$(CR^8R^9)$—, —$NR^{10}$—, O or S, wherein $R^8$, $R^9$ and $R^{10}$ are independently hydrogen or $C_{1-3}$ alkyl;

X is —$(CR^{11}R^{12})_m$— or —(C═O)—, wherein each $R^{11}$ is independently hydrogen or $C_{1-3}$ alkyl, and each $R^{12}$ is independently hydrogen or C1-C3 alkyl;

m=1, 2 or 3;

B is 6-10 membered aryl or 5-8 membered heteroaryl, wherein the 6-10 membered aryl or the 5-8 membered heteroaryl is unsubstituted or optionally substituted by one or more $R^{13}$;

each $R^{13}$ is independently halogen, hydroxy, amino, $C_{1-3}$ alkylamino, $(C_{1-3}\ alkyl)_2$amino, $C_{1-6}$ alkyl, $C_{1-6}$ haloalkyl, $C_{3-6}$ carbocyclyl, $C_{1-3}$ alkoxy, or $C_{1-3}$ haloalkoxy;

Y is —$NR^{14}$—, wherein $R^{14}$ is hydrogen, $C_{1-6}$ alkyl, $C_{1-6}$ haloalkyl or $C_{3-6}$ carbocyclyl;

Z is —$(CR^{15}R^{16})$—, wherein $R^{15}$ and $R^{16}$ are independently hydrogen or $C_{1-3}$ alkyl.

In a preferred embodiment, $R^2$ is hydrogen, optionally substituted $C_{1-4}$ alkyl, optionally substituted saturated or unsaturated 3-8 membered carbocyclyl, optionally substituted saturated or unsaturated 4-12 membered heterocyclyl, optionally substituted saturated or unsaturated 3-8 membered heterocyclyl fused 6-10 membered aryl, optionally substituted saturated or unsaturated 3-8 membered heterocyclyl fused 5-10 membered heteroaryl, optionally substituted 6-10 membered aryl or optionally substituted 5-10 membered heteroaryl, wherein the substituents for optionally substituted described in the $R^2$ are selected from: deuterium, halogen, hydroxyl, cyano, oxo, $C_{1-3}$ alkoxy, —$NR^cR^d$, —$CO_2R^7$, —$CONR^eR^f$, $C_{1-4}$ alkyl sulfoxide, $C_{1-4}$ alkyl sulfonyl, —$SO_2NR^gR^h$, optionally substituted 3-8 membered saturated or unsaturated carbocyclyl and optionally substituted 4-8 membered saturated or unsaturated heterocyclyl;

$R^c$ and $R^d$ are each independently selected from hydrogen, optionally substituted $C_{1-6}$ alkyl, optionally substituted 3-8 membered carbocyclyl and optionally substituted 4-8 membered heterocyclyl, or $R^c$ and $R^d$ together with N to which they are connected form an optionally substituted 4-8 membered heterocycle;

$R^e$ and $R^f$ are each independently selected from hydrogen, optionally substituted $C_{1-6}$ alkyl, optionally substituted 3-8 membered carbocyclyl and optionally substituted 4-8 membered heterocyclyl, or $R^e$ and $R^f$ together with N to which they are connected form an optionally substituted 4-8 membered heterocycle;

$R^g$ and $R^h$ are each independently selected from hydrogen, optionally substituted $C_{1-6}$ alkyl, optionally substituted 3-8 membered carbocyclyl and optionally substituted 4-8 membered heterocyclyl, or $R^g$ and $R^h$ together with N to which they are connected form an optionally substituted 4-8 membered heterocycle;

$R^7$ is hydrogen or optionally substituted $C_{1-4}$ alkyl;

preferably, $L^2$ is absent, —O—, —S—, or —$NR^6$—, wherein $R^6$ is hydrogen or $C_{1-4}$ alkyl;

preferably, $R^a$ is hydrogen, fluorine, optionally substituted $C_{1-3}$ alkyl, optionally substituted 4-6 membered saturated heterocyclyl or acetyl;

wherein the substituents for optionally substituted described in $R^a$ are selected from the group consisting of methyl, ethyl, —$N(R^5)_2$, halogen, $C_{1-3}$ alkoxy, and 4-6 membered saturated heterocyclyl;

each $R^5$ is independently hydrogen or $C_{1-3}$ alkyl;

preferably, $R^{a'}$ and $R^b$ are independently hydrogen, fluorine or $C_{1-3}$ alkyl;

preferably, W is —$(CR^8R^9)$— or —$NR^{10}$—, wherein $R^8$, $R^9$ and $R^{10}$ are independently hydrogen or $C_{1-3}$ alkyl;

preferably, X is —$(CR^{11}R^{12})_m$—; wherein each $R^{11}$ is independently hydrogen or $C_{1-3}$ alkyl, and each $R^{12}$ is independently hydrogen or $C_{1-3}$ alkyl; m is 1, 2 or 3; further preferably, m is 1 or 2.

In another preferred embodiment, the moiety represented by

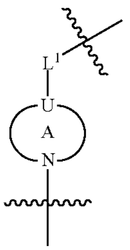

is selected from the group consisting of:

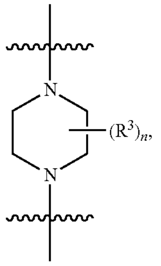
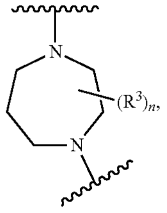
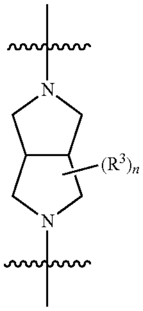
,

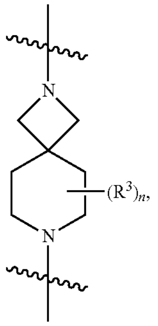
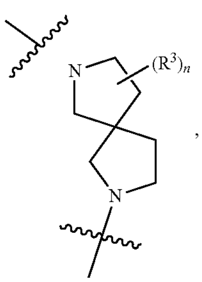
,
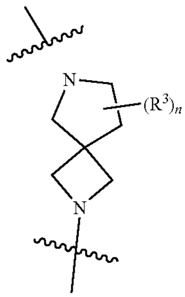
,

-continued

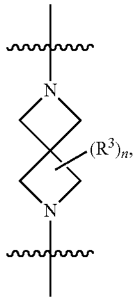
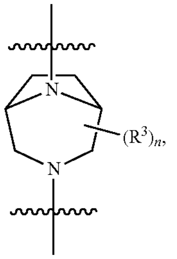
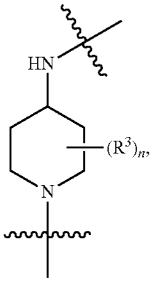

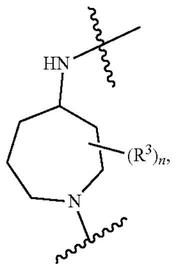
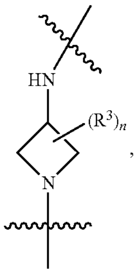
,
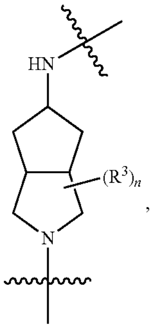
,

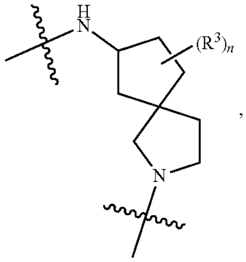
, and
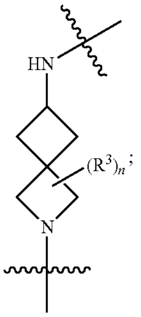

n represents the number of $R^3$, and n is 0, 1, 2 or 3;

each $R^3$ is independently oxo, $C_{1-3}$ alkyl, $C_{2-4}$ alkenyl, $C_{2-4}$ alkynyl, cyano, —$C(O)OR^4$, —$CON(R^4)_2$, or —$N(R^4)_2$, wherein $C_{1-3}$ alkyl can be optionally substituted by cyano, halogen, —$OR^4$, or —$N(R^4)_2$;

each $R^4$ is independently hydrogen or $C_{1-3}$ alkyl;

preferably, the moiety represented by

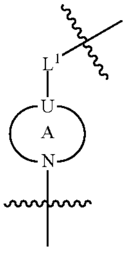

is selected from the group consisting of:

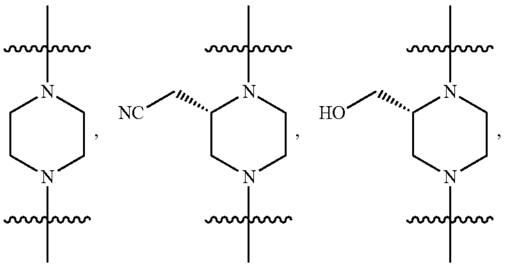

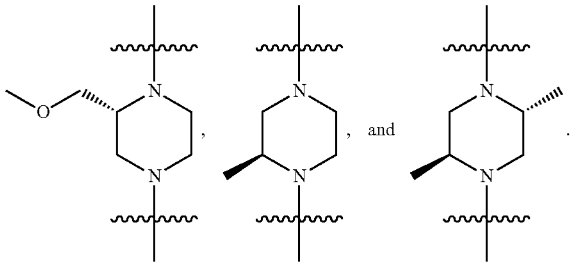

and

In another preferred embodiment, R is

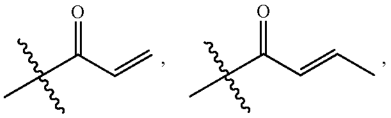

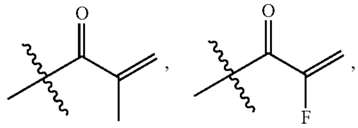

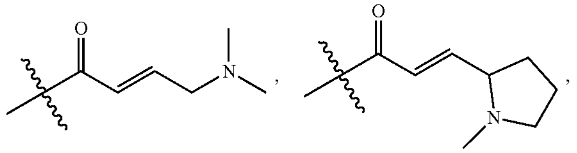

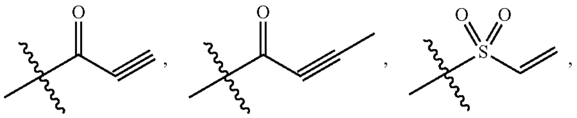

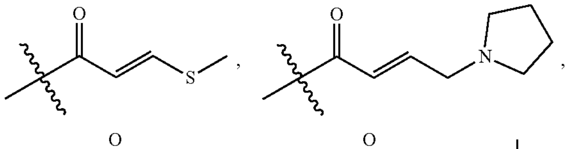

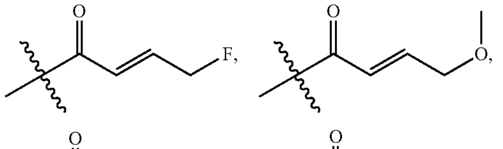

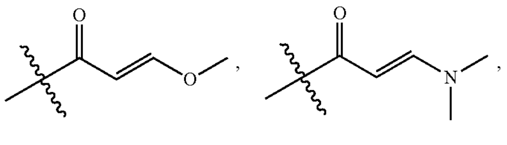

-continued

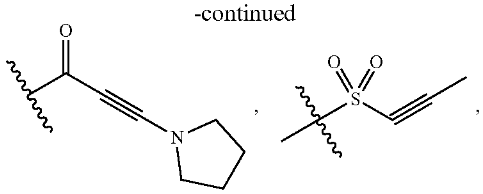

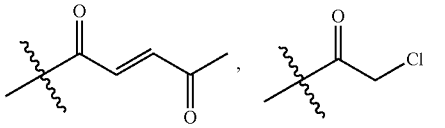

or

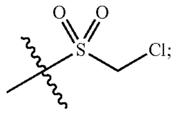

preferably, $R^1$ is

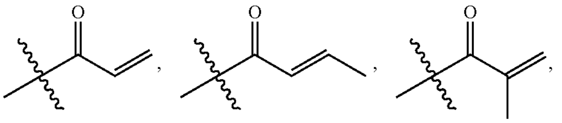

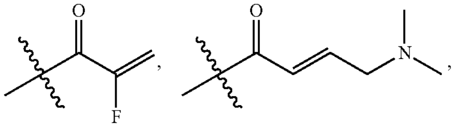

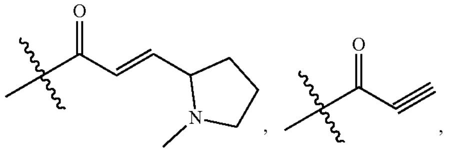

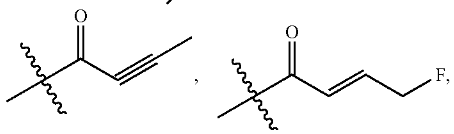

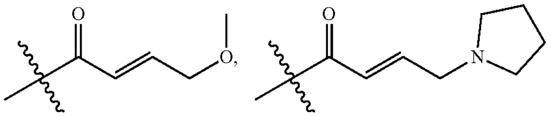

or

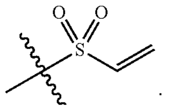

In another preferred embodiment, $R^2$ is hydrogen, optionally substituted $C_{1-4}$ alkyl, optionally substituted 6-10 membered aryl or optionally substituted 5-10 membered heteroaryl; wherein the substituents for optionally substituted described in $R^2$ are selected from: halogen, hydroxy, cyano, oxo, $C_{1-3}$ alkoxy, —$NR^cR^d$, —$CO_2R^7$, —$CONR^eR^f$, $C_{1-4}$ alkyl sulfoxide, $C_{1-4}$ alkyl sulfonyl, —$SO_2NR^gR^h$, optionally substituted 3-8 membered saturated or unsaturated carbocyclyl, and optionally substituted 4-8 membered saturated or unsaturated heterocyclyl;

$R^c$ and $R^d$ are each independently selected from hydrogen, optionally substituted $C_{1-6}$ alkyl, optionally substituted 3-8 membered carbocyclyl and optionally substituted 4-8 membered heterocyclyl, or $R^c$ and $R^d$ together with N to which they are connected form an optionally substituted 4-8 membered heterocycle;

$R^e$ and $R^f$ are each independently selected from hydrogen, optionally substituted $C_{1-6}$ alkyl, optionally substituted 3-8 membered carbocyclyl and optionally substituted 4-8 membered heterocyclyl, or $R^e$ and $R^f$ together with N to which they are connected form an optionally substituted 4-8 membered heterocycle;

$R^g$ and $R^h$ are each independently selected from hydrogen, optionally substituted $C_{1-6}$ alkyl, optionally substituted 3-8 membered carbocyclyl and optionally substituted 4-8 membered heterocyclyl, or $R^g$ and $R^h$ together with N to which they are connected form an optionally substituted 4-8 membered heterocycle;

$R^7$ is hydrogen or optionally substituted $C_{1-4}$ alkyl.

Preferably, $R^2$ is

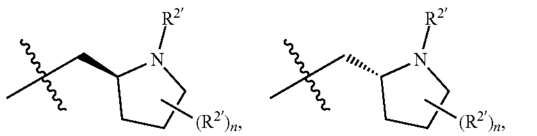

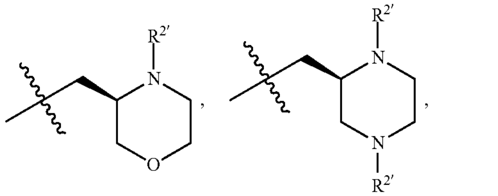

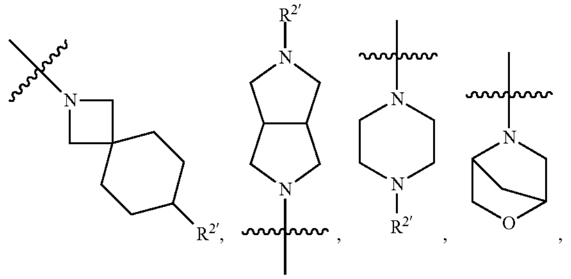

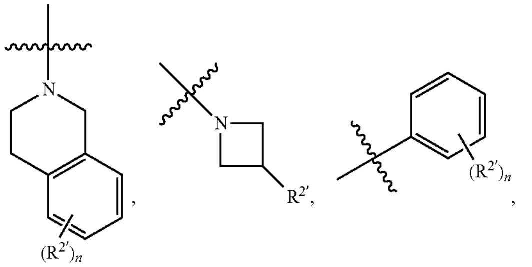

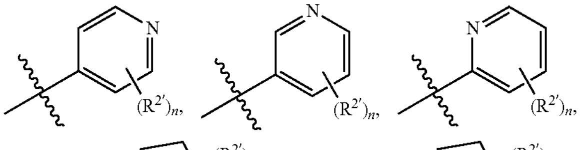

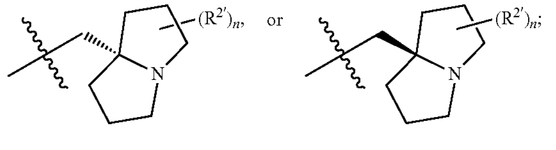

wherein n represents the number of $R^{2'}$, and selected from: 0, 1, 2 and 3; each $R^{2'}$ is independently halogen, $C_{1-3}$ alkyl, $C_{1-3}$ haloalkyl, hydroxy, cyano, oxo, $C_{1-3}$ alkoxy, —$NR^cR^d$, —$CO_2R^7$, —$CONR^eR^f$, $C_{1-4}$ alkyl sulfoxide, $C_{1-4}$ alkyl sulfonyl, —$SO_2NR^gR^h$, optionally substituted 3-8 membered saturated or unsaturated carbocyclyl, and optionally substituted 4-8 membered saturated or unsaturated heterocyclyl;

$R^c$ and $R^d$ are each independently selected from hydrogen, optionally substituted $C_{1-6}$ alkyl, optionally substituted 3-8 membered carbocyclyl and optionally substituted 4-8 membered heterocyclyl, or $R^c$ and $R^d$ together with N to which they are connected form an optionally substituted 4-8 membered heterocycle;

$R^e$ and $R^f$ are each independently selected from hydrogen, optionally substituted $C_{1-6}$ alkyl, optionally substituted 3-8 membered carbocyclyl and optionally substituted 4-8 membered heterocyclyl, or $R^e$ and $R^f$ together with N to which they are connected form an optionally substituted 4-8 membered heterocycle;

$R^g$ and $R^h$ are each independently selected from hydrogen, optionally substituted $C_{1-6}$ alkyl, optionally substituted 3-8 membered carbocyclyl and optionally substituted 4-8 membered heterocyclyl, or $R^g$ and $R^h$ together with N to which they are connected form an optionally substituted 4-8 membered heterocycle;

$R^7$ is hydrogen or optionally substituted $C_{1-4}$ alkyl.

In another preferred embodiment, the spiro ring represented by

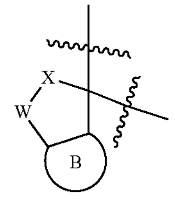

is selected from the group consisting of:

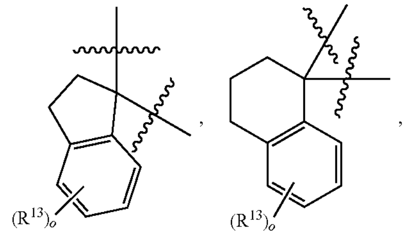

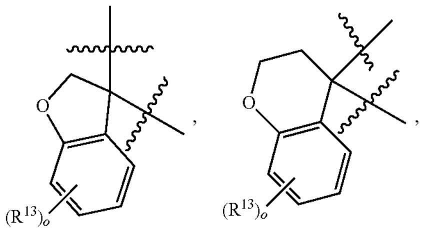

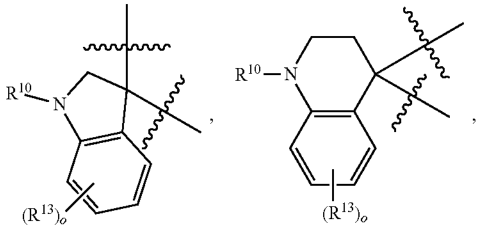

-continued
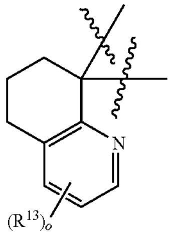,
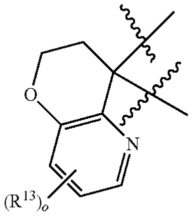,
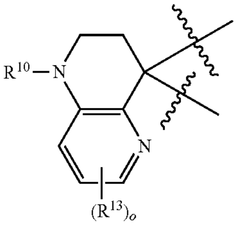,
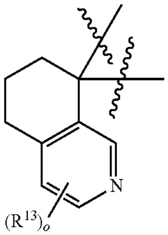,
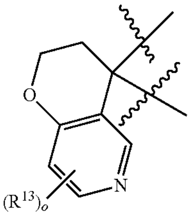,
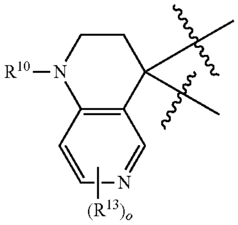,
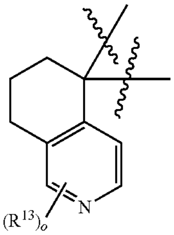,
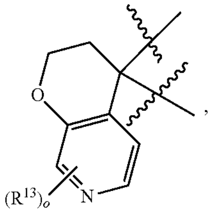,
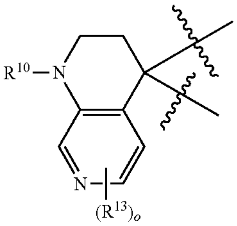,
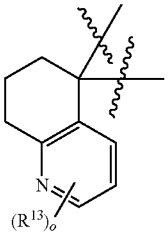,
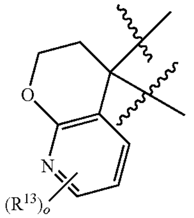,
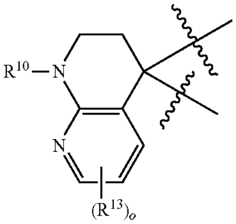,
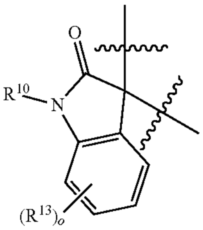,
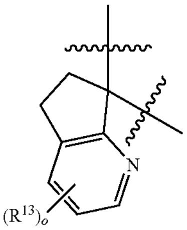,
-continued
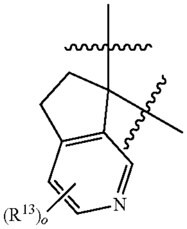,
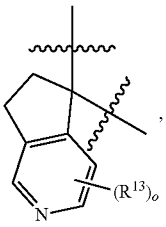,
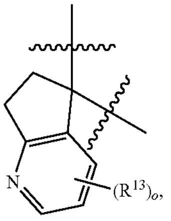
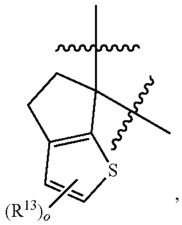,
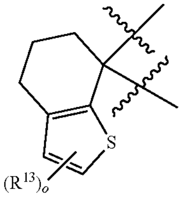,
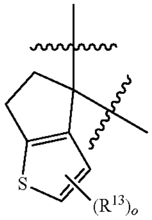, and 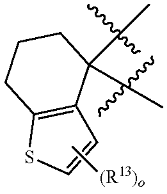;
wherein, $R^{10}$ is independently hydrogen or $C_{1-3}$ alkyl; o represents the number of $R^{13}$, and o is 0, 1, 2 or 3; and each $R^{13}$ is independently halogen, $C_{1-6}$ alkyl, $C_{1-6}$ haloalkyl, $C_{3-6}$ carbocyclyl, $C_{1-3}$ alkoxy, or $C_{1-3}$ haloalkoxy.
In another preferred embodiment, the compound is selected from the group consisting of:
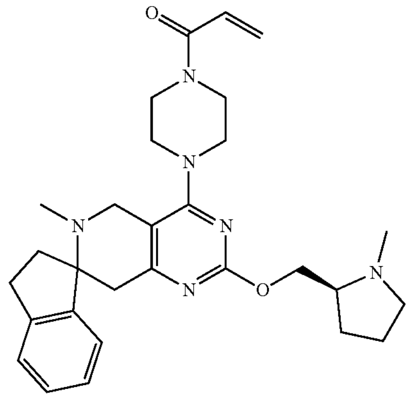

-continued
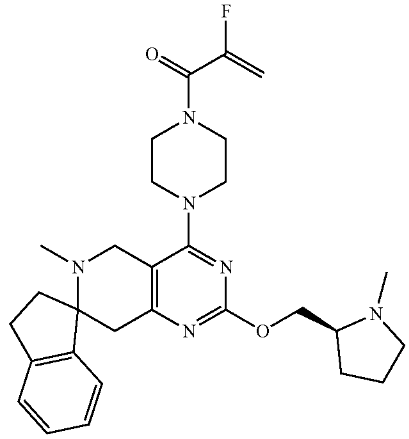
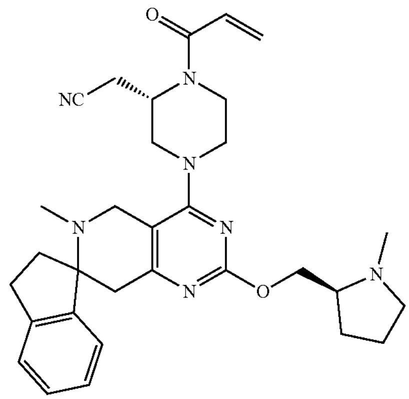
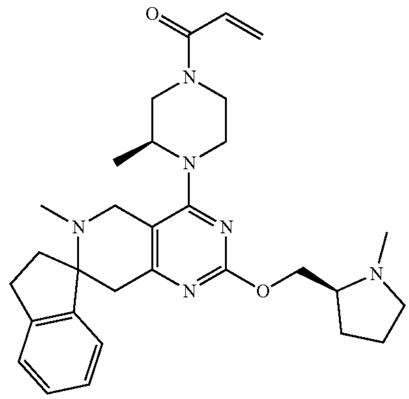
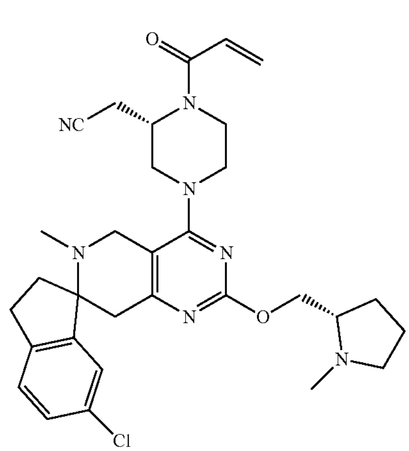
-continued
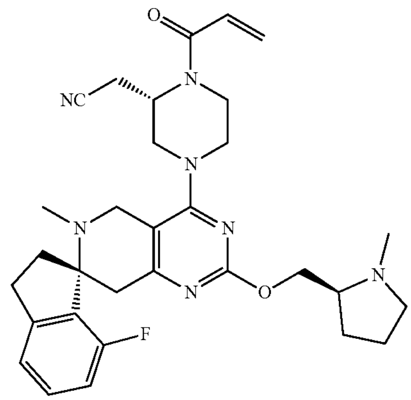
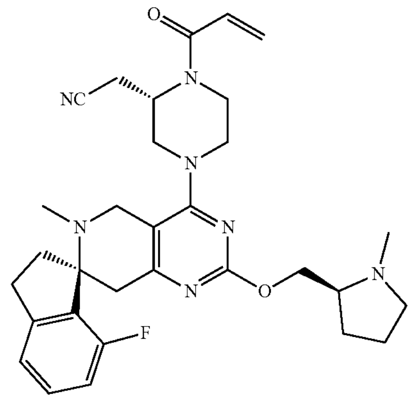
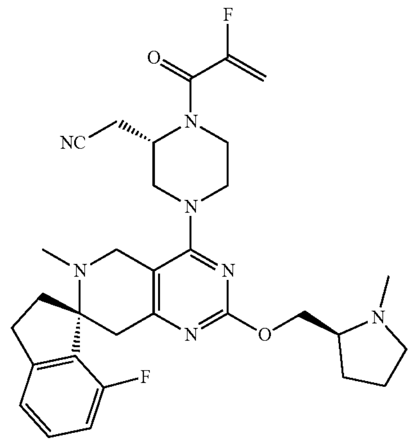
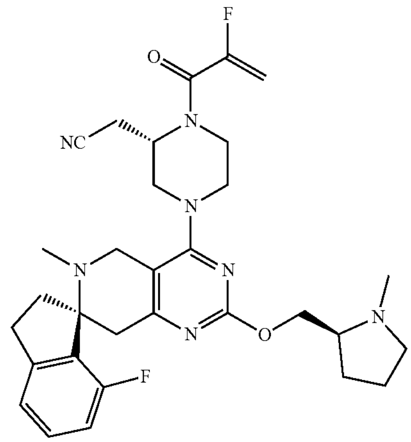

-continued
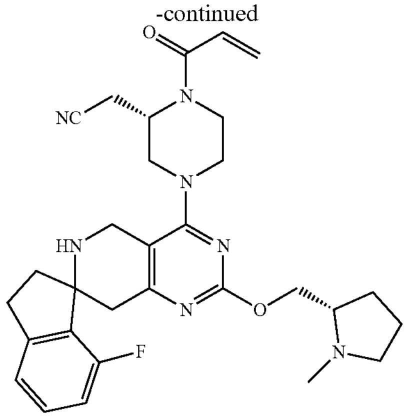
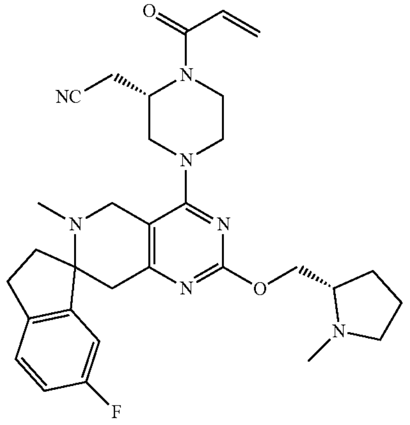
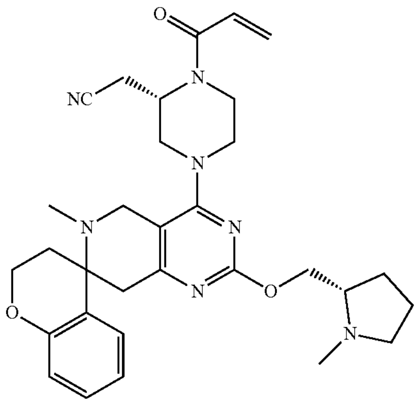
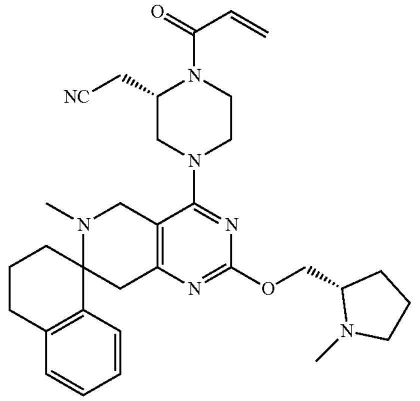
-continued
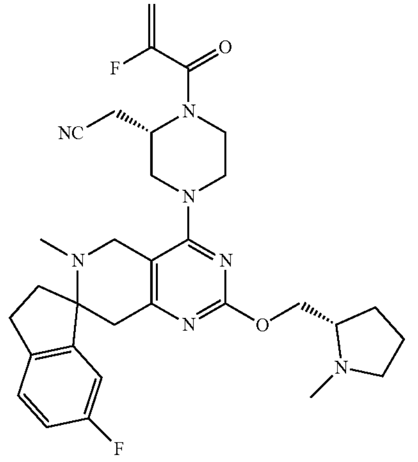
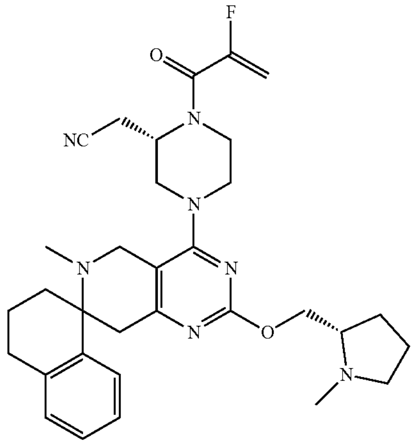
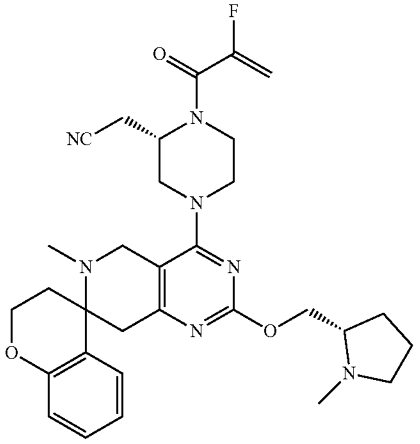

-continued
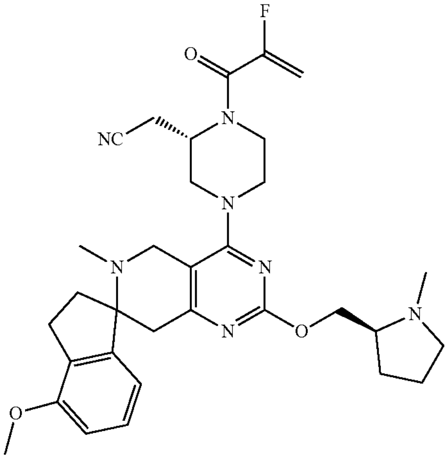
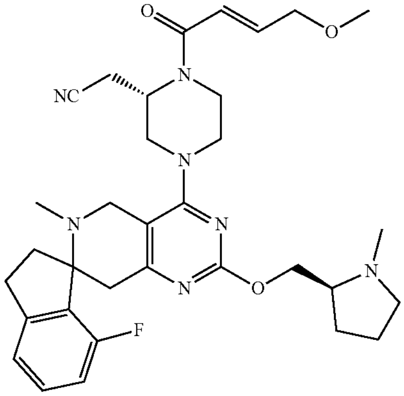
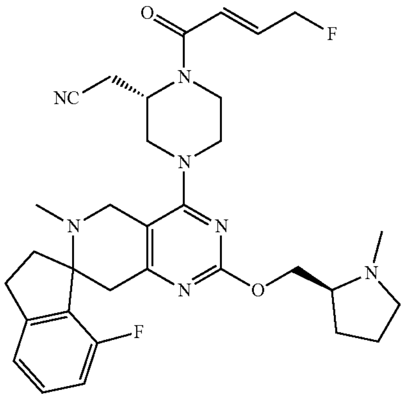
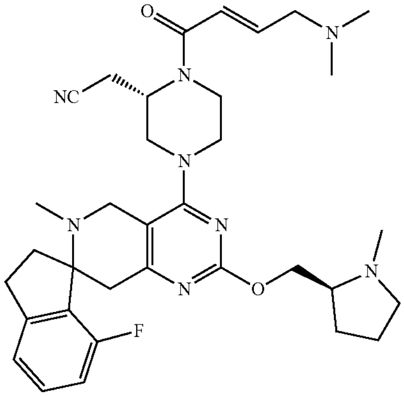
-continued
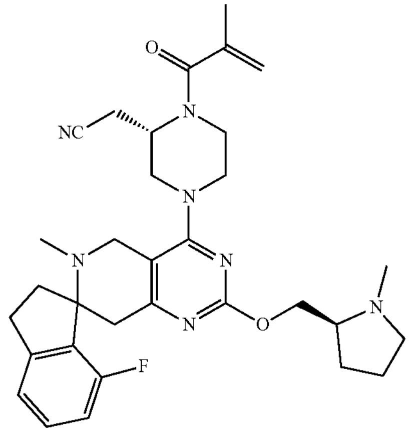
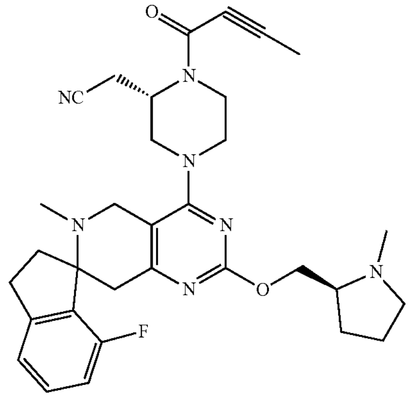
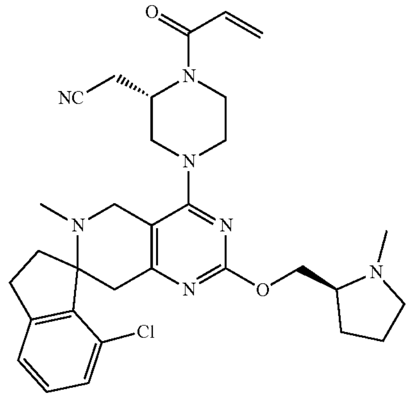
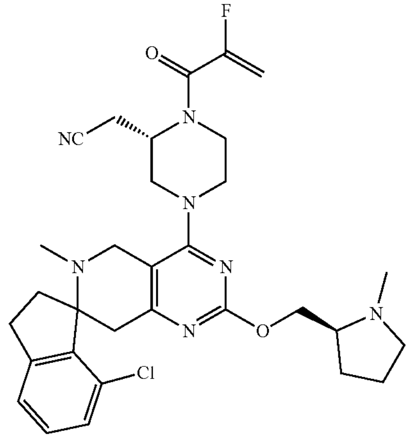

-continued
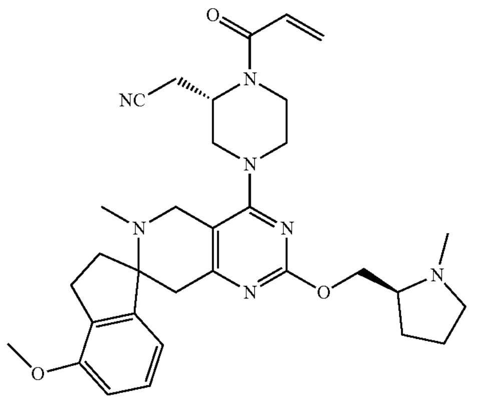
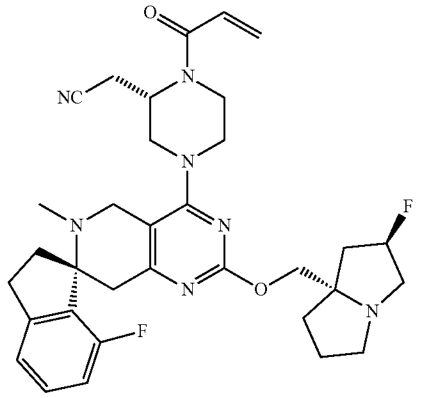
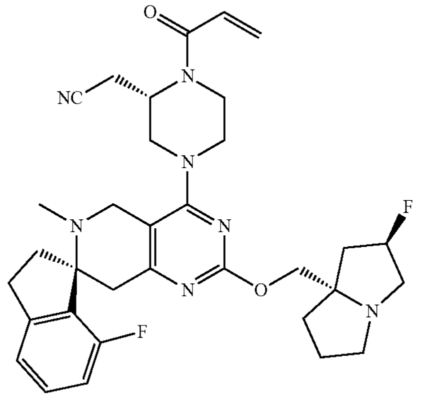
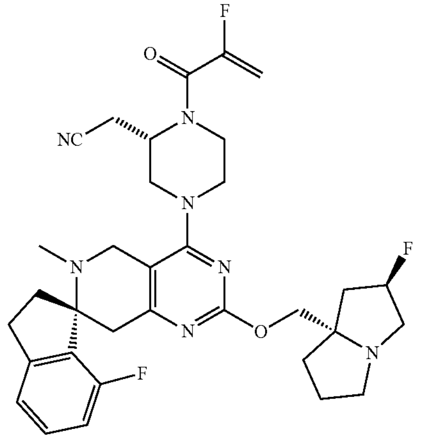
-continued
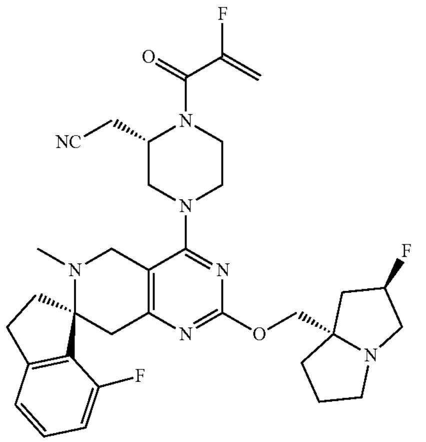
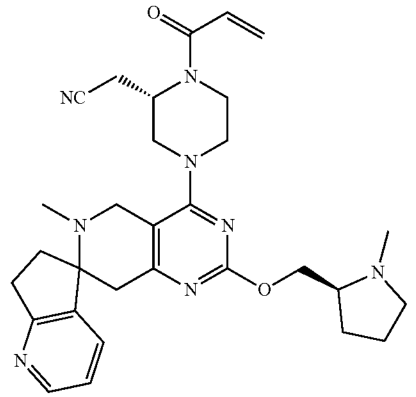
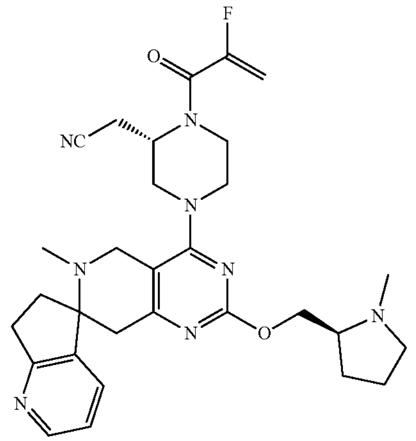
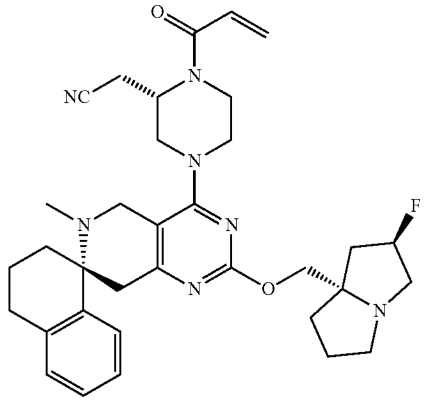

-continued
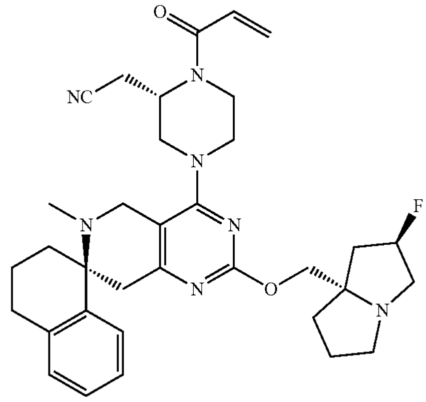
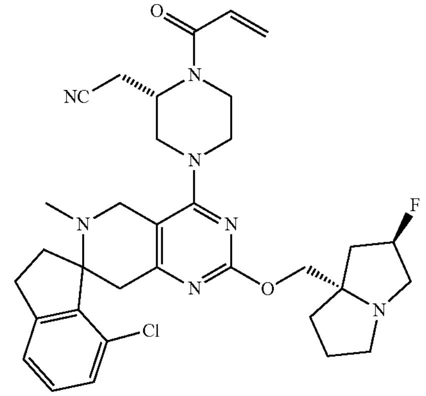
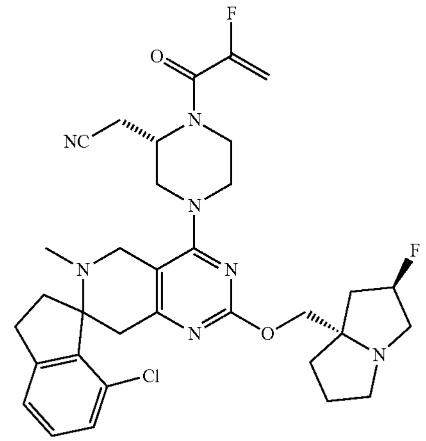
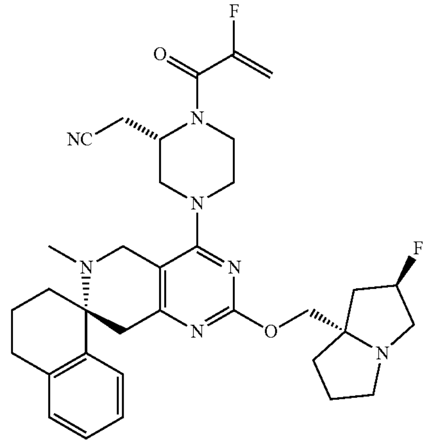
-continued
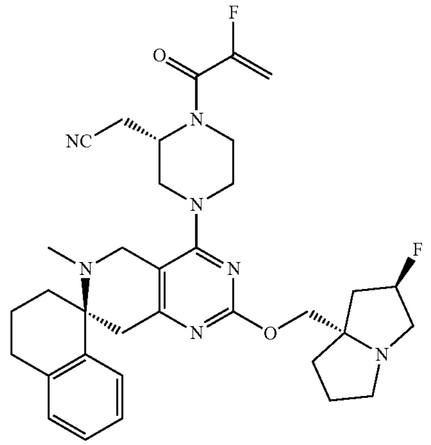
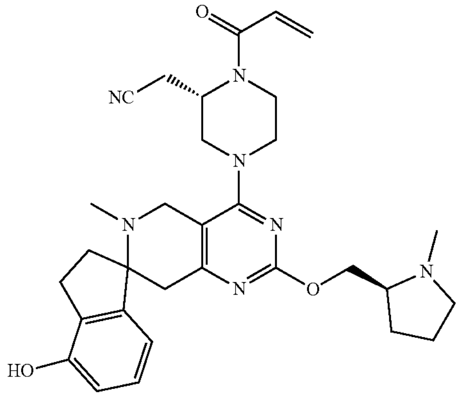
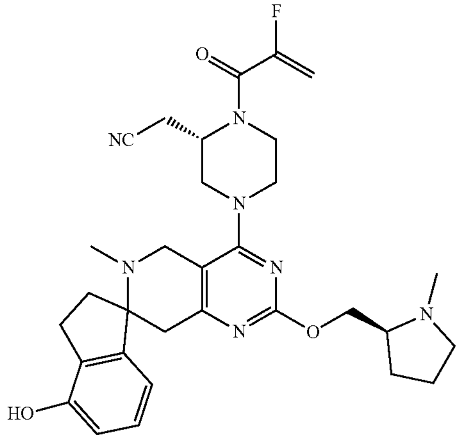
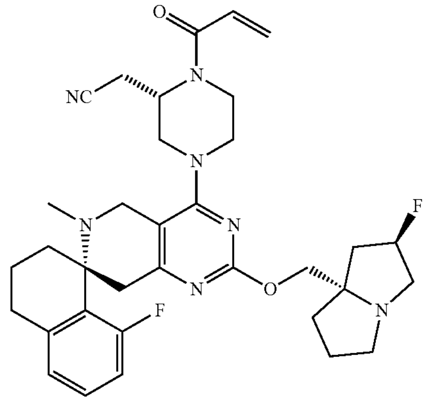

-continued
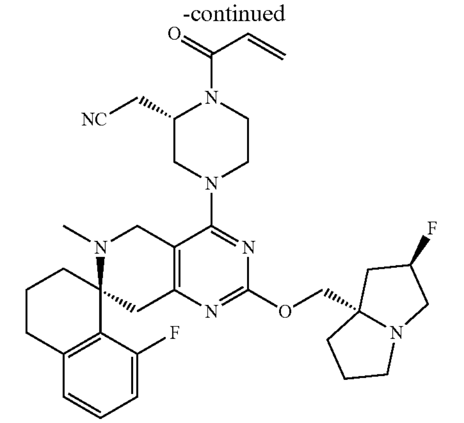
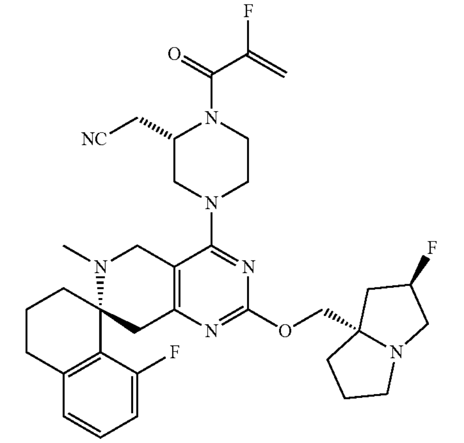
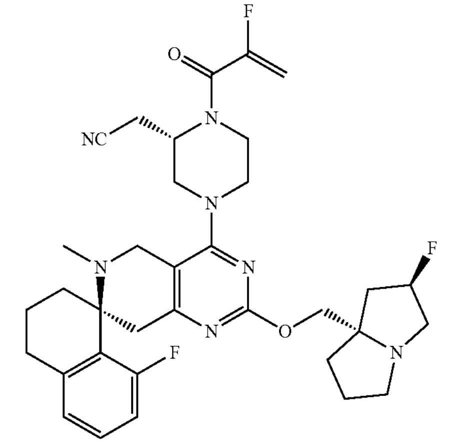
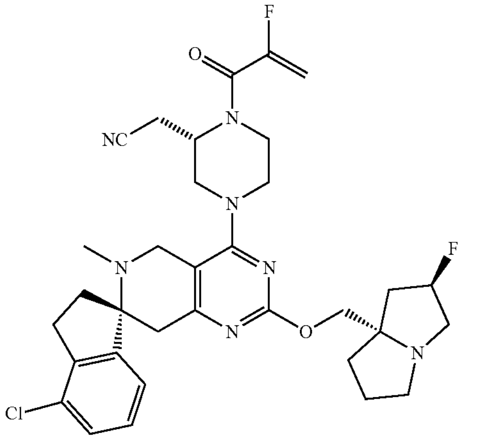
-continued
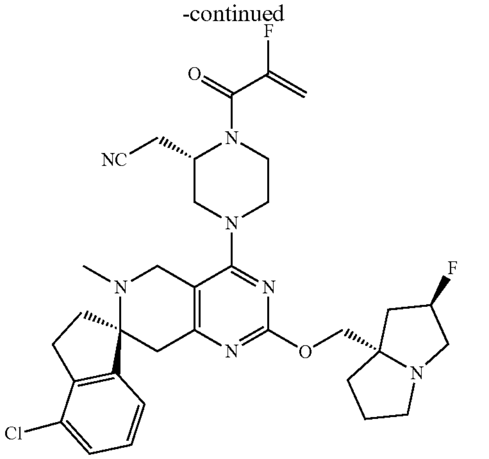
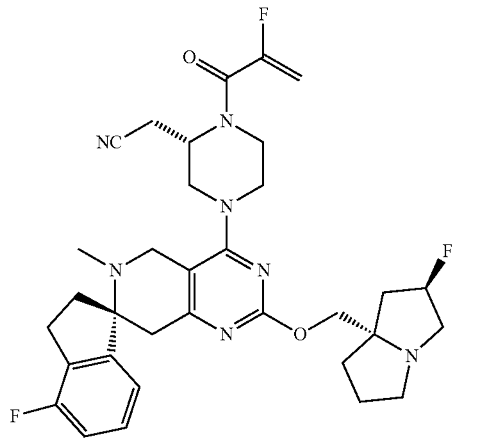
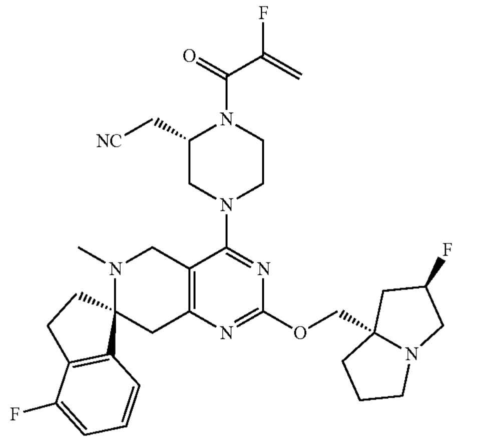

-continued

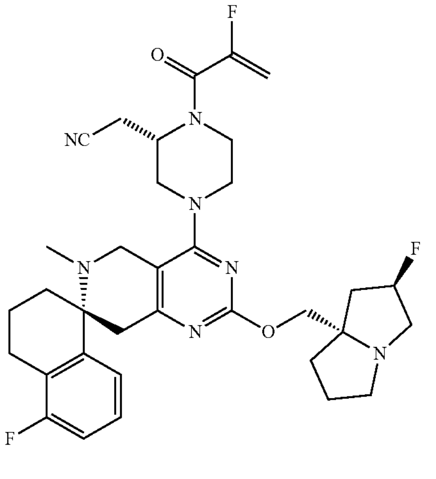

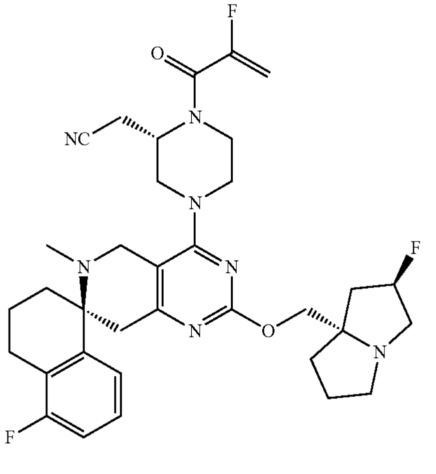

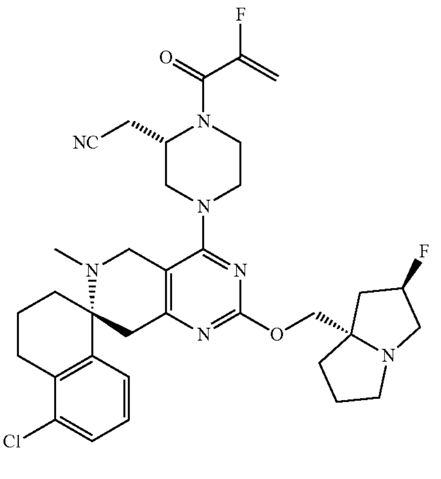

and

-continued

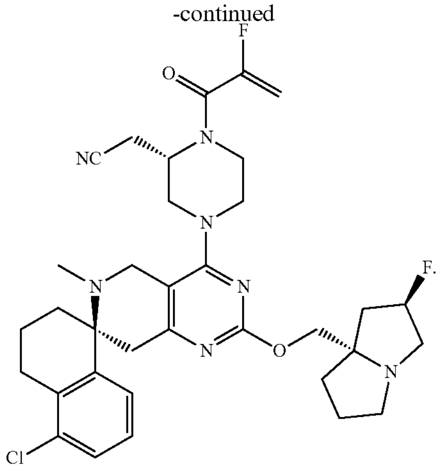

The compound of the present invention can be prepared according to the synthetic methods described in examples or methods similar thereto.

In the second aspect of the present invention, provided is a pharmaceutical composition comprising:

(1) a therapeutically effective amount of one or more of the compounds of the present invention, pharmaceutically acceptable salts thereof, enantiomers, diastereomers, tautomers, cis-trans isomers, solvates, polymorphs, and deuterates thereof as an active ingredient; and (2) optionally, pharmaceutically acceptable excipients.

In addition, the pharmaceutical composition may further include other pharmaceutically acceptable therapeutic agents or be used in combination with other pharmaceutically acceptable therapeutic agents, especially other anti-tumor drugs. The therapeutic agents include, but are not limited to: anti-tumor drugs that act on the chemical structure of DNA, such as cisplatin; anti-tumor drugs that affect nucleic acid synthesis, such as methotrexate (MTX), 5-fluorouracil (5FU), etc.; anti-tumor drugs that affect nucleic acid transcription, such as adriamycin, epirubicin, aclacinomycin, mithramycin, etc.; anti-tumor drugs that act on tubulin synthesis, such as paclitaxel, vinorelbine; aromatase inhibitors such as aminoglutethimide, lentaron, letrozole, anastrozole, etc; cell signaling pathway inhibitors such as epidermal growth factor receptor inhibitors gefitinib (Gefitinib), erlotinib (Erlotinib), lapatinib (Lapatinib), etc; mitogen-activated extracellular signal-regulated kinase (MEK) inhibitors such as trametinib (Trametinib), cobimetinib (Cobimetinib), etc.; cyclin-dependent kinase 4/6(CDK4/6) inhibitors such as Palbociclib, etc.; Src homologous tyrosine phosphatase (SHP2) inhibitor; SOS1 inhibitor; programmed death receptor-1/programmed death ligand-1(PD-1/PD-L1) inhibitors such as nivolumab (Nivolumab), pembrolizumab (Pembrolizumab), etc.

In the third aspect of the present invention, provided is a use of the compound of the present invention as described above, or pharmaceutically acceptable salts thereof, enantiomers, diastereomers, tautomers, cis-trans isomers, solvates, polymorphs, deuterates, or a pharmaceutical composition thereof in the preparation of medicaments for preventing or treating cancer mediated by KRAS G12C mutation. In a preferred embodiment, the cancer mediated by KRAS G12C is selected from the group consisting of: lung cancer (including non-small cell lung cancer), pancreatic cancer, colorectal cancer, leukemia, Ewing's sarcoma, breast cancer, prostate cancer, T-cell lymphoma, B-cell lymphoma, malignant rhabdomyoma, synovial sarcoma, endometrioma, gastric cancer, liver cancer, renal cancer, melanoma, ovarian cancer, brain glioma, cholangiocarcinoma, nasopharyngeal carcinoma, cervical cancer, head and neck cancer, esophageal cancer, thyroid cancer and bladder cancer. In another preferred embodiment, the cancer mediated by KRAS G12C is selected from non-small cell lung cancer, pancreatic cancer and colorectal cancer.

It should be understood that, within the scope of the present invention, each of the above technical features of the present invention and each of the technical features specifically described in the following (such as the examples) can be combined with each other to constitute a new or preferred technical solution. Due to space limitations, it will not be repeated herein.

DESCRIPTION OF TERMS

Figure 1:
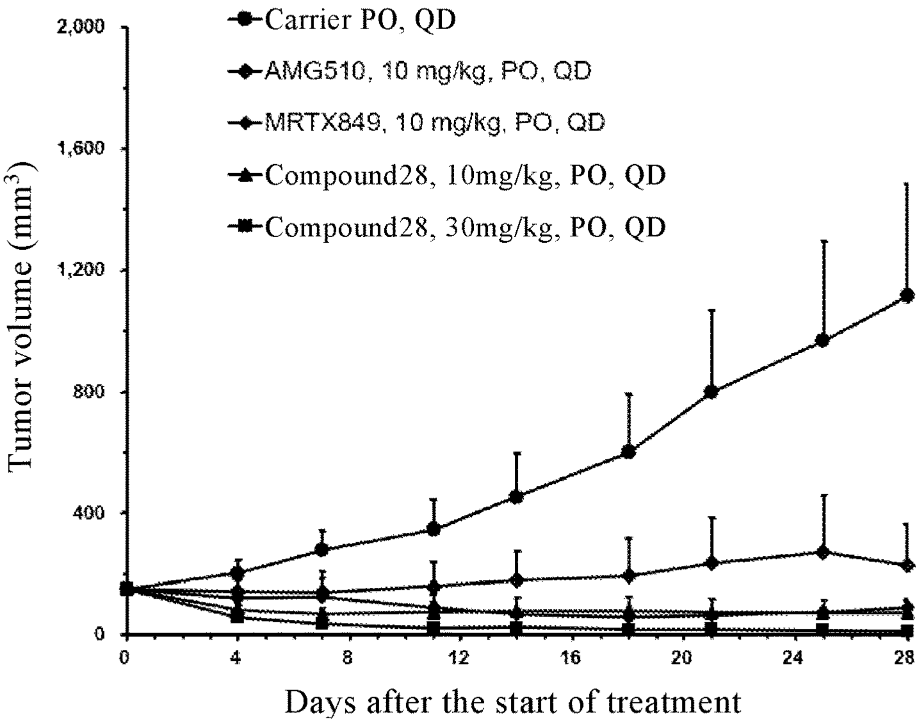
FIG. 1 shows the in vivo efficacy results of the test substances in the female BALB/c nude mouse model with subcutaneous transplantation of NCI-H358 tumors.

Unless otherwise defined, all technical and scientific terms used herein have the same meaning as those commonly understood by those of ordinary skill in the art of the invention.

As used herein, term “contain” or “include (comprise)” may be open, semi-closed, and closed. In other words, said term also includes “consisting essentially of” or “consisting of”.

Definition of Groups

Definitions for standard chemical terms can be found in references including Carey and Sundberg “ADVANCED ORGANIC CHEMISTRY 4TH ED.” Vols. A (2000) and B (2001), Plenum Press, New York. Unless otherwise indicated, conventional methods within the skill of the art are used, such as mass spectrometry, NMR, IR and UV/VIS spectroscopy and pharmacological methods. Unless specifically defined, the terms used herein in the relevant descriptions of analytical chemistry, organic synthetic chemistry, and pharmaceuticals and medicinal chemistry are known in the art. Standard techniques can be used in chemical synthesis, chemical analysis, pharmaceutical preparation, formulation and delivery, and treatment of patients. For example, the reaction and purification can be carried out using the manufacturer’s instructions for use of the kit, or in a manner well known in the art or as described herein. The above-mentioned techniques and methods can generally be carried out in accordance with conventional methods well known in the art, or as described in the various general and more specific documents cited and discussed in this specification. In the present specification, the groups and substituents thereof can be selected by those skilled in the art to provide stable structural moieties and compounds.

When a substituent is described by a conventional formula written from left to right, the substituent likewise includes the chemically equivalent substituent obtained when the formula is written from right to left. For example, $—CH_2O—$ is equivalent to $—OCH_2—$.

The section headings used herein are for the purpose of organizing the article only and should not be interpreted as limitations on the subject matter described. All documents or part of documents cited in this application, including but not limited to patents, patent applications, articles, books, manuals, and papers, are hereby incorporated by reference in their entirety.

Certain chemical groups defined herein are preceded by a simplified symbol to indicate the total number of carbon atoms present in that group. For example, $C_{1-6}$ alkyl refers to an alkyl group as defined below having 1 to 6 carbon atoms. The total number of carbon atoms in the simplified symbol does not include carbons that may be present in substituent of the group.

In addition to the foregoing, the following terms, when used in the present specification and claims, have the meanings set forth below unless otherwise specified.

As used herein, the term “halogen” refers to fluorine, chlorine, bromine or iodine.

“Hydroxy” refers to —OH group.

“Hydroxyalkyl” refers to an alkyl group, as defined below, substituted by a hydroxy (—OH) group.

“Carbonyl” refers to —C(═O)— group.

“Nitro” refers to $—NO_2$.

“Cyano” refers to —CN.

“Amino” refers to $—NH_2$.

“Substituted amino” refers to an amino group substituted by one or two substituents as defined below: alkyl, alkylcarbonyl, aryl alkyl, heteroarylalkyl group, e.g., monoalkylamino, dialkylamino, alkylamido, arylalkylamino, heteroarylalkylamino.

“Carboxyl” refers to —COOH.

As used herein, the term “alkyl” as a group or part of another group (e.g., in the case of halogen-substituted alkyl. etc.) refers to a fully saturated straight or branched hydrocarbon chain group consisting only of carbon and hydrogen atoms, having, for example, from 1 to 12 (preferably from 1 to 8, more preferably from 1 to 6) carbon atoms, and linked to the rest of the molecule by a single bond, for example including but not limited to methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, nonyl, and decyl, and the like. For the purposes of the present invention, the term “alkyl” preferably refers to an alkyl group containing 1 to 6 carbon atoms.

As used herein, the term “alkenyl”, as a group or part of another group, refers to a straight or branched hydrocarbon chain group consisting only of carbon and hydrogen atoms, and at least one double bond, having, for example, from 2 to 14 (preferably from 2 to 10, more preferably from 2 to 6) carbon atoms, linked to the rest of the molecule by a single bond, for example, but not limited to, vinyl, propenyl, allyl group, but-1-enyl, but-2-enyl, pent-1-enyl, pent-1,4-dienyl, and the like.

As a group or part of another group, the term “alkynyl” refers to a straight or branched hydrocarbon chain group consisting only of carbon and hydrogen atoms, containing at least one C≡C, having, for example, from 2 to 14 (preferably from 2 to 10, more preferably from 2 to 6) carbon atoms, and linked to the rest of the molecule by a single bond, for example, but not limited to, ethynyl, 1-propynyl, 1-butynyl, heptynyl, octynyl, and the like.

As used herein, as a group or part of another group, the term “carbocyclyl (carbocyclic group, carbocycle)” refers to a stable non-aromatic monocyclic or polycyclic hydrocarbon group consisting only of carbon and hydrogen atoms, which may include fused ring system, bridged ring system or spiro ring system, having from 3 to 15 carbon atoms, preferably from 3 to 10 carbon atoms, more preferably from 3 to 8 carbon atoms, and it is saturated or unsaturated and can be attached to the rest of the molecule by a single bond via any suitable carbon atom. Unless otherwise specifically indicated in the specification, the carbon atom in the carbocyclyl may be optionally oxidized. Examples of the carbocyclic group include, but are not limited to, cyclopropyl, cyclobutyl, cyclopentyl, cyclohexyl, cycloheptyl, cyclooctyl, adamantyl, 2,3-dihydroindenyl, octahydro-4, 7-methylene-1H-indenyl, 1,2, 3,4-tetrahydro-naphthyl, 5,6,7, 8-tetrahydro-naphthyl, cyclopentenyl, cyclohexenyl, cyclohexadienyl, 1H-indenyl, 8,9-dihydro-7H-benzocyclohepten-6-yl, 6,7,8,9-tetrahydro-5H-benzocycloheptenyl, 5,6,7,8,9, 10-hexahydro-benzocyclooctenyl, fluorenyl, bicyclo [2.2.1] heptyl, 7,7-dimethyl-bicyclo [2.2.1] heptyl, bicyclo [2.2.1] heptenyl, bicyclo [2.2.2] octyl, bicyclo [3.1.1] heptyl, bicyclo [3.2.1] octyl, bicyclo [2.2.2] octenyl, bicyclo [3.2.1] octenyl and octahydro-2, 5-methylene-cyclopentadienyl, etc.

As used herein, as a group or part of another group, the term “heterocyclyl (heterocycle)” refers to a stable 3- to 20-membered non-aromatic cyclic group consisting of 2 to 14 carbon atoms and 1 to 6 heteroatoms selected from nitrogen, phosphorus, oxygen and sulfur. Unless otherwise specifically indicated in the specification, a heterocyclyl may be a monocyclic, bicyclic, tricyclic, or more ring systems, which may include fused ring system, bridged ring system, or spiro ring system; and the nitrogen, carbon, or sulfur atom in heterocyclyl may be optionally oxidized; the nitrogen atom may be optionally quaternized; and the heterocyclyl may be partially or fully saturated. A heterocyclyl may be attached to the rest of the molecule by a single bond via a carbon atom or a heteroatom. In heterocyclyl containing fused rings, one or more of the rings may be an aryl or heteroaryl as defined below, provided that the point of attachment to the rest of the molecule is a non-aromatic ring atom. For the purposes of the present invention, the heterocyclyl is preferably a stable 4- to 11-membered non-aromatic monocyclic, bicyclic, bridged or spiro ring group containing 1 to 3 heteroatoms selected from nitrogen, oxygen and sulfur, more preferred a stable 4- to 8-membered non-aromatic monocyclic, bicyclic, bridged or spirocyclic groups comprising 1 to 3 heteroatoms selected from nitrogen, oxygen and sulfur. Examples of heterocyclyl include, but are not limited to, pyrrolidinyl, morpholinyl, piperazinyl, homopiperazinyl, piperidinyl, thiomorpholinyl, 2,7-diaza-spiro [3.5] nonan-7-yl, 2-oxa-6-aza-spiro [3.3] heptan-6-yl, 2, 5-diaza-bicyclo [2.2.1] heptan-2-yl, azetidinyl, pyranyl, tetrahydropyranyl, thiopyranyl, tetrahydrofuryl, oxazinyl, dioxocyclopentyl, tetrahydroisoquinolinyl, decahydroisoquinolinyl, imidazolinyl, imidazolidinyl, quinazinyl, thiazolidinyl, isothiazolidinyl, isoxazolidinyl, dihydroindolyl, octahydroindolyl, pyrrolidinyl, pyrazolidinyl, phthalimide, etc.

As used herein, the term “aromatic ring (aryl)”, as a group or part of another group, refers to a conjugated hydrocarbon ring system group having from 6 to 18 carbon atoms, preferably having from 6 to 10 carbon atoms. For the purposes of the present invention, an aromatic ring (aryl) may be a monocyclic, bicyclic, tricyclic or polycyclic ring system and may also be fused with the carbocyclyl or heterocyclyl as defined above, provided that the aromatic ring (aryl) attached to the rest of the molecule by a single bond via an atom on the aromatic ring. Examples of the aromatic ring (aryl) include, but are not limited to, phenyl, naphthyl, anthryl, phenanthryl, fluorenyl, 2,3-dihydro-1H-isoindolyl, 2-benzoxazoliabsent, 2H-1, 4-benzoxazin-3 (4H)-one-7-yl, and the like.

As used herein, the term “arylalkyl” refers to an alkyl group as defined above substituted by an aryl as defined above.

As used herein, the term “heteroaromatic ring (heteroaryl)” as a group or part of another group refers to a 5- to 16-membered conjugated ring system group having from 1 to 15 carbon atoms (preferably from 1 to 10 carbon atoms) and 1 to 6 heteroatoms selected from nitrogen, oxygen and sulfur in the ring. Unless specifically indicated in the specification, the heteroaromatic ring (heteroaryl) may be a monocyclic, bicyclic, tricyclic or polycyclic ring system and may also be fused with a carbocyclyl or heterocyclyl as defined above, provided that the heteroaromatic ring (heteroaryl) is attached to the rest of the molecule by a single bond via an atom on the heteroaromatic ring. The nitrogen, carbon or sulfur atom in the heteroaromatic ring (heteroaryl) may optionally be oxidized; the nitrogen atom may optionally be quaternized. For the purposes of the present invention, the heteroaromatic ring (heteroaryl) is preferably a stable 5- to 12-membered aromatic group containing 1 to 5 heteroatoms selected from nitrogen, oxygen and sulfur, more preferred a stable 5- to 10-membered aromatic group containing 1 to 4 heteroatoms selected from nitrogen, oxygen and sulfur or 5- to 6-membered aromatic group containing 1 to 3 heteroatoms selected from nitrogen, oxygen and sulfur. Examples of heteroaromatic ring (heteroaryl) include, but are not limited to, thienyl, imidazolyl, pyrazolyl, thiazolyl, oxazolyl, oxadiazolyl, isoxazolyl, pyridinyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolinyl, isoquinolinyl, diazanaphthalenyl, naphthyridyl, quinoxalinyl, pteridinyl, carbazolyl, carbolinyl, phenanthridinyl, phenanthrolinyl, acridinyl, phenazinyl, isothiazolyl, benzothiazolyl, benzothiophenyl, oxatriazolyl, cinnolinyl, quinazolinyl, thiophenyl, indolizinyl, phenanthrolinyl, isoxazolyl, phenoxazinyl, phenothiazinyl, 4,5,6,7-tetrahydrobenzo [b] thienyl, naphthopyridyl, [1,2,4] triazolo [4,3-b] pyridazine, [1,2,4]triazolo [4,3-a] pyrazine, [1,2,4]triazolo [4,3-c]pyrimidine, [1,2,4]triazolo [4,3-a] pyridine, imidazo [1,2-a] pyridine, imidazo [1,2-b] pyridazine, imidazo [1,2-a] pyrazine and the like.

As used herein, the term “heteroarylalkyl” refers to an alkyl group as defined above substituted by a heteroaryl as defined above.

In the present application, the term “absent” means that the two sides of the group defined above are directly linked by chemical bonds. For example, “B is absent in A-B—C” means “A-C”.

In the present application,

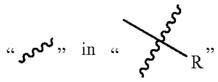

represents the connection position of group R.

In the present application, unless otherwise specified in the claims, “optionally” and “optionally substituted” mean that the subsequently described event or condition may or may not occur, and the description includes both the occurrence and non-occurrence of the event or condition. For example, “optionally substituted aryl” means that the hydrogen on the aryl is substituted or unsubstituted, and the description includes both substituted aryl and unsubstituted aryl. For example, without explicit listing of substituents, as used herein, the term "optionally substituted", "substituted" or "substituted by" refer to one or more hydrogen atoms on a given atom or group independently substituted by one or more, e.g., 1, 2, 3, or 4, substituents independently selected from: deuterium (D), halogen, —OH, sulfydryl, cyano, —$CD_3$, —$C_1$-$C_6$alkyl (preferred —$C_{1-3}$alkyl), $C_2$-$C_6$alkenyl, $C_2$-$C_6$alkynyl, cycloalkyl (preferably 3-8 membered cycloalkyl), aryl, heterocyclyl (preferably 3-8 membered heterocyclyl), heteroaryl, aryl-$C_1$-$C_6$alkyl, heteroaryl $C_1$-$C_6$alkyl, $C_1$-$C_6$haloalkyl-, —$OC_1$-$C_6$alkyl (preferred —$OC_1$-$C_3$alkyl), —$OC_2$-$C_6$alkenyl, —$OC_1$-$C_6$alkyl phenyl, —$C_1$-$C_6$alkyl-OH (preferred —$C_1$-$C_4$alkyl OH), —$C_1$-$C_6$alkyl SH, —$C_1$-$C_6$alkyl O—$C_1$-$C_6$alkyl, —$OC_1$-$C_6$haloalkyl, —$NH_2$, $C_1$-$C_6$alkyl-$NH_2$ (preferably —$C_1$-$C_3$alkyl-$NH_2$), —N($C_1$-$C_6$alkyl)$_2$ (preferably —N($C_1$-$C_3$alkyl)$_2$), —NH($C_1$-$C_6$alkyl) (preferably —NH($C_1$-$C_3$alkyl)), —N($C_1$-$C_6$alkyl)($C_1$-$C_6$alkyl phenyl), —NH($C_1$-$C_6$alkyl phenyl), nitro, —C(O)—OH, C(O)$OC_1$-$C_6$alkyl (preferably —C(O)$OC_1$-$C_3$alkyl), —CON$R^iR^{ii}$ (wherein, $R^i$ and $R^{ii}$ is H, D and $C_{1-6}$alkyl, preferably $C_{1-3}$alkyl), —NHC(O)($C_1$-$C_6$alkyl), —NHC(O)(phenyl), —N($C_1$-$C_6$alkyl) C(O)($C_1$-$C_6$alkyl), —N($C_1$-$C_6$alkyl) C(O)(phenyl), —C(O) $C_1$-$C_6$alkyl, —C(O) heteroaryl (preferably —C(O)-5-7 membered heteroaryl), —C(O)$C_1$-$C_6$alkyl phenyl, —C(O) $C_1$-$C_6$haloalkyl, —OC(O)$C_1$-$C_6$alkyl (preferably —OC(O) $C_1$-$C_3$alkyl), —S(O)$_2$—$C_1$-$C_6$alkyl, —S(O)—$C_1$-$C_6$alkyl, —S(O)$_2$-phenyl, —S(O)$_2$—$C_1$-$C_6$haloalkyl, —S(O)$_2$$NH_2$, —S(O)$_2$NH($C_1$-$C_6$alkyl), —S(O)$_2$NH (phenyl), —NHS(O)$_2$ ($C_1$-$C_6$alkyl), —NHS(O)$_2$(phenyl) and —NHS(O)$_2$($C_1$-$C_6$haloalkyl), wherein each of the alkyl, cycloalkyl, phenyl, aryl, heterocyclyl and heteroaryl is optionally further substituted by one or more substituents selected from halogen, —OH, —$NH_2$, cycloalkyl, 3-8 membered heterocyclyl, $C_1$-$C_4$alkyl, $C_1$-$C_4$haloalkyl-, —$OC_1$-$C_4$alkyl, —$C_1$-$C_4$alkyl-OH, —$C_1$-$C_4$alkyl O—$C_1$-$C_4$alkyl, —$OC_1$-$C_4$haloalkyl, cyano, nitro, —C(O)—OH, —C(O)$OC_1$-$C_6$alkyl, —CON($C_1$-$C_6$alkyl)$_2$, —CONH($C_1$-$C_6$alkyl), —$CONH_2$—NHC(O)($C_1$-$C_6$alkyl), —NH($C_1$-$C_6$alkyl) C(O)($C_1$-$C_6$alkyl), —$SO_2$($C_1$-$C_6$alkyl), —$SO_2$(phenyl), —$SO_2$($C_1$-$C_6$haloalkyl), —$SO_2NH_2$, —$SO_2$NH($C_1$-$C_6$alkyl), —$SO_2$NH (phenyl), —$NHSO_2$($C_1$-$C_6$alkyl), —$NHSO_2$(phenyl) and —$NHSO_2$($C_1$-$C_6$haloalkyl). When an atom or group is substituted with various substituents, the substituents may be the same or different. As used herein, the terms "moiety," "structure moiety," "chemical moiety," "group," "chemical group" refer to a specific fragment or functional group in a molecule. A chemical moiety is generally considered to be a chemical entity embedded in or attached to a molecule.

"Stereoisomer" refers to compound composed of the same atoms, bonded by the same bonds, but with different three-dimensional structures. The present invention is intended to encompass various stereoisomers and mixtures thereof.

When the compound of the present invention contains olefinic double bonds, the compound of the present invention is intended to include both E- and Z-geometric isomers unless otherwise specified.

The term "tautomer" refers to an isomer formed by the transfer of a proton from one atom of a molecule to another atom of the same molecule. All tautomeric forms of the compound of the invention will also be included within the scope of the invention.

The compounds of the present invention, or pharmaceutically acceptable salts thereof, may contain one or more chiral carbon atoms, and thus may give rise to enantiomers, diastereomers, and other stereoisomeric forms. Each chiral carbon atom may be defined as (R)- or (S)-based on stereochemistry. The present invention is intended to include all possible isomers, as well as racemates and optically pure forms thereof. Racemates, diastereomers or enantiomers can be selected as starting materials or intermediates in the preparation of the compounds of the present invention. Isomers with optical activity can be prepared using chiral synthons or chiral reagents, or resolved using conventional techniques, such as crystallization and chiral chromatography.

Conventional techniques for the preparation/separation of individual isomers include chiral synthesis from appropriate optically pure precursors, or resolution of the racemate (or racemate of salts or derivatives) using, for example, chiral high performance liquid chromatography, see, for example, Gerald Gubitz and Martin G. Schmid (Eds.), Chiral Separations, Methods and Protocols, Methods in Molecular Biology, Vol. 243, 2004; A. M. Stalcup, Chiral Separations. *Annu. Rev. Anal. Chem.* 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, *Acc. Chem. Res.* 1990, 23, 128.

As used herein, the term "pharmaceutically acceptable salts" includes pharmaceutically acceptable acid addition salts and pharmaceutically acceptable base addition salts.

The term "pharmaceutically acceptable acid addition salts" refers to salts formed with inorganic or organic acids that retain the bioavailability of the free base without exerting other adverse effects. The inorganic acid salts include but are not limited to hydrochloride, hydrobromide, sulfate, nitrate, phosphate, etc.; the organic acid salts include but are not limited to formate, acetate, 2, 2-dichloro acetate, trifluoroacetate, propionate, caproate, caprylate, caprate, undecylenate, glycolate, gluconate, lactate, sebacate, adipate, glutarate, malonate, oxalate, maleate, succinate, fumarate, tartrate, citrate, palmitate, stearate, oleate, cinnamate, lauroleate, malate, glutamate, pyroglutamate, aspartate, benzoate, mesylate, benzene sulfonate, p-toluenesulfonate, alginate, ascorbate, salicylate, 4-aminosalicylate, naphthalene disulfonate, etc. These salts can be prepared by methods known in the art.

The term "pharmaceutically acceptable base addition salts" refers to salts formed with inorganic or organic bases that retain bioavailability of the free acid without exerting other adverse effects. Salts derived from inorganic bases include, but are not limited to, sodium salts, potassium salts, lithium salts, ammonium salts, calcium salts, magnesium salts, ferric salts, zinc salts, copper salts, manganese salts, aluminum salts, and the like. Preferred inorganic salts are ammonium salts, sodium salts, potassium salts, calcium salts and magnesium salts. Salts derived from organic bases include, but are not limited to, primary, secondary and tertiary amines; substituted amines, including natural substituted amines, cyclic amines and basic ion exchange resins, such as ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, dicyclohexylamine, lysine, arginine, histidine, caffeine, procaine, choline, betaine, ethylenediamine, glucamine, methylglucamine, theobromine, purine, piperazine, piperidine, N-ethylpiperidine, polyamine resin, and the like. Preferred organic bases include isopropylamine, diethylamine, ethanolamine, trimethylamine, dicyclohexylamine, choline and caffeine. These salts can be prepared by methods known in the art.

As used herein, the term "pharmaceutical composition" refers to a formulation of a compound of the present invention in combination with a medium generally acceptable in the art for the delivery of a biologically active compound to a mammal (e. g., a human). The medium includes pharmaceutically acceptable carriers. The purpose of the pharmaceutical composition is to promote the administration of the organism, facilitate the absorption of active ingredients and thereby exert biological activity.

As used herein, the term "pharmaceutically acceptable" refers to a substance (e. g., a carrier or diluent) that does not affect the biological activity or properties of the compound of the invention, and is relatively non-toxic, i.e., the substance can be administered to an individual without causing any adverse biological reaction or interacting in an adverse manner with any of the components contained in the composition.

In the present application, "pharmaceutically acceptable carriers" include, but are not limited to, any adjuvant, carrier, excipient, glidant, sweetener, diluent, preservative, dye/colorant, flavoring agent, surfactant, wetting agent, dispersant, suspending agent, stabilizer, isotonic agent, solvent or emulsifier licensed by relevant governmental regulatory authority as acceptable for human or livestock use.

As used herein, the term "tumors" include but are not limited to lung cancer, pancreatic cancer, colorectal cancer, leukemia, Ewing's sarcoma, breast cancer, prostate cancer, T cell lymphoma, B cell lymphoma, malignant rhabdomyoma, synovial sarcoma, endometrioma, gastric cancer, liver cancer, renal cancer, melanoma, ovarian cancer, brain glioma, cholangiocarcinoma, nasopharyngeal carcinoma, cervical carcinoma, head and neck cancer, esophageal cancer, thyroid cancer and bladder cancer, etc.

As used herein, the terms "prophylactic", "preventing" and "prevention" include reducing the possibility of the occurrence or worsening of a disease or disorder in patients.

As used herein, the term "treatment" and other similar synonyms include the following meanings:

(i) Preventing the occurrence of the disease or disorder in mammals, especially when such mammals are susceptible to such diseases or disorders but have not been diagnosed as having it;

(ii) Inhibiting the disease or disorder, i.e. curbing its development;

(iii) Alleviating disease or disorder, i.e., abating the condition of the disease or disorder; or (iv) Alleviating the symptoms caused by the disease or disorder.

As used herein, the terms "effective amount," "therapeutically effective amount," or "pharmaceutically effective amount" refer to an amount of at least one agent or compound that, upon administration, is sufficient to alleviate to some extent of one or more of the symptoms of the disease or condition being treated. The result can be the reduction and/or alleviation of signs, symptoms, or causes, or any other desired change in a biological system. For example, an "effective amount" for treatment is the amount of a composition comprising the compound disclosed herein required to provide a clinically significant condition-relieving effect. An effective amount appropriate in any individual case can be determined using techniques such as dose escalation assays.

As used herein, the terms "administration," "administed" "administering" and the like refer to methods that enable the delivery of a compound or composition to the desired site for biological action. These methods include, but are not limited to, oral routes, transduodenal routes, parenteral injection (including intravenous, subcutaneous, intraperitoneal, intramuscular, intra-arterial injection or infusion), topical administration, and rectal administration. Those skilled in the art are familiar with the application techniques of the compounds and methods described herein, such as those discussed in Goodman and Gilman, The Pharmacological of Therapeutics, current ed.; Pergamon; and Remington's, Pharmaceutical Sciences (current edition), Mack Publishing Co., Easton, Pa. In preferred examples, the compounds and compositions discussed herein are administered orally.

As used herein, the terms "pharmaceutical combination", "administrated in combination", "combined administration", "administration of other treatments", "administration of other therapeutic agents" and the like refer to pharmaceutical treatments obtained by admixing or combining more than one active ingredients, which includes both fixed and non-fixed combinations of active ingredients. The term "fixed combination" refers to the simultaneous administration of at least one compound described herein and at least one synergists to a patient in the form of a single entity or single dosage form. The term "non-fixed combination" refers to that at least one compound described herein and at least one synergistic formulation are administered simultaneously, concomitantly, or sequentially at variable intervals to a patient as separate entities. These are also applied to cocktail therapies, for example the administration of three or more active ingredients.

It should also be understood by those of skill in the art that in the methods described below, the functional group of the intermediate compound may need to be protected by an appropriate protecting group. Such functional groups include hydroxyl, amino, sulfydryl, and carboxylic acid. Suitable hydroxyl protecting groups include trialkylmethanosilyl or diaromatic cyclic alkylmethanosilyl (e.g. tert-butyldimethylmethanosilyl, tert-butyl diphenylmethanosilyl or trimethylmethanosilyl), tetrahydropyranyl, benzyl, etc. Suitable protecting groups for amino, amidinyl and guanidinyl include tert-butoxycarbonyl, benzyloxycarbonyl and the like. Suitable thiol protecting groups include —C(O)—R" (wherein R" is alkyl, aryl or arylalkyl), p-methoxybenzyl, trityl, and the like. Suitable carboxy protecting groups include alkyl, aryl or aryl alkyl esters.

Protecting groups can be introduced and removed according to standard techniques known to those skilled in the art and as described herein. The use of protecting groups is described in detail in Greene, T. W. and P. G. M. Wuts, Protective Groups in Organi Synthesis, (1999), 4th Ed., in Wiley. The protecting group may also be polymer resin.

Beneficial Effect

1. Provided a compound of formula I or pharmaceutically acceptable salts thereof.
2. Provided a structurally novel pharmaceutical composition for the prevention and treatment of diseases mediated by KRAS G12C mutation.

DETAILED DESCRIPTION OF EMBODIMENTS

The present invention was further specified with specific examples. It should be clear to those skilled in the art that the examples are merely intended to assist in understanding the present invention and should not be considered as specific limitations to the present invention.

The experimental methods without specific conditions in the following examples generally follow the conventional conditions or the conditions suggested by the manufacturer. Unless otherwise stated, percentages and portions are calculated by weight.

Unless otherwise specified, the experimental materials and reagents used in the following examples are commercially available.

In each example, $^1$H NMR was recorded on a BRUKER AVANCE NEO 400 MHz Nuclear Magnetic Resonance instrument with chemical shifts reported as δ (ppm); Liquid chromatography-mass spectrometry (LCMS) was recorded on Shimadzu LC-20AD, SIL-20A, CTO-20AC, SPD-M20A, CBM-20A, LCMS-2020 mass spectrometer; preparative HPLC separation used Gilson-281 liquid chromatograph.

Preparation of Intermediates

1. Preparation of Intermediate A

A

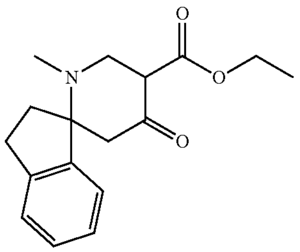

The synthetic route of intermediate A is shown below:

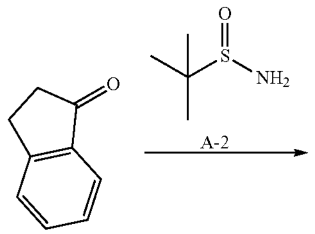

A-1

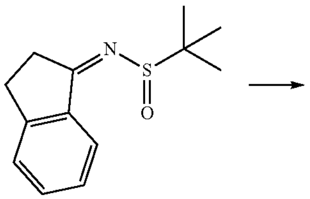

A-3

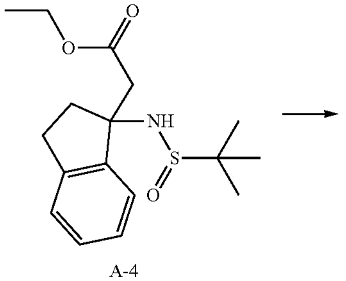

A-4

-continued

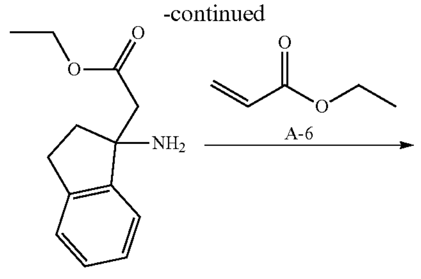

A-5

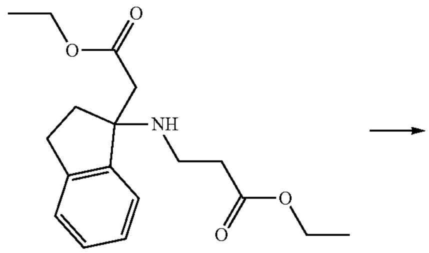

A-7

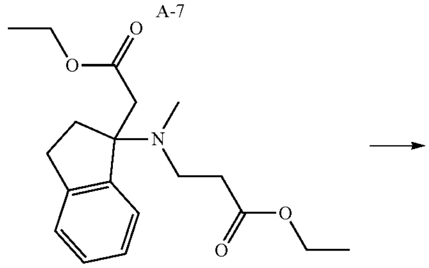

A-8

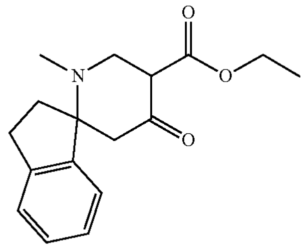

A (1) To a solution of compound A-1 (59.9 g, 454 mmol) in toluene (500 mL) was added compound A-2 (50.0 g, 413 mmol) and tetraethyl titanate (188 g, 825 mmol). The reaction solution was stirred at 130° C. for 12 h under nitrogen protection. Then the reaction solution was added with water (400 mL), and extracted with ethyl acetate (400 mL×2). The combined organic phase was washed with saturated NaCl aqueous solution (500 mL×1), dried over anhydrous sodium sulfate, filtered, and concentrated under reduced pressure. The crude product was isolated by silica gel column chromatography (petroleum ether/ethyl acetate=1:0 to 0:1) to obtain compound A-3.

MS-ESI [M+H]$^+$, calculated: 236, found: 236.

(2) To a solution of compound A-3 (50.8 g, 216 mmol), and ethyl acetate (95.1 g, 1.08 mol) in tetrahydrofuran (500 mL) was added dropwise with lithium diisopropylamide (2 mol/L, 216 mL, tetrahydrofuran solution) at −78° C. under nitrogen protection. The reaction solution was stirred at −78° C. for 3 hours. After warming to 0° C., the reaction solution was quenched with saturated aqueous ammonium chloride solution (500 mL), and extracted with ethyl acetate (1000 mL×2). The combined organic phase was dried over anhydrous sodium sulfate, filtered, and concentrated under reduced pressure. The crude product was separated by silica gel column chromatography (petroleum ether/ethyl acetate=1:0 to 0:1) to obtain compound A-4.

MS-ESI $[M+H]^+$, calculated: 324, found: 324.

$^1$H NMR (400 MHz, $CDCl_3$) δ 7.18-7.26 (m, 4H), 5.21 (s, 1H), 4.17 (qd, J=7.2, 3.2 Hz, 2H), 3.17 (ddd, J=16.4, 8.4, 5.6 Hz, 1H), 2.88-2.93 (m, 1H), 2.73-2.87 (m, 2H), 2.64-2.72 (m, 1H), 2.32 (ddd, J=13.6, 8.4, 5.6 Hz, 1H), 1.24-1.27 (m, 3H), 1.19 (s, 9H).

(3) To a solution of compound A-4 (15.6 g, 48.2 mmol) in ethanol (100 mL) was added a solution of hydrochloric acid in dioxane (4 mol/L, 30 mL). The reaction solution was stirred at 25° C. for 5 hours under nitrogen protection. The reaction solution was concentrated under reduced pressure to afford crude product of hydrochloride of compound A-5.

MS-ESI $[M-NH_2+H]^+$, calculated: 203, found: 203.

(4) To a solution of hydrochloride of compound A-5 (12.0 g, 46.9 mmol) in ethanol (50.0 mL) was added compound A-6 (46.9 g, 469 mmol), copper oxide (373 mg, 4.69 mmol) and triethylamine (4.75 g, 46.9 mmol). The reaction solution was reacted at 85° C. for 4 hours in a sealed tube under nitrogen protection. Then the reaction solution was added with water (500 mL), and extracted with ethyl acetate (500 mL×2). The combined organic phase was washed with saturated NaCl aqueous solution (500 mL×1), dried over anhydrous sodium sulfate, filtered and concentrated under reduced pressure. The crude product was separated by silica gel column chromatography (petroleum ether/ethyl acetate=1:0 to 0:1) to obtain compound A-7.

MS-ESI $[M+H]^+$, calculated: 320, found: 320.

$^1$H NMR (400 MHz, $CDCl_3$) δ 7.13-7.26 (m, 4H), 4.09-4.15 (m, 4H), 2.87-2.99 (m, 2H), 2.76 (q, J=6.8 Hz, 2H), 2.63 (br d, J=14.8 Hz, 1H), 2.54 (dd, J=11.2, 6.4 Hz, 1H), 2.42-2.45 (m, 2H), 2.28-2.36 (m, 1H), 2.17 (ddd, J=13.2, 8.4, 4.8 Hz, 1H), 1.18-1.26 (m, 6H).

(5) To a solution of compound A-7 (13.7 g, 42.9 mmol) in ethanol (100 mL) was added paraformaldehyde (6.44 g) and sodium cyanoborohydride (8.09 g, 129 mmol). The reaction solution was reacted at 25° C. for 1 hour under nitrogen protection. Then the reaction solution was added with water (150 mL), and extracted with ethyl acetate (200 mL×2). The combined organic phase was washed with saturated NaCl aqueous solution (150 mL×1), dried over anhydrous sodium sulfate, filtered, and concentrated under reduced pressure. The crude product was isolated by silica gel column chromatography (petroleum ether/ethyl acetate=3:1) to obtain compound A-8.

MS-ESI $[M+H]^+$, calculated: 334, found: 334.

$^1$H NMR (400 MHz, $CDCl_3$) δ 7.11-7.26 (m, 4H), 4.07-4.12 (m, 2H), 3.81-3.97 (m, 2H), 2.79-3.00 (m, 3H), 2.74-2.78 (m, 1H), 2.57-2.73 (m, 2H), 2.24-2.48 (m, 4H), 2.17 (s, 3H), 1.22-1.26 (m, 3H), 1.01 (t, J=7.2 Hz, 3H).

(6) To a solution of compound A-8 (13.4 g, 40.2 mmol) in tetrahydrofuran (500 mL) was added potassium bis (trimethylsilyl) amide (1 mol/L, 121 mL, tetrahydrofuran solution) at −78° C. The reaction solution was reacted at −78° C. for 1 hour under nitrogen protection. Then the reaction solution was added with water (500 mL), and extracted with ethyl acetate (500 mL×2). The combined organic phase was washed with saturated NaCl aqueous solution (500 mL×1), dried over anhydrous sodium sulfate, filtered, and concentrated under reduced pressure to obtain the crude compound A.

MS-ESI $[M+H]^+$, calculated: 288, found: 288.

$^1$H NMR (400 MHz, $CDCl_3$) δ 7.19-7.27 (m, 4H), 4.20-4.31 (m, 2H), 3.44-3.61 (m, 1H), 3.18-3.31 (m, 1H), 2.90-2.99 (m, 2H), 2.69 (br t, J=13.2 Hz, 1H), 2.30-2.44 (m, 1H), 2.16-2.29 (m, 1H), 2.06-2.15 (m, 3H), 1.61-1.96 (m, 2H), 1.30-1.34 (m, 3H).

Example 1 Synthesis of Compound 1

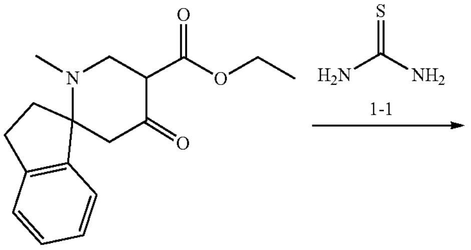

A

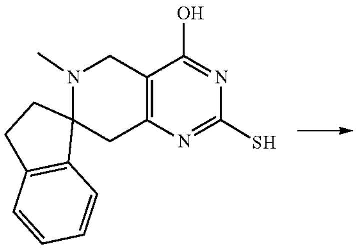

1-2

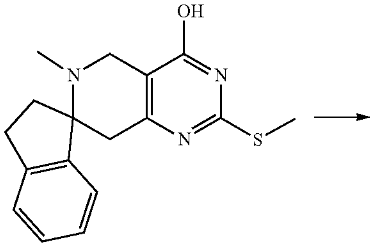

1-3

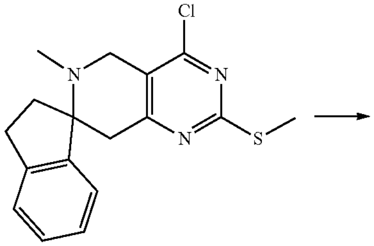

1-4

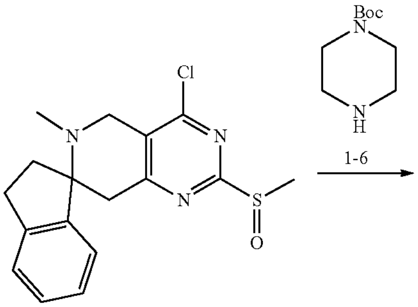

1-5

-continued

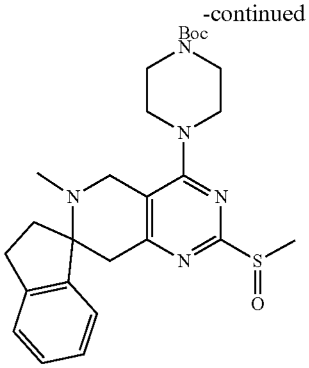

1-7

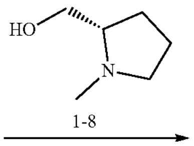

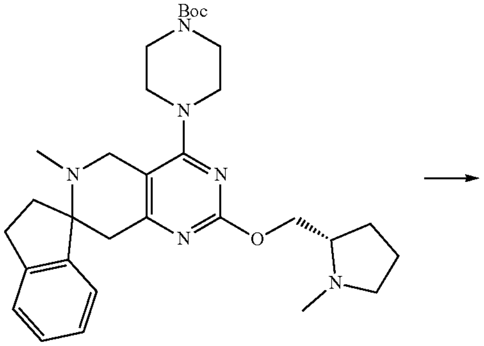

1-9

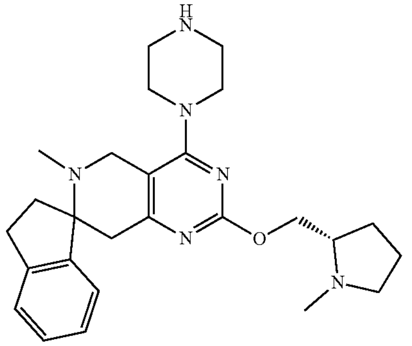

1-10

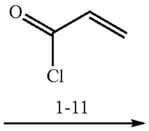

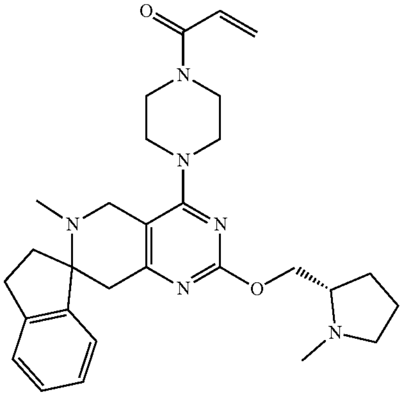

1

(1) To a solution of intermediate A (2.0 g, 6.96 mmol) in ethanol (30.0 mL) was added compound 1-1 (1.06 g, 13.9 mmol) and sodium ethoxide (1.42 g, 20.9 mmol), and the reaction solution was stirred at 80° C. for 16 hours under nitrogen protection. After concentrated under reduced pressure, the reaction solution was added with ethanol (15.0 mL) and water (5.0 mL) and its pH was adjusted to 6 with hydrochloric acid (1 mol/L). The resulting solution was precipitated, and filtered, and the filter cake was dried to obtain compound 1-2.

MS-ESI $[M+H]^+$, calculated: 300, found: 300.

$^1$H NMR (400 MHz, DMSO-d6) δ 12.43 (br s, 1H), 12.28 (br s, 1H), 7.23-7.27 (m, 3H), 7.21 (br s, 1H), 3.49 (br d, J=16.8 Hz, 1H), 3.05 (br d, J=16.4 Hz, 1H), 2.84-2.95 (m, 2H), 2.57-2.69 (m, 1H), 2.40-2.48 (m, 1H), 2.15 (dt, J=13.2, 8.4 Hz, 1H), 1.98 (s, 3H), 1.59-1.69 (m, 1H).

(2) To a solution of compound 1-2 (1.66 g, 5.54 mmol) in water (15.0 mL) was added sodium hydroxide (443 mg, 11.1 mmol), and dimethyl sulfate (1.93 mg, 15.3 mmol), and the reaction solution was stirred at 0° C. for 2 hours under nitrogen protection. The reaction solution was added with water (100 mL), and extracted with ethyl acetate (100 mL×3). The combined organic phase was dried over anhydrous sodium sulfate, filtered, and concentrated under reduced pressure. The crude product was separated by silica gel column chromatography (petroleum ether/ethyl acetate=1:0 to 1:2) to obtain compound 1-3.

MS-ESI $[M+H]^+$, calculated: 314, found: 314.

$^1$H NMR (400 MHz, DMSO-d6) δ 12.66 (br s, 1H), 7.21-7.26 (m, 3H), 7.15-7.20 (m, 1H), 3.55 (br d, J=17.2 Hz, 1H), 3.12-3.20 (m, 1H), 2.90 (br t, J=7.2 Hz, 2H), 2.77 (br d, J=17.6 Hz, 1H), 2.54 (br d, J=18.4 Hz, 1H), 2.44 (s, 3H), 2.18 (dt, J=13.2, 8.4 Hz, 1H), 2.00 (s, 3H), 1.61 (dt, J=13.2, 6.4 Hz, 1H).

(3) To a solution of compound 1-3 (840 mg, 2.68 mmol) in chloroform (4.0 mL) was added phosphorus oxychloride (6.60 g, 43.0 mmol), and the reaction solution was stirred at 80° C. for 1 hour under nitrogen protection. Then the reaction solution was concentrated under reduced pressure, added with ice water (50.0 mL), and extracted with dichloromethane (50.0 mL×1). The organic phase was washed with saturated sodium bicarbonate aqueous solution (50.0 mL×2) and saturated NaCl aqueous solution (500 mL×1), dried over anhydrous sodium sulfate, filtered, and concentrated under reduced pressure to obtain compound 1-4.

MS-ESI $[M+H]^+$, calculated: 332, found: 332.

$^1$H NMR (400 MHz, $CDCl_3$) δ 7.27 (br s, 1H), 7.18-7.26 (m, 3H), 3.95 (br d, J=16.8 Hz, 1H), 3.48-3.60 (m, 1H), 3.04-3.22 (m, 1H), 2.97-3.04 (m, 1H), 2.89-2.97 (m, 2H), 2.54 (s, 3H), 2.23-2.31 (m, 1H), 2.20 (s, 3H), 1.65-1.71 (m, 1H).

(4) To a solution of compound 1-4 (200 mg, 603 μmol) in dichloromethane (5.0 mL) was added m-chloroperoxybenzoic acid (123 mg, 606 μmol), and the reaction solution was stirred at 0° C. for 5 hours under nitrogen protection. Then the reaction solution was added with saturated sodium sulfite aqueous solution (30.0 mL), and extracted with dichloromethane (20.0 mL). The organic phase was washed with saturated sodium bicarbonate aqueous solution (20.0 mL×2) and saturated NaCl aqueous solution (20.0 mL×1), dried over anhydrous sodium sulfate, filtered, and concentrated under reduced pressure to obtain compound 1-5.

MS-ESI $[M+H]^+$, calculated: 348, found: 348.

(5) To a solution of compound 1-5 (206 mg, 592 μmol) in N,N-Dimethylformamide (10.0 mL) was added compound 1-6 (552 mg 2.96 mmol), and the reaction solution was stirred at 25° C. for 16 hours under nitrogen protection. Then the reaction solution was added with ethyl acetate (30.0 mL), washed with saturated NaCl aqueous solution (20.0 mL×5), dried over anhydrous sodium sulfate, filtered, and concentrated under reduced pressure. The crude product was separated by preparative thin layer chromatography (dichloromethane/methanol=10:1) to obtain compound 1-7.

MS-ESI [M+H]$^+$, calculated: 498, found: 498.

(6) To a solution of compound 1-7 (32.0 mg, 64.3 μmol) in tetrahydrofuran (3.0 mL) was added compound 1-8 (22.2 mg, 193 μmol), and sodium tert-butoxide (18.6 mg, 194 mol), and the reaction solution was stirred at 25° C. for 1 hour under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure to afford compound 1-9.

MS-ESI [M+H]$^+$, calculated: 549, found: 549.

(7) To a solution of compound 1-9 (35.0 mg, 63.8 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 1-10.

MS-ESI [M+H]$^+$, calculated: 449, found: 449.

(8) To a solution of trifluoroacetate of compound 1-10 (35.0 mg, 62.2 μmol) in dichloromethane (2.0 mL) was added triethylamine (31.5 mg, 331 μmol) and compound 1-11 (16.9 mg, 187 μmol), and the reaction solution was stirred at −78° C. for 1 hour under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (3_Phenomenex Luna C18, 70 mm×30 mm 3 μm, A: water (10 mmol/L ammonium bicarbonate); B: acetonitrile, 20%-70%: 40 min) to obtain compound 1.

MS-ESI [M+H]$^+$, calculated: 503, found: 503.

$^1$H NMR (400 MHz, MeOD) δ 7.20-7.31 (m, 4H), 6.81 (dd, J=16.8, 10.4 Hz, 1H), 6.26 (dd, J=16.8, 1.6 Hz, 1H), 5.80 (dd, J=10.4, 1.6 Hz, 1H), 4.34-4.41 (m, 1H), 4.27-4.33 (m, 1H), 3.85 (br d, J=3.2 Hz, 2H), 3.74-3.81 (m, 2H), 3.63-3.72 (m, 4H), 3.54 (br s, 2H), 3.08 (dt, J=9.6, 4.8 Hz, 1H), 2.95-3.04 (m, 2H), 2.82-2.94 (m, 2H), 2.70-2.78 (m, 1H), 2.49 (s, 3H), 2.39-2.46 (m, 1H), 2.35 (q, J=8.8 Hz, 1H), 2.20 (s, 3H), 2.05-2.13 (m, 1H), 1.85-1.91 (m, 1H), 1.76-1.84 (m, 2H), 1.65-1.74 (m, 1H).

Example 2 Synthesis of Compound 2

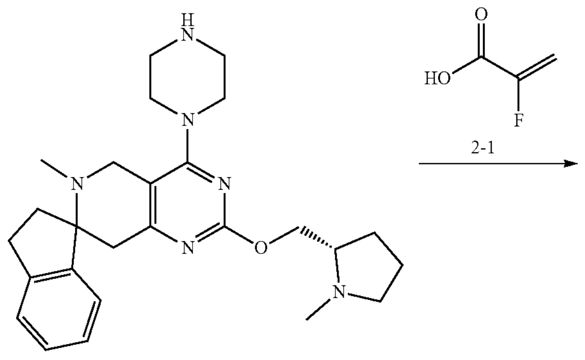

2-1

1-10

-continued

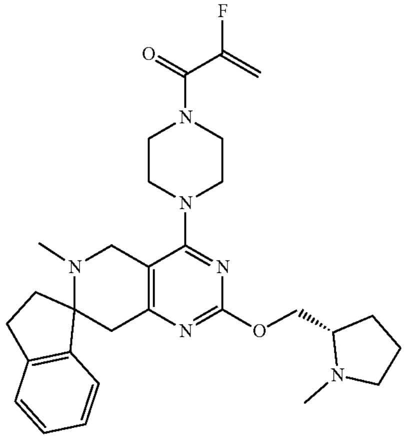

2

To a solution of compound 2-1 (19.2 mg, 213 μmol) in dichloromethane (2.0 mL) was added triethylamine (108 ng, 1.07 μmol) and 2-(7-azabenzotriazole)-N,N,N',N'-tetramethylurea hexafluorophosphate (81.2 mg, 214 μmol), and the reaction solution was stirred at 25° C. for 0.5 hours under nitrogen protection, and the reaction solution was added with trifluoroacetate of compound 1-10 (60.0 mg, 107 μmol), and continued stirring for 0.5 hours at 25° C. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 70 mm×30 mm 3 μm, A: water (0.225% formic acid); B: acetonitrile, 0%-30%: 35 min) to obtain formate of compound 2.

MS-ESI [M+H]$^+$, calculated: 521, found: 521.

$^1$HNMR (400 MHz, MeOD) δ 7.25-7.30 (m, 4H), 5.28-5.35 (m, 1H), 5.24 (dd, J=19.2, 4.0 Hz, 1H), 4.70 (dt, J=12.4, 3.6 Hz, 1H), 4.47-4.55 (m, 1H), 3.81-3.90 (m, 3H), 3.73-3.78 (m, 4H), 3.61-3.71 (m, 3H), 3.52-3.61 (m, 2H), 3.21 (dt, J=11.2, 8.0 Hz, 1H), 3.04-3.12 (m, 1H), 3.02 (s, 3H), 2.95-3.01 (m, 2H), 2.88-2.94 (m, 1H), 2.47 (dt, J=13.2, 8.4 Hz, 1H), 2.32-2.40 (m, 1H), 2.24 (s, 3H), 2.14-2.20 (m, 1H), 2.09 (br dd, J=14.4, 7.2 Hz, 1H), 1.97-2.04 (m, 1H), 1.89 (ddd, J=13.2, 8.4, 4.4 Hz, 1H).

Example 3 Synthesis of Compound 3

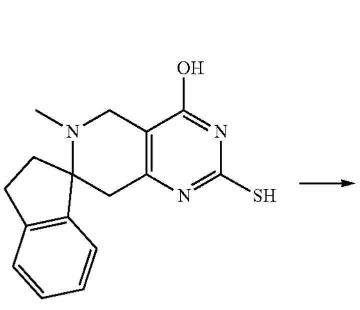

1-2

-continued

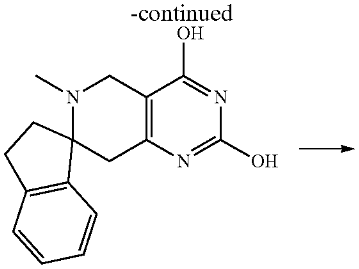

3-1

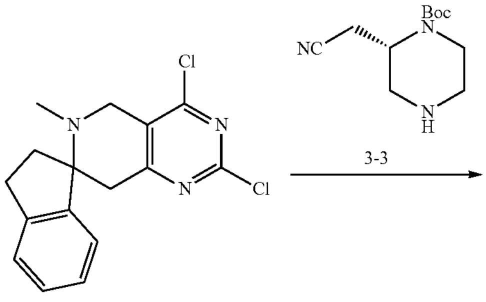

3-2

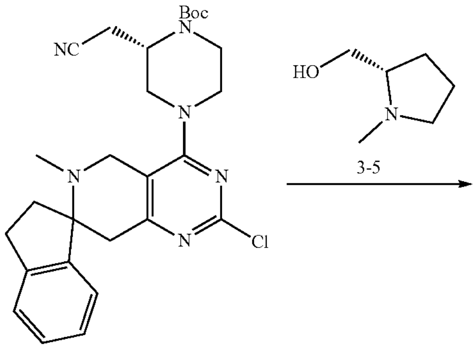

3-4

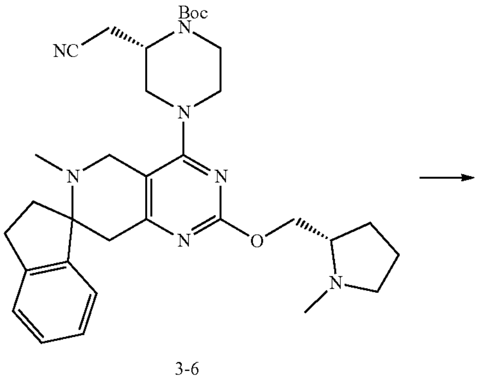

3-6

-continued

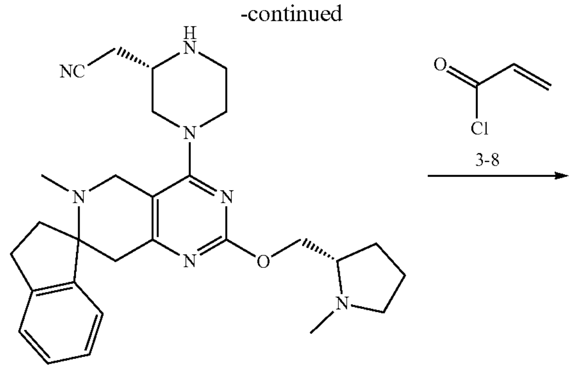

3-7

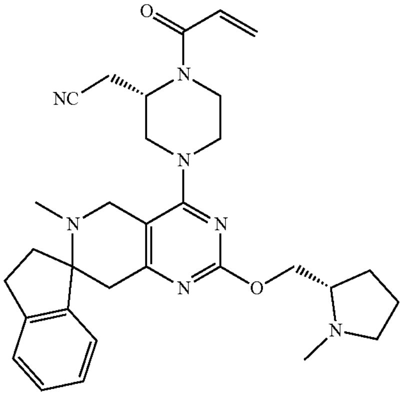

3

(1) To a solution of intermediate 1-2 (500 mg, 1.67 mmol) in water (10.0 mL) was added chloroacetic acid (1.27 g, 13.9 mmol), and the reaction solution was stirred at 100° C. for 16 hours under nitrogen protection. After the reaction solution was filtered, the filtrate was adjusted to pH 8 with saturated sodium bicarbonate aqueous solution to give precipitate. After filtration, the filter cake was dried to obtain compound 3-1.

MS-ESI $[M+H]^+$, calculated: 284, found: 284.

$^1$H NMR (400 MHz, DMSO-d6) δ 11.01 (s, 1H), 10.76 (s, 1H), 7.22-7.27 (m, 3H), 7.18-7.22 (m, 1H), 3.41-3.45 (m, 1H), 3.02 (br d, J=16.0 Hz, 1H), 2.81-2.93 (m, 2H), 2.56 (br d, J=17.2 Hz, 1H), 2.32 (d, J=17.2 Hz, 1H), 2.16 (dt, J=13.2, 8.4 Hz, 1H), 1.97 (s, 3H), 1.62 (ddd, J=13.2, 8.4, 4.4 Hz, 1H).

(2) Compound 3-1 (328 mg, 1.16 mmol) was dissolved in phosphorus oxychloride (4.95 g, 32.3 mmol), and the reaction solution was stirred at 80° C. for 16 hours under nitrogen protection. Then the reaction solution was concentrated under reduced pressure, added with ice water (50.0 mL), and extracted with dichloromethane (50.0 mL×1). The organic phase was washed with saturated sodium bicarbonate aqueous solution (50.0 mL×2) and saturated NaCl aqueous solution (500 mL×1), dried over anhydrous sodium sulfate, filtered, and concentrated under reduced pressure to obtain compound 3-2.

MS-ESI $[M+H]^+$, calculated: 320, found: 320.

$^1$H NMR (400 MHz, $CDCl_3$) δ 7.27 (br d, J=5.2 Hz, 3H), 7.19 (br d, J=4.4 Hz, 1H), 3.98 (d, J=17.6 Hz, 1H), 3.55 (br d, J=17.6 Hz, 1H), 3.11-3.22 (m, 1H), 2.91-3.05 (m, 3H), 2.23-2.31 (m, 1H), 2.20 (s, 3H), 1.62 (td, J=8.8, 4.4 Hz, 1H).

(3) To a solution of compound 3-2 (140 mg, 437 μmol) in N,N-Dimethylformamide (5.0 mL) was added potassium carbonate (151 mg, 1.09 mmol) and compound 3-3 (82.1 mg, 364 mol), and the reaction solution was stirred at 50° C. for 6 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure. The crude product was separated by preparative thin layer chromatography (petroleum ether/ethyl acetate=1:1) to obtain compound 3-4.

MS-ESI $[M+H]^+$, calculated: 509, found: 509.

(4) To a solution of compound 3-4 (120 mg, 236 μmol) in dioxane (5.0 mL) was added compound 3-5 (81.5 mg 708 μmol), cesium carbonate (231 mg, 709 μmol) and (2-dicyclohexylphosphino-2',6'-diisopropoxy-1,1'-biphenyl) [2-(2'-amino-1,1'-biphenyl)]palladium(II) methanesulfonate (39.4 mg, 47.1 μmol), and the reaction solution was stirred at 110° C. for 4 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by preparative thin layer chromatography (petroleum ether/ethyl acetate=1:2) to obtain compound 3-6.

MS-ESI $[M+H]^+$, calculated: 588, found: 588.

$^1$H NMR (400 MHz, MeOD) δ 7.19-7.29 (m, 4H), 4.59-4.65 (m, 1H), 4.30-4.41 (m, 2H), 3.92-4.16 (m, 3H), 3.68-3.76 (m, 2H), 3.41 (br dd, J=14.0, 3.6 Hz, 1H), 3.14-3.25 (m, 2H), 2.96-3.11 (m, 4H), 2.73-2.95 (m, 4H), 2.54 (br d, J=3.6 Hz, 3H), 2.43 (td, J=13.2, 8.4 Hz, 2H), 2.21 (d, J=2.8 Hz, 3H), 2.07-2.17 (m, 1H), 1.81-1.92 (m, 3H), 1.67-1.77 (m, 1H), 1.51 (s, 9H).

(5) To a solution of compound 3-6 (30.0 mg, 51.0 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 3-7.

MS-ESI $[M+H]^+$, calculated: 488, found: 488.

(6) To a solution of trifluoroacetate of compound 3-7 (30.0 mg, 49.9 μmol) in dichloromethane (2.0 mL) was added triethylamine (25.2 mg, 249 μmol) and compound 3-8 (13.6 mg, 150 μmol), and the reaction solution was stirred at −78° C. for 1 hour under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 3.

MS-ESI $[M+H]^+$, calculated: 542, found: 542.

$^1$H NMR (400 MHz, MeOD) δ 7.25-7.31 (m, 4H), 6.82 (br d, J=11.6 Hz, 1H), 6.30 (br d, J=16.4 Hz, 1H), 5.84 (br d, J=10.4 Hz, 1H), 5.04 (br s, 1H), 4.72 (dt, J=12.4, 3.2 Hz, 1H), 4.54 (dd, J=12.4, 7.2 Hz, 1H), 4.18-4.40 (m, 1H), 3.96-4.18 (m, 2H), 3.79-3.88 (m, 3H), 3.65-3.71 (m, 1H), 3.45-3.62 (m, 1H), 3.31-3.44 (m, 1H), 3.13-3.26 (m, 2H), 3.04-3.13 (m, 2H), 3.03 (d, J=5.2 Hz, 3H), 2.89-3.01 (m, 4H), 2.43-2.52 (m, 1H), 2.32-2.40 (m, 1H), 2.26 (d, J=2.4 Hz, 3H), 2.14-2.20 (m, 1H), 2.09 (br dd, J=14.0, 7.6 Hz, 1H), 1.99-2.05 (m, 1H), 1.87-1.96 (m, 1H).

Example 4 Synthesis of Compound 4

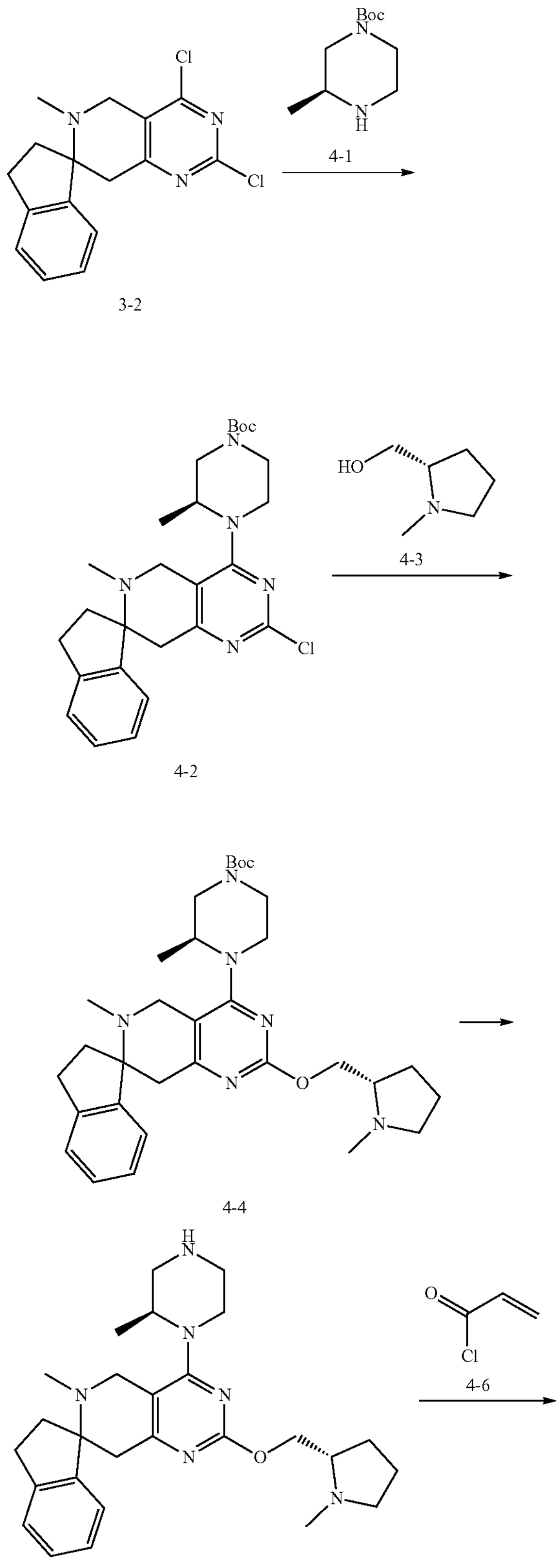

3-2

4-1

4-3

4-2

4-4

4-6

4-5

-continued

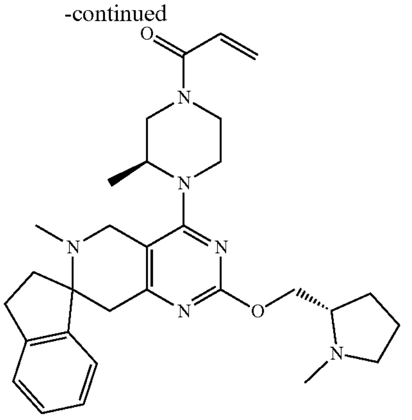

4

(1) To a solution of compound 3-2 (200 mg, 625 μmol) in N-methylpyrrolidone (5.0 mL) was added potassium carbonate (259 mg, 1.87 mmol) and compound 4-1 (250 mg, 1.25 mmol), and the reaction solution was stirred at 50° C. for 16 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure. The crude product was separated by preparative thin layer chromatography (petroleum ether/ethyl acetate=1:0 to 4:1) to give compound 4-2.

MS-ESI $[M+H]^+$, calculated: 484, found: 484.

(2) To a solution of compound 4-2 (160 mg, 331 μmol) in dioxane (5.0 mL) was added compound 4-3 (115 mg, 999 μmol), cesium carbonate (323 mg, 991 μmol) and ((2-dicyclohexylphosphino-2',6'-diisopropoxy-1,1'-biphenyl) [2-(2'-amino-1,1'-biphenyl)]palladium(II) methanesulfonate (55.3 mg, 66.1 μmol), and the reaction solution was stirred at 110° C. for 4 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by preparative thin layer chromatography (dichloromethane/methanol=10:1) to obtain compound 4-4.

MS-ESI $[M+H]^+$, calculated: 563, found: 563.

$^1H$ NMR (400 MHz, MeOD) δ 7.18-7.30 (m, 4H), 4.32-4.40 (m, 2H), 4.21 (br s, 1H), 4.02 (br s, 1H), 3.76-3.98 (m, 2H), 3.50-3.75 (m, 3H), 3.38-3.50 (m, 1H), 3.32-3.38 (m, 1H), 3.07-3.20 (m, 2H), 2.97-3.05 (m, 2H), 2.87-2.96 (m, 2H), 2.84 (br d, J=2.8 Hz, 1H), 2.54 (s, 2H), 2.38-2.48 (m, 2H), 2.19 (s, 3H), 2.05-2.14 (m, 1H), 1.80-1.93 (m, 3H), 1.68-1.77 (m, 1H), 1.49 (d, J=0.8 Hz, 9H), 1.17-1.37 (in, 3H).

(3) To a solution of compound 4-4 (80.0 mg, 142 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 4-5.

MS-ESI $[M+H]^+$, calculated: 463, found: 463.

(4) To a solution of trifluoroacetate of compound 4-5 (70.0 mg, 121 μmol) in dichloromethane (2.0 mL) was added triethylamine (61.4 mg, 607 μmol) and compound 4-6 (33.0 mg, 365 μmol), and the reaction solution was stirred at −78° C. for 1 hour under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 4.

MS-ESI $[M+H]^+$, calculated: 517, found: 517.

$^1H$ NMR (400 MHz, MeOD) δ 7.23-7.33 (m, 4H), 6.73-6.90 (m, 1H), 6.29 (br dd, J=16.4, 2.4 Hz, 1H), 5.81 (dd, J=10.4, 1.6 Hz, 1H), 4.71 (dd, J=12.4, 3.2 Hz, 1H), 4.40-4.54 (m, 2H), 4.11-4.33 (m, 1H), 3.90-4.02 (m, 1H), 3.64-3.87 (m, 5H), 3.50-3.62 (m, 1H), 3.37-3.49 (m, 1H), 3.09-3.29 (m, 2H), 3.04-3.09 (m, 1H), 3.03 (s, 3H), 2.87-3.02 (m, 3H), 2.43-2.53 (m, 1H), 2.31-2.42 (m, 1H), 2.25 (s, 3H), 2.14-2.22 (m, 1H), 2.06-2.13 (m, 1H), 1.98-2.05 (m, 1H), 1.88-1.97 (m, 1H), 1.17-1.38 (m, 3H).

Example 5 Synthesis of Compound 5

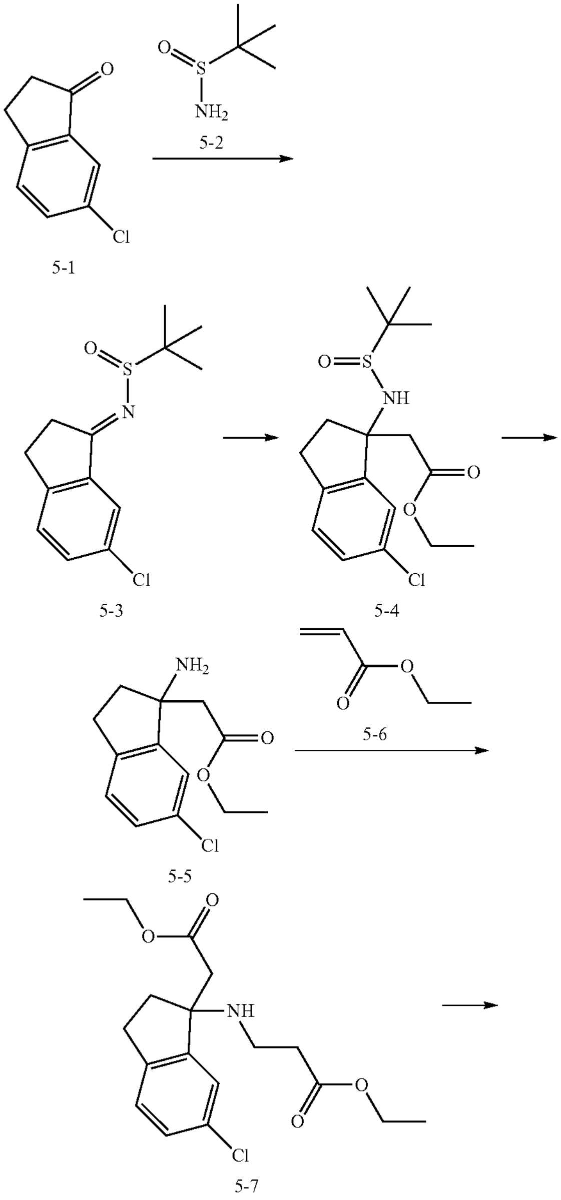

-continued
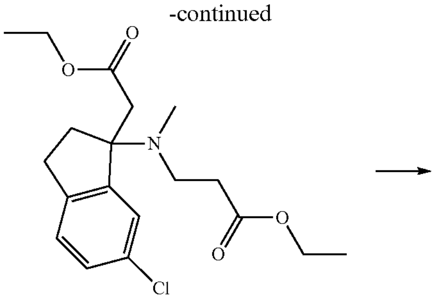
5-8
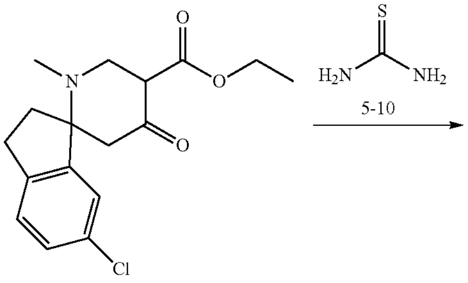
5-9
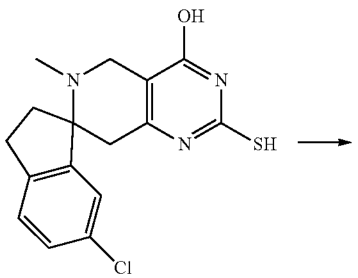
5-11
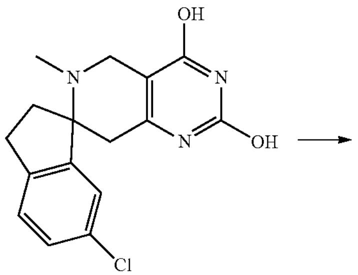
5-12
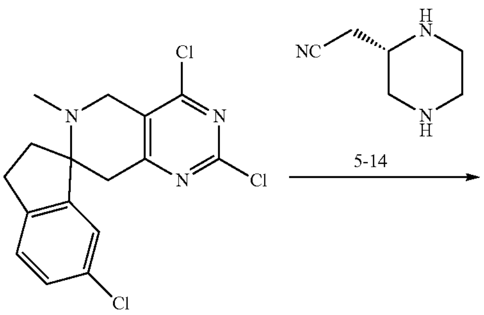
5-13
-continued
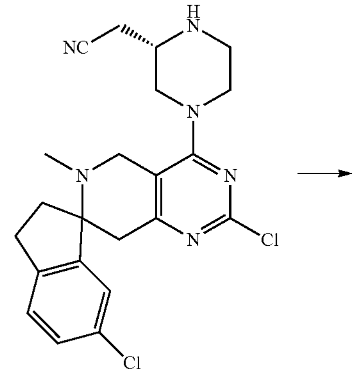
5-15
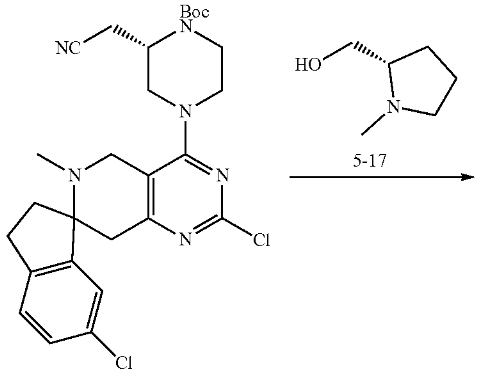
5-16
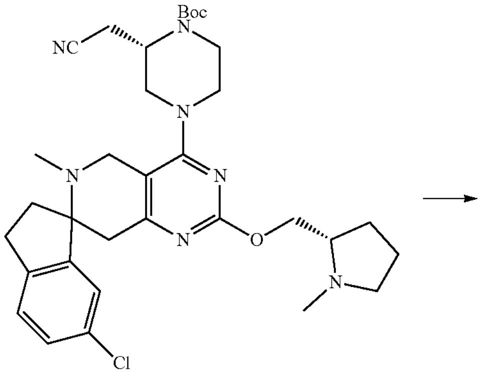
5-18
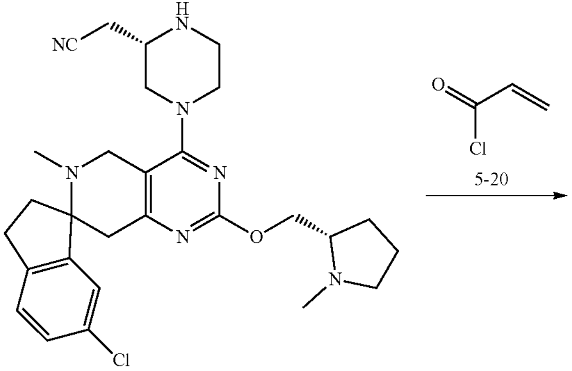
5-19

-continued

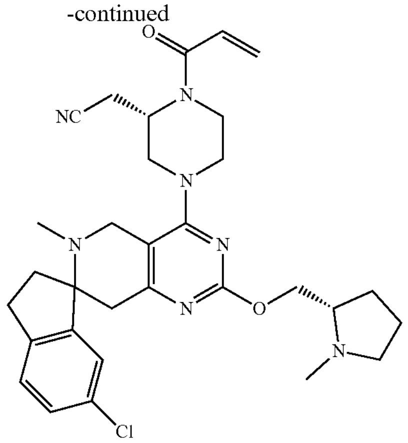

5

(1) To a solution of compound 5-1 (25.0 g, 150 mmol) in toluene (400 mL) was added compound 5-2 (16.6 g, 137 mmol), tetraethyl titanate (62.3 g, 273 mmol), and the reaction solution was stirred at 120° C. for 16 hours under nitrogen protection. Then the reaction solution was added with water (200 mL), and extracted with ethyl acetate (400 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 2:1) to obtain compound 5-3.

MS-ESI $[M+H]^+$, calculated: 270, found: 270.

$^1$H NMR (400 MHz, $CDCl_3$) δ 7.73 (d, J=2.0 Hz, 1H), 7.44 (dd, J=8.0, 2.0 Hz, 1H), 7.33 (d, J=8.0 Hz, 1H), 3.43-3.53 (m, 1H), 3.10-3.13 (m, 2H), 3.04-3.10 (m, 1H), 1.32 (s, 9H).

(2) To a solution of ethyl acetate (22.9 g, 260 mmol) in tetrahydrofuran (300 mL) was added dropwise with lithium diisopropylamide (2 mol/L, 52.0 mL, tetrahydrofuran solution) at −78° C. under nitrogen protection and the reaction solution was stirred at −78° C. for 1 hour. Then the reaction solution was added dropwise with a solution of compound 5-3 (14.0 g, 51.9 mmol) in tetrahydrofuran (50.0 mL), and continued stirring for 3 hours at −78° C. After warming to 0° C., then quenched with saturated ammonium chloride aqueous solution (200 mL), and extracted with ethyl acetate (200 mL×1). The combined organic phase was washed with saturated ammonium chloride aqueous solution (200 mL×1) and saturated NaCl aqueous solution (200 mL×1), dried over anhydrous sodium sulfate, filtered, and concentrated under reduced pressure. The crude product was separated by silica gel column chromatography (petroleum ether/ethyl acetate=1:0 to 4:1) to obtain compound 5-4.

MS-ESI $[M+H]^+$, calculated: 358, found: 358.

$^1$H NMR (400 MHz, $CDCl_3$) δ 7.21-7.24 (m, 1H), 7.15-7.20 (m, 2H), 5.24 (s, 1H), 4.15-4.21 (m, 2H), 3.13 (ddd, J=16.4, 8.8, 5.2 Hz, 1H), 2.83-2.90 (m, 1H), 2.73-2.83 (m, 2H), 2.67-2.73 (m, 1H), 2.33 (ddd, J=13.2, 8.4, 5.2 Hz, 1H), 1.25-1.28 (m, 3H), 1.20 (s, 9H).

(3) To a solution of compound 5-4 (5.10 g, 14.3 mmol) in ethanol (40.0 mL) was added hydrochloric acid in dioxane (4 mol/L, 15.0 mL), and the reaction solution was stirred at 25° C. for 2 hours under nitrogen protection. Then the reaction solution was concentrated under reduced pressure to obtain crude product of hydrochloride of compound 5-5.

MS-ESI $[M-NH_2+H]^+$, calculated: 237, found: 237.

(4) To a solution of hydrochloride of compound 5-5 (4.0 g, 13.8 mmol) in ethanol (20.0 mL) was added compound 5-6 (15.7 g, 157 mmol), copper oxide (219 mg, 2.75 mmol), triethylamine (4.18 g, 41.4 mmol), and the reaction solution was reacted at 85° C. in a sealed tube for 8 hours under nitrogen protection. Then the reaction solution was added with water (200 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 6:1) to obtain compound 5-7.

MS-ESI $[M+H]^+$, calculated: 354, found: 354.

$^1$H NMR (400 MHz, $CDCl_3$) δ 7.02-7.25 (m, 3H), 4.07-4.16 (m, 4H), 2.86-2.91 (m, 1H), 2.77-2.85 (m, 1H), 2.69-2.77 (m, 2H), 2.58-2.65 (m, 1H), 2.37-2.58 (m, 4H), 2.32 (dt, J=13.2, 8.4 Hz, 1H), 2.16 (ddd, J=13.2, 8.4, 4.4 Hz, 1H), 1.25 (t, J=7.2 Hz, 3H), 1.20 (t, J=7.2 Hz, 3H).

(5) To a solution of compound 5-7 (1.0 g, 2.83 mmol) in ethanol (15.0 mL) was added paraformaldehyde (500 mg) and sodium cyanoborohydride (533 mg, 8.48 mmol), and the reaction solution was reacted for 16 hours at 25° C. under nitrogen protection. Then the reaction solution was added with water (50.0 mL), and extracted with ethyl acetate (50 mL×1). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 2:1) to obtain compound 5-8.

MS-ESI $[M+H]^+$, calculated: 368, found: 368.

$^1$H NMR (400 MHz, $CDCl_3$) δ 7.13-7.21 (m, 2H), 7.06-7.10 (m, 1H), 4.08-4.16 (m, 2H), 3.87-3.94 (m, 2H), 2.83-2.89 (m, 3H), 2.73-2.77 (m, 1H), 2.59-2.70 (m, 2H), 2.41 (dt, J=7.6, 6.4 Hz, 2H), 2.31-2.37 (m, 1H), 2.20-2.28 (m, 1H), 2.17 (s, 3H), 1.25 (t, J=7.2 Hz, 3H), 1.04 (t, J=7.2 Hz, 3H).

(6) To a solution of compound 5-8 (600 mg, 1.63 mmol) in tetrahydrofuran (10.0 mL) was added potassium bis (trimethylsilyl) amide (1 mol/L, 4.89 mL, tetrahydrofuran solution) at −78° C., and the reaction solution was reacted at −78° C. for 2 hours under nitrogen protection. Then the reaction solution was added with saturated ammonium chloride aqueous solution (50.0 mL), and extracted with ethyl acetate (50.0 mL×1). The combined organic phase was washed with saturated NaCl aqueous solution (50.0 mL×1), dried over anhydrous sodium sulfate, filtered, and concentrated under reduced pressure. The crude product was separated by silica gel column chromatography (petroleum ether/ethyl acetate=1:0 to 6:1) to obtain compound 5-9.

MS-ESI $[M+H]^+$, calculated: 322, found: 322.

$^1$H NMR (400 MHz, $CDCl_3$) δ 7.17-7.23 (m, 2H), 7.11-7.15 (m, 1H), 4.22-4.32 (m, 2H), 3.50 (d, J=15.2 Hz, 1H), 3.22-3.33 (m, 1H), 3.08-3.16 (m, 1H), 2.86-2.93 (m, 2H), 2.54-2.64 (m, 1H), 2.20-2.37 (m, 2H), 2.09 (s, 3H), 1.78 (ddd, J=13.2, 8.4, 4.4 Hz, 1H), 1.30-1.34 (m, 3H).

(7) To a solution of compound 5-9 (440 mg, 1.37 mmol) in ethanol (10.0 mL) was added compound 5-10 (208 mg, 2.37 mmol) and sodium ethoxide (279 mg, 4.10 mmol), and the reaction solution was stirred at 80° C. for 12 hours under nitrogen protection. After concentrated under reduced pressure, the reaction solution was added with ethanol (15.0 mL) and water (5.0 mL) and its pH was adjusted to 6 with hydrochloric acid (1 mol/L). The resulting solution was precipitated, and filtered, and the filter cake was dried to obtain compound 5-11.

MS-ESI $[M+H]^+$, calculated: 334, found: 334.

$^1$H NMR (400 MHz, DMSO-d6) δ 12.20-12.60 (m, 2H), 7.19-7.36 (m, 3H), 3.36-3.56 (m, 1H), 3.06 (br s, 1H), 2.84-2.94 (m, 2H), 2.65-2.77 (m, 1H), 2.37-2.49 (m, 3H), 2.20 (br s, 1H), 1.99 (br s, 1H), 1.68 (br s, 1H).

(8) To a solution of intermediate 5-11 (360 mg, 1.08 mmol) in water (10.0 mL) was added chloroacetic acid (590 mg, 6.24 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 5-12.

MS-ESI [M+H]$^+$, calculated: 318, found: 318.

$^1$H NMR (400 MHz, DMSO-d6) δ 11.03 (s, 1H), 10.78 (s, 1H), 7.27-7.32 (m, 2H), 7.21 (d, J=1.6 Hz, 1H), 3.43 (br d, J=16.0 Hz, 1H), 3.01 (br d, J=16.0 Hz, 1H), 2.83-2.93 (m, 2H), 2.62 (br d, J=17.6 Hz, 1H), 2.32 (d, J=17.2 Hz, 1H), 2.19 (dt, J=13.2, 8.4 Hz, 1H), 1.97 (s, 3H), 1.65 (ddd, J=13.2, 8.4, 4.4 Hz, 1H).

(9) Compound 5-12 (210 mg, 661 μmol) was dissolved in phosphorus oxychloride (8.25 g, 53.8 mmol), and the reaction solution was stirred at 80° C. for 2 hours under nitrogen protection, and the reaction solution was concentrated under reduced pressure, added with iced water (50.0 mL), and extracted with dichloromethane (50.0 mL×1). The organic phase was washed with saturated sodium bicarbonate aqueous solution (50.0 mL×2) and saturated NaCl aqueous solution (500 mL×1), dried over anhydrous sodium sulfate, filtered, and concentrated under reduced pressure to obtain compound 5-13.

MS-ESI [M+H]$^+$, calculated: 356, found: 356.

$^1$H NMR (400 MHz, $CDCl_3$) δ 7.28-7.37 (m, 2H), 7.22 (s, 1H), 3.87-4.04 (m, 1H), 3.51 (br d, J=18.0 Hz, 1H), 3.14 (br d, J=17.6 Hz, 1H), 2.88-2.96 (m, 3H), 2.23 (dt, J=13.2, 8.4 Hz, 1H), 2.10 (s, 3H), 1.58-1.69 (m, 1H).

(10) To a solution of compound 5-13 (150 mg, 423 μmol) in N-methylpyrrolidone (5.0 mL) was added potassium carbonate (292 mg, 2.11 mmol) and hydrochloride of compound 5-14 (126 mg, 107 μmol), and the reaction solution was stirred at 50° C. for 12 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure to obtain compound 5-15.

MS-ESI [M+H]$^+$, calculated: 443, found: 443.

(11) To a solution of compound 5-15 (187 mg, 422 μmol) in dichloromethane (10.0 mL) was added triethylamine (214 mg, 2.11 mmol) and di-tert-butyl carbonate (920 mg, 4.22 mmol), and the reaction solution was stirred at 25° C. for 12 hours. Then the reaction solution was added with dichloromethane (20.0 mL), washed with saturated NaCl aqueous solution (20.0 mL×2), dried over anhydrous sodium sulfate, and concentrated under reduced pressure. The crude product was separated by silica gel column chromatography (petroleum ether/ethyl acetate=6:1) to obtain compound 5-16.

MS-ESI [M+H]$^+$, calculated: 543, found: 543.

(12) To a solution of compound 5-16 (80.0 mg, 147 μmol) in dioxane (5.0 mL) was added compound 5-17 (50.9 mg, 442 μmol), potassium carbonate (61.0 mg, 441 μmol), tris (dibenzylideneacetone) dipalladium (27.0 mg, 29.5 μmol) and dicyclohexyl(2',4',6'-triisopropyl-[1,1'-biphenyl]-2-yl) phosphine (28.1 mg, 58.9 μmol), and the reaction solution was stirred at 110° C. for 6 hours under nitrogen protection. Then the reaction solution was added with ethyl acetate (40.0 mL), washed with saturated NaCl aqueous solution (40.0 mL×2), dried over anhydrous sodium sulfate, filtered, and concentrated under reduced pressure. The crude product was separated by preparative thin layer chromatography (dichloromethane/methanol=1:0 to 15:1) to obtain compound5-18.

MS-ESI [M+H]$^+$, calculated: 622, found: 622.

$^1$H NMR (400 MHz, MeOD) δ 7.18-7.31 (m, 3H), 4.62-4.67 (m, 1H), 4.49 (br s, 1H), 4.39-4.45 (m, 1H), 3.89-4.23 (m, 4H), 3.67-3.77 (m, 2H), 3.43 (br d, J=14.0 Hz, 2H), 3.24 (br dd, J=14.0, 3.6 Hz, 2H), 2.88-3.03 (m, 5H), 2.73 (br s, 3H), 2.41-2.50 (m, 1H), 2.24-2.41 (m, 1H), 2.20-2.24 (m, 3H), 2.09-2.20 (m, 1H), 1.93-2.05 (m, 2H), 1.76-1.92 (m, 3H), 1.51 (d, J=1.6 Hz, 9H).

(13) To a solution of compound 5-18 (70.0 mg, 113 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 5-19.

MS-ESI [M+H]$^+$, calculated: 522, found: 522.

(14) To a solution of trifluoroacetate of compound 5-19 (60.0 mg, 94.3 μmol) in dichloromethane (2.0 mL) was added triethylamine (28.6 mg, 283 μmol) and compound 5-20 (17.1 mg, 189 μmol), and the reaction solution was stirred at −78° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 5.

MS-ESI [M+H]$^+$, calculated: 576, found: 576.

$^1$H NMR (400 MHz, MeOD) δ 7.25-7.30 (m, 2H), 7.22 (d, J=17.6 Hz, 1H), 6.80 (br s, 1H), 6.30 (br d, J=16.4 Hz, 1H), 5.84 (br d, J=10.8 Hz, 1H), 5.03 (br s, 1H), 4.69 (br dd, J=12.4, 3.6 Hz, 1H), 4.50 (ddd, J=12.4, 7.2, 1.6 Hz, 1H), 4.17-4.36 (m, 1H), 3.94-4.16 (m, 2H), 3.72-3.84 (m, 3H), 3.59-3.65 (m, 1H), 3.41-3.58 (m, 1H), 3.28 (br d, J=1.6 Hz, 1H), 3.08-3.18 (m, 2H), 2.97-3.06 (m, 5H), 2.84-2.96 (m, 4H), 2.42-2.51 (m, 1H), 2.30-2.40 (m, 1H), 2.24 (d, J=1.6 Hz, 3H), 2.11-2.19 (m, 1H), 2.07 (br dd, J=14.4, 7.6 Hz, 1H), 1.96-2.03 (m, 1H), 1.87-1.95 (m, 1H).

Example 6 Synthesis of Compounds 6 and 7

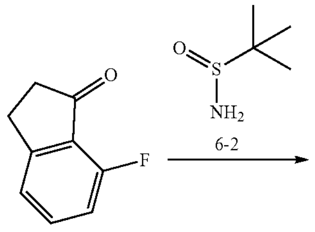

6-1

-continued
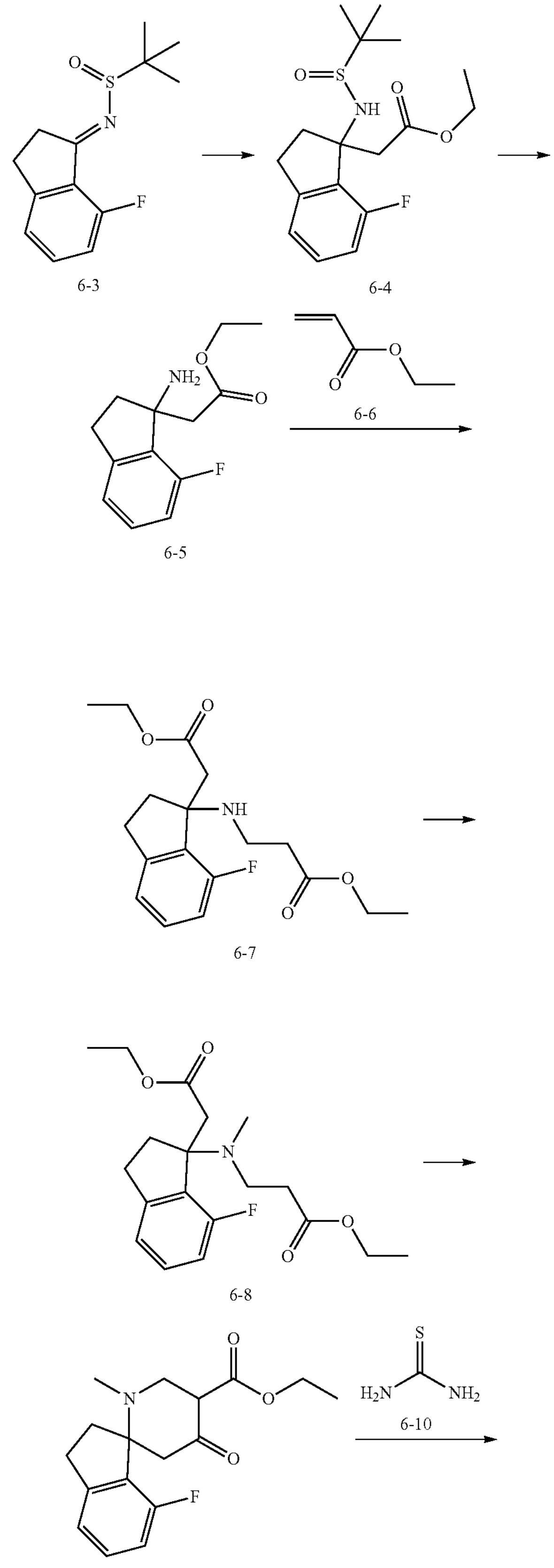
6-3 6-4 6-5 6-7 6-8 6-9
-continued
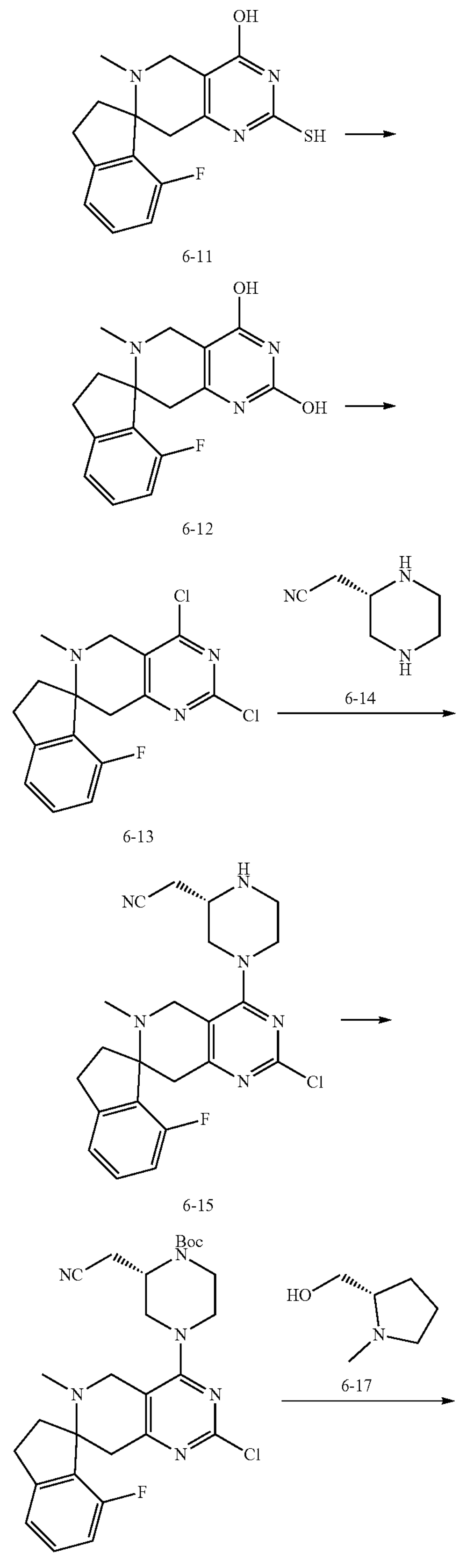
6-11 6-12 6-13 6-15 6-16

-continued

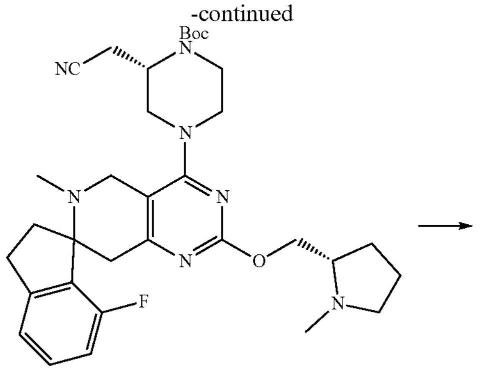

6-18

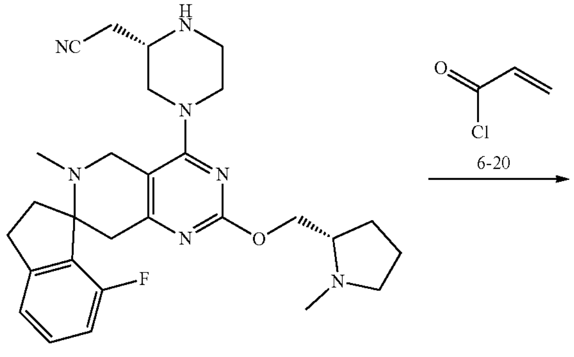

6-19

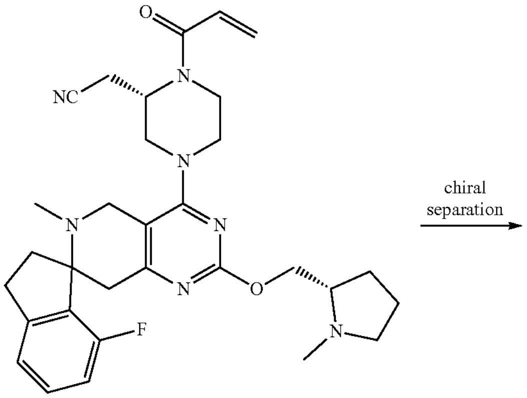

6-21

Compound 6 and 7

(1) To a solution of compound 6-1 (25.0 g, 166 mmol) in toluene (400 mL) was added compound 6-2 (18.3 g, 151 mmol), tetraethyl titanate (69.0 g, 302 mmol), and the reaction solution was stirred at 120° C. for 16 hours under nitrogen protection. Then the reaction solution was added with water (400 mL), and extracted with ethyl acetate (400 mL×2). The combined organic phase was washed with saturated NaCl aqueous solution (500 mL×1), dried over anhydrous sodium sulfate, filtered, and concentrated under reduced pressure. The crude product was separated by silica gel column chromatography (petroleum ether/ethyl acetate (1:0 to 0:1) to obtain compound 6-3.

MS-ESI $[M+H]^+$, calculated: 254, found: 254.

$^1H$ NMR (400 MHz, $CDCl_3$) δ 7.42-7.48 (m, 1H), 7.16-7.20 (m, 1H), 6.93-7.00 (m, 1H), 3.46-3.56 (m, 1H), 3.05-3.21 (m, 3H), 1.30-1.36 (s, 9H).

(2) To a solution of ethyl acetate (22.4 g, 254 mmol) in tetrahydrofuran (200 mL) was added dropwise with lithium diisopropylamide (2 mol/L, 50.9 mL, tetrahydrofuran solution) at −78° C. under nitrogen protection, and the reaction solution was stirred at −78° C. for 1 hour. Then the reaction solution was added dropwise with a solution of compound 6-3 (12.9 g, 50.9 mmol) in tetrahydrofuran (50.0 mL), and continued stirring for 3 hours at −78° C. After warming to 0° C., the reaction solution was quenched with saturated ammonium chloride aqueous solution (200 mL), and extracted with ethyl acetate (200 mL×1). The combined organic phase was washed with saturated ammonium chloride aqueous solution (200 mL×1) and saturated NaCl aqueous solution (200 mL×1), dried over anhydrous sodium sulfate, filtered, and concentrated under reduced pressure. The crude product was separated by silica gel column chromatography (petroleum ether/ethyl acetate=1:0 to 4:1) to obtain compound 6-4.

MS-ESI $[M+H]^+$, calculated: 342, found: 342.

$^1H$ NMR (400 MHz, $CDCl_3$) δ 7.27-7.30 (m, 1H), 7.01-7.07 (m, 1H), 6.82-6.90 (m, 1H), 5.05-5.11 (s, 1H), 4.15-4.24 (m, 2H), 3.29-3.39 (m, 2H), 2.88-2.98 (m, 1H), 2.64-2.73 (m, 1H), 2.28-2.39 (m, 1H), 1.25-1.30 (t, 3H), 1.16-1.20 (s, 9H).

(3) To a solution of compound 6-4 (12.4 g, 36.3 mmol) in ethanol (120 mL) was added hydrochloric acid in dioxane (4 mol/L, 40.0 mL). Then the reaction solution was stirred at 25° C. for 2 hours under nitrogen protection. Then the reaction solution was concentrated under reduced pressure to obtain crude product of hydrochloride of compound 6-5.

MS-ESI $[M-NH_2+H]^+$, calculated: 221, found: 221.

(4) To a solution of hydrochloride of compound 6-5 (9.94 g, 36.3 mmol) in ethanol (80.0 mL) was added compound 6-6 (37.6 g, 376 mmol), copper oxide (577 mg, 7.26 mmol), and triethylamine (3.67 g, 36.3 mmol), and the reaction solution was reacted at 85° C. in a sealed tube for 8 hours under nitrogen protection. Then the reaction solution was added with water (200 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 6:1) to obtain compound 6-7.

MS-ESI $[M+H]^+$, calculated: 338, found: 338.

$^1H$ NMR (400 MHz, $CDCl_3$) δ 7.16-7.22 (m, 1H), 6.96-7.01 (m, 1H), 6.80-6.87 (m, 1H), 4.06-4.17 (m, 4H), 2.95-3.07 (m, 2H), 2.86-2.94 (m, 1H), 2.65-2.81 (m, 3H), 2.26-2.51 (m, 5H), 1.22-1.26 (t, 3H), 1.14-1.20 (t, 3H).

(5) To a solution of compound 6-7 (3.0 g, 8.89 mmol) in ethanol (15.0 mL) was added paraformaldehyde (1.33 g) and sodium cyanoborohydride (1.68 g, 26.6 mmol), and the reaction solution was reacted for 16 hours at 25° C. under nitrogen protection. Then the reaction solution was added with water (50.0 mL), and extracted with ethyl acetate (50 mL×1). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 4:1) to obtain compound 6-8.

MS-ESI $[M+H]^+$, calculated: 352, found: 352.

$^1H$ NMR (400 MHz, $CDCl_3$) δ 7.16-7.22 (m, 1H), 6.93-6.99 (m, 1H), 6.79-6.86 (m, 1H), 4.07-4.14 (m, 2H), 3.88-3.99 (m, 2H), 2.95-3.08 (m, 3H), 2.83-2.92 (m, 1H), 2.72-2.80 (m, 1H), 2.60-2.68 (m, 1H), 2.29-2.46 (m, 4H), 2.19-2.23 (s, 3H), 1.22-1.27 (t, 3H), 1.00-1.06 (t, 3H).

(6) To a solution of compound 6-8 (3.00 g, 8.54 mmol) in tetrahydrofuran (30.0 mL) was added potassium bis (trimethylsilyl) amide (1 mol/L, 25.6 mL, tetrahydrofuran solution) at −78° C., and the reaction solution was reacted at −78° C. for 2 hours under nitrogen protection. Then the reaction solution was added with saturated ammonium chloride aqueous solution (50.0 mL), and extracted with ethyl acetate (50.0 mL×1). The combined organic phase was washed with saturated NaCl aqueous solution (50.0 mL×1), dried over anhydrous sodium sulfate, filtered, and concentrated under reduced pressure. The crude product was separated by silica gel column chromatography (petroleum ether/ethyl acetate=1:0 to 6:1) to obtain compound 6-9.

MS-ESI $[M+H]^+$, calculated: 306, found: 306.

$^1$H NMR (400 MHz, $CDCl_3$) δ 7.21-7.26 (m, 1H), 6.99-7.02 (m, 1H), 6.87-6.93 (m, 1H), 4.19-4.36 (m, 2H), 3.58-3.64 (m, 1H), 2.85-3.30 (m, 5H), 2.25-2.35 (m, 2H), 2.18-2.22 (m, 3H), 1.72-1.81 (m, 1H), 1.30-1.35 (m, 3H).

(7) To a solution of compound 6-9 (2.00 g, 6.55 mmol) in ethanol (20.0 mL) was added compound 6-10 (997 mg, 13.1 mmol) and sodium ethoxide (1.34 g, 19.6 mmol), and the reaction solution was stirred at 80° C. for 12 hours under nitrogen protection. After concentrated under reduced pressure, the reaction solution was added with ethanol (50.0 mL) and its pH was adjusted to 6 with hydrochloric acid (1 mol/L). The resulting solution was precipitated, and filtered, and the filter cake was dried to obtain compound 6-11.

MS-ESI $[M+H]^+$, calculated: 318, found: 318.

$^1$H NMR (400 MHz, DMSO-d6) δ 11.61-12.93 (s, 2H), 7.28-7.36 (m, 1H), 7.06-7.14 (m, 1H), 6.97-7.04 (m, 1H), 3.44-3.53 (m, 2H), 2.79-3.04 (m, 4H), 2.16-2.28 (m, 1H), 1.98-2.11 (s, 3H), 1.61-1.70 (m, 1H).

(8) To a solution of intermediate 6-11 (1.90 g, 5.99 mmol) in water (10.0 mL) was added chloroacetic acid (2.26 g, 23.9 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 6-12.

MS-ESI $[M+H]^+$, calculated: 302, found: 302.

$^1$H NMR (400 MHz, DMSO-d6) δ 10.98-11.04 (s, 1H), 10.73-10.80 (s, 1H), 7.29-7.36 (m, 1H), 7.07-7.12 (m, 1H), 6.96-7.04 (m, 1H), 3.39-3.47 (m, 1H), 2.76-3.02 (m, 4H), 2.29-2.37 (m, 1H), 2.18-2.27 (m, 1H), 2.02-2.08 (s, 3H), 1.60-1.68 (m, 1H).

(9) Compound 6-12 (800 mg, 2.66 mmol) was dissolved in phosphorus oxychloride (13.2 g, 86.0 mmol), and the reaction solution was stirred at 80° C. for 2 hours under nitrogen protection. Then the reaction solution was concentrated under reduced pressure, added with iced water (10.0 mL) and saturated sodium bicarbonate aqueous solution (50.0 mL), and extracted with dichloromethane (50.0 mL×1). The organic phase was washed with saturated sodium bicarbonate aqueous solution (50.0 mL×2) and saturated NaCl aqueous solution (50.0 mL×1), dried over anhydrous sodium sulfate, filtered, and concentrated under reduced pressure to obtain compound 6-13.

MS-ESI $[M+H]^+$, calculated: 338, found: 338.

(10) To a solution of compound 6-13 (500 mg, 1.48 mmol) in N-methylpyrrolidone (5.0 mL) was added potassium carbonate (1.02 g, 7.39 mmol) and hydrochloride of compound 6-14 (439 mg, 2.22 mmol), and the reaction solution was stirred at 50° C. for 12 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure to obtain compound 6-15.

MS-ESI $[M+H]^+$, calculated: 427, found: 427.

$^1$H NMR (400 MHz, DMSO-d6) δ 7.26-7.37 (m, 1H), 7.07-7.16 (m, 1H), 6.95-7.05 (m, 1H), 3.36-3.96 (m, 6H), 3.22-3.31 (m, 1H), 2.65-3.11 (m, 8H), 2.23-2.39 (m, 1H), 2.09-2.19 (m, 3H), 1.55-1.83 (m, 1H), 1.19-1.39 (m, 1H).

(11) To a solution of compound 6-15 (1.40 g, 3.28 mmol) in dichloromethane (20.0 mL) was added triethylamine (2.14 g, 21.1 mmol) and di-tert-butyl carbonate (3.58 mg, 16.4 mmol), and the reaction solution was stirred at 25° C. for 12 hours. Then the reaction solution was added with dichloromethane (20.0 mL), washed with saturated NaCl aqueous solution (20.0 mL×2), dried over anhydrous sodium sulfate, and concentrated under reduced pressure. The crude product was separated by silica gel column chromatography (petroleum ether/ethyl acetate=1:0 to 6:1) to obtain compound 6-16.

MS-ESI $[M+H]^+$, calculated: 527, found: 527.

(12) To a solution of compound 6-16 (900 mg, 1.71 mmol) in dioxane (10.0 mL) was added compound 6-17 (590 mg, 5.12 mmol), cesium carbonate (1.67 g, 5.12 mmol) and (2-dicyclohexylphosphino-2',6'-diisopropoxy-1,1'-biphenyl) [2-(2'-amino-1,1'-biphenyl)]palladium(II) methanesulfonate (285.6 mg, 341 μmol), and the reaction solution was stirred at 110° C. for 6 hours under nitrogen protection. Then the reaction solution was added with ethyl acetate (40.0 mL), washed with saturated NaCl aqueous solution (40.0 mL×2), dried over anhydrous sodium sulfate, filtered, and concentrated under reduced pressure. The crude product was separated by silica gel column chromatography (dichloromethane/methanol=1:0 to 15:1) to obtain compound 6-18.

MS-ESI $[M+H]^+$, calculated: 606, found: 606.

$^1$H NMR (400 MHz, $CDCl_3$) δ 7.22-7.26 (m, 1H), 7.01-7.06 (m, 1H), 6.87-6.94 (m, 1H), 4.54-4.64 (m, 1H), 4.24-4.40 (m, 1H), 3.78-4.08 (m, 3H), 3.51-3.77 (m, 3H), 3.19-3.39 (m, 3H), 2.80-3.16 (m, 7H), 2.64-2.73 (m, 3H), 2.29-2.35 (s, 3H), 1.79-1.99 (m, 4H), 1.55-1.75 (m, 4H), 1.49-1.55 (s, 9H).

(13) To a solution of compound 6-18 (342 mg, 564 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 6-19.

MS-ESI $[M+H]^+$, calculated: 506, found: 506.

(14) To a solution of trifluoroacetate of compound 6-19 (110 mg, 217 μmol) in dichloromethane (2.0 mL) was added triethylamine (22.0 mg, 217 μmol) and compound 6-20 (29.5 mg, 326 μmol), and the reaction solution was stirred at −78° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by reverse column chromatography (acetonitrile/water=0:1 to 1:19) to obtain compound 6-21.

MS-ESI $[M+H]^+$, calculated: 560, found: 560.

(15) Compound 6-21 was separated by chiral supercritical fluid chromatography to obtain compounds 6 and 7.

Separation conditions: Chromatographic column model: AD-H; Column specification: 0.46 cm I.D.×15 cm L; Injection volume: 2 μL; Mobile phase: carbondioxide:ethanol (0.1% triethylamine)=70:30; Detection wavelength: 254 nm; Column temperature: 25.

Compound 6: retention time: 4.071 minutes, 99.42% ee.

MS-ESI $[M+H]^+$, calculated: 560, found: 560.

$^1$H NMR (400 MHz, DMSO-d6) δ 7.31 (td, J=7.6, 5.2 Hz, 1H), 7.10 (d, J=7.6 Hz, 1H), 7.03-6.97 (m, 1H), 6.95-6.78

(m, 1H), 6.19 (d, J=16.8 Hz, 1H), 5.77 (d, J=8.8 Hz, 1H), 5.00-4.72 (m, 1H), 4.24 (d, J=6.8 Hz, 1H), 4.00 (dd, J=10.8, 6.4 Hz, 2H), 3.93-3.80 (m, 2H), 3.74-3.58 (m, 2H), 3.53-3.45 (m, 1H), 3.29-3.12 (m, 2H), 3.07-2.96 (m, 4H), 2.96-2.89 (m, 2H), 2.84-2.74 (m, 2H), 2.40-2.28 (m, 4H), 2.20-2.08 (m, 4H), 1.91 (dq, J=12.4, 8.4 Hz, 1H), 1.77-1.68 (m, 1H), 1.68-1.62 (m, 2H), 1.60-1.51 (m, 1H).

Compound 7: retention time: 4.436 minutes, 98.76% ee. MS-ESI $[M+H]^+$, calculated: 560, found: 560.

$^1H$ NMR (400 MHz, DMSO-d6) δ 7.31 (dt, J=12.8, 6.4 Hz, 1H), 7.11 (d, J=7.2 Hz, 1H), 7.04-6.95 (m, 1H), 6.91-6.79 (m, 1H), 6.18 (d, J=17.2 Hz, 1H), 5.78 (d, J=8.8 Hz, 1H), 5.00-4.55 (m, 1H), 4.27-4.17 (m, 1H), 4.13-3.91 (m, 2H), 3.91-3.72 (m, 2H), 3.67-3.47 (m, 3H), 3.14-2.90 (m, 9H), 2.81 (d, J=17.6 Hz, 1H), 2.39-2.24 (m, 4H), 2.16 (s, 3H), 2.09-1.99 (m, 1H), 1.96-1.85 (m, 1H), 1.83-1.70 (m, 1H), 1.69-1.60 (m, 2H), 1.60-1.49 (m, 1H).

Example 7 Synthesis of Compounds 8 and 9

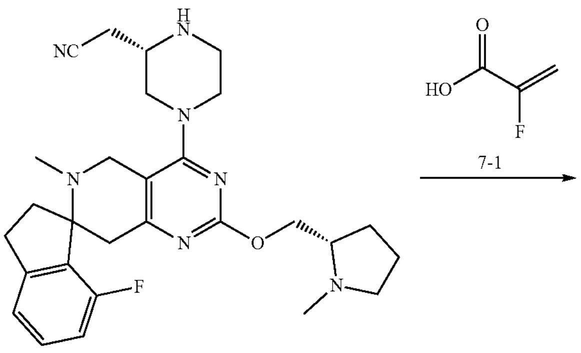

6-19

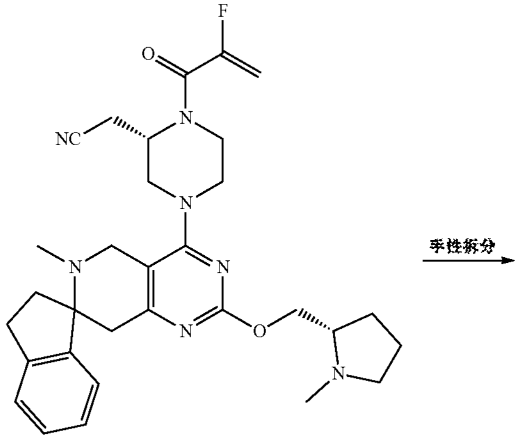

7-2 chiral separation
化合物8和9
Compound8and9

(1) To a solution of compound 6-19 (160 mg, 316 μmol) in dichloromethane (2.0 mL) was added triethylamine (32.0 mg, 316 μmol) and propanephosphonic acid anhydride (503 mg, 791 μmol, 470 μL, 50% ethyl acetate solution) and hydrochloride of compound 7-1 (600 mg, 4.75 mmol), and the reaction solution was stirred at 25° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure to obtain crude compound 7-2.

MS-ESI $[M+H]^+$, calculated: 578, found: 578.

(2) Compound 7-2 was separated by chiral supercritical fluid chromatography to obtain compounds 8 and 9.

Separation conditions: Chromatographic column model: AD-H; Column specification: 0.46 cm I.D.×15 cm L; Injection volume: 2 μL; Mobile phase: carbondioxide:ethanol (0.1% triethylamine)=70:30; Detection wavelength: 254 nm; Column temperature: 25° C.

Compound 8: retention time: 3.689 minutes, 98.44% ee.

MS-ESI $[M+H]^+$, calculated: 578, found: 578.

$^1H$ NMR (400 MHz, DMSO-d6) δ 7.35-7.27 (m, 1H), 7.10 (d, J=7.6 Hz, 1H), 7.02-6.95 (m, 1H), 5.43-5.35 (m, 1H), 5.35-5.20 (m, 1H), 4.30-4.22 (m, 1H), 4.06 (s, 1H), 3.97-3.88 (m, 1H), 3.86-3.83 (m, 1H), 3.71 (d, J=14.4 Hz, 2H), 3.20 (dd, J=13.6, 3.6 Hz, 1H), 3.05-2.89 (m, 6H), 2.84-2.75 (m, 1H), 2.44-2.32 (m, 4H), 2.26 (s, 1H), 2.13 (s, 3H), 1.98-1.89 (m, 1H), 1.77-1.65 (m, 3H), 1.65--1.52 (m, 1H), 1.52-1.41 (m, 2H), 1.20 (s, 1H), 0.91 (t, J=6.8 Hz, 2H).

Compound 9: retention time: 4.059 minutes, 97.90% ee.

MS-ESI $[M+H]^+$, calculated: 578, found: 578.

$^1H$ NMR (400 MHz, DMSO-d6) δ 7.31 (d, J=5.2 Hz, 1H), 7.11 (d, J=8.0 Hz, 1H), 7.05-6.92 (m, 1H), 5.39 (d, J=13.6 Hz, 1H), 5.35-5.17 (m, 1H), 4.22 (d, J=10.4 Hz, 1H), 4.09-3.98 (m, 1H), 3.90 (d, J=13.6 Hz, 1H), 3.85-3.74 (m, 1H), 3.53 (d, J=7.3 Hz, 2H), 3.14-3.06 (m, 2H), 3.06-2.92 (m, 5H), 2.85-2.78 (m, 1H), 2.39-2.28 (m, 4H), 2.22-2.09 (m, 4H), 1.91 (s, 2H), 1.82-1.71 (m, 1H), 1.70-1.62 (m, 2H), 1.58-1.51 (m, 1H), 1.22-1.11 (m, 1H), 1.08-0.77 (m, 2H).

Example 8 Synthesis of Compound 10

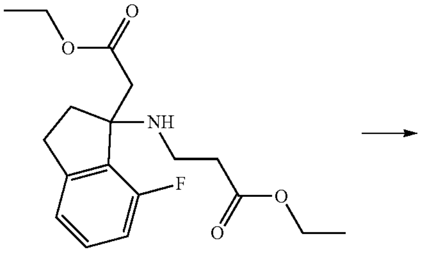

6-7

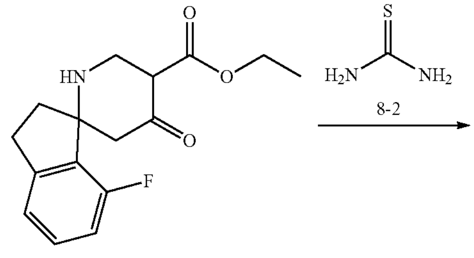

8-1

-continued

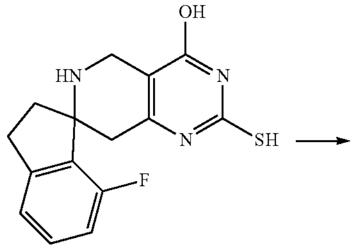

8-3

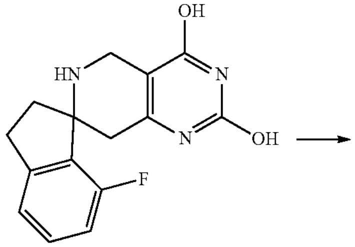

8-4

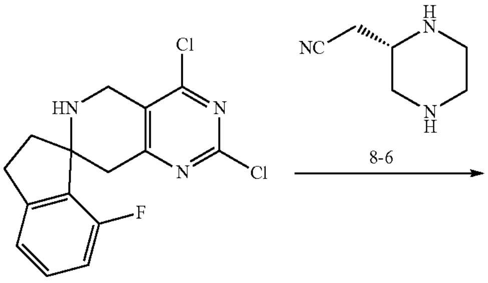

8-5

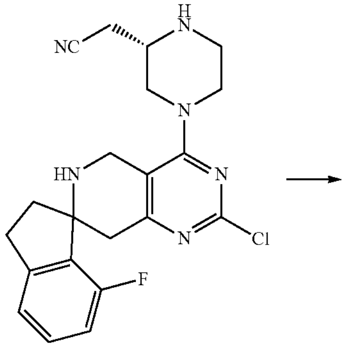

8-7

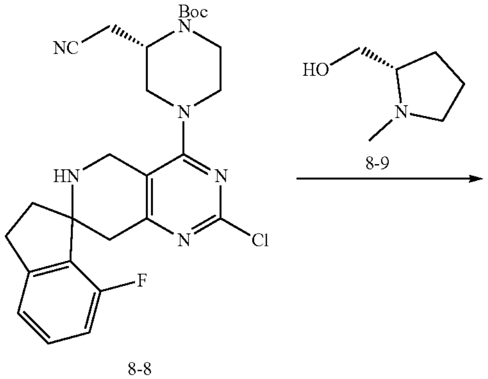

8-8

-continued

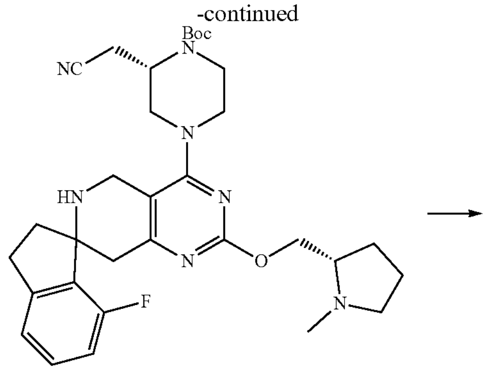

8-10

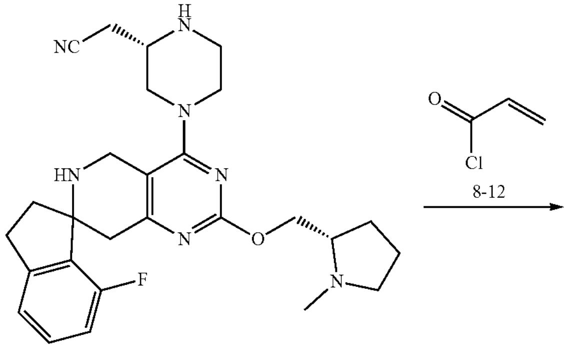

8-11

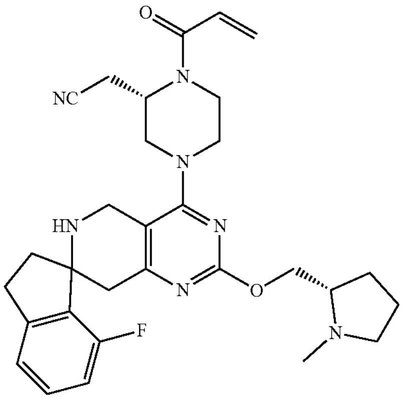

10

(1) To a solution of compound 6-7 (1.00 g, 2.96 mmol) in tetrahydrofuran (10.0 mL) was added potassium bis (trimethylsilyl) amide (1 mol/L, 9.0 mL, tetrahydrofuran solution) at −78° C., and the reaction solution was reacted at −78° C. for 2 hours under nitrogen protection. Then the reaction solution was added with saturated ammonium chloride aqueous solution (50.0 mL), and extracted with ethyl acetate (50.0 mL×1). The combined organic phase was washed with saturated NaCl aqueous solution (50.0 mL×1), dried over anhydrous sodium sulfate, filtered, and concentrated under reduced pressure. The crude product was separated by silica gel column chromatography (petroleum ether/ethyl acetate=1:0 to 6:1) to obtain compound 8-1.

MS-ESI $[M+H]^+$, calculated: 292, found: 292.

$^1$HNMR (400 MHz, $CDCl_3$) δ 7.18-7.25 (m, 1H), 7.00-7.05 (m, 1H), 6.89 (t, J=9.2 Hz, 1H), 4.22-4.29 (m, 2H), 3.35-3.57 (m, 1H), 3.14-3.27 (m, 1H), 3.01-3.14 (m, 1H), 2.85-2.99 (m, 2H), 2.42-2.69 (m, 2H), 2.34 (br d, J=6.0 Hz, 1H), 2.08-2.20 (m, 2H), 1.30-1.34 (m, 3H).

(2) To a solution of compound 8-1 (970 mg, 3.33 mmol) in ethanol (10.0 mL) was added compound 8-2(507 mg, 6.66 mmol) and sodium ethoxide (679 mg, 9.98 mmol), and the reaction solution was stirred at 80° C. for 16 hours under nitrogen protection. After concentrated under reduced pressure, the reaction solution was adjusted to pH 6 with hydrochloric acid (1 mol/L). The resulting solution was precipitated, and filtered, and the filter cake was dried to obtain compound 8-3.

MS-ESI $[M+H]^+$, calculated: 304, found: 304.

$^1$H NMR (400 MHz, DMSO-d6) δ 12.39 (br s, 1H), 12.25 (br s, 1H), 7.29 (td, J=7.6, 5.2 Hz, 1H), 7.10 (d, J=7.6 Hz, 1H), 6.93-7.01 (m, 1H), 3.50 (br s, 1H), 3.39-3.40 (m, 1H), 3.00-3.08 (m, 1H), 2.81-2.90 (m, 1H), 2.66-2.74 (m, 1H), 2.56 (s, 1H), 1.97-2.16 (m, 2H).

(3) To a solution of intermediate 8-3 (470 mg, 1.55 mmol) in water (10.0 mL) was added chloroacetic acid (560 mg, 5.93 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 8-4.

MS-ESI $[M+H]^+$, calculated: 288, found: 288.

$^1$H NMR (400 MHz, DMSO-d6) δ 11.03 (s, 1H), 10.78 (s, 1H), 7.27-7.32 (m, 2H), 7.21 (d, J=1.6 Hz, 1H), 3.43 (br d, J=16.0 Hz, 1H), 3.01 (br d, J=16.0 Hz, 1H), 2.83-2.93 (m, 2H), 2.62 (br d, J=17.6 Hz, 1H), 2.32 (d, J=17.2 Hz, 1H), 2.19 (dt, J=13.2, 8.4 Hz, 1H), 1.97 (s, 3H), 1.65 (ddd, J=13.2, 8.4, 4.4 Hz, 1H).

(4) Compound 8-4 (200 mg, 696 μmol) was dissolved in phosphorus oxychloride (8.25 g, 53.8 mmol), and the reaction solution was added with triethylamine (141 mg, 1.39 mmol) and then stirred at 85° C. for 16 hours under nitrogen protection. Then the reaction solution was added with iced water (10.0 mL) and saturated sodium bicarbonate aqueous solution (50.0 mL), and extracted with dichloromethane (50.0 mL×1). The organic phase was washed with saturated sodium bicarbonate aqueous solution (50.0 mL×2) and saturated NaCl aqueous solution (50.0 mL×1), dried over anhydrous sodium sulfate, filtered, and concentrated under reduced pressure to give compound 8-5.

MS-ESI $[M+H]^+$, calculated: 324, found: 324.

$^1$H NMR (400 MHz, DMSO-d6) δ 7.29 (td, J=7.6, 5.2 Hz, 1H), 7.13 (d, J=7.6 Hz, 1H), 6.89-7.01 (m, 1H), 3.83-3.96 (m, 1H), 3.66-3.77 (m, 1H), 3.18 (s, 1H), 3.04-3.15 (m, 3H), 2.84-2.96 (m, 1H), 2.03-2.15 (m, 2H).

(5) To a solution of compound 8-5 (200 mg, 617 μmol) in N-methylpyrrolidone (5.0 mL) was added potassium carbonate (426 mg, 3.08 mmol) and hydrochloride of compound 8-6(183 mg, 924 μmol), and the reaction solution was stirred at 50° C. for 12 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure to obtain compound 8-7.

MS-ESI $[M+H]^+$, calculated: 413, found: 413.

(6) To a solution of compound 8-7 (250 mg, 605 μmol) in dichloromethane (10.0 mL) was added triethylamine (307 mg, 3.03 mmol) and di-tert-butyl carbonate (264 mg, 1.21 mmol), and the reaction solution was stirred at 25° C. for 12 hours. Then the reaction solution was added with dichloromethane (20.0 mL), washed with saturated NaCl aqueous solution (20.0 mL×2), dried over anhydrous sodium sulfate, and concentrated under reduced pressure. The crude product was separated by silica gel column chromatography (petroleum ether/ethyl acetate=1:0 to 1:1) to obtain compound 8-8.

MS-ESI $[M+H]^+$, calculated: 513, found: 513.

$^1$H NMR (400 MHz, $CDCl_3$) δ 7.28-7.43 (m, 1H), 7.03-7.17 (m, 1H), 6.87-6.94 (m, 1H), 4.31-4.95 (m, 2H), 4.18-4.26 (m, 1H), 3.93-4.00 (m, 1H), 3.64-3.91 (m, 2H), 3.32-3.45 (m, 3H), 3.07-3.30 (m, 3H), 2.89-3.07 (m, 2H), 2.66-2.85 (m, 3H), 2.21-2.38 (m, 1H), 1.50-1.52 (m, 9H).

(7) To a solution of compound 8-8 (205 mg, 400 μmol) in dioxane (5.0 mL) was added compound 8-9 (138 mg, 1.20 mmol), cesium carbonate (391 mg, 1.20 mmol) and (2-dicyclohexylphosphino-2',6'-diisopropoxy-1,1'-biphenyl) [2-(2'-amino-1,1'-biphenyl)]palladium(II) methanesulfonate (66.9 mg, 80.0 μmol), and the reaction solution was stirred at 110° C. for 6 hours under nitrogen protection. Then the reaction solution was added with ethyl acetate (40.0 mL), washed with saturated NaCl aqueous solution (40.0 mL×2), dried over anhydrous sodium sulfate, filtered, and concentrated under reduced pressure. The crude product was separated by preparative thin layer chromatography (dichloromethane/methanol=1:0 to 10:1) to obtain compound 8-10.

MS-ESI $[M+H]^+$, calculated: 592, found: 592.

$^1$H NMR (400 MHz, MeOD) δ 7.25-7.32 (m, 1H), 7.08-7.17 (m, 1H), 6.88-6.98 (m, 1H), 4.62-4.67 (m, 1H), 4.41 (br s, 2H), 3.93-4.08 (m, 3H), 3.77-3.91 (m, 2H), 3.59-3.75 (m, 1H), 3.09-3.17 (m, 2H), 2.97-3.08 (m, 4H), 2.94 (s, 1H), 2.75-2.90 (m, 2H), 2.64 (br s, 3H), 2.13-2.31 (m, 4H), 1.90 (br s, 2H), 1.80 (br s, 1H), 1.58 (br s, 1H), 1.51 (s, 9H).

(8) To a solution of compound 8-10 (100 mg, 169 μmol) in dichloromethane (3.0 mL) was added trifluoroacetic acid (1.0 mL), and the reaction solution was stirred at 25° C. for 0.5 hours under nitrogen protection. Then the reaction solution was concentrated under reduced pressure to obtain crude trifluoroacetate of compound 8-11.

MS-ESI $[M+H]^+$, calculated: 492, found: 492.

(9) To a solution of trifluoroacetate of compound 8-11 (40.0 mg, 66.1 μmol) in dichloromethane (2.0 mL) was added triethylamine (20.1 mg, 199 μmol) and compound 8-12 (6.6 mg, 72.9 μmol), and the reaction solution was stirred at −78° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 10.

MS-ESI $[M+H]^+$, calculated: 546, found: 546.

$^1$H NMR (400 MHz, MeOD) δ 7.32 (tdd, J=8.0, 5.2, 3.2 Hz, 1H), 7.15 (dd, J=7.2, 3.2 Hz, 1H), 6.89-6.98 (m, 1H), 6.72-6.89 (m, 1H), 6.29 (br d, J=16.4 Hz, 1H), 5.83 (br d, J=10.4 Hz, 1H), 5.04 (br s, 1H), 4.64-4.84 (m, 2H), 4.51-4.57 (m, 1H), 4.07-4.27 (m, 2H), 3.90-4.05 (m, 2H), 3.77-3.90 (m, 2H), 3.52-3.74 (m, 2H), 3.10-3.27 (m, 5H), 3.04 (d, J=4.4 Hz, 3H), 2.92-3.03 (m, 3H), 2.27-2.43 (m, 3H), 2.18 (br dd, J=12.8, 6.8 Hz, 1H), 2.10 (br dd, J=14.4, 7.2 Hz, 1H), 2.01-2.07 (m, 1H).

Example 9 Synthesis of Compound 11
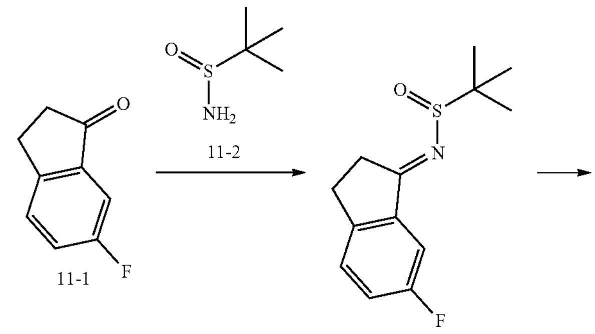
11-3
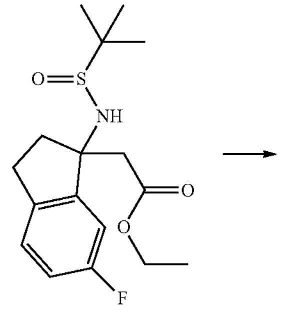
11-4
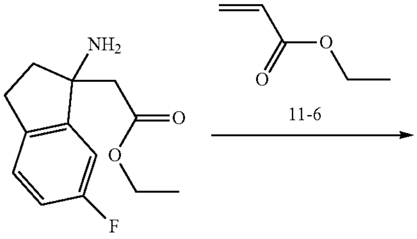
11-4
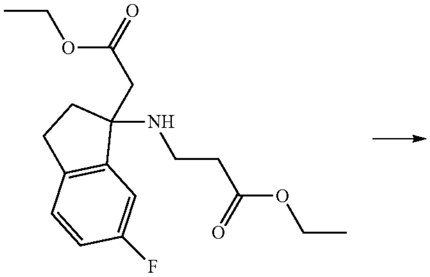
11-7
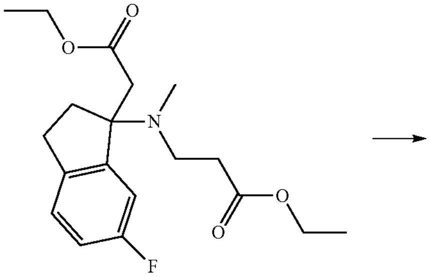
11-8
-continued
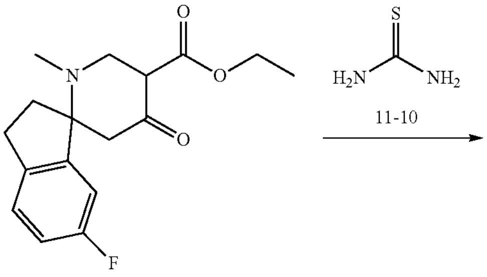
11-9
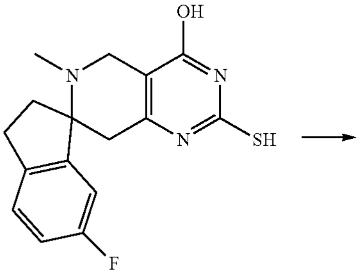
11-11
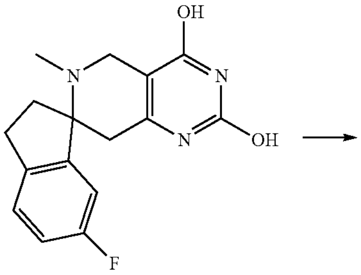
11-12
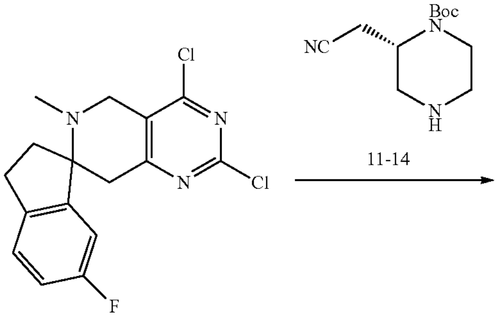
11-13
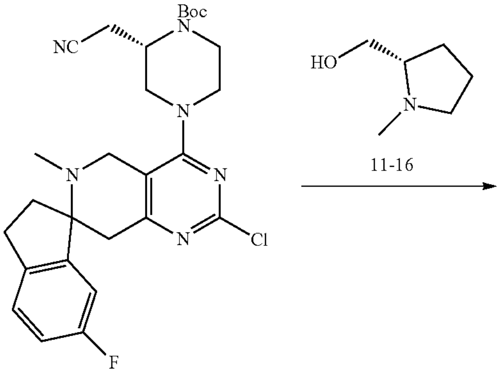
11-15

-continued

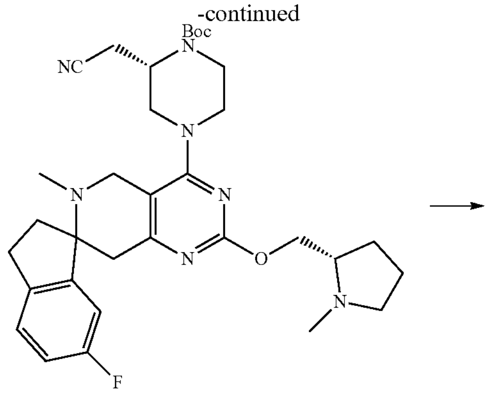

11-17

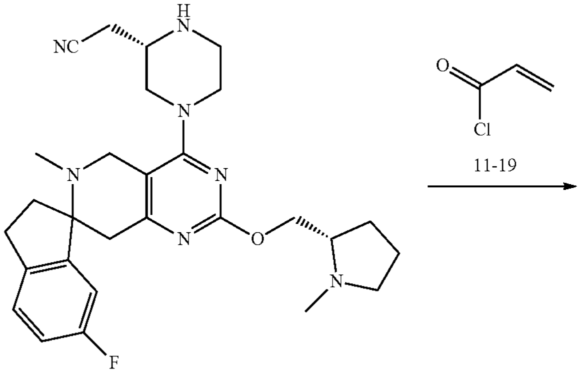

11-18

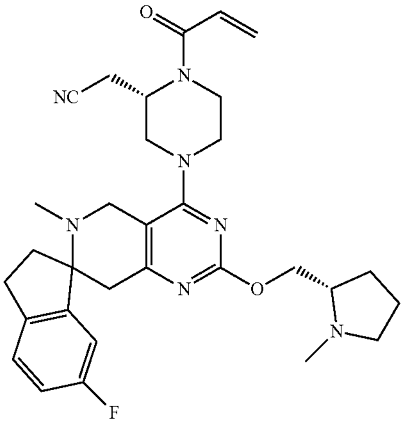

11

(1) To a solution of compound 11-1 (30.0 g, 200 mmol) in toluene (400 mL) was added compound 11-2 (29.1 g, 240 mmol), tetraethyl titanate (91.4 g, 401 mmol), and the reaction solution was stirred at 120° C. for 16 hours under nitrogen protection. Then the reaction solution was added with water (200 mL), and extracted with ethyl acetate (200 mL×5). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 10:1) to obtain compound 11-3.

MS-ESI $[M+H]^+$, calculated: 254, found: 254.

$^1H$ NMR (400 MHz, $CDCl_3$) δ 7.41 (dd, J=8.0, 2.4 Hz, 1H), 7.35 (dd, J=8.4, 4.8 Hz, 1H), 7.20 (td, J=8.4, 2.4 Hz, 1H), 3.45-3.55 (m, 1H), 3.11-3.17 (m, 1H), 3.07-3.11 (m, 2H), 1.32 (s, 9H).

(2) To a solution of ethyl acetate (32.9 g, 260 mmol) in tetrahydrofuran (200 mL) was added dropwise with lithium diisopropylamide (2 mol/L, 56.0 mL, tetrahydrofuran solution) at −78° C. under nitrogen protection, and the reaction solution stirred at −78° C. for 1 hour. Then the reaction solution was added dropwise with a solution of compound 11-3 (18.9 g, 74.6 mmol) in tetrahydrofuran (100 mL), and then continued stirring for 3 hours at −65° C. After warming to 0° C., the reaction solution was quenched with saturated ammonium chloride aqueous solution (500 mL), and extracted with ethyl acetate (500 mL×2). The combined organic phase was washed with saturated ammonium chloride aqueous solution (500 mL×1) and saturated NaCl aqueous solution (500 mL×1), dried over anhydrous sodium sulfate, filtered, and concentrated under reduced pressure. The crude product was separated by silica gel column chromatography (petroleum ether/ethyl acetate=1:0 to 1:1) to obtain compound 11-4.

MS-ESI $[M+H]^+$, calculated: 342, found: 342.

$^1H$ NMR (400 MHz, $CDCl_3$) δ 7.18 (dd, J=8.4, 5.2 Hz, 1H), 6.92-7.00 (m, 1H), 6.88 (dd, J=8.8, 2.4 Hz, 1H), 5.24 (s, 1H), 4.14-4.22 (m, 2H), 3.06-3.17 (m, 1H), 2.82-2.89 (m, 1H), 2.75-2.81 (m, 2H), 2.68-2.74 (m, 1H), 2.34 (ddd, J=13.2, 8.4, 5.2 Hz, 1H), 1.26 (t, J=7.2 Hz, 3H), 1.20 (s, 9H).

(3) To a solution of compound 11-4 (6.90 g, 19.6 mmol) in ethanol (60.0 mL) was added hydrochloric acid in dioxane (4 mol/L, 20.0 mL), and the reaction solution was stirred at 25° C. for 1 hour under nitrogen protection. Then the reaction solution was concentrated under reduced pressure to obtain crude product of hydrochloride of compound 11-5.

MS-ESI $[M-NH_2+H]^+$, calculated: 221, found: 221.

(4) To a solution of hydrochloride of compound 11-5 (5.37 g, 19.6 mmol) in ethanol (30.0 mL) was added compound 11-6 (19.9 g, 198 mmol), copper oxide (312 mg, 3.92 mmol), triethylamine (5.96 g, 58.9 mmol), and the reaction solution was reacted at 85° C. in a sealed tube for 8 hours under nitrogen protection. Then the reaction solution was added with water (200 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 4:1) to obtain compound 11-7.

MS-ESI $[M+H]^+$, calculated: 338, found: 338.

$^1H$ NMR (400 MHz, $CDCl_3$) δ 7.12 (dd, J=8.0, 5.2 Hz, 1H), 6.85-6.96 (m, 2H), 4.06-4.15 (m, 4H), 2.81-2.94 (m, 2H), 2.70-2.80 (m, 2H), 2.58-2.70 (m, 2H), 2.49-2.55 (m, 1H), 2.41-2.45 (m, 2H), 2.34 (dt, J=13.6, 8.4 Hz, 1H), 2.17 (ddd, J=13.2, 8.4, 4.4 Hz, 1H), 1.25 (t, J=7.2 Hz, 3H), 1.20 (t, J=7.2 Hz, 3H).

(5) To a solution of compound 11-7 (5.93 g, 17.6 mmol) in ethanol (80.0 mL) was added paraformaldehyde (5.28 g) and sodium cyanoborohydride (3.31 g, 52.7 mmol), and the reaction solution was reacted for 16 hours at 25° C. under nitrogen protection. Then the reaction solution was added with water (100 mL), and extracted with ethyl acetate (100 mL×1). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 9:1) to obtain compound 11-8.

MS-ESI $[M+H]^+$, calculated: 352, found: 352.

$^1H$ NMR (400 MHz, $CDCl_3$) δ 7.09 (dd, J=8.0, 5.2 Hz, 1H), 6.87-6.95 (m, 2H), 4.11 (qd, J=7.2, 2.0 Hz, 2H), 3.91 (qd, J=7.2, 1.2 Hz, 2H), 2.82-2.88 (m, 3H), 2.72-2.76 (m,

1H), 2.62 (td, J=7.2, 3.2 Hz, 2H), 2.38-2.46 (m, 2H), 2.32-2.37 (m, 1H), 2.21-2.28 (m, 1H), 2.18 (s, 3H), 1.25 (t, J=7.2 Hz, 3H), 1.03 (t, J=7.2 Hz, 3H).

(6) To a solution of compound 11-8 (2.00 g, 5.69 mmol) in tetrahydrofuran (20.0 mL) was added potassium bis (trimethylsilyl) amide (1 mol/L, 17.1 mL, tetrahydrofuran solution) at −78° C., and the reaction solution was reacted at −65° C. for 2 hours under nitrogen protection. Then the reaction solution was added with saturated ammonium chloride aqueous solution (100 mL), and extracted with ethyl acetate (100 mL×1). The combined organic phase was washed with saturated NaCl aqueous solution (100 mL×1), dried over anhydrous sodium sulfate, filtered, and concentrated under reduced pressure. The crude product was separated by silica gel column chromatography (petroleum ether/ethyl acetate=1:0 to 10:1) to obtain compound 11-9.

MS-ESI $[M+H]^+$, calculated: 306, found: 306.

$^1$H NMR (400 MHz, $CDCl_3$) δ 7.10-7.18 (m, 1H), 6.87-7.03 (m, 2H), 4.21-4.32 (m, 2H), 3.49 (d, J=13.2 Hz, 1H), 2.92-3.37 (m, 2H), 2.76-2.92 (m, 2H), 2.49-2.67 (m, 1H), 2.33-2.44 (m, 1H), 2.19-2.31 (m, 1H), 2.06-2.13 (m, 3H), 1.76-1.86 (m, 1H), 1.32 (t, J=7.2 Hz, 3H).

(7) To a solution of compound 11-9 (1.33 g, 4.36 mmol) in ethanol (15.0 mL) was added compound 11-10(663 mg, 8.71 mmol) and sodium ethoxide (889 mg, 13.1 mmol), and the reaction solution was stirred at 80° C. for 12 hours under nitrogen protection. After concentrated under reduced pressure, the reaction solution was adjusted to pH 6 with hydrochloric acid (1 mol/L). The resulting solution was precipitated, and filtered, and the filter cake was dried to obtain compound 11-11.

MS-ESI $[M+H]^+$, calculated: 318, found: 318.

$^1$H NMR (400 MHz, DMSO-d6) δ 7.27 (dd, J=8.4, 5.2 Hz, 1H), 7.07 (td, J=8.8, 2.4 Hz, 1H), 6.98 (d, J=9.2 Hz, 1H), 3.47 (d, J=16.4 Hz, 1H), 3.03 (d, J=16.4 Hz, 1H), 2.81-2.92 (m, 2H), 2.62 (d, J=17.6 Hz, 1H), 2.41 (d, J=17.6 Hz, 1H), 2.19 (dt, J=13.6, 8.4 Hz, 1H), 1.98 (s, 3H), 1.66 (ddd, J=13.2, 8.4, 4.4 Hz, 1H).

(8) To a solution of compound 11-11 (1.36 g, 1.08 mmol) in water (15.0 mL) was added chloroacetic acid (1.77 g, 18.7 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 11-12.

MS-ESI $[M+H]^+$, calculated: 302, found: 302.

$^1$H NMR (400 MHz, DMSO-d6) δ 11.01 (s, 1H), 10.76 (s, 1H), 7.27 (dd, J=8.4, 5.2 Hz, 1H), 7.08 (td, J=8.8, 2.4 Hz, 1H), 6.99 (dd, J=9.2, 2.4 Hz, 1H), 3.44 (d, J=16.0 Hz, 1H), 3.01 (d, J=16.0 Hz, 1H), 2.80-2.91 (m, 2H), 2.61 (d, J=17.6 Hz, 1H), 2.33 (d, J=17.2 Hz, 1H), 2.21 (dt, J=13.2, 8.4 Hz, 1H), 1.98 (s, 3H), 1.67 (ddd, J=13.2, 8.4, 4.4 Hz, 1H).

(9) Compound 11-12 (1.00 g, 3.32 mmol) was dissolved in phosphorus oxychloride (16.5 g, 108 mmol), and the reaction solution was stirred at 80° C. for 2 hours under nitrogen protection. Then the reaction solution was concentrated under reduced pressure, added with iced water (100 mL), and extracted with dichloromethane (100 mL×1). The organic phase was washed with saturated sodium bicarbonate aqueous solution (100 mL×2) and saturated NaCl aqueous solution (100 mL×1), dried over anhydrous sodium sulfate, filtered, and concentrated under reduced pressure. The crude product was separated by silica gel column chromatography (petroleum ether/ethyl acetate=1:0 to 10:1) to obtain compound 11-13.

MS-ESI $[M+H]^+$, calculated: 338, found: 338.

$^1$H NMR (400 MHz, DMSO-$d_6$) δ 7.29 (dd, J=8.4, 5.2 Hz, 1H), 7.09 (td, J=8.8, 2.4 Hz, 1H), 6.98 (dd, J=9.2, 2.4 Hz, 1H), 3.93 (d, J=17.6 Hz, 1H), 3.51 (d, J=17.6 Hz, 1H), 3.12 (d, J=18.0 Hz, 1H), 2.87-2.97 (m, 3H), 2.25 (dt, J=13.2, 8.4 Hz, 1H), 2.11 (s, 3H), 1.66 (dt, J=13.2, 6.4 Hz, 1H).

(10) To a solution of compound 11-13 (200 mg, 591 μmol) in N-methylpyrrolidone (5.0 mL) was added potassium carbonate (245 mg, 1.77 mmol) and compound 11-14 (200 mg, 888 mol), and the reaction solution was stirred at 50° C. for 10 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure. The crude product was separated by silica gel column chromatography (petroleum ether/ethyl acetate=1:0 to 3:1) to give compound 11-15.

MS-ESI $[M+H]^+$, calculated: 527, found: 527.

$^1$H NMR (400 MHz, MeOD) δ 7.21-7.30 (m, 1H), 7.01 (td, J=8.8, 2.4 Hz, 1H), 6.89-6.98 (m, 1H), 4.63 (s, 1H), 4.09-4.28 (m, 1H), 3.92-4.05 (m, 2H), 3.68-3.85 (m, 2H), 3.45 (dd, J=14.0, 3.6 Hz, 1H), 3.25 (dd, J=13.6, 3.6 Hz, 1H), 3.06-3.20 (m, 1H), 2.80-3.03 (m, 6H), 2.39-2.50 (m, 1H), 2.23 (d, J=1.6 Hz, 3H), 1.89 (ddt, J=13.2, 7.6, 4.0 Hz, 1H), 1.51 (d, J=1.2 Hz, 9H).

(11) To a solution of compound 11-15 (220 mg, 417 μmol) in dioxane (8.0 mL) was added compound 11-16 (144 mg, 1.20 mmol), cesium carbonate (409 mg, 1.20 mmol) and (2-dicyclohexylphosphino-2',6'-diisopropoxy-1,1'-biphenyl) [2-(2'-amino-1,1'-biphenyl)]palladium(II) methanesulfonate (70.0 mg, 83.7 μmol), and the reaction solution was stirred at 110° C. for 4 hours under nitrogen protection. Then the reaction solution was added with ethyl acetate (50.0 mL), washed with saturated NaCl aqueous solution (50.0 mL×2), dried over anhydrous sodium sulfate, filtered, and concentrated under reduced pressure. The crude product was separated by silica gel column chromatography (dichloromethane/methanol=1:0 to 9:1) to obtain compound 11-17.

MS-ESI $[M+H]^+$, calculated: 606, found: 606.

$^1$H NMR (400 MHz, MeOD) δ 7.26 (t, J=5.6 Hz, 1H), 6.98-7.08 (m, 1H), 6.86-6.98 (m, 1H), 4.63 (d, J=7.6 Hz, 1H), 4.26-4.46 (m, 2H), 3.92-4.17 (m, 3H), 3.65-3.82 (m, 2H), 3.42 (dd, J=13.6, 3.6 Hz, 1H), 3.14-3.29 (m, 2H), 3.07-3.13 (m, 1H), 2.95-3.06 (m, 3H), 2.88-2.94 (m, 2H), 2.77-2.88 (m, 2H), 2.53 (d, J=4.0 Hz, 3H), 2.34-2.49 (m, 2H), 2.23 (d, J=2.0 Hz, 3H), 2.04-2.16 (m, 1H), 1.78-1.94 (m, 3H), 1.67-1.78 (m, 1H), 1.51 (d, J=1.6 Hz, 9H).

(12) To a solution of compound 11-17 (70.0 mg, 281 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 11-18.

MS-ESI $[M+H]^+$, calculated: 506, found: 506.

(13) To a solution of trifluoroacetate of compound 11-18 (160.0 mg, 258 μmol) in dichloromethane (5.0 mL) was added triethylamine (78.1 mg, 775 μmol) and compound 11-19 (46.7 mg, 516 μmol), and the reaction solution was stirred at −65° C. for 0.5 hours under nitrogen protection. Then the reaction solution was added with dichloromethane (30.0 mL), washed with saturated NaCl aqueous solution (30.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 11.

MS-ESI $[M+H]^+$, calculated: 560, found: 560.

$^1$H NMR (400 MHz, MeOD) δ 7.28 (t, J=6.0 Hz, 1H), 6.93-7.11 (m, 2H), 6.81 (s, 1H), 6.29 (d, J=16.4 Hz, 1H), 5.84 (d, J=10.4 Hz, 1H), 4.90-5.14 (m, 1H), 4.68-4.75 (m, 1H), 4.55 (dd, J=12.4, 7.2 Hz, 1H), 4.17-4.38 (m, 1H), 3.89-4.16 (m, 2H), 3.80 (d, J=15.6 Hz, 3H), 3.65-3.72 (m, 1H), 3.54 (s, 1H), 3.04-3.30 (m, 4H), 3.02 (d, J=5.2 Hz, 3H), 2.89-3.01 (m, 5H), 2.44-2.54 (m, 1H), 2.32-2.41 (m, 1H), 2.26 (s, 3H), 2.13-2.20 (m, 1H), 2.09 (dd, J=14.4, 7.6 Hz, 1H), 1.97-2.05 (m, 1H), 1.88-1.96 (m, 1H).

Example 10 Synthesis of Compound 12

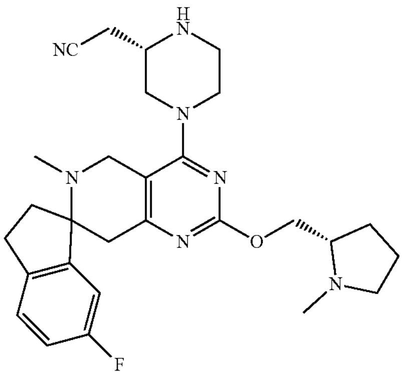
11-18

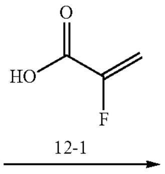

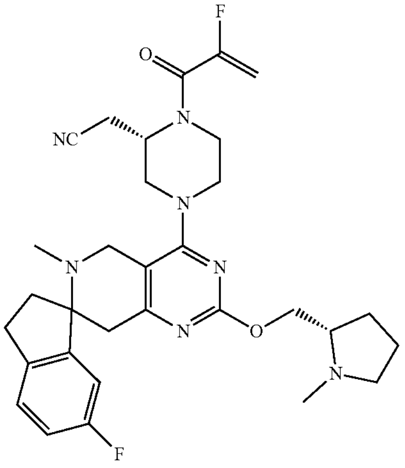
12

To a solution of compound 12-1 (65.4 mg, 726 μmol) in dichloromethane (5.0 mL) was added triethylamine (73.5 mg, 726 μmol), trifluoroacetate of compound 11-18(150 mg, 242 mol) and propanephosphonic acid anhydride (462 mg, 726 μmol, 50% ethyl acetate solution), and the reaction solution was stirred at 25° C. for 1 hour. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 70 mm×30 mm 3 μm, A: water (0.225% formic acid); B: acetonitrile, 0%-30%: 8 min) to obtain formate of compound 12.

MS-ESI $[M+H]^+$, calculated: 578, found: 578.

$^1$H NMR (400 MHz, MeOD) δ 7.23-7.31 (m, 1H), 7.02 (td, J=8.8, 2.0 Hz, 1H), 6.95 (ddd, J=11.2, 9.2, 2.4 Hz, 1H), 5.21-5.43 (m, 2H), 4.58 (dt, J=12.0, 4.4 Hz, 1H), 4.43-4.50 (m, 1H), 3.97-4.35 (m, 3H), 3.71-3.82 (m, 2H), 3.39-3.60 (m, 3H), 3.32 (s, 1H), 3.26-3.30 (m, 1H), 3.03-3.23 (m, 2H), 2.88-3.03 (m, 6H), 2.85 (d, J=7.6 Hz, 3H), 2.43-2.53 (m, 1H), 2.25-2.33 (m, 1H), 2.24 (d, J=2.0 Hz, 3H), 1.96-2.10 (m, 2H), 1.85-1.95 (m, 2H).

Example 11 Synthesis of Compound 13

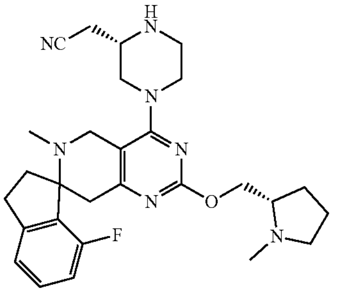
6-19

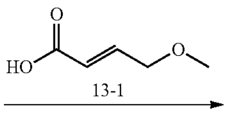

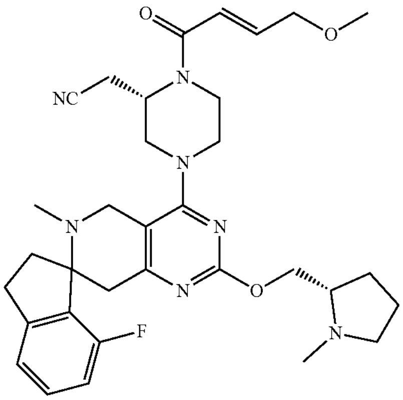
13

To a solution of compound 13-1 (45.3 mg, 435 μmol) in dichloromethane (2.0 mL) was added triethylamine (14.7 mg, 145 μmol), trifluoroacetate of compound 6-19 (90.0 mg, 145 mol) and 2-(7-azabenzotriazole)-N, N, N', N'-tetramethylurea hexafluorophosphate (110 mg, 290 μmol), and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Gemini-NX C18, 70 mm×30 mm 3 μm, A: water (10 mmol/L $NH_4HCO_3$); B: acetonitrile, 35%-75%: 11 minutes) to obtain compound 13.

MS-ESI $[M+H]^+$, calculated: 604, found: 604.

$^1$H NMR (400 MHz, MeOD) δ 7.28-7.35 (m, 1H), 7.06-7.13 (m, 1H), 6.89-6.98 (t, 1H), 6.10-6.20 (m, 1H), 4.88-5.04 (m, 1H), 4.48-4.54 (m, 1H), 4.29-4.40 (m, 2H), 3.89-4.23 (m, 3H), 3.63-3.71 (m, 5H), 3.40-3.58 (m, 1H), 3.14-3.27 (m, 4H), 2.83-3.13 (m, 7H), 2.71-2.79 (m, 1H), 2.45-2.54 (m, 4H), 2.32-2.39 (m, 1H), 2.25-2.30 (s, 3H), 2.04-2.14 (m, 1H), 1.78-1.93 (m, 3H), 1.66-1.75 (m, 1H).

Example 12 Synthesis of Compound 14

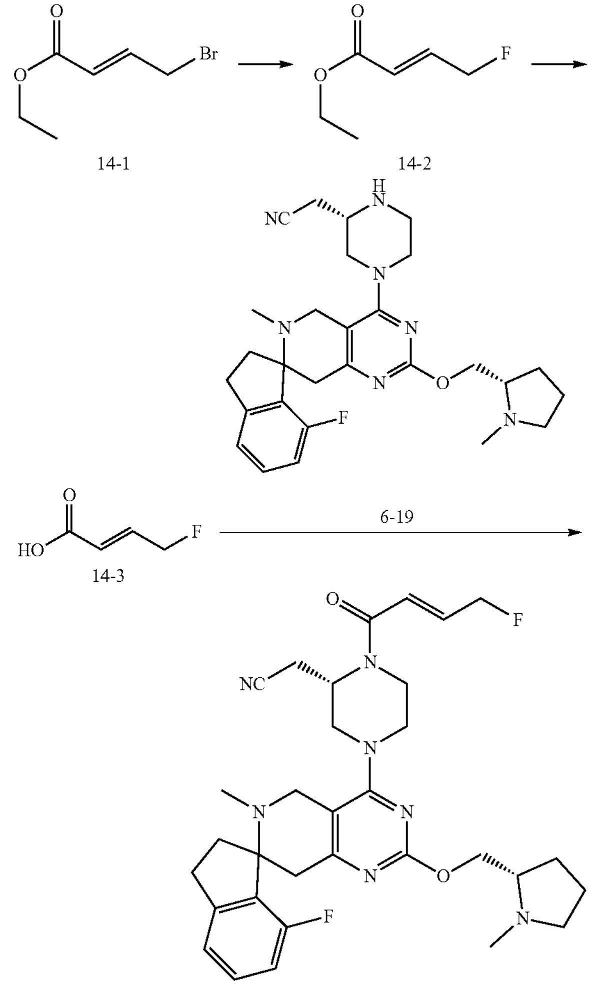

14-1 14-2 6-19 14-3 14

(1) To a solution of compound 14-1 (1.0 g, 5.18 mmol) in acetonitrile (10.0 mL) was added silver fluoride (1.97 g, 15.5 mmol), and the reaction solution was stirred at 25° C. for 24 hours under nitrogen protection. Then the reaction solution was filtered and concentrated under reduced pressure to obtain compound 14-2.

$^1$H NMR (400 MHz, $CDCl_3$) δ 6.90-7.04 (m, 1H), 6.07-6.16 (m, 1H), 5.09-5.14 (m, 1H), 4.98-5.03 (m, 1H), 4.19-4.26 (m, 2H), 1.29-1.33 (m, 3H).

(2) To a solution of compound 14-2 (400 mg, 3.03 mmol) in tetrahydrofuran (3.0 mL) was added lithium hydroxide (381 mg, 9.08 mmol) and water (3.0 mL), and the reaction solution was stirred at 25° C. for 12 hours under nitrogen protection. Then the reaction solution was added with hydrochloric acid (20 mL, 1 mol/L), and extracted with ethyl acetate (50.0 mL×2). The combined organic phase was washed with saturated NaCl aqueous solution (50.0 mL×2), dried over anhydrous sodium sulfate, filtered, and concentrated under reduced pressure to give compound 14-3.

$^1$H NMR (400 MHz, DMSO-$d_6$) δ 12.36-12.68 (s, 1H), 6.80-6.96 (m, 1H), 5.88-6.04 (m, 1H), 5.03-5.22 (m, 2H).

(3) To a solution of compound 14-3 (45.3 mg, 435 μmol) in dichloromethane (2.0 mL) was added triethylamine (14.7 mg, 145 μmol), trifluoroacetate of compound 6-19 (90.0 mg, 145 μmol) and 2-(7-azabenzotriazole)-N, N, N', N'-tetramethylurea hexafluorophosphate (110 mg, 290 μmol), and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Gemini-NX C18, 70 mm×30 mm 3 μm, A: water (10 mmol/L $NH_4HCO_3$); B: acetonitrile, 35%-75%: 11 minutes) to obtain compound 14.

MS-ESI $[M+H]^+$, calculated: 592, found: 592.

$^1$H NMR (400 MHz, MeOD) δ 7.28-7.35 (m, 1H), 7.06-7.13 (m, 1H), 6.89-6.98 (t, 1H), 6.56-6.84 (m, 1H), 5.02-5.19 (m, 1H), 4.28-4.41 (m, 2H), 3.86-4.19 (m, 3H), 3.65-3.74 (m, 2H), 3.34-3.61 (m, 3H), 2.83-3.28 (m, 10H), 2.70-2.80 (m, 1H), 2.43-2.53 (m, 4H), 2.32-2.40 (m, 1H), 2.25-2.31 (s, 3H), 2.04-2.13 (m, 1H), 1.78-1.94 (m, 3H), 1.65-1.75 (m, 1H).

Example 13 Synthesis of Compound 15

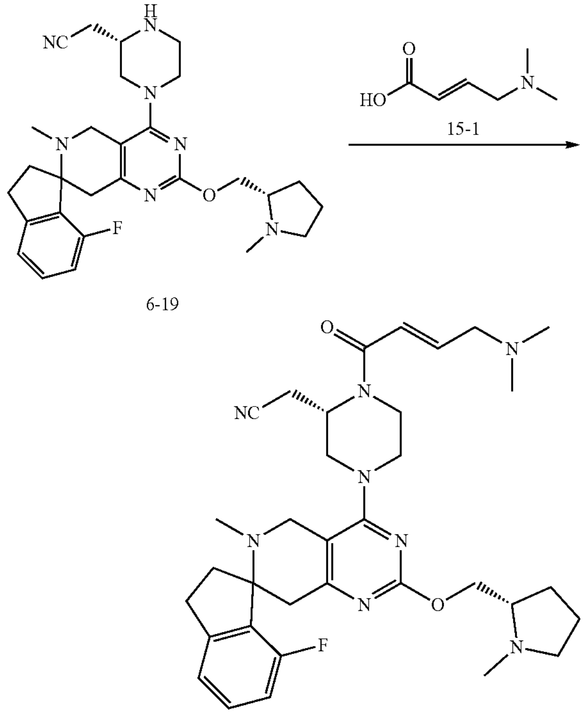

6-19 15-1 15

To a solution of compound 15-1 (45.3 mg, 435 μmol) in dichloromethane (2.0 mL) was added triethylamine (14.7 mg, 145 μmol), trifluoroacetate of compound 6-19 (90.0 mg, 145 mol) and 2-(7-azabenzotriazole)-N, N, N', N'-tetramethylurea hexafluorophosphate (110 mg, 290 μmol), and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A:

water (0.225% formic acid); B: acetonitrile, 0%-20%: 8 minutes) to obtain formate of compound 15.

MS-ESI $[M+H]^+$, calculated: 617, found: 617.

$^1H$ NMR (400 MHz, MeOD) δ 7.29-7.37 (m, 1H), 7.07-7.15 (m, 1H), 6.73-7.03 (m, 3H), 4.90-5.20 (m, 1H), 4.65-4.73 (m, 1H), 4.51-4.57 (m, 1H), 3.85-4.47 (m, 3H), 3.61-3.82 (m, 6H), 3.42-3.59 (m, 1H), 3.04-3.29 (m, 6H), 2.87-3.03 (m, 6H), 2.67-2.80 (m, 6H), 2.34-2.56 (m, 2H), 2.26-2.33 (m, 3H), 1.88-2.20 (m, 4H).

Example 14 Synthesis of Compound 16

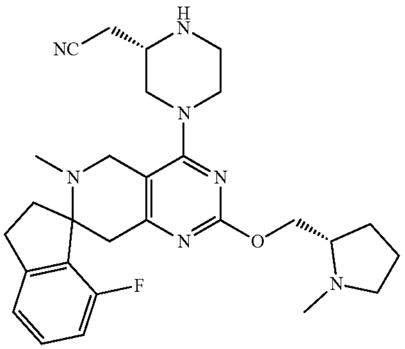

6-19

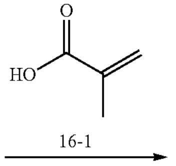

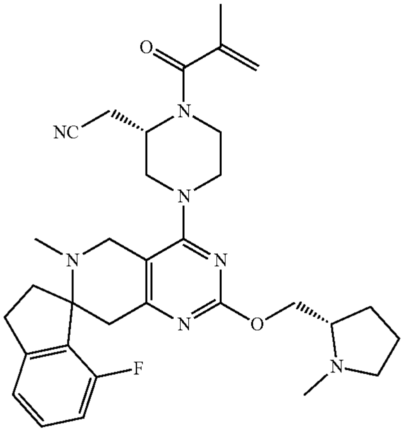

16

To a solution of compound 16-1 (45.3 mg, 435 μmol) in dichloromethane (2.0 mL) was added triethylamine (14.7 mg, 145 μmol), trifluoroacetate of compound 6-19 (90.0 mg, 145 μmol) and 2-(7-azabenzotriazole)-N, N, N', N'-tetramethylurea hexafluorophosphate (110 mg, 290 μmol), and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-20%: 8 minutes) to obtain formate of compound 16.

MS-ESI $[M+H]^+$, calculated: 574, found: 574.

$^1H$ NMR (400 MHz, MeOD) δ 7.29-7.36 (m, 1H), 7.08-7.14 (m, 1H), 6.90-6.99 (m, 1H), 5.31-5.39 (m, 1H), 5.14-5.24 (m, 1H), 4.89-5.07 (m, 1H), 4.67-4.73 (m, 1H), 4.48-4.56 (m, 1H), 3.89-4.32 (m, 3H), 3.76-3.85 (m, 1H), 3.63-3.74 (m, 3H), 3.34-3.49 (m, 1H), 3.15-3.27 (m, 3H), 2.85-3.14 (m, 9H), 2.45-2.56 (m, 1H), 2.33-2.41 (m, 1H), 2.27-2.32 (m, 3H), 2.02-2.22 (m, 3H), 1.97-2.01 (m, 3H), 1.87-1.95 (m, 1H).

Example 15 Synthesis of Compound 17

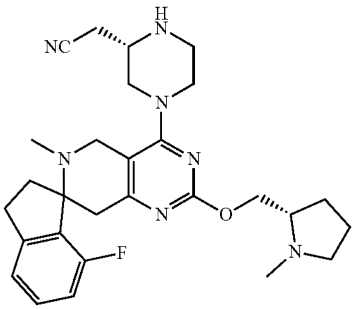

6-19

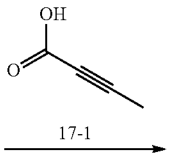

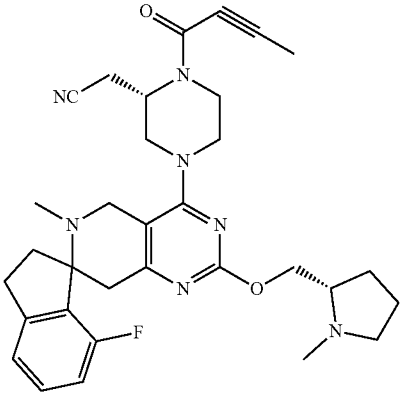

17

To a solution of compound 17-1 (45.3 mg, 435 μmol) in dichloromethane (2.0 mL) was added triethylamine (14.7 mg, 145 μmol), trifluoroacetate of compound 6-19 (90.0 mg, 145 mol) and 2-(7-azabenzotriazole)-N, N, N', N'-tetramethylurea hexafluorophosphate (110 mg, 290 μmol), and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-20%: 8 minutes) to obtain formate of compound 17.

MS-ESI $[M+H]^+$, calculated: 572, found: 572.

$^1H$ NMR (400 MHz, MeOD) δ 7.29-7.36 (m, 1H), 7.06-7.15 (m, 1H), 6.90-6.99 (m, 1H), 4.66-4.75 (m, 1H), 4.35-4.58 (m, 2H), 4.01-4.32 (m, 2H), 3.66-3.86 (m, 4H), 3.39-3.60 (m, 1H), 2.85-3.27 (m, 12H), 2.34-2.57 (m, 2H), 2.27-2.33 (m, 3H), 2.06-2.21 (m, 5H), 1.87-2.04 (m, 2H), 1.61-1.75 (m, 1H).

Example 16 Synthesis of Compound 18
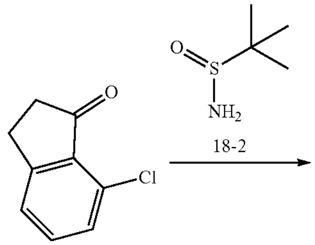
18-1
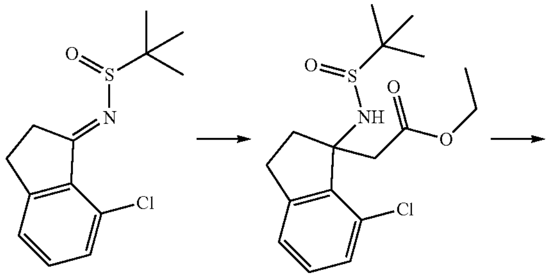
18-3
18-4
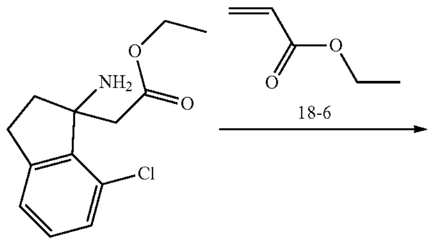
18-5
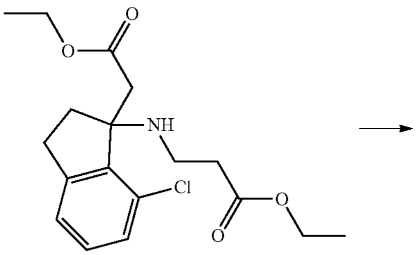
18-7
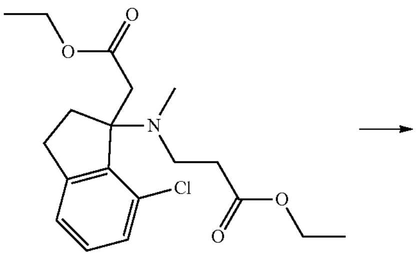
18-8
-continued
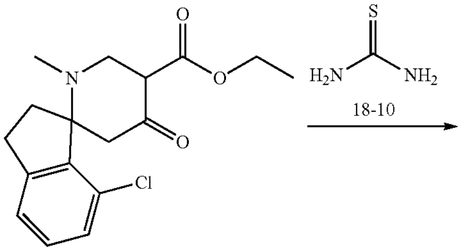
18-9
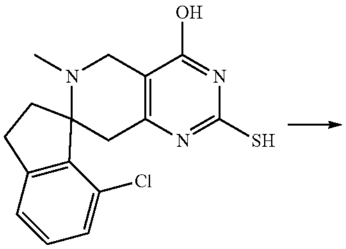
18-11
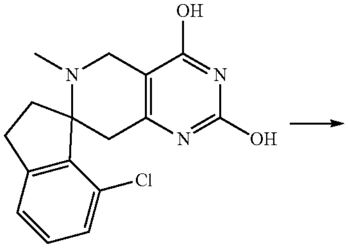
18-12
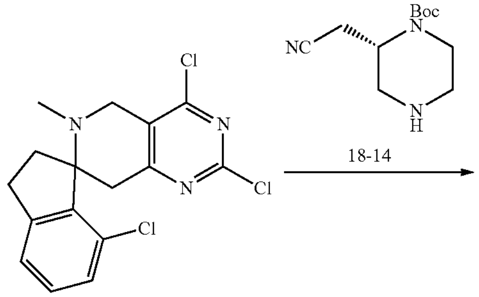
18-13
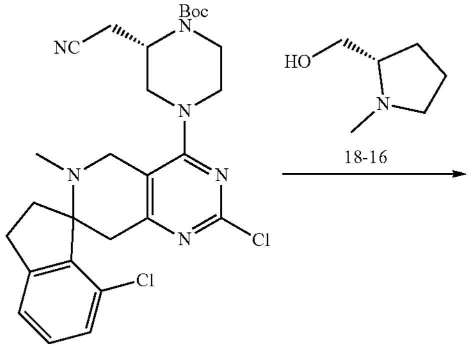
18-15

-continued

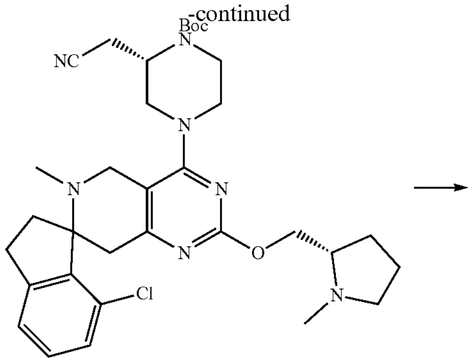

18-17

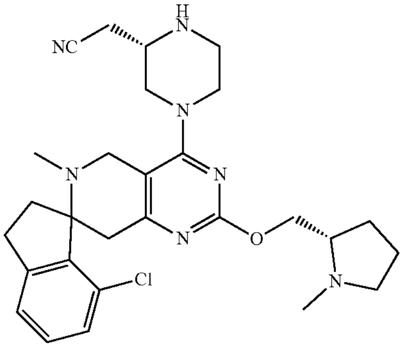

18-18

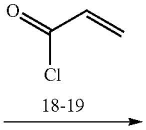

18-19

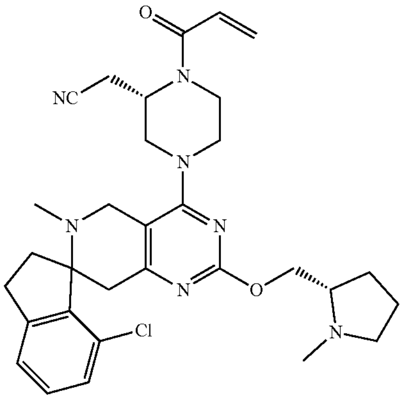

18

(1) To a solution of compound 18-1 (24.0 g, 144 mmol) in toluene (300 mL) was added compound 18-2 (21.0 g, 173 mmol), and tetraethyl titanate (65.9 g, 289 mmol), and then the reaction solution was stirred at 120° C. for 12 hours under nitrogen protection. Then the reaction solution was added with water (100 mL) and ethyl acetate (400 mL). After filtration, the filter cake was washed with ethyl acetate (400 mL×4). The combined organic phase was washed with saturated NaCl aqueous solution (400 mL×2), dried over anhydrous sodium sulfate, filtered, and concentrated under reduced pressure. The crude product was separated by silica gel column chromatography (petroleum ether/ethyl acetate=1:0 to 5:1) to obtain compound 18-3.

MS-ESI $[M+H]^+$, calculated: 270, found: 270.

$^1$H NMR (400 MHz, $CDCl_3$) δ 7.35-7.40 (m, 1H), 7.27-7.32 (m, 2H), 3.45-3.60 (m, 1H), 3.06-3.15 (m, 3H), 1.36 (s, 9H).

(2) To a solution of ethyl acetate (3.27 g, 37.1 mmol) in tetrahydrofuran (20.0 mL) was added dropwise with lithium diisopropylamide (2 mol/L, 7.4 mL, tetrahydrofuran solution) at −65° C. under nitrogen protection, and the reaction solution was stirred at −78° C. for 1 hour. Then the reaction solution was added dropwise with a solution of compound 18-3 (2.00 g, 7.41 mmol) in tetrahydrofuran (20.0 mL), and then continued stirring for 2 hours at −65° C. After warming to 0° C., the reaction solution was quenched with saturated ammonium chloride aqueous solution (50.0 mL), and extracted with ethyl acetate (50.0 mL×2). The combined organic phase was washed with saturated ammonium chloride aqueous solution (50.0 mL×1) and saturated NaCl aqueous solution (50.0 mL×1), dried over anhydrous sodium sulfate, filtered, and concentrated under reduced pressure. The crude product was separated by silica gel column chromatography (petroleum ether/ethyl acetate=1:0 to 3:1) to obtain compound 18-4.

MS-ESI $[M+H]^+$, calculated: 358, found: 358.

$^1$H NMR (400 MHz, $CDCl_3$) δ 7.21-7.25 (m, 1H), 7.14-7.19 (m, 2H), 5.14 (s, 1H), 4.11-4.20 (m, 2H), 3.68 (d, J=15.6 Hz, 1H), 3.33 (dt, J=16.4, 8.4 Hz, 1H), 2.90 (ddd, J=16.4, 9.2, 3.6 Hz, 1H), 2.78 (d, J=15.6 Hz, 1H), 2.68 (ddd, J=13.2, 9.2, 3.6 Hz, 1H), 2.29-2.38 (m, 1H), 1.23-1.27 (m, 3H), 1.20 (s, 9H).

(3) To a solution of compound 18-4 (1.40 g, 3.91 mmol) in ethanol (15.0 mL) was added hydrochloric acid in dioxane (4 mol/L, 5.0 mL), and the reaction solution was stirred at 25° C. for 1 hour under nitrogen protection. Then the reaction solution was concentrated under reduced pressure to obtain crude product of hydrochloride of compound 18-5.

MS-ESI $[M+H]^+$, calculated: 254, found: 254.

(4) To a solution of hydrochloride of compound 18-5 (1.14 g, 3.93 mmol) in ethanol (12.0 mL) was added compound 18-6 (8.17 g, 81.6 mmol), copper oxide (62.5 mg, 786 μmol), and triethylamine (1.19 g, 11.8 mmol), and the reaction solution was then reacted at 85° C. in a sealed tube for 8 hours under nitrogen protection. Then the reaction solution was added with water (100 mL), and extracted with ethyl acetate (100 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 10:1) to obtain compound 18-7.

MS-ESI $[M+H]^+$, calculated: 354, found: 354.

$^1$H NMR (400 MHz, $CDCl_3$) δ 7.02-7.18 (m, 3H), 4.09-4.14 (m, 2H), 4.02 (q, J=7.2 Hz, 2H), 2.86-3.03 (m, 3H), 2.72-2.86 (m, 2H), 2.63-2.72 (m, 1H), 2.41-2.50 (m, 4H), 2.29 (m, 1H), 1.22-1.26 (t, J=7.2 Hz, 3H), 1.12 (t, J=7.2 Hz, 3H).

(5) To a solution of compound 18-7 (900 mg, 2.54 mmol) in ethanol (15.0 mL) was added paraformaldehyde (900 mg) and sodium cyanoborohydride (480 mg, 7.64 mmol), and then the reaction solution was reacted for 10 hours at 25° C. under nitrogen protection. Then the reaction solution was added with water (30.0 mL), and extracted with ethyl acetate (30.0 mL×1). The combined organic phase was washed with saturated NaCl aqueous solution (30.0 mL×2), dried over anhydrous sodium sulfate, filtered, and concentrated under reduced pressure. The crude product was separated by silica gel column chromatography (petroleum ether/ethyl acetate=1:0 to 15:1) to obtain compound 18-8.

MS-ESI $[M+H]^+$, calculated: 368, found: 368.

$^1$H NMR (400 MHz, $CDCl_3$) δ 7.08-7.16 (m, 2H), 7.01-7.06 (m, 1H), 4.10 (q, J=7.2 Hz, 2H), 3.80 (dtt, J=10.4, 7.2, 3.6 Hz, 2H), 3.32 (d, J=13.6 Hz, 1H), 2.94 (d, J=13.6 Hz, 1H), 2.87-2.92 (m, 2H), 2.74 (dt, J=12.8, 7.2 Hz, 1H), 2.50-2.56 (m, 1H), 2.43-2.49 (m, 2H), 2.35 (dt, J=14.0, 8.0 Hz, 1H), 2.20-2.28 (m, 1H), 2.14 (s, 3H), 1.24 (t, J=7.2 Hz, 3H), 0.91 (t, J=7.2 Hz, 3H).

(6) To a solution of compound 18-8 (780 mg, 2.12 mmol) in tetrahydrofuran (10.0 mL) was added potassium bis (trimethylsilyl) amide (1 mol/L, 6.4 mL, tetrahydrofuran solution) at −78° C., and the reaction solution was reacted at −65° C. for 2 hours under nitrogen protection. Then the reaction solution was added with saturated ammonium chloride aqueous solution (50.0 mL), and extracted with ethyl acetate (50.0 mL×1). The combined organic phase was washed with saturated NaCl aqueous solution (50.0 mL×1), dried over anhydrous sodium sulfate, filtered, and concentrated under reduced pressure. The crude product was separated by silica gel column chromatography (petroleum ether/ethyl acetate=1:0 to 19:1) to obtain compound 18-9.

MS-ESI $[M+H]^+$, calculated: 322, found: 322.

$^1$H NMR (400 MHz, $CDCl_3$) δ 7.15-7.20 (m, 2H), 7.10-7.14 (m, 1H), 4.26-4.34 (m, 1H), 4.17-4.25 (m, 1H), 3.61 (d, J=15.2 Hz, 1H), 3.04-3.17 (m, 2H), 2.71-3.04 (m, 3H), 2.24-2.30 (m, 1H), 2.15-2.22 (m, 1H), 2.14 (s, 3H), 1.76 (ddd, J=13.2, 8.4, 2.4 Hz, 1H), 1.31 (t, J=7.2 Hz, 3H).

(7) To a solution of compound 18-9 (475 mg, 1.48 mmol) in ethanol (10.0 mL) was added compound 18-10 (225 mg, 2.96 mmol) and sodium ethoxide (301 mg, 4.42 mmol), and the reaction solution was stirred at 80° C. for 12 hours under nitrogen protection. After concentrated under reduced pressure, the reaction solution was adjusted to pH 6 with hydrochloric acid (1 mol/L). The resulting solution was precipitated, and filtered, and the filter cake was dried to obtain compound 18-11.

MS-ESI $[M+H]^+$, calculated: 334, found: 334.

$^1$H NMR (400 MHz, DMSO-d6) δ 12.41 (s, 1H), 12.27 (s, 1H), 7.23-7.31 (m, 3H), 3.52 (d, J=16.4 Hz, 1H), 2.88-3.04 (m, 4H), 2.30-2.37 (m, 1H), 2.16-2.25 (m, 1H), 2.03 (s, 3H), 1.66 (t, J=10.0 Hz, 1H).

(8) To a solution of compound 18-11 (320 mg, 959 μmol) in water (10.0 mL) was added chloroacetic acid (410 g, 4.34 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 18-12.

MS-ESI $[M+H]^+$, calculated: 318, found: 318.

$^1$H NMR (400 MHz, DMSO-d6) δ 11.00 (s, 1H), 10.76 (s, 1H), 7.22-7.33 (m, 3H), 3.47 (d, J=15.2 Hz, 1H), 2.85-2.99 (m, 4H), 2.13-2.25 (m, 2H), 2.02 (s, 3H), 1.59-1.69 (m, 1H).

(9) Compound 18-12 (260 mg, 818 μmol) was dissolved in phosphorus oxychloride (8.25 g, 53.8 mmol), and the reaction solution was stirred at 80° C. for 6 hours under nitrogen protection. Then the reaction solution was diluted with dichloromethane (30.0 mL) and added with saturated sodium bicarbonate aqueous solution (30.0 mL) to adjust pH value to 8. The separated organic phase was washed with saturated sodium bicarbonate aqueous solution (30.0 mL×2) and saturated NaCl aqueous solution (30.0 mL×1), dried over anhydrous sodium sulfate, filtered, and concentrated under reduced pressure to give compound 18-13.

MS-ESI $[M+H]^+$, calculated: 356, found: 356.

$^1$H NMR (400 MHz, $CDCl_3$) δ 7.15-7.26 (m, 3H), 3.72-4.23 (m, 2H), 3.43-3.69 (m, 2H), 3.00-3.08 (m, 1H), 2.81-2.96 (m, 2H), 2.31 (s, 3H), 0.77-1.27 (m, 1H).

(10) To a solution of compound 18-13 (180 mg, 508 μmol) in N-methylpyrrolidone (5.0 mL) was added potassium carbonate (211 mg, 1.53 mmol) and compound 18-14 (137 mg, 608 mol), and the reaction solution was stirred at 50° C. for 10 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure. The crude product was separated by silica gel column chromatography (petroleum ether/ethyl acetate=1:0 to 6:1) to give compound 18-15.

MS-ESI $[M+H]^+$, calculated: 543, found: 543.

$^1$H NMR (400 MHz, MeOD) δ 7.14-7.34 (m, 3H), 4.64 (s, 1H), 4.10-4.25 (m, 1H), 3.88-4.10 (m, 3H), 3.71 (d, J=9.6 Hz, 2H), 3.33-3.49 (m, 2H), 3.15-3.30 (m, 2H), 3.01 (dt, J=17.6, 8.8 Hz, 3H), 2.75 (dd, J=18.0, 3.6 Hz, 1H), 2.38-2.52 (m, 1H), 2.24 (d, J=0.8 Hz, 3H), 1.78-1.87 (m, 1H), 1.51 (d, J=1.6 Hz, 9H).

(11) To a solution of compound 18-15 (150 mg, 276 μmol) in dioxane (5.0 mL) was added compound 18-16 (95.4 mg, 828 μmol), potassium carbonate (115 mg, 832 μmol), dicyclohexyl(2',4',6'-triisopropyl-[1,1'-biphenyl]-2-yl)phosphine (52.6 mg, 110 mol) and bis (di benzylidene acetone) palladium (50.6 mg, 55.3 μmol), and the reaction solution was stirred at 110° C. for 4 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 10:1) to obtain compound 18-17.

MS-ESI $[M+H]^+$, calculated: 622, found: 622.

$^1$H NMR (400 MHz, MeOD) δ 7.16-7.31 (m, 3H), 4.62 (s, 1H), 4.38-4.54 (m, 2H), 4.13-4.25 (m, 1H), 3.91-4.12 (m, 3H), 3.62-3.72 (m, 2H), 3.36-3.51 (m, 2H), 3.12-3.20 (m, 2H), 2.91-3.08 (m, 4H), 2.65-2.76 (m, 4H), 2.48 (d, J=8.4 Hz, 1H), 2.24 (s, 3H), 2.07-2.22 (m, 2H), 1.93 (d, J=8.4 Hz, 2H), 1.77-1.88 (m, 3H), 1.51 (d, J=2.4 Hz, 9H).

(12) To a solution of compound 18-17 (20.0 mg, 193 μmol) in dichloromethane (3.0 mL) was added trifluoroacetic acid (1.0 mL), and the reaction solution was stirred at 25° C. for 1 hour under nitrogen protection. Then the reaction solution was concentrated under reduced pressure to obtain crude trifluoroacetate of compound 18-18.

MS-ESI $[M+H]^+$, calculated: 522, found: 522.

(13) To a solution of trifluoroacetate of compound 18-18 (50.0 mg, 78.6 μmol) in dichloromethane (2.0 mL) was added triethylamine (23.9 mg, 236 μmol) and compound 18-19 (14.3 mg, 158 μmol), and the reaction solution was stirred at −65° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 18.

MS-ESI $[M+H]^+$, calculated: 576, found: 576.

$^1$H NMR (400 MHz, MeOD) δ 7.21-7.29 (m, 3H), 6.80 (s, 1H), 6.30 (d, J=16.8 Hz, 1H), 5.84 (d, J=10.0 Hz, 1H), 4.67 (d, J=12.4 Hz, 1H), 4.46-4.53 (m, 1H), 4.18-4.38 (m, 1H), 4.00-4.18 (m, 2H), 3.62-3.84 (m, 4H), 3.45-3.62 (m, 2H), 3.33-3.38 (m, 1H), 3.15-3.28 (m, 2H), 2.98-3.14 (m, 4H), 2.96 (d, J=9.2 Hz, 3H), 2.91 (d, J=4.0 Hz, 1H), 2.73 (dd, J=17.6, 3.2 Hz, 1H), 2.44-2.51 (m, 1H), 2.33 (dt, J=8.4, 6.4 Hz, 1H), 2.25 (s, 3H), 2.10-2.17 (m, 1H), 2.02-2.09 (m, 1H), 1.93-2.02 (m, 1H), 1.79-1.88 (m, 1H).

Example 17 Synthesis of Compound 19

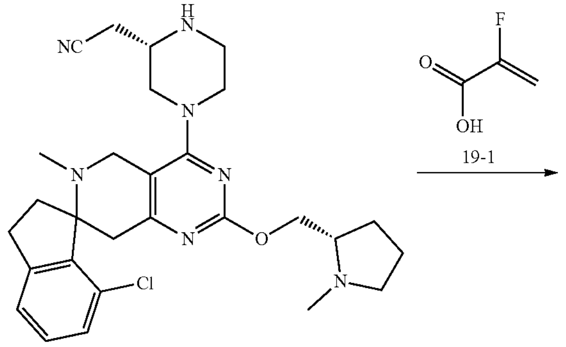

18-18

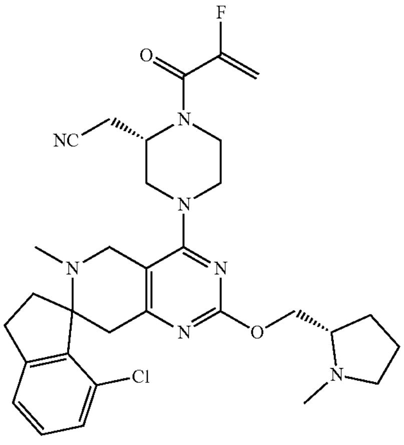

19

To a solution of compound 19-1 (21.3 mg, 237 μmol) in dichloromethane (2.0 mL) was added triethylamine (23.9 mg, 236 μmol), trifluoroacetate of compound 18-18 (90.0 mg, 145 mol) and propylphosphonic acid anhydride solution (150 mg, 236 μmol, 50% ethyl acetate solution), and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-20%: 8 min) to obtain formate of compound 19.

MS-ESI $[M+H]^+$, calculated: 594, found: 595.

$^1H$ NMR (400 MHz, MeOD) δ 7.21-7.29 (m, 3H), 5.37 (d, J=17.6 Hz, 1H), 5.29 (d, J=7.6 Hz, 1H), 4.64 (d, J=10.0 Hz, 1H), 4.48 (dt, J=12.0, 5.6 Hz, 2H), 4.34 (d, J=13.2 Hz, 1H), 4.08-4.26 (m, 2H), 4.03 (d, J=10.4 Hz, 1H), 3.66-3.73 (m, 2H), 3.48-3.63 (m, 3H), 3.37 (s, 1H), 3.18-3.25 (m, 1H), 2.95-3.07 (m, 4H), 2.92 (d, J=10.0 Hz, 3H), 2.73 (dd, J=18.0, 3.6 Hz, 1H), 2.49 (q, J=10.4 Hz, 1H), 2.28-2.36 (m, 1H), 2.25 (s, 3H), 2.00-2.12 (m, 2H), 1.92-1.99 (m, 1H), 1.79-1.86 (m, 1H), 1.67 (s, 1H).

Example 18 Synthesis of Compound 20

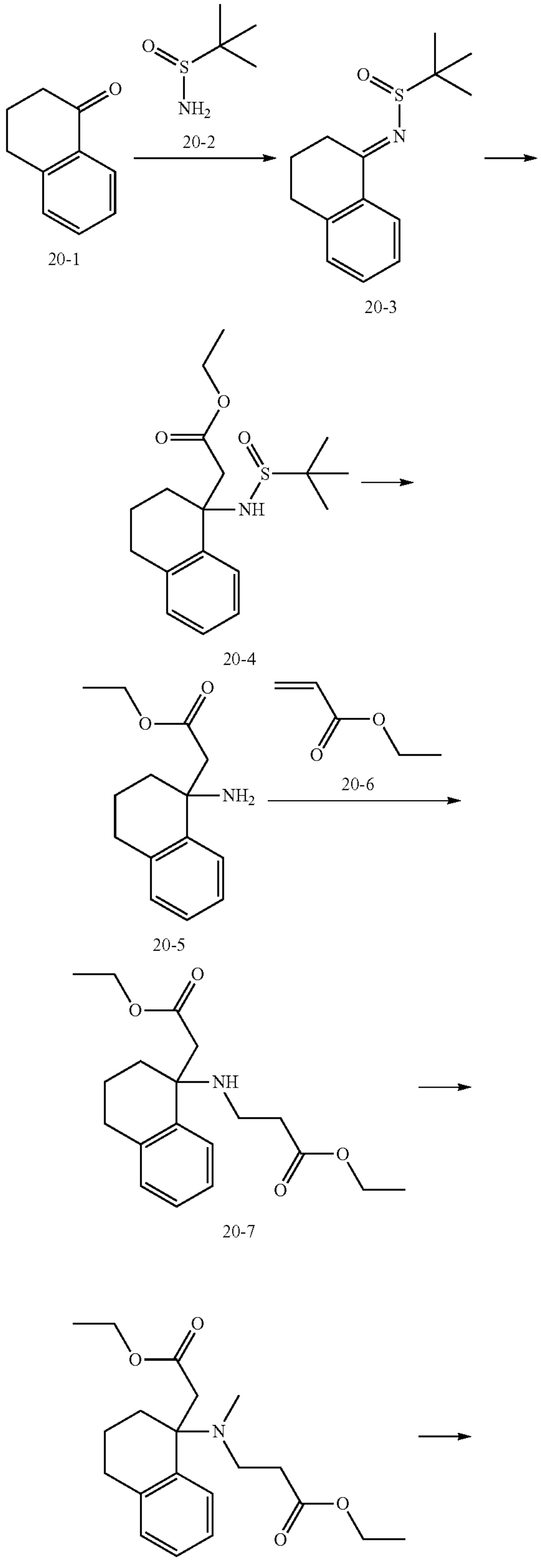

20-1

20-3

20-4

20-5

20-7

20-8

-continued

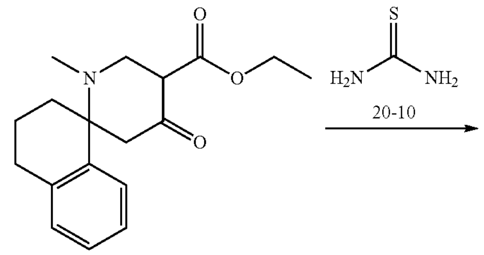

20-9

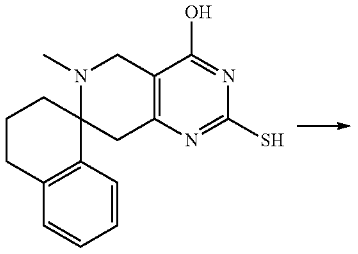

20-11

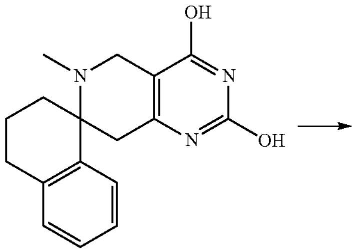

20-12

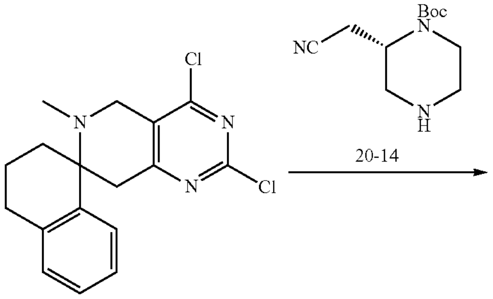

20-13

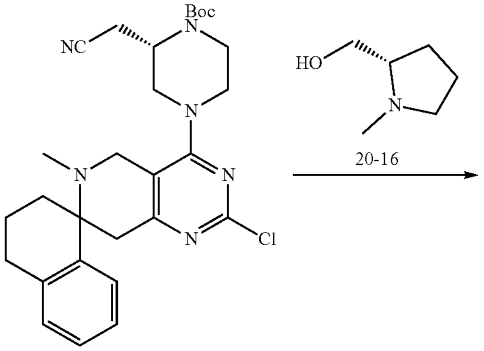

20-15

-continued

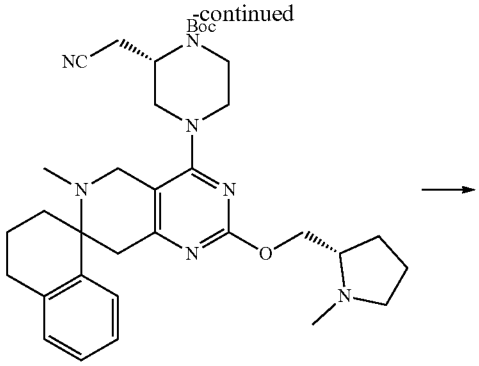

20-17

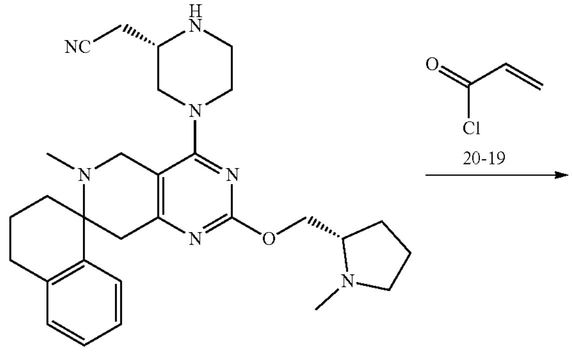

20-18

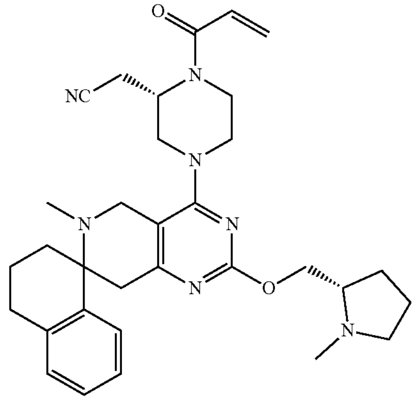

20

(1) To a solution of compound 20-1 (30.0 g, 205 mmol) in toluene (500 mL) was added compound 20-2 (29.9 g, 247 mmol), tetraethyl titanate (93.6 g, 410 mmol), and the reaction solution was stirred at 110° C. for 16 hours under nitrogen protection. Then the reaction solution was added with water (200 mL) and ethyl acetate (300 mL). After filtration, the filter cake was washed with ethyl acetate (300 mL×4). The combined organic phase was washed with saturated NaCl aqueous solution (300 mL×2), dried over anhydrous sodium sulfate, filtered, and concentrated under reduced pressure. The crude product was separated by silica gel column chromatography (petroleum ether/ethyl acetate=1:0 to 11:1) to obtain compound 20-3.

MS-ESI $[M+H]^+$, calculated: 250, found: 250.

$^1H$ NMR (400 MHz, CDCl3) δ 8.17 (d, J=8.0 Hz, 1H), 7.35-7.42 (m, 1H), 7.22-7.26 (m, 1H), 7.19 (d, J=7.6 Hz, 1H), 3.23-3.34 (m, 1H), 3.06 (m, 1H), 2.85-2.90 (m, 2H), 1.95-2.07 (m, 2H), 1.33 (s, 9H).

(2) To a solution of ethyl acetate (60.1 g, 682 mmol) in tetrahydrofuran (400 mL) was added dropwise with lithium diisopropylamide (2 mol/L, 137 mL, tetrahydrofuran solution) at −65° C. under nitrogen protection, and the reaction solution was stirred at −65° C. for 1 hour. Then the reaction solution was added dropwise with a solution of compound 20-3 (34.0 g, 136 mmol) in tetrahydrofuran (200 mL), and continued stirring for 2 hours at −65° C. After warming to 0° C., the reaction solution was quenched with saturated ammonium chloride aqueous solution (500 mL), and extracted with ethyl acetate (500 mL×2). The combined organic phase was washed with saturated ammonium chloride aqueous solution (500 mL×1) and saturated NaCl aqueous solution (500 mL×1), dried over anhydrous sodium sulfate, filtered, and concentrated under reduced pressure. The crude product was separated by silica gel column chromatography (petroleum ether/ethyl acetate=1:0 to 2:1) to obtain compound 20-4.

MS-ESI $[M+H]^+$, calculated: 338, found: 338.

$^1$H NMR (400 MHz, $CDCl_3$) δ7.32-7.40 (m, 1H), 7.13-7.21 (m, 2H), 7.08-7.13 (m, 1H), 5.19 (s, 1H), 4.11-4.20 (m, 2H), 2.86-2.98 (m, 1H), 2.80-2.86 (m, 2H), 2.70-2.78 (m, 1H), 2.42-2.51 (m, 1H), 2.04-2.17 (m, 2H), 1.76-1.86 (m, 1H), 1.24-1.28 (m, 3H), 1.23 (s, 9H).

(3) To a solution of compound 20-4 (6.0 g, 17.8 mmol) in ethanol (60.0 mL) was added hydrochloric acid in dioxane (4 mol/L, 20.0 mL), and the reaction solution was stirred at 25° C. for 1 hour under nitrogen protection. Then the reaction solution was concentrated under reduced pressure to obtain crude product of hydrochloride of compound 20-5.

MS-ESI $[M-NH_2+H]^+$, calculated: 217, found: 217.

(4) To a solution of hydrochloride of compound 20-5 (4.80 g, 17.8 mmol) in ethanol (60.0 mL) was added compound 20-6 (18.2 g, 182 mmol), copper oxide (283 mg, 3.56 mmol), and triethylamine (5.40 g, 53.4 mmol), and the reaction solution was reacted at 85° C. in a sealed tube for 8 hours under nitrogen protection. Then the reaction solution was added with water (200 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 10:1) to obtain compound 20-7.

MS-ESI $[M+H]^+$, calculated: 334, found: 334.

$^1$H NMR (400 MHz, $CDCl_3$) δ7.53 (d, J=6.4 Hz, 1H), 7.09-7.18 (m, 2H), 7.03-7.08 (m, 1H), 4.09-4.15 (m, 4H), 2.73-2.80 (m, 4H), 2.62 (d, J=14.0 Hz, 2H), 2.40-2.46 (m, 3H), 2.08 (d, J=10.0 Hz, 1H), 1.85-1.99 (m, 3H), 1.25 (t, J=7.2 Hz, 3H), 1.21 (t, J=7.2 Hz, 3H).

(5) To a solution of compound 20-7 (4.32 g, 13.0 mmol) in ethanol (60.0 mL) was added paraformaldehyde (3.89 g) and sodium cyanoborohydride (2.45 g, 38.9 mmol), and the reaction solution was reacted for 16 hours at 25° C. under nitrogen protection. Then the reaction solution was added with water (100 mL), and extracted with ethyl acetate (100 mL×1). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 10:1) to obtain compound 20-8.

MS-ESI $[M+H]^+$, calculated: 348, found: 348.

$^1$H NMR (400 MHz, MeOD) δ 7.43-7.52 (m, 1H), 7.05-7.13 (m, 2H), 6.95-7.04 (m, 1H), 4.04-4.12 (m, 2H), 3.73-3.83 (m, 2H), 2.79 (s, 2H), 2.76 (d, J=7.2 Hz, 1H), 2.71 (t, J=6.4 Hz, 2H), 2.56-2.63 (m, 1H), 2.39-2.48 (m, 1H), 2.30-2.38 (m, 1H), 2.21 (s, 3H), 2.10-2.15 (m, 2H), 1.81-1.90 (m, 1H), 1.70-1.80 (m, 1H), 1.22 (t, J=7.2 Hz, 3H), 0.94 (t, J=7.2 Hz, 3H).

(6) To a solution of compound 20-8 (3.10 g, 8.92 mmol) in tetrahydrofuran (60.0 mL) was added potassium bis (trimethylsilyl) amide (1 mol/L, 17.8 mL mL, tetrahydrofuran solution) at −65° C., and the reaction solution was reacted at −65° C. for 2 hours under nitrogen protection. Then the reaction solution was added with saturated ammonium chloride aqueous solution (100 mL), and extracted with ethyl acetate (100 mL×1). The organic phase was washed successively with saturated ammonium chloride aqueous solution (100 mL×1) and saturated NaCl aqueous solution (100 mL×1), dried over anhydrous sodium sulfate, filtered, and concentrated under reduced pressure. The crude product was separated by silica gel column chromatography (petroleum ether/ethyl acetate=1:0 to 10:1) to obtain compound 20-9.

MS-ESI $[M+H]^+$, calculated: 302, found: 302.

$^1$H NMR (400 MHz, $CDCl_3$) δ7.49-7.75 (m, 1H), 7.21 (t, J=6.4 Hz, 1H), 7.10-7.17 (m, 1H), 7.05 (d, J=7.6 Hz, 1H), 4.20-4.33 (m, 2H), 3.45-3.63 (m, 1H), 3.14-3.28 (m, 1H), 2.64-2.76 (m, 3H), 2.51-2.63 (m, 1H), 2.01-2.14 (m, 3H), 1.80-2.00 (m, 2H), 1.63-1.80 (m, 3H), 1.30-1.34 (m, 3H).

(7) To a solution of compound 20-9 (3.78 g, 12.5 mmol) in ethanol (70.0 mL) was added compound 20-10 (1.91 g, 25.1 mmol) and sodium ethoxide (2.56 g, 37.6 mmol), and the reaction solution was stirred at 80° C. for 8 hours under nitrogen protection. After concentrated under reduced pressure, the reaction solution was adjusted to pH 6 with hydrochloric acid (1 mol/L). The resulting solution was precipitated, and filtered, and the filter cake was dried to obtain compound 20-11.

MS-ESI $[M+H]^+$, calculated: 314, found: 314.

(8) To a solution of intermediate 20-11 (3.36 g, 10.7 mmol) in water (80.0 mL) was added chloroacetic acid (4.05 g, 42.9 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 20-12.

MS-ESI $[M+H]^+$, calculated: 298, found: 298.

$^1$H NMR (400 MHz, DMSO-d6) δ 10.98 (s, 1H), 10.69 (s, 1H), 7.45-7.51 (m, 1H), 7.17-7.24 (m, 1H), 7.11-7.17 (m, 1H), 7.04-7.10 (m, 1H), 3.46-3.52 (m, 1H), 2.99-3.07 (m, 1H), 2.65-2.72 (m, 2H), 2.52-2.55 (m, 2H), 1.95 (s, 3H), 1.84-1.91 (m, 1H), 1.71-1.80 (m, 1H), 1.51-1.64 (m, 2H).

(9) Compound 20-12 (1.00 g, 3.36 mmol) was dissolved in phosphorus oxychloride (10 mL), and the reaction solution was stirred at 100° C. in a sealed tube under nitrogen protection for 12 hours. Then the reaction solution was concentrated under reduced pressure, added with iced water (100 mL), and extracted with dichloromethane (100 mL×1). The organic phase was washed with saturated sodium bicarbonate aqueous solution (100 mL×2) and saturated NaCl aqueous solution (100 mL×1), dried over anhydrous sodium sulfate, filtered, and concentrated under reduced pressure to obtain compound 20-13.

MS-ESI $[M+H]^+$, calculated: 334, found: 334.

(10) To a solution of compound 20-13 (782 mg, 2.34 mmol) in N-methylpyrrolidone (10.0 mL) was added potassium carbonate (970 mg, 7.02 mmol) and compound 20-14 (633 mg, 2.81 mmol), and the reaction solution was stirred at 50° C. for 12 hours under nitrogen protection. Then the reaction solution was poured into water (30.0 mL) and extracted with ethyl acetate (30.0 mL×2). The organic phases were combined, washed with saturated NaCl aqueous solution (30.0 mL×2), dried over anhydrous sodium sulfate, filtered, and concentrated under reduced pressure. The crude product was separated by silica gel column chromatography (petroleum ether/ethyl acetate=1:0 to 0:1) to obtain compound 20-15. MS-ESI $[M+H]^+$, calculated: 523, found: 523.

(11) To a solution of compound 20-15 (500 mg, 956 μmol) in dioxane (10.0 mL) was added compound 20-16 (330 mg, 2.87 mmol), cesium carbonate (934 mg, 2.88 mmol) and (2-dicyclohexylphosphino-2',6'-diisopropoxy-1,1'-biphenyl) [2-(2'-amino-1,1'-biphenyl)]palladium(II) methanesulfonate (160 mg, 191 μmol), and the reaction solution was stirred at 110° C. for 12 hours under nitrogen protection. Then the reaction solution was added with ethyl acetate (50.0 mL), washed with saturated NaCl aqueous solution (50.0 mL×2), dried over anhydrous sodium sulfate, filtered, and concentrated under reduced pressure. The crude product was separated by silica gel column chromatography (dichloromethane/methanol=1:0 to 9:1) to obtain compound 20-17.

MS-ESI $[M+H]^+$, calculated: 602, found: 602.

(12) To a solution of compound 20-17 (368 mg, 611 μmol) in dichloromethane (6.0 mL) was added trifluoroacetic acid (3.08 g, 27.0 mmol), and the reaction solution was stirred at 25° C. for 0.5 hours under nitrogen protection. Then the reaction solution was concentrated under reduced pressure to obtain crude trifluoroacetate of compound 20-18.

MS-ESI $[M+H]^+$, calculated: 502, found: 502.

(13) To a solution of trifluoroacetate of compound 20-18 (175 mg, 284 μmol) in dichloromethane (3.0 mL) was added triethylamine (28.8 mg, 284 μmol), then cooled to −78° C. and added with compound 20-19 (38.6 mg, 426 μmol), and the reaction solution was stirred at −78° C. for 5 minutes under nitrogen protection. Then the reaction solution was added with dichloromethane (30.0 mL), washed with saturated NaCl aqueous solution (30.0 mL×2), dried over anhydrous sodium sulfate, filtered, and concentrated under reduced pressure. The crude product was separated by preparative high performance liquid chromatography (Xtimate C18, 100 mm×30 mm 10 μm, A: water (0.225% formic acid); B: acetonitrile, 0%-30%: 10 min) to obtain formate of compound 20.

MS-ESI $[M+H]^+$, calculated: 556, found: 556.

$^1H$ NMR (400 MHz, MeOD) δ 7.47-7.58 (m, 1H), 7.07-7.28 (m, 3H), 6.70-6.95 (m, 1H), 5.84-5.84 (m, 1H), 5.77-5.90 (m, 1H), 4.66-4.67 (m, 1H), 4.46-4.53 (m, 1H), 4.29-4.41 (m, 1H), 3.96-4.25 (m, 3H), 3.72-3.87 (m, 3H), 3.56-3.70 (m, 2H), 3.20-3.28 (m, 1H), 3.09-3.18 (m, 2H), 3.01-3.08 (m, 2H), 2.94-3.00 (m, 3H), 2.85-2.93 (m, 1H), 2.63-2.84 (m, 3H), 2.29-2.40 (m, 1H), 2.11-2.22 (m, 4H), 1.93-2.10 (m, 4H), 1.75-1.87 (m, 2H).

Example 19 Synthesis of Compound 21

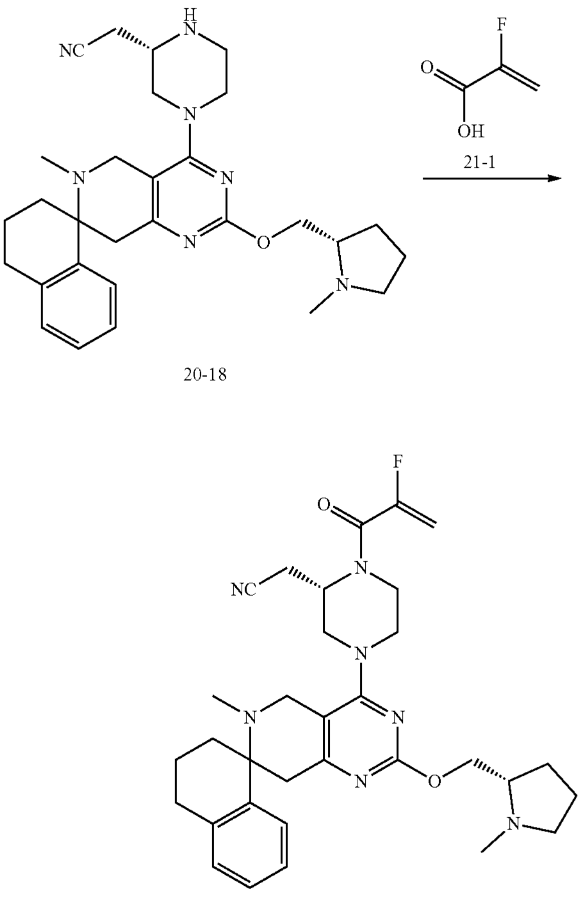

20-18

21

To a solution of compound 20-18 in dichloromethane was added triethylamine to adjust the pH of the solution to 7. Then the reaction solution was cooled to 0° C. and added with compound 21-1 (92.2 mg, 1.02 mmol) and propanephosphonic acid anhydride (279 mg, 438 mol), and the reaction solution was then heated to 25° C. and reacted for 0.5 hours. Then the reaction solution was poured into water (30.0 mL), and extracted with dichloromethane (30.0 mL×2). The organic phases were combined and washed with saturated NaCl aqueous solution (30.0 mL×1), dried over anhydrous sodium sulfate, filtered, and concentrated under reduced pressure. The crude product was separated by preparative high performance liquid chromatography (Xtimate C18, 100 mm×30 mm 10 μm, A: water (0.225% formic acid); B: acetonitrile, 0%-30%: 8 min) to obtain formate of compound 21.

MS-ESI $[M+H]^+$, calculated: 574, found: 574.

$^1H$ NMR (400 MHz, MeOD) δ 7.52-7.53 (m, 1H), 7.19-7.26 (m, 1H), 7.14-7.18 (m, 1H), 7.09-7.13 (m, 1H), 5.22-5.47 (m, 2H), 4.66-4.70 (m, 1H), 4.46-4.53 (m, 1H), 4.16-4.17 (m, 2H), 3.66-3.86 (m, 4H), 3.46-3.65 (m, 2H), 3.33-3.40 (m, 1H), 3.22-3.29 (m, 1H), 3.05-3.19 (m, 4H), 3.01-3.04 (m, 1H), 2.90-3.00 (m, 4H), 2.72-2.82 (m, 2H), 2.28-2.40 (m, 1H), 2.09-2.15 (m, 4H), 1.92-2.06 (m, 4H), 1.75-1.86 (m, 2H).

Example 20 Synthesis of Compound 22
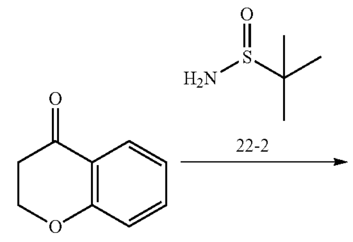
22-1
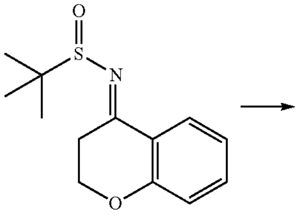
22-3
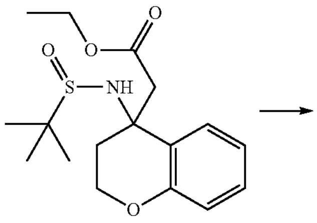
22-4
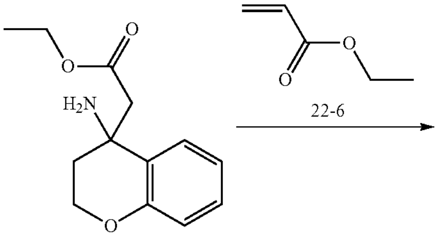
22-5
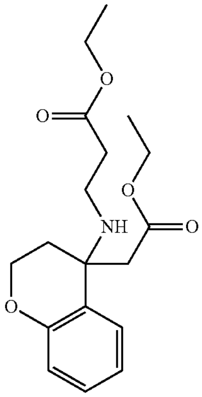
22-7
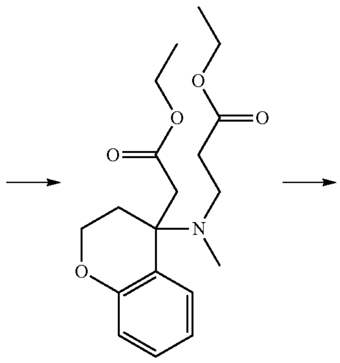
22-8
-continued
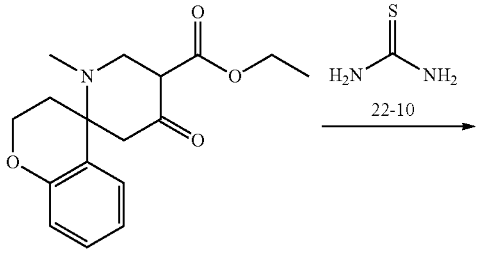
22-9
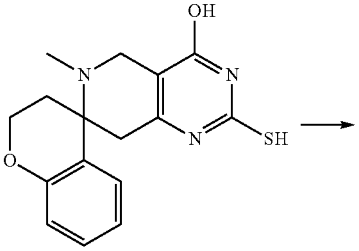
22-11
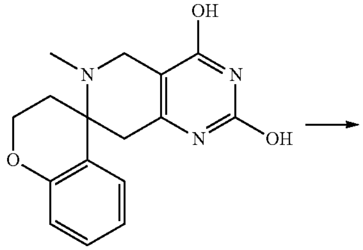
22-12
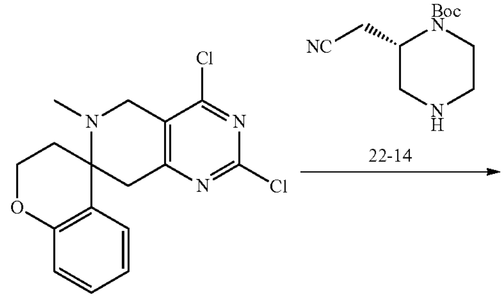
22-13
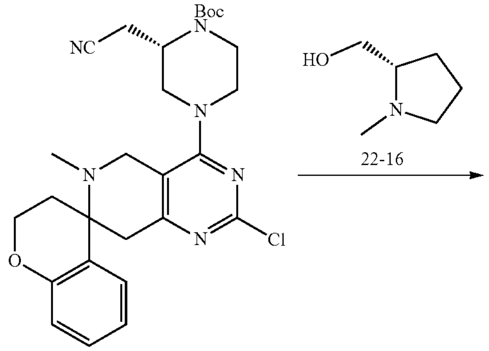
22-15

-continued

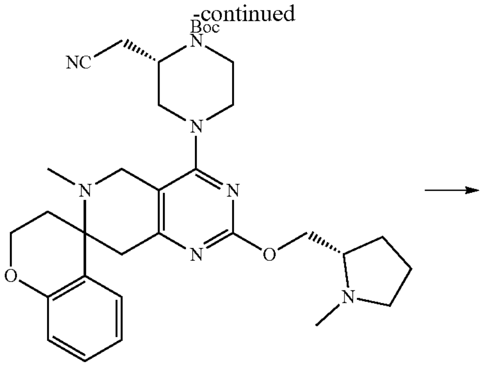

22-17

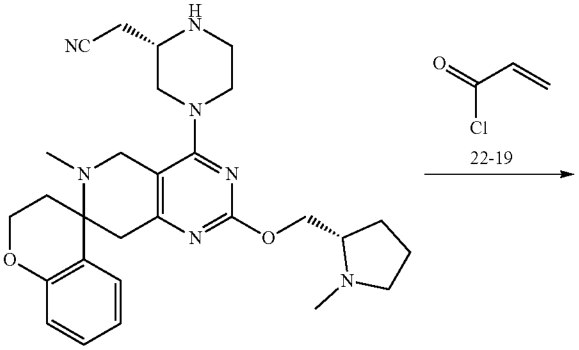

22-18

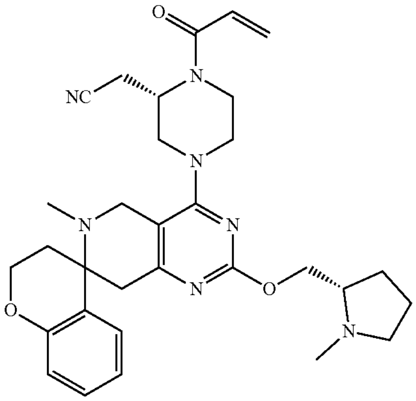

22

(1) To a solution of compound 22-1 (25.0 g, 168 mmol) in toluene (500 mL) was added compound 22-2 (26.5 g, 219 mmol), and tetraethyl titanate (77.0 g, 337 mmol), and then the reaction solution was stirred at 120° C. for 12 hours under nitrogen protection. Then the reaction solution was added with water (400 mL), and filtered. The filtrate was washed with ethyl acetate (400 mL×2). The combined organic phase was washed with saturated NaCl aqueous solution (500 mL), dried over anhydrous sodium sulfate, filtered, and concentrated under reduced pressure. The crude product was separated by silica gel column chromatography (petroleum ether/ethyl acetate=1:0 to 0:1) to obtain compound 22-3.

MS-ESI $[M+H]^+$, calculated: 252, found: 252.

$^1H$ NMR (400 MHz, $CDCl_3$) δ 7.98-8.03 (m, 1H), 7.35-7.42 (m, 1H), 6.89-7.02 (m, 2H), 4.27-4.42 (m, 2H), 3.46-3.56 (m, 1H), 3.22-3.34 (m, 1H), 1.32-1.34 (s, 9H).

(2) To a solution of ethyl acetate (54.6 g, 620 mmol) in tetrahydrofuran (1000 mL) was added dropwise with lithium diisopropylamide (2 mol/L, 155 mL, tetrahydrofuran solution) at −78° C. under nitrogen protection, and the reaction solution was stirred at −78° C. for 1 hour. Then the reaction solution was added dropwise with a solution of compound 22-3 (39.0 g, 155 mmol) in tetrahydrofuran (500 mL), and continued stirring for 3 hours at −78° C. Then the reaction solution was quenched with saturated ammonium chloride aqueous solution (2000 mL), and extracted with ethyl acetate (2000 mL×1). The combined organic phase was washed with saturated ammonium chloride aqueous solution (2000 mL) and saturated NaCl aqueous solution (2000 mL), dried over anhydrous sodium sulfate, filtered, and concentrated under reduced pressure. The crude product was separated by silica gel column chromatography (petroleum ether/ethyl acetate=1:0 to 4:1) to obtain compound 22-4.

MS-ESI $[M+H]^+$, calculated: 340, found: 340.

(3) To a solution of compound 22-4 (5.00 g, 14.7 mmol) in ethanol (50.0 mL) was added hydrochloric acid in dioxane (4 mol/L, 15.0 mL), and the reaction solution was stirred at 25° C. for 2 hours under nitrogen protection. Then the reaction solution was concentrated under reduced pressure to obtain crude product of hydrochloride of compound 22-5.

MS-ESI $[M-NH_2+H]^+$, calculated: 219, found: 219.

(4) To a solution of hydrochloride of compound 22-5 (4.00 g, 14.7 mmol) in ethanol (40.0 mL) was added compound 22-6 (14.7 g, 147 mmol), copper oxide (234 mg, 2.94 mmol), triethylamine (1.49 g, 14.7 mmol), and the reaction solution was reacted at 85° C. in a sealed tube for 8 hours under nitrogen protection. Then the reaction solution was added with water (100 mL), and extracted with ethyl acetate (200 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 6:1) to obtain compound 22-7.

MS-ESI $[M+H]^+$, calculated: 336, found: 336.

$^1H$ NMR (400 MHz, $CDCl_3$) δ 7.34-7.42 (m, 1H), 7.08-7.16 (m, 1H), 6.85-6.95 (m, 1H), 6.77-6.83 (m, 1H), 4.30-4.37 (m, 1H), 4.18-4.26 (m, 1H), 4.11-4.15 (m, 5H), 2.75-2.79 (m, 2H), 2.48-2.59 (m, 2H), 2.42-2.45 (m, 2H), 2.28-2.37 (m, 1H), 2.05-2.12 (m, 1H), 1.25-1.27 (m, 3H), 1.20-1.24 (m, 3H).

(5) To a solution of compound 22-7 (3.00 g, 8.94 mmol) in ethanol (30.0 mL) was added paraformaldehyde (1.34 g) and sodium cyanoborohydride (1.69 g, 26.8 mmol), and the reaction solution was reacted for 16 hours at 25° C. under nitrogen protection. Then the reaction solution was added with water (100 mL), and extracted with ethyl acetate (100 mL). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 4:1) to obtain compound 22-8.

MS-ESI $[M+H]^+$, calculated: 350, found: 350.

$^1H$ NMR (400 MHz, $CDCl_3$) δ 7.33-7.37 (m, 1H), 7.09-7.15 (m, 1H), 6.82-6.88 (m, 1H), 6.74-6.81 (m, 1H), 4.26-4.34 (m, 1H), 4.15-4.23 (m, 1H), 4.06-4.14 (m, 2H), 3.88-3.99 (m, 2H), 2.89-2.98 (m, 1H), 2.70-2.81 (m, 3H), 2.32-2.46 (m, 3H), 2.24-2.30 (m, 1H), 2.22-2.24 (m, 3H), 1.20-1.27 (m, 3H), 1.02-1.08 (t, 3H).

(6) To a solution of compound 22-8 (1.75 g, 5.01 mmol) in tetrahydrofuran (30.0 mL) was added potassium bis(trimethylsilyl) amide (1 mol/L, 15 mL, tetrahydrofuran solution) at −78° C., and the reaction solution was reacted at −78° C. for 2 hours under nitrogen protection. Then the reaction solution was added with saturated ammonium chloride aqueous solution (70 mL), and extracted with ethyl acetate (500 mL×1). The combined organic phase was washed with saturated NaCl aqueous solution (50 mL×1), dried over anhydrous sodium sulfate, filtered, and concentrated under reduced pressure. The crude product was separated by silica gel column chromatography (petroleum ether/ethyl acetate=1:0 to 6:1) to obtain compound 22-9.

MS-ESI $[M+H]^+$, calculated: 304, found: 304.

(7) To a solution of compound 22-9 (1.03 g, 3.40 mmol) in ethanol (30.0 mL) was added compound 22-10 (516 mg, 6.79 mmol) and sodium ethoxide (693 mg, 10.1 mmol), and the reaction solution was stirred at 80° C. for 12 hours under nitrogen protection. After concentrated under reduced pressure, the reaction solution was adjusted to pH 6 with hydrochloric acid (1 mol/L). The resulting solution was precipitated, and filtered, and the filter cake was dried to obtain compound 22-11.

MS-ESI $[M+H]^+$, calculated: 316, found: 316.

$^1$H NMR (400 MHz, DMSO-d6) δ 11.54-12.84 (m, 2H), 7.37-7.42 (m, 1H), 7.12-7.18 (m, 1H), 6.92-6.99 (m, 1H), 6.75-6.81 (m, 1H), 4.22-4.31 (m, 1H), 3.92-4.01 (t, 1H), 3.51-3.60 (d, 1H), 3.02-3.11 (d, 1H), 2.70-2.77 (s, 2H), 2.03-2.13 (m, 1H), 1.88-1.96 (m, 3H), 1.54-1.63 (d, 1H).

(8) To a solution of intermediate 22-11 (1.05 g, 3.33 mmol) in water (100.0 mL) was added chloroacetic acid (1.26 g, 13.3 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 22-12.

MS-ESI $[M+H]^+$, calculated: 300, found: 300.

(9) Compound 22-12 (1.70 g, 5.68 mmol) was dissolved in phosphorus oxychloride (16.5 g, 107 mmol), and the reaction solution was stirred at 100° C. for 12 hours under nitrogen protection. Then the reaction solution was concentrated under reduced pressure, and extracted with dichloromethane (40 mL). The organic phase was washed with saturated sodium bicarbonate aqueous solution (20 mL×2) and saturated NaCl aqueous solution (200 mL), dried over anhydrous sodium sulfate, filtered, and concentrated under reduced pressure to obtain compound 22-13.

MS-ESI $[M+H]^+$, calculated: 336, found: 336.

(10) To a solution of compound 22-13 (1.00 g, 2.97 mmol) in N-methylpyrrolidone (10.0 mL) was added potassium carbonate (1.23 g, 8.92 mmol) and compound 22-14 (846 mg, 3.57 mmol), and the reaction solution was stirred at 50° C. for 12 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure to obtain compound 22-15.

MS-ESI $[M+H]^+$, calculated: 525, found: 525.

(11) To a solution of compound 22-15 (700 mg, 1.33 mmol) in dioxane (10.0 mL) was added compound 22-16 (460 mg, 4.00 mmol), cesium carbonate (1.30 g, 4.00 mmol) and (2-dicyclohexylphosphino-2',6'-diisopropoxy-1,1'-biphenyl) [2-(2'-amino-1,1'-biphenyl)]palladium(II) methanesulfonate (223 mg, 266 μmol), and the reaction solution was stirred at 110° C. for 6 hours under nitrogen protection. Then the reaction solution was added with ethyl acetate (40.0 mL), washed with saturated NaCl aqueous solution (40.0 mL×2), dried over anhydrous sodium sulfate, filtered, and concentrated under reduced pressure. The crude product was separated by silica gel column chromatography (dichloromethane/methanol=1:0 to 15:1) to obtain compound 22-17.

MS-ESI $[M+H]^+$, calculated: 604, found: 604.

(12) To a solution of compound 22-17 (150.0 mg, 248 μmol) in dichloromethane (3.0 mL) was added trifluoroacetic acid (1.54 g), and the reaction solution was stirred at 25° C. for 1 hour. Then the reaction solution was extracted by ethyl acetate (50 mL×2) and the organic phase was washed by saturated sodium bicarbonate aqueous solution (50 mL×1) and saturated NaCl aqueous solution (50 mL×1), dried over anhydrous sodium sulfate, filtered, and concentrated under reduced pressure to obtain crude trifluoroacetate of compound 22-18.

MS-ESI $[M+H]^+$, calculated: 504, found: 504.

(13) To a solution of trifluoroacetate of compound 22-18 (120.0 mg, 194 μmol) in dichloromethane (2.0 mL) was added triethylamine (14.7 mg, 145 μmol) and compound 22-19 (26.3 mg, 291 μmol), and the reaction solution was stirred at −78° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 μm, A: water (0.225% formic acid); B: acetonitrile, 0%-30%: 8 min) to obtain formate of compound 22.

MS-ESI $[M+H]^+$, calculated: 558, found: 558.

$^1$H NMR (400 MHz, MeOD) δ 7.40-7.46 (m, 1H), 7.13-7.19 (m, 1H), 6.94-7.00 (m, 1H), 6.73-6.90 (m, 2H), 6.22-6.35 (m, 1H), 5.77-5.88 (m, 1H), 4.95-5.12 (m, 1H), 4.67-4.73 (m, 1H), 4.48-4.55 (m, 1H), 3.99-4.39 (m, 5H), 3.56-3.84 (m, 5H), 3.36-3.53 (m, 1H), 3.09-3.28 (m, 5H), 2.97-3.02 (m, 3H), 2.84-2.93 (m, 1H), 2.31-2.44 (m, 2H), 1.97-2.19 (m, 6H), 1.68-1.79 (m, 1H).

Example 21 Synthesis of Compound 23

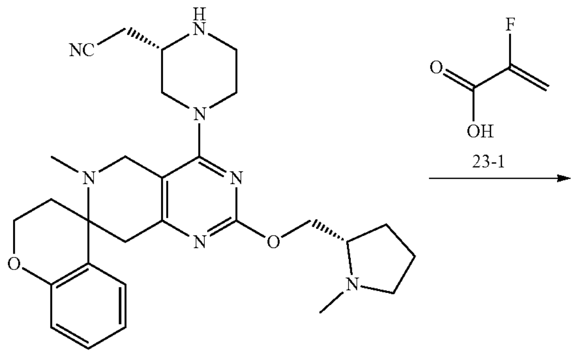

22-18

23-1

-continued

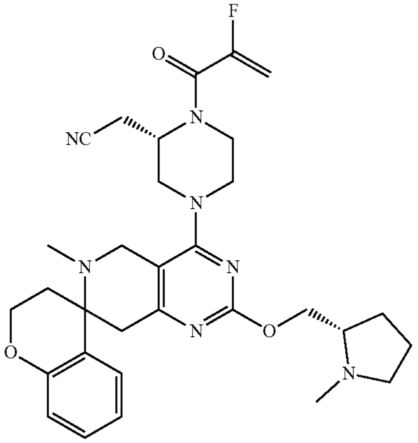

23

To a solution of compound 22-18 (220 mg, 356 μmol) in dichloromethane (2.0 mL) was added triethylamine (14.7 mg, 145 μmol), compound 23-1 (160.0 mg, 1.78 μmol) and propanephosphonic acid anhydride solution (679.98 mg, 1.07 mol, 50% ethyl acetate) at 0° C., and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Genimi NX C18, 150 mm×40 mm 5 μm, A: water (0.05% hydrochloric acid); B: acetonitrile, 58%-35%: 10 min) to obtain hydrochloride of compound 23.

MS-ESI $[M+H]^+$, calculated: 576, found: 576.

$^1H$ NMR (400 MHz, MeOD) δ 7.83-7.96 (m, 1H), 7.38-7.44 (m, 1H), 7.11-7.19 (m, 1H), 6.97-7.04 (m, 1H), 5.19-5.51 (m, 2H), 4.95-5.16 (m, 2H), 4.37-4.72 (m, 4H), 3.98-4.30 (m, 4H), 3.59-3.82 (m, 5H), 3.19-3.27 (m, 1H), 3.03-3.13 (m, 4H), 2.67-2.76 (m, 4H), 2.37-2.54 (m, 2H), 1.77-2.30 (m, 6H).

Example 22 Synthesis of Compound 24

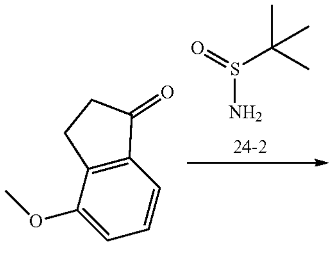

24-1

-continued

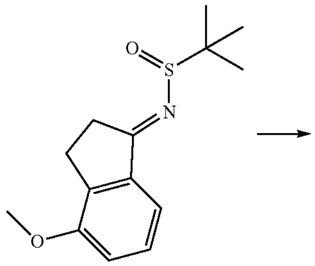

24-3

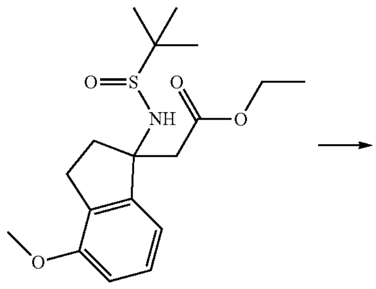

24-4

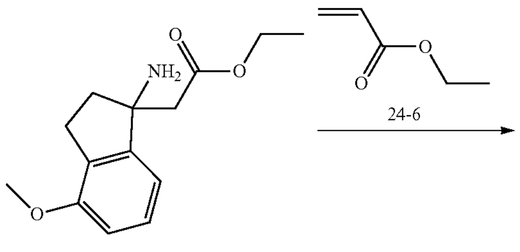

24-5

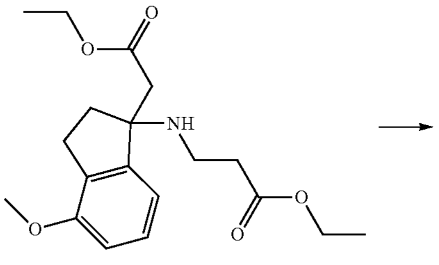

24-7

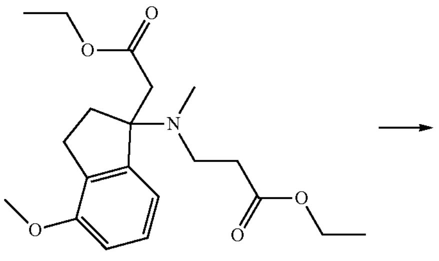

24-8

-continued

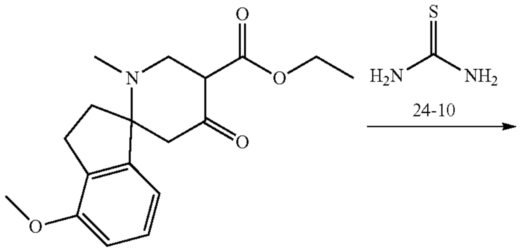

24-9

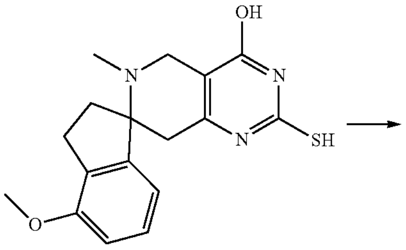

24-11

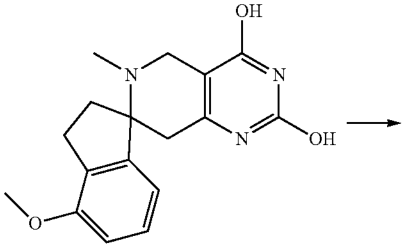

24-12

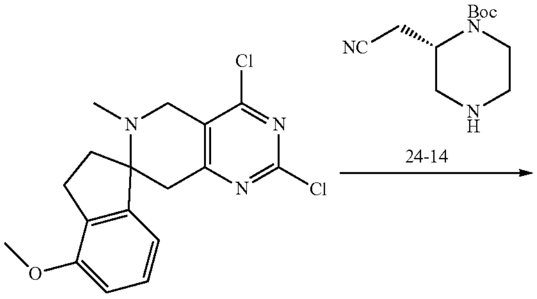

24-13

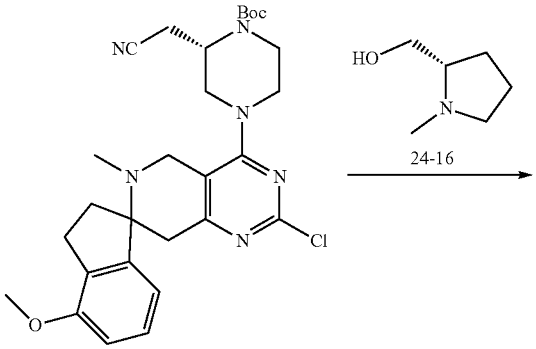

24-15

-continued

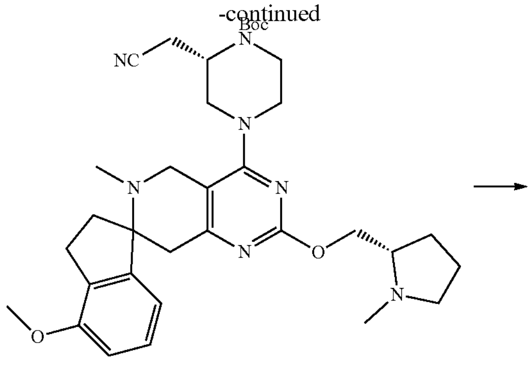

24-17

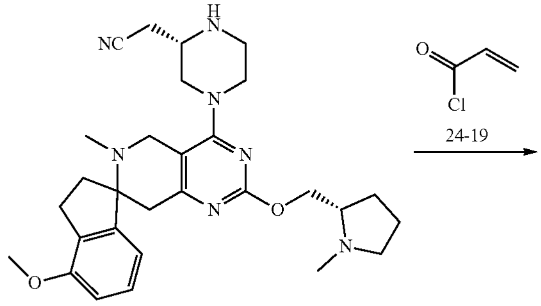

24-18

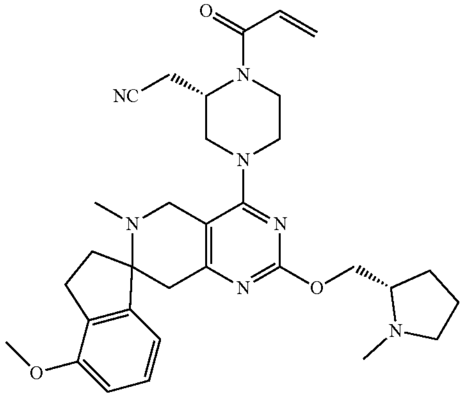

24

(1) To a solution of compound 24-1 (20.0 g, 123 mmol) in toluene (500 mL) was added compound 24-2 (19.4 g, 160 mmol), and tetraethyl titanate (56.2 g, 246 mmol), and the reaction solution was stirred at 120° C. for 12 hours under nitrogen protection. Then the reaction solution was added with water (400 mL), and filtered. The filtrate was washed with ethyl acetate (400 mL×2). The combined organic phase was washed with saturated NaCl aqueous solution (500 mL), dried over anhydrous sodium sulfate, filtered, and concentrated under reduced pressure. The crude product was separated by silica gel column chromatography (petroleum ether/ethyl acetate=1:0 to 0:1) to obtain compound 24-3.

MS-ESI $[M+H]^+$, calculated: 266, found: 266.

$^1H$ NMR (400 MHz, $CDCl_3$) δ 7.38-7.43 (m, 1H), 7.28-7.34 (m, 1H), 6.93-6.98 (m, 1H), 3.87-3.90 (m, 3H), 3.40-3.51 (m, 1H), 3.01-3.08 (m, 3H), 1.31-1.34 (s, 9H).

(2) To a solution of ethyl acetate (15.8 g, 179 mmol) in tetrahydrofuran (500 mL) was added dropwise with lithium diisopropylamide (2 mol/L, 44.8 mL, tetrahydrofuran solution) at −78° C. under nitrogen protection, and the reaction solution was stirred at −78° C. for 1 hour. Then the reaction solution was added dropwise with a solution of compound 24-3 (11.9 g, 44.8 mmol) in tetrahydrofuran (500 mL), and continued stirring for 3 hours at −78° C. Then the reaction solution was quenched with saturated ammonium chloride aqueous solution (1000 mL), and extracted with ethyl acetate (1000 mL×1). The combined organic phase was washed with saturated ammonium chloride aqueous solution (1000 mL) and saturated NaCl aqueous solution (1000 mL), dried over anhydrous sodium sulfate, filtered, and concentrated under reduced pressure. The crude product was separated by silica gel column chromatography (petroleum ether/ethyl acetate=1:0 to 4:1) to obtain compound 24-4.

MS-ESI $[M+H]^+$, calculated: 354, found: 354.

(3) To a solution of compound 24-4 (8.00 g, 22.6 mmol) in ethanol (50.0 mL) was added hydrochloric acid in dioxane (4 mol/L, 15.0 mL), and the reaction solution was stirred at 25° C. for 2 hours under nitrogen protection. Then the reaction solution was concentrated under reduced pressure to obtain crude product of hydrochloride of compound 24-5.

MS-ESI $[M-NH_2+H]^+$, calculated: 233, found: 233.

(4) To a solution of hydrochloride of compound 24-5 (6.40 g, 22.4 mmol) in ethanol (40.0 mL) was added compound 24-6 (22.4 g, 223 mmol), copper oxide (356 mg, 4.48 mmol), and triethylamine (2.27 g, 22.4 mmol), and the reaction solution was reacted at 85° C. in a sealed tube for 8 hours under nitrogen protection. Then the reaction solution was added with water (100 mL), and extracted with ethyl acetate (200 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 6:1) to obtain compound 24-7.

MS-ESI $[M+H]^+$, calculated: 350, found: 350.

(5) To a solution of compound 24-7 (3.80 g, 10.8 mmol) in ethanol (30.0 mL) was added paraformaldehyde (1.60 g) and sodium cyanoborohydride (2.05 g, 32.6 mmol), and the reaction solution was reacted for 16 hours at 25° C. under nitrogen protection. Then the reaction solution was added with water (100 mL), and extracted with ethyl acetate (100 mL). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 4:1) to obtain compound 24-8.

MS-ESI $[M+H]^+$, calculated: 364, found: 364.

$^1H$ NMR (400 MHz, $CDCl_3$) δ 7.12-7.21 (m, 1H), 6.82-6.89 (m, 1H), 6.67-6.75 (m, 1H), 4.08-4.16 (m, 3H), 3.91-3.94 (m, 1H), 3.80-3.83 (m, 3H), 2.75-2.94 (m, 4H), 2.60-2.68 (m, 2H), 2.27-2.48 (m, 4H), 2.13-2.21 (m, 3H), 1.24-1.27 (m, 3H), 1.01-1.07 (t, 3H).

(6) To a solution of compound 24-8 (4.60 g, 12.6 mmol) in tetrahydrofuran (100.0 mL) was added potassium bis(trimethylsilyl) amide (1 mol/L, 38 mL, tetrahydrofuran solution) at −78° C., and the reaction solution was reacted at −78° C. for 2 hours under nitrogen protection. Then the reaction solution was added with saturated ammonium chloride aqueous solution (70 mL), and extracted with ethyl acetate (200 mL). The combined organic phase was washed with saturated NaCl aqueous solution (50 mL), dried over anhydrous sodium sulfate, filtered, and concentrated under reduced pressure. The crude product was separated by silica gel column chromatography (petroleum ether/ethyl acetate=1:0 to 6:1) to obtain compound 24-9.

MS-ESI $[M+H]^+$, calculated: 318, found: 318.

(7) To a solution of compound 24-9 (2.00 g, 6.30 mmol) in ethanol (30.0 mL) was added compound 24-10 (959 mg, 12.6 mmol) and sodium ethoxide (1.29 g, 18.9 mmol), and the reaction solution was stirred at 80° C. for 12 hours under nitrogen protection. After concentrated under reduced pressure, the reaction solution was adjusted to pH 6 with hydrochloric acid (1 mol/L). The resulting solution was precipitated, and filtered. The filter cake was dried to obtain compound 24-11.

MS-ESI $[M+H]^+$, calculated: 330, found: 330.

$^1H$ NMR (400 MHz, DMSO-d6) δ 12.19-12.46 (m, 2H), 7.21-7.27 (m, 1H), 6.83-6.88 (m, 1H), 6.75-6.82 (m, 1H), 3.77-3.81 (m, 3H), 3.43-3.53 (m, 1H), 2.98-3.10 (m, 1H), 2.58-2.83 (m, 3H), 2.38-2.45 (m, 1H), 2.09-2.19 (m, 1H), 1.91-2.02 (s, 3H), 1.58-1.69 (m, 1H).

(8) To a solution of intermediate 24-11 (1.72 g, 5.22 mmol) in water (10.0 mL) was added chloroacetic acid (1.97 g, 20.8 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 24-12.

MS-ESI $[M+H]^+$, calculated: 314, found: 314.

$^1H$ NMR (400 MHz, DMSO-d6) δ 10.95-11.02 (s, 1H), 10.70-10.76 (s, 1H), 7.20-7.26 (t, 1H), 6.77-6.87 (dd, 2H), 3.78-3.81 (m, 3H), 3.37-3.46 (m, 1H), 2.96-3.04 (m, 1H), 2.55-2.87 (m, 3H), 2.27-2.35 (m, 1H), 2.09-2.20 (m, 1H), 1.94-1.99 (s, 3H), 1.57-1.68 (m, 1H).

(9) Compound 24-12 (1.34 g, 4.28 mmol) was dissolved in phosphorus oxychloride (16.5 g, 107 mmol), and the reaction solution was stirred at 100° C. for 12 hours under nitrogen protection. Then the reaction solution was concentrated under reduced pressure, and extracted with dichloromethane (40 mL). The organic phase was washed with saturated sodium bicarbonate aqueous solution (20 mL×2) and saturated NaCl aqueous solution (100 mL×2), dried over anhydrous sodium sulfate, filtered, and concentrated under reduced pressure to obtain compound 24-13.

MS-ESI $[M+H]^+$, calculated: 350, found: 350.

(10) To a solution of compound 24-13 (1.12 g, 3.20 mmol) in N-methylpyrrolidone (10.0 mL) was added potassium carbonate (1.33 g, 9.59 mmol) and compound24-14 (864 mg, 3.84 mmol), and the reaction solution was stirred at 50° C. for 12 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure to obtain compound 24-15.

MS-ESI $[M+H]^+$, calculated: 539, found: 539.

(11) To a solution of compound 24-15 (700 mg, 1.30 mmol) in dioxane (10.0 mL) was added compound 24-16 (448 mg, 3.90 mmol), cesium carbonate (1.27 g, 3.90 mmol) and (2-dicyclohexylphosphino-2',6'-diisopropoxy-1,1'-biphenyl) [2-(2'-amino-1,1'-biphenyl)]palladium(II) methanesulfonate (217 mg, 259 μmol), and the reaction solution was stirred at 110° C. for 6 hours under nitrogen protection. Then the reaction solution was added with ethyl acetate (40.0 mL), washed with saturated NaCl aqueous solution (40.0 mL×2), dried over anhydrous sodium sulfate, filtered, and concentrated under reduced pressure. The crude product was separated by silica gel column chromatography (dichloromethane/methanol=1:0 to 15:1) to obtain compound 24-17.

MS-ESI $[M+H]^+$, calculated: 618, found: 618.

(12) To a solution of compound 24-17 (430 mg, 696 μmol) in dichloromethane (3.0 mL) was added trifluoroacetic acid (1.54 g), and the reaction solution was stirred at 25° C. for 1 hour under nitrogen protection. Then the reaction solution was extracted with ethyl acetate (50 mL×2) and the organic phase was washed by saturated sodium bicarbonate aqueous solution (50 mL) and saturated NaCl aqueous solution (50 mL), dried over anhydrous sodium sulfate, filtered, and concentrated under reduced pressure to obtain crude trifluoroacetate of compound 24-18.

MS-ESI $[M+H]^+$, calculated: 518, found: 518.

(13) To a solution of trifluoroacetate of compound 24-18 (100.0 mg, 158 μmol) in dichloromethane (2.0 mL) was added triethylamine (16.0 mg, 158 μmol) and compound 24-19 (21.4 mg, 237 μmol), and the reaction solution was stirred at −78° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm×3 μm, A: water (0.225% formic acid); B: acetonitrile, 0%-30%: 8 min) to obtain formate of compound 24.

MS-ESI $[M+H]^+$, calculated: 558, found: 572.

$^1$H NMR (400 MHz, MeOD) δ 7.24-7.31 (m, 1H), 6.78-6.94 (m, 3H), 6.23-6.36 (m, 1H), 5.79-5.88 (m, 1H), 4.61-4.86 (m, 2H), 4.52-4.60 (m, 1H), 3.91-4.36 (m, 4H), 3.76-3.90 (m, 6H), 3.58-3.74 (m, 2H), 3.06-3.28 (m, 4H), 3.01-3.04 (m, 3H), 2.86-3.00 (m, 4H), 2.35-2.52 (m, 2H), 2.28-2.32 (m, 3H), 1.92-2.21 (m, 4H).

Example 23 Synthesis of Compound 25

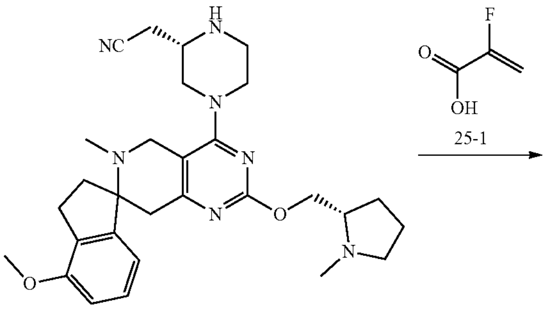

24-18

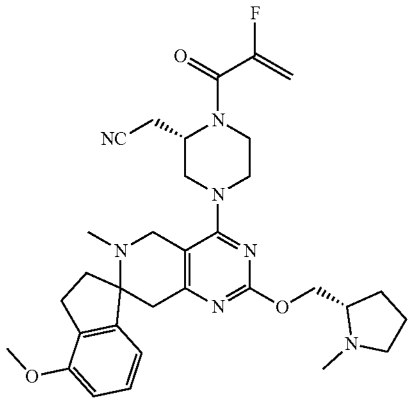

25

To a solution of compound 24-18 (100 mg, 158 μmol) in dichloromethane (2.0 mL) was added triethylamine (14.7 mg, 145 μmol), compound 25-1 (71.2 mg, 791 μmol) and propanephosphonic acid anhydride solution (302 mg, 474 μmol, 50% ethyl acetate solution) at 0° C., and the reaction solution was stirred at 25° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm×3 μm, A: water (0.225% formic acid); B: acetonitrile, 0%-30%: 8 min) to obtain formate of compound 25.

MS-ESI $[M+H]^+$, calculated: 590, found: 590.

$^1$H NMR (400 MHz, MeOD) δ 7.21-7.32 (m, 1H), 6.83-6.90 (m, 2H), 5.23-5.43 (m, 2H), 4.69-4.74 (m, 1H), 4.50-4.57 (m, 1H), 4.00-4.36 (m, 3H), 3.63-3.88 (m, 8H), 3.40-3.58 (m, 1H), 2.81-3.29 (m, 12H), 2.34-2.50 (m, 2H), 2.23-2.28 (m, 3H), 1.89-2.21 (m, 4H).

Example 24 Synthesis of Compounds 26 and 27

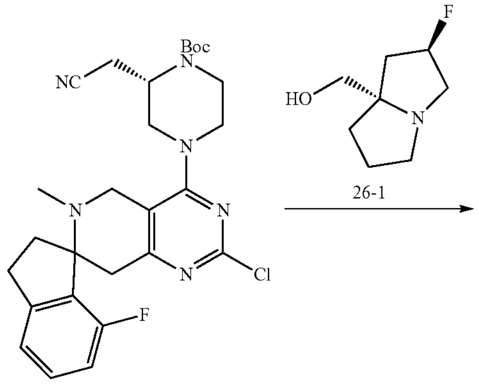

8-8

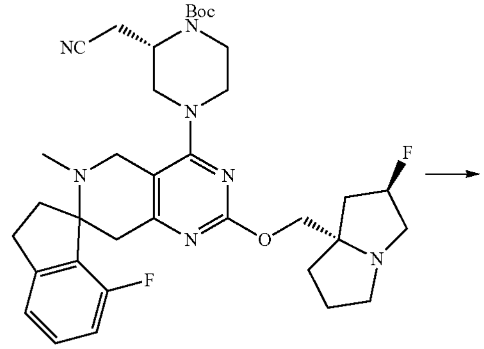

26-2

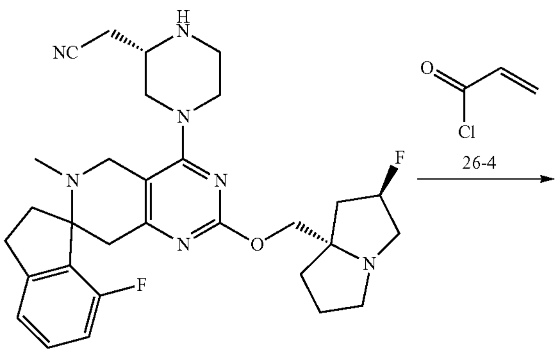

26-3

-continued

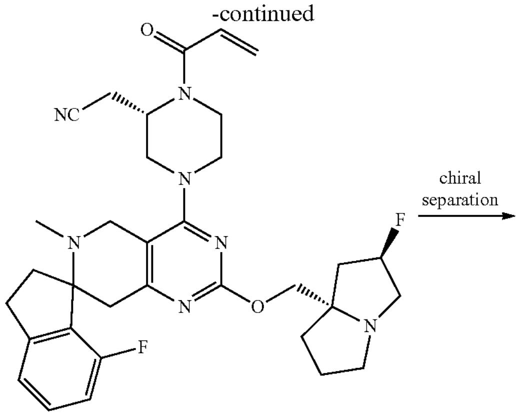

26-5

Compound 26 and 27

(1) To a solution of compound 8-8 (3.00 g, 5.69 mmol) in dioxane (80.0 mL) was added compound 26-1 (1.81 mg, 11.4 mmol), cesium carbonate (5.56 g, 17.1 mmol) and (2-dicyclohexylphosphino-2',6'-diisopropoxy-1,1'-biphenyl) [2-(2'-amino-1,1'-biphenyl)] palladium(II) methanesulfonate (300 mg, 359 μmol), and the reaction solution was stirred at 110° C. for 4 hours under nitrogen protection. Then the reaction solution was added with ethyl acetate (200 mL), washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 8:1) to give compound 26-2.

MS-ESI $[M+H]^+$, calculated: 650, found: 650.

(2) To a solution of compound 26-2 (3.24 g, 4.99 mmol) in dichloromethane (50.0 mL) was added hydrochloric acid in dioxane (1.25 mL, 4 mol/L), and the reaction solution was stirred at 25° C. for 0.5 hours under nitrogen protection. Then the reaction solution was concentrated under reduced pressure to obtain crude product of hydrochloride of compound 26-3.

MS-ESI $[M+H]^+$, calculated: 550, found: 550.

(3) To a solution of hydrochloride of compound 26-3 (2.60 g, 4.44 mmol) in dichloromethane (30.0 mL) was added triethylamine (1.35 g, 13.3 mmol) and compound 26-4 (803 mg, 8.87 μmol), and then the reaction solution was stirred at −78° C. for 0.5 hours under nitrogen protection. Then the reaction solution was added with dichloromethane (60.0 mL), washed with saturated NaCl aqueous solution (30.0 mL×2), dried over anhydrous sodium sulfate, filtered, and concentrated under reduced pressure. The crude product was separated by silica gel column chromatography (dichloromethane/methanol=1:0 to 25:1) to obtain compound 26-5.

(4) Compound 26-5 was separated by chiral supercritical fluid chromatography to obtain compounds 26 and 27.

Separation conditions: Chromatographic column model: Chiralpak OX-3; Column specification: 100×4.6 mm I.D., 3 m; Injection volume: 10 μL; Mobile phase: carbon dioxide: isopropyl alcohol (0.05% diethylamine)=60:40; Detection wavelength: 254 nm; Column temperature: 35° C.

Compound 26: retention time 2.047 minutes, 99.28% ee.

MS-ESI $[M+H]^+$, calculated: 604, found: 604.

$^1$H NMR (400 MHz, MeOD) δ 7.31 (td, J=7.6, 5.2 Hz, 1H), 7.10 (d, J=7.6 Hz, 1H), 6.91-6.97 (m, 1H), 6.71-6.90 (m, 1H), 6.28 (d, J=16.4 Hz, 1H), 5.83 (d, J=10.4 Hz, 1H), 5.19-5.37 (m, 1H), 5.03 (s, 1H), 4.54 (s, 1H), 4.16-4.22 (m, 1H), 4.10 (d, J=10.4 Hz, 3H), 3.52-3.79 (m, 3H), 3.39-3.51 (m, 1H), 3.21-3.28 (m, 2H), 3.19 (d, J=9.6 Hz, 2H), 3.11 (d, J=3.2 Hz, 1H), 3.04-3.09 (m, 1H), 2.99-3.04 (m, 2H), 2.89-2.98 (m, 2H), 2.85 (s, 1H), 2.49 (dt, J=13.2, 8.8 Hz, 1H), 2.27-2.32 (m, 3H), 2.19-2.27 (m, 1H), 2.12-2.19 (m, 1H), 2.05-2.12 (m, 1H), 1.93-2.02 (m, 2H), 1.84-1.93 (m, 2H).

Compound 27: retention time 3.558 minutes, 98.36% ee.

MS-ESI $[M+H]^+$, calculated: 604, found: 604.

$^1$H NMR (400 MHz, MeOD) δ 7.32 (td, J=7.6, 5.2 Hz, 1H), 7.10 (d, J=7.6 Hz, 1H), 6.91-6.97 (m, 1H), 6.72-6.91 (m, 1H), 6.29 (d, J=16.4 Hz, 1H), 5.83 (d, J=10.4 Hz, 1H), 5.22-5.39 (m, 1H), 5.07 (s, 1H), 4.50-4.78 (m, 1H), 4.18-4.27 (m, 2H), 4.14 (d, J=10.4 Hz, 1H), 3.91-4.13 (m, 2H), 3.62-3.74 (m, 2H), 3.37-3.61 (m, 1H), 3.25-3.29 (m, 2H), 3.20-3.24 (m, 2H), 3.08-3.20 (m, 3H), 3.06 (d, J=5.2 Hz, 1H), 2.98-3.05 (m, 2H), 2.90 (d, J=18.0 Hz, 1H), 2.48 (dt, J=13.2, 8.4 Hz, 1H), 2.28-2.37 (m, 1H), 2.24-2.28 (m, 3H), 2.18-2.24 (m, 1H), 2.10-2.16 (m, 1H), 1.94-2.03 (m, 2H), 1.90 (ddd, J=13.2, 8.4, 4.4 Hz, 2H).

Example 25 Synthesis of Compound 28 and 29

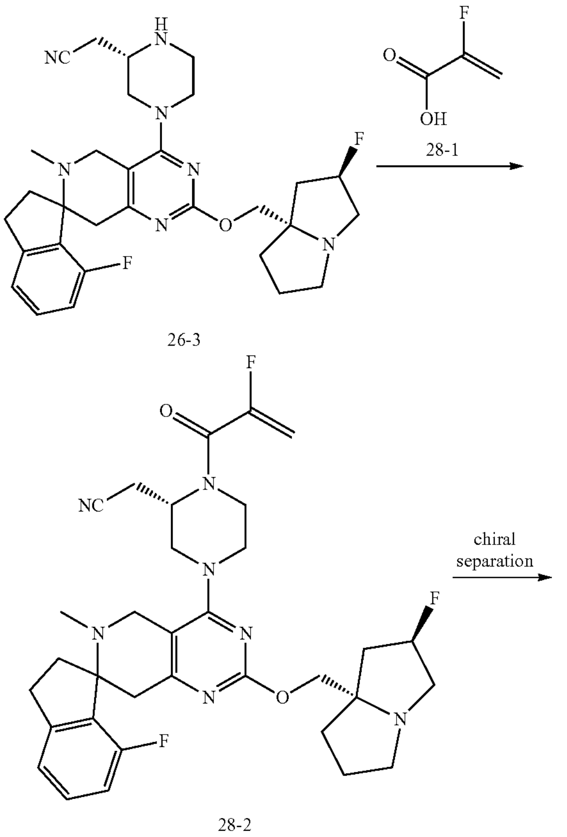

28-1

26-3

28-2

Compounds 28 and 29

To a solution of compound 28-1 (848 mg, 9.42 mmol) in ethyl acetate (20.0 mL) was added 4A molecular sieve (1.80 g), triethylamine (1.59 g, 1.57 mmol), hydrochloride of compound 26-3 (1.84 g, 3.14 mmol) and propanephosphonic acid anhydride solution (5.99 g, 9.42 mmol, 50% ethyl acetate solution), and the reaction solution was stirred at 25° C. for 0.5 hours. After filtration, the filter cake was washed with ethyl acetate (10.0 mL×3), and the filtrate was washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 24:1) to obtain compound 28-2.

(4) Compound 28-2 was separated by chiral supercritical fluid chromatography to obtain compounds 28 and 29.

Separation conditions: Chromatographic column model: Chiralpak OX-3; Column specification: 50×4.6 mm I.D., 3 m; Injection volume: 10 μL; Mobile phase: A: carbon dioxide, B: ethanol (0.05% diethylamine), B %: 5%-40% gradient elution for 2.5 minutes, 40% fixed concentration elution for 0.5 minutes, 5% fixed concentration elution for 1 minute; Detection wavelength: 254 nm; Column temperature: 35° C.

Compound 28: retention time 1.457 minutes, 100% ee.

MS-ESI $[M+H]^+$, calculated: 622, found: 622.

$^1H$ NMR (400 MHz, MeOD) δ 7.32 (td, J=7.6, 5.2 Hz, 1H), 7.10 (d, J=7.6 Hz, 1H), 6.90-6.97 (m, 1H), 5.34-5.41 (m, 1H), 5.28-5.34 (m, 1H), 5.19-5.28 (m, 1H), 4.92 (s, 1H), 4.79-4.88 (m, 1H), 4.15-4.23 (m, 1H), 4.13 (s, 1H), 4.06-4.11 (m, 2H), 3.90-4.06 (m, 1H), 3.69 (s, 2H), 3.45 (d, J=13.2 Hz, 1H), 3.23-3.29 (m, 1H), 3.17-3.23 (m, 2H), 3.16 (d, J=5.2 Hz, 1H), 3.10-3.15 (m, 1H), 3.06-3.10 (m, 1H), 3.04 (d, J=8.8 Hz, 2H), 2.98-3.01 (m, 1H), 2.93-2.98 (m, 1H), 2.87 (d, J=18.0 Hz, 1H), 2.49 (dt, J=13.2, 8.8 Hz, 1H), 2.27-2.32 (m, 3H), 2.19-2.27 (m, 1H), 2.13-2.18 (m, 1H), 2.06-2.12 (m, 1H), 1.96-2.02 (m, 1H), 1.92-1.96 (m, 1H), 1.88-1.92 (m, 1H), 1.79-1.88 (m, 1H).

Compound 29: retention time 1.588 minutes, 95.44% ee.

MS-ESI $[M+H]^+$, calculated: 622, found: 622.

$^1H$ NMR (400 MHz, MeOD) δ 7.32 (td, J=7.6, 5.2 Hz, 1H), 7.11 (d, J=7.6 Hz, 1H), 6.91-6.97 (m, 1H), 5.38 (s, 1H), 5.29-5.35 (m, 1H), 5.25 (d, J=13.6 Hz, 1H), 4.91 (s, 1H), 4.86-4.87 (m, 1H), 4.24 (d, J=14.0 Hz, 1H), 4.14-4.22 (m, 2H), 3.96-4.12 (m, 2H), 3.63-3.71 (m, 2H), 3.27 (d, J=3.6 Hz, 2H), 3.24 (d, J=3.2 Hz, 2H), 3.20 (s, 1H), 3.13-3.18 (m, 2H), 3.06-3.13 (m, 2H), 2.99-3.06 (m, 2H), 2.89 (d, J=18.0 Hz, 1H), 2.44-2.51 (m, 1H), 2.28 (s, 3H), 2.22-2.26 (m, 1H), 2.19 (s, 1H), 2.12 (d, J=9.2 Hz, 1H), 1.96-2.04 (m, 2H), 1.90 (td, J=8.8, 4.4 Hz, 2H).

Example 26 Synthesis of Compound 30

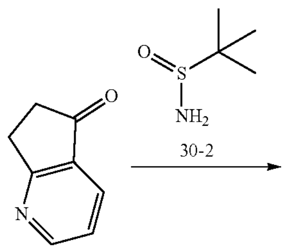

30-1

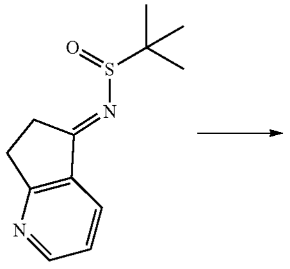

30-3

-continued

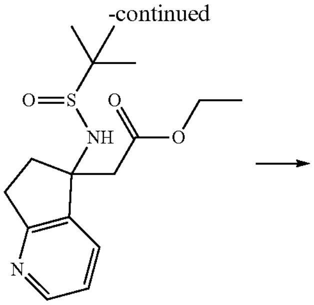

30-4

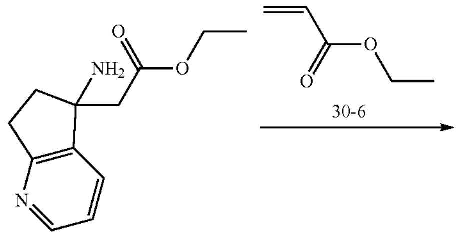

30-5

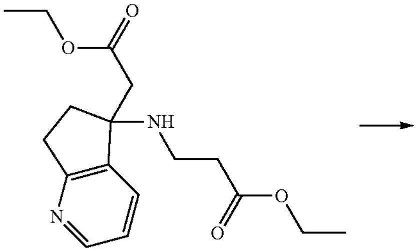

30-7

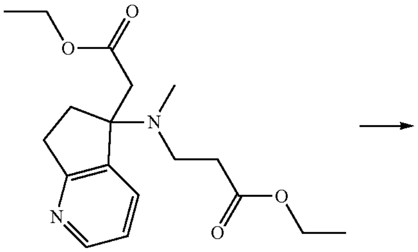

30-8

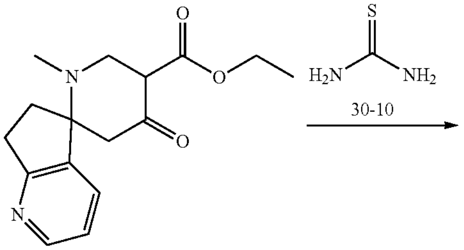

30-9

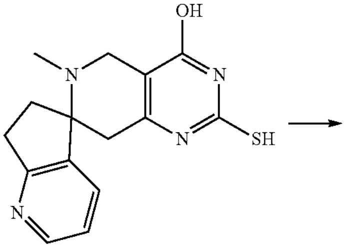

30-11

-continued

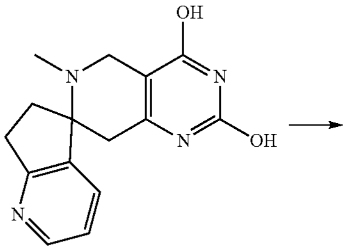

30-12

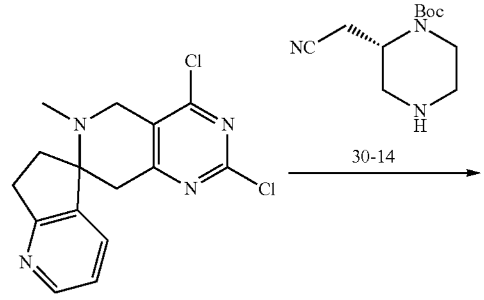

30-13

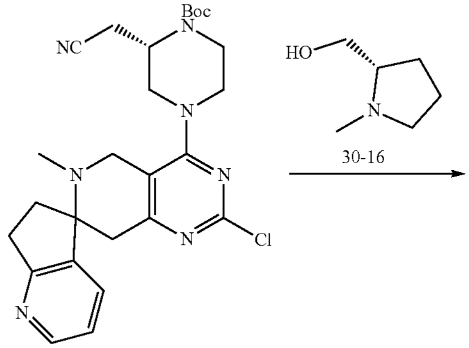

30-15

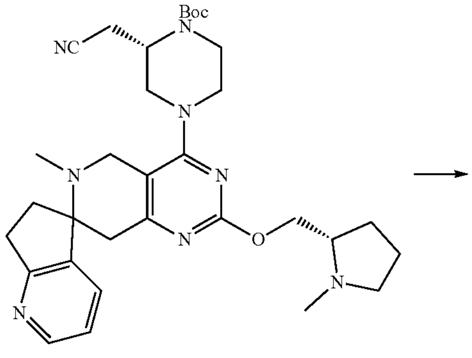

30-17

-continued

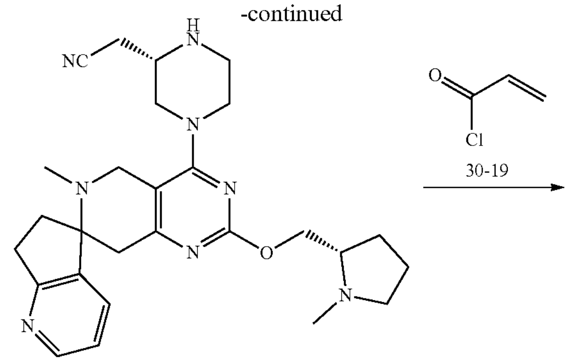

30-18

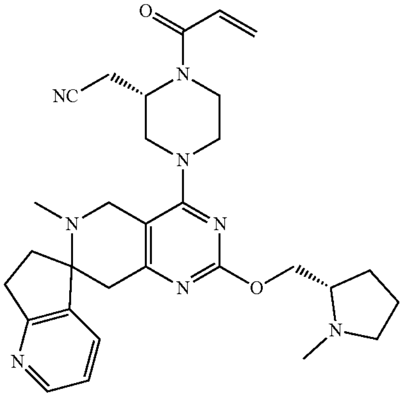

30

(1) To a solution of compound 30-1 (20.0 g, 150 mmol) in toluene (500 mL) was added compound 30-2 (21.9 g, 181 mmol), and tetraethyl titanate (68.5 g, 300 mmol), and then the reaction solution was stirred at 110° C. for 12 hours under nitrogen protection. Then the reaction solution was added with water (200 mL) and ethyl acetate (500 mL). After filtration, the filter cake was washed with ethyl acetate (500 mL×4). The combined organic phase was washed with saturated NaCl aqueous solution (500 mL×2), dried over anhydrous sodium sulfate, filtered, and concentrated under reduced pressure. The crude product was separated by silica gel column chromatography (petroleum ether/ethyl acetate=1:0 to 1:2) to obtain compound 30-3.

MS-ESI $[M+H]^+$, calculated: 237, found: 237.

$^1H$ NMR (400 MHz, $CDCl_3$) δ 8.71 (dd, J=4.8, 1.6 Hz, 1H), 8.05 (dd, J=7.6, 1.6 Hz, 1H), 7.28 (dd, J=8.0, 4.8 Hz, 1H), 3.49-3.59 (m, 1H), 3.25-3.31 (m, 2H), 3.11-3.20 (m, 1H), 1.33 (s, 9H).

(2) To a solution of ethyl acetate (24.3 g, 276 mmol) in tetrahydrofuran (150 mL) was added dropwise with lithium diisopropylamide (2 mol/L, 55 mL, tetrahydrofuran solution) at −65° C. under nitrogen protection, and the reaction solution was stirred at −65° C. for 1 hour. Then the reaction solution was added dropwise with a solution of compound 30-3 (13.0 g, 55.0 mmol) in tetrahydrofuran (150 mL), and then continued stirring for 2 hours at −65° C. After warming to 0° C., the reaction solution was quenched with saturated ammonium chloride aqueous solution (200 mL), and extracted with ethyl acetate (200 mL×2). The combined organic phase was washed with saturated ammonium chloride aqueous solution (200 mL×1) and saturated NaCl aqueous solution (200 mL×1), dried over anhydrous sodium sulfate, filtered, and concentrated under reduced pressure.

The crude product was separated by silica gel column chromatography (dichloromethane/methanol=1:0 to 32:1) to obtain compound 30-4.

MS-ESI $[M+H]^+$, calculated: 325, found: 325.

$^1H$ NMR (400 MHz, MeOD) δ 8.42 (d, J=5.2 Hz, 1H), 7.77-7.83 (m, 1H), 7.25-7.33 (m, 1H), 4.08-4.19 (m, 2H), 3.17-3.25 (m, 1H), 2.97-3.15 (m, 2H), 2.85-2.97 (m, 1H), 2.60-2.69 (m, 1H), 2.41-2.54 (m, 1H), 1.17-1.22 (m, 12H).

(3) To a solution of compound 30-4 (7.40 g, 22.8 mmol) in ethanol (60.0 mL) was added hydrochloric acid in dioxane (4 mol/L, 20.0 mL), and the reaction solution was stirred at 25° C. for 1 hour under nitrogen protection. Then the reaction solution was concentrated under reduced pressure to obtain crude product of hydrochloride of compound 30-5.

MS-ESI $[M+H]^+$, calculated: 221, found: 221.

(4) To a solution of hydrochloride of compound 30-5 (5.86 g, 22.8 mmol) in ethanol (50.0 mL) was added compound 30-6 (23.1 g, 231 mmol), copper oxide (363 mg, 4.56 mmol), and triethylamine (6.94 g, 68.6 mmol), and the reaction solution was reacted at 85° C. in a sealed tube for 8 hours under nitrogen protection. Then the reaction solution was added with water (200 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 2:1) to obtain compound 30-7.

MS-ESI $[M+H]^+$, calculated: 321, found: 321.

$^1H$ NMR (400 MHz, MeOD) δ 8.37 (d, J=4.4 Hz, 1H), 7.75 (dd, J=7.6, 1.2 Hz, 1H), 7.26 (dd, J=7.6, 5.2 Hz, 1H), 4.13 (q, J=7.2 Hz, 2H), 4.06 (q, J=7.2 Hz, 2H), 2.97-3.10 (m, 2H), 2.82-2.87 (m, 1H), 2.75-2.80 (m, 1H), 2.71 (dt, J=10.8, 6.0 Hz, 1H), 2.48-2.59 (m, 1H), 2.43-2.48 (m, 2H), 2.28-2.39 (m, 2H), 1.24 (t, J=7.2 Hz, 3H), 1.15 (t, J=7.2 Hz, 3H).

(5) To a solution of compound 30-7 (1.00 g, 3.12 mmol) in ethanol (15.0 mL) was added paraformaldehyde (937 mg) and sodium cyanoborohydride (589 mg, 9.37 mmol), and the reaction solution was reacted for 14 hours at 25° C. under nitrogen protection. Then the reaction solution was added with water (100 mL), and extracted with ethyl acetate (100 mL×1). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 3:1) to obtain compound 30-8.

MS-ESI $[M+H]^+$, calculated: 335, found: 335.

$^1H$ NMR (400 MHz, MeOD) δ8.36 (dd, J=5.2, 1.6 Hz, 1H), 7.72 (dd, J=7.6, 1.6 Hz, 1H), 7.25 (dd, J=7.6, 5.2 Hz, 1H), 4.07-4.13 (m, 2H), 3.90 (qd, J=7.2, 1.2 Hz, 2H), 2.98-3.04 (m, 2H), 2.94-2.97 (m, 1H), 2.84-2.89 (m, 1H), 2.64-2.71 (m, 1H), 2.57-2.63 (m, 1H), 2.40-2.46 (m, 3H), 2.25-2.32 (m, 1H), 2.20 (s, 3H), 1.24 (t, J=7.2 Hz, 3H), 1.02 (t, J=7.2 Hz, 3H).

(6) To a solution of compound 30-8 (900 mg, 2.69 mmol) in tetrahydrofuran (20.0 mL) was added potassium bis (trimethylsilyl) amide (1 mol/L, 8.0 mL, tetrahydrofuran solution) at −65° C., and the reaction solution was reacted at −65° C. for 2 hours under nitrogen protection. Then the reaction solution was added with saturated ammonium chloride aqueous solution (100 mL), and extracted with ethyl acetate (100 mL×1). The organic phase was washed successively with saturated ammonium chloride aqueous solution (100 mL×1) and saturated NaCl aqueous solution (100 mL×1), dried over anhydrous sodium sulfate, filtered, and concentrated under reduced pressure. The crude product was separated by silica gel column chromatography (petroleum ether/ethyl acetate=1:0 to 3:1) to obtain compound 30-9.

MS-ESI $[M+H]^+$, calculated: 289, found: 289.

$^1H$ NMR (400 MHz, MeOD) δ 8.42 (dd, J=5.2, 1.6 Hz, 1H), 7.71 (dd, J=7.6, 1.6 Hz, 1H), 7.32 (dd, J=7.6, 5.2 Hz, 1H), 4.28 (q, J=7.2 Hz, 2H), 3.45 (d, J=15.2 Hz, 1H), 3.32-3.39 (m, 1H), 3.22-3.28 (m, 1H), 3.04-3.11 (m, 2H), 2.58-2.69 (m, 1H), 2.44-2.49 (m, 1H), 2.34-2.40 (m, 1H), 2.07 (s, 3H), 1.85-1.93 (m, 1H), 1.32 (t, J=7.2 Hz, 3H).

(7) To a solution of compound 30-9 (510 mg, 1.77 mmol) in ethanol (8.0 mL) was added compound 30-10 (269 mg, 3.53 mmol) and sodium ethoxide (361 mg, 5.30 mmol), and the reaction solution was stirred at 80° C. for 16 hours under nitrogen protection. After concentrated under reduced pressure, the reaction solution was adjusted to pH 6 with hydrochloric acid (1 mol/L). The resulting solution was precipitated, and filtered. The filter cake was dried to obtain compound 30-11.

MS-ESI $[M+H]^+$, calculated: 301, found: 301.

$^1H$ NMR (400 MHz, DMSO-$d_6$) δ 12.77 (s, 1H), 12.64 (s, 1H), 8.66-8.73 (m, 1H), 8.59 (s, 1H), 7.56 (s, 1H), 4.10 (s, 1H), 3.96 (d, J=14.4 Hz, 1H), 3.43 (d, J=18.8 Hz, 4H), 3.18 (s, 2H), 2.89 (d, J=16.0 Hz, 1H), 2.67 (s, 1H), 2.20 (s, 1H).

(8) To a solution of intermediate 30-11 (531 mg, 1.77 mmol) in water (10.0 mL) was added chloroacetic acid (670 mg, 7.09 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 30-12.

MS-ESI $[M+H]^+$, calculated: 285, found: 285.

$^1H$ NMR (400 MHz, DMSO-d6) δ 10.92 (s, 2H), 8.44 (dd, J=4.8, 1.6 Hz, 1H), 7.58 (dd, J=7.6, 1.6 Hz, 1H), 7.24 (dd, J=7.6, 4.8 Hz, 1H), 3.39 (s, 1H), 3.07 (d, J=16.0 Hz, 1H), 2.90-2.99 (m, 2H), 2.61 (d, J=17.2 Hz, 1H), 2.39 (d, J=17.6 Hz, 1H), 2.21 (dt, J=13.6, 8.4 Hz, 1H), 1.96 (s, 3H), 1.70 (ddd, J=13.6, 8.0, 5.6 Hz, 1H).

(9) Compound 30-12 (300 mg, 1.06 mmol) was dissolved in phosphorus oxychloride (9.90 g, 64.6 mmol), and the reaction solution was stirred at 100° C. in a sealed tube under nitrogen protection for 12 hours. Then the reaction solution was concentrated under reduced pressure, slowly added with iced water (50 mL), and extracted with dichloromethane (50 mL×1). The organic phase was washed with saturated sodium carbonate solution (20 mL×2) and saturated NaCl aqueous solution (20 mL×1), dried over anhydrous sodium sulfate, filtered, and concentrated under reduced pressure to obtain compound 30-13.

MS-ESI $[M+H]^+$, calculated: 321, found: 321.

(10) To a solution of compound 30-13 (338 mg, 1.05 mmol) in N-methylpyrrolidone (5.0 mL) was added potassium carbonate (436 mg, 3.15 mmol) and compound 30-14 (284 mg, 1.26 mmol), and the reaction solution was stirred at 50° C. for 3 hours under nitrogen protection. Then the reaction solution was poured into water (30.0 mL) and extracted with ethyl acetate (30.0 mL×2). The organic phases were combined, washed with saturated NaCl aqueous solution (30.0 mL×2), dried over anhydrous sodium sulfate, filtered, and concentrated under reduced pressure. The crude product was separated by silica gel column chromatography (petroleum ether/ethyl acetate=1:0 to 3:1) to obtain compound 30-15.

MS-ESI $[M+H]^+$, calculated: 510, found: 510.

$^1H$ NMR (400 MHz, MeOD) δ 8.44 (d, J=4.4 Hz, 1H), 7.65-7.74 (m, 1H), 7.28-7.37 (m, 1H), 4.43 (s, 2H), 3.98-4.08 (m, 2H), 3.87 (d, J=14.4 Hz, 2H), 3.68-3.80 (m, 2H), 2.97 (d, J=5.2 Hz, 2H), 2.93 (s, 2H), 2.83-2.87 (m, 2H), 2.82 (d, J=4.0 Hz, 2H), 2.45-2.54 (m, 1H), 2.21 (s, 3H), 1.48 (s, 9H).

(11) To a solution of compound 30-15 (300 mg, 588 μmol) in dioxane (10.0 mL) was added compound 30-16 (203 mg, 1.76 mmol), cesium carbonate (575 mg, 1.76 mmol) and (2-dicyclohexylphosphino-2',6'-diisopropoxy-1,1'-biphenyl)[2-(2'-amino-1,1'-biphenyl)]palladium(II) methanesulfonate (98.4 mg, 118 μmol), and the reaction solution was stirred at 110° C. for 4 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 5:1) to obtain compound 30-17.

MS-ESI [M+H]$^+$, calculated: 589, found: 589.

(12) To a solution of compound 30-17 (110 mg, 187 μmol) in dichloromethane (3.0 mL) was added trifluoroacetic acid (1.54 g, 13.5 mmol), and the reaction solution was stirred at 25° C. for 1 hour under nitrogen protection. Then the reaction solution was concentrated under reduced pressure to obtain crude trifluoroacetate of compound 30-18.

MS-ESI [M+H]$^+$, calculated: 489, found: 489.

(13) To a solution of trifluoroacetate of compound 30-18 (90.0 mg, 149 μmol) in dichloromethane (5.0 mL) was added triethylamine (45.0 mg, 445 μmol), then cooled to −78° C. and added with compound 30-19 (27.0 mg, 298 μmol), and the reaction solution was stirred at −65° C. for 0.5 hours under nitrogen protection. Then the reaction solution was added with dichloromethane (30.0 mL), washed with saturated NaCl aqueous solution (30.0 mL×2), dried over anhydrous sodium sulfate, filtered, and concentrated under reduced pressure. The crude product was separated by preparative high performance liquid chromatography (Gemini-NX C18, 75×30 mm×3 μm, A: water (10 mmM ammonium bicarbonate); B: acetonitrile, 10%-40%: 10 min) to obtain compound 30.

MS-ESI [M+H]$^+$, calculated: 543, found: 543.

$^1$H NMR (400 MHz, MeOD) δ 8.44 (d, J=4.8 Hz, 1H), 7.62-7.75 (m, 1H), 7.27-7.37 (m, 1H), 6.83 (d, J=13.2 Hz, 1H), 6.29 (d, J=16.4 Hz, 1H), 5.84 (d, J=10.4 Hz, 1H), 4.43-4.68 (m, 1H), 4.29-4.41 (m, 2H), 4.19 (d, J=14.0 Hz, 1H), 4.10 (s, 1H), 4.00 (d, J=10.0 Hz, 1H), 3.71-3.82 (m, 2H), 3.44-3.64 (m, 1H), 3.27 (s, 1H), 3.15-3.23 (m, 1H), 3.04-3.15 (m, 4H), 2.88-2.99 (m, 3H), 2.74 (dt, J=14.0, 6.8 Hz, 1H), 2.50-2.56 (m, 1H), 2.49 (d, J=2.4 Hz, 3H), 2.35 (qd, J=8.8, 2.0 Hz, 1H), 2.21 (s, 3H), 2.09 (dq, J=12.4, 8.4 Hz, 1H), 1.91-2.01 (m, 1H), 1.77-1.86 (m, 2H), 1.63-1.75 (m, 1H).

Example 27 Synthesis of Compound 31

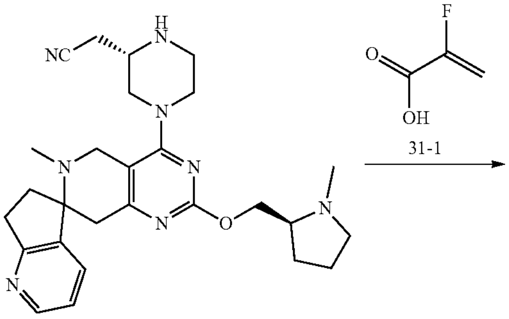

30-18

31-1

-continued

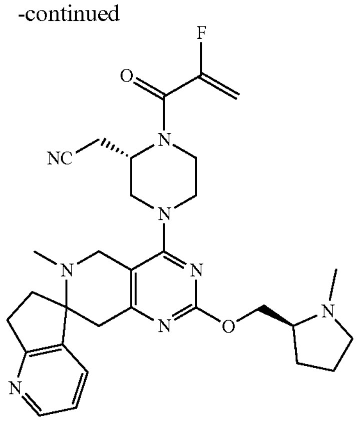

31

To a solution of compound 31-1 (58.3 mg, 648 μmol) in dichloromethane (5.0 mL) was added 4A molecular sieve (130 mg), triethylamine (65.6 mg, 648 μmol), trifluoroacetate of compound 30-18 (130 mg, 216 μmol) and propanephosphonic acid anhydride solution (549 mg, 863 μmol, 50% ethyl acetate solution), and the reaction solution was stirred at 25° C. for 0.5 hours. After filtration, the filter cake was washed with ethyl acetate (10.0 mL×3), and the filtrate was washed with saturated NaCl aqueous solution (20.0 mL×2), dried over anhydrous sodium sulfate, filtered, and concentrated under reduced pressure. The crude product was separated by preparative high performance liquid chromatography (Phenomenex Gemini-NX C18, 75 mm×30 mm 3 μm, A: water (10 mmol/L ammonium bicarbonate); B: acetonitrile, 25%-50%: 8 minutes) to obtain compound 31.

MS-ESI [M+H]$^+$, calculated: 561, found: 561.

$^1$H NMR (400 MHz, MeOD) δ 8.44 (d, J=4.8 Hz, 1H), 7.69 (ddd, J=13.2, 7.6, 1.6 Hz, 1H), 7.33 (dt, J=7.6, 5.2 Hz, 1H), 5.32-5.44 (m, 1H), 5.20-5.32 (m, 1H), 4.28-4.39 (m, 2H), 4.14-4.26 (m, 1H), 4.10 (d, J=5.2 Hz, 1H), 3.93-4.07 (m, 1H), 3.63-3.80 (m, 2H), 3.37-3.57 (m, 1H), 3.32-3.34 (m, 1H), 3.20-3.30 (m, 1H), 3.04-3.20 (m, 5H), 2.95-3.04 (m, 1H), 2.94 (d, J=6.4 Hz, 2H), 2.76 (dt, J=13.6, 6.8 Hz, 1H), 2.50 (d, J=2.4 Hz, 3H), 2.47 (d, J=3.6 Hz, 1H), 2.33-2.42 (m, 1H), 2.21 (d, J=1.2 Hz, 3H), 2.09 (dq, J=12.4, 8.4 Hz, 1H), 1.91-2.01 (m, 1H), 1.77-1.87 (m, 2H), 1.65-1.76 (m, 1H).

Example 28 Synthesis of Compounds 32 and 33

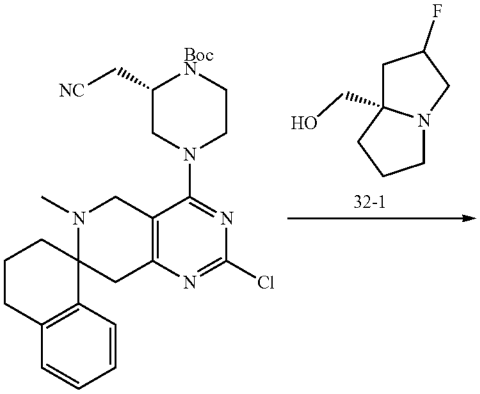

20-15

32-1

-continued

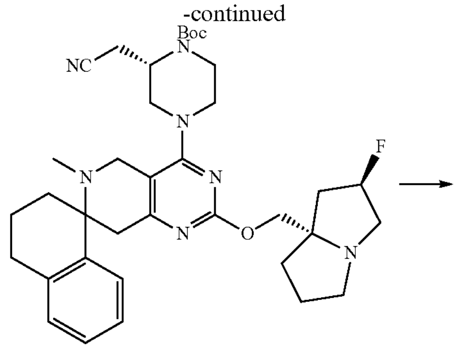

32-2

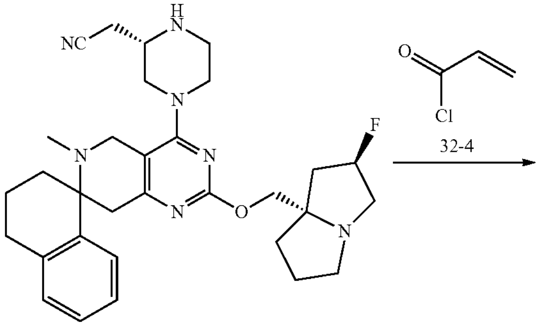

32-3

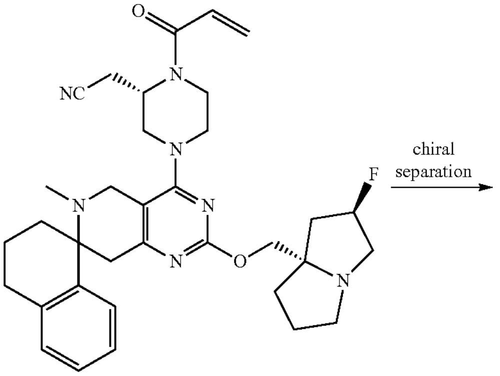

32-5

Compound 32 and 33

(1) To a solution of compound 20-15 (800 mg, 1.53 mmol) in dioxane (15.0 mL) was added compound 32-1 (487 mg, 3.06 mmol), cesium carbonate (382 mg, 2.76 mmol) and (2-dicyclohexylphosphino-2',6'-diisopropoxy-1, 1'-biphenyl) [2-(2'-amino-1,1'-biphenyl)]palladium methanesulfonate (80.0 mg, 95.7 μmol), and the reaction solution was stirred at 110° C. for 3 hours under nitrogen protection. Then the reaction solution was added with ethyl acetate (80.0 mL), washed with water (50.0 mL×1) and saturated NaCl aqueous solution (50.0 mL×3), dried over anhydrous sodium sulfate, filtered, and concentrated under reduced pressure. The crude product was separated by silica gel column chromatography (dichloromethane/methanol=1:0 to 16:1) to obtain compound 32-2.

MS-ESI $[M+H]^+$, calculated: 646, found: 646.

$^1$H NMR (400 MHz, $CDCl_3$) δ 7.53 (t, J=7.2 Hz, 1H), 7.19-7.24 (m, 1H), 7.14 (t, J=6.8 Hz, 1H), 7.06-7.09 (m, 1H), 4.59 (s, 1H), 4.09 (s, 2H), 3.96 (s, 1H), 3.63-3.83 (m, 3H), 3.34 (dd, J=14.0, 3.2 Hz, 1H), 3.23 (s, 2H), 3.16 (d, J=8.0 Hz, 1H), 3.05-3.14 (m, 3H), 2.79-3.05 (m, 4H), 2.74

(d, J=5.6 Hz, 2H), 2.69 (d, J=2.8 Hz, 1H), 2.27 (s, 1H), 2.21 (s, 1H), 2.10-2.16 (m, 3H), 1.89-1.99 (m, 4H), 1.84 (d, J=10.0 Hz, 2H), 1.77 (s, 1H), 1.67-1.76 (m, 2H), 1.51 (s, 9H).

(2) To a solution of compound 32-2 (810 g, 1.25 mmol) in dichloromethane (10.0 mL) was added hydrochloric acid in dioxane (3.12 mL, 4 mol/L), and the reaction solution was stirred at 25° C. for 1 hour under nitrogen protection. Then the reaction solution was concentrated under reduced pressure to obtain crude product of hydrochloride of compound 32-3.

MS-ESI $[M+H]^+$, calculated: 546, found: 546.

(3) To a solution of hydrochloride of compound 32-3 (830 g, 1.43 mmol) in dichloromethane (3.0 mL) was added triethylamine (433 mg, 4.28 mmol) and compound 32-4 (258 mg, 2.85 mmol), and then the reaction solution was stirred at −78° C. for 1 hour under nitrogen protection. Then the reaction solution was added with dichloromethane (60.0 mL), washed with saturated NaCl aqueous solution (30.0 mL×3), dried over anhydrous sodium sulfate, filtered, and concentrated under reduced pressure. The crude product was separated by silica gel column chromatography (dichloromethane/methanol=1:0 to 16:1) to obtain compound 32-5.

(4) Compound 32-5 was separated by chiral supercritical fluid chromatography to obtain compounds 32 and 33.

Separation conditions: Chromatographic column model: Chiralpak OX-3; Column specification: 50×4.6 mm I.D., 3 m; Injection volume: 10 μL; Mobile phase: A: Carbon dioxide, B: Ethanol (0.05% diethylamine), B %: 5%-40% gradient elution for 2.5 minutes, 40% fixed concentration elution for 0.5 minutes, 5% fixed concentration elution for 1 minute; Detection wavelength: 254 nm; Column temperature: 35° C.

Compound32: retention time 1.759 minutes, 100% ee.

MS-ESI $[M+H]^+$, calculated: 600, found: 600.

$^1$H NMR (400 MHz, MeOD) δ 7.51 (d, J=8.0 Hz, 1H), 7.19-7.25 (m, 1H), 7.13-7.18 (m, 1H), 7.07-7.12 (m, 1H), 6.80 (s, 1H), 6.29 (d, J=16.4 Hz, 1H), 5.83 (d, J=10.4 Hz, 1H), 5.21-5.42 (m, 1H), 5.02 (s, 1H), 4.23-4.53 (m, 1H), 4.22 (s, 1H), 4.13 (d, J=8.4 Hz, 2H), 4.09 (s, 1H), 3.75-3.87 (m, 2H), 3.57-3.75 (m, 1H), 3.35-3.57 (m, 2H), 3.15 (d, J=15.2 Hz, 1H), 3.04-3.12 (m, 2H), 2.93-3.04 (m, 2H), 2.88 (s, 2H), 2.76 (d, J=5.6 Hz, 2H), 2.26-2.39 (m, 1H), 2.13-2.26 (m, 2H), 2.12 (s, 3H), 2.03-2.10 (m, 1H), 2.01 (d, J=8.4 Hz, 2H), 1.92-1.99 (m, 2H), 1.90 (d, J=6.8 Hz, 1H), 1.66-1.84 (m, 2H).

Compound33: retention time: 1.966 minutes, 99.36% ee.

MS-ESI $[M+H]^+$, calculated: 600, found: 600.

$^1$H NMR (400 MHz, MeOD) δ 7.51 (d, J=7.6 Hz, 1H), 7.19-7.25 (m, 1H), 7.13-7.18 (m, 1H), 7.07-7.12 (m, 1H), 6.82 (d, J=10.0 Hz, 1H), 6.29 (d, J=16.4 Hz, 1H), 5.84 (d, J=10.4 Hz, 1H), 5.25-5.43 (m, 1H), 5.07 (s, 1H), 4.32 (d, J=14.0 Hz, 1H), 4.18-4.29 (m, 2H), 4.11 (d, J=10.0 Hz, 1H), 4.00 (d, J=11.2 Hz, 1H), 3.70-3.85 (m, 2H), 3.46-3.69 (m, 1H), 3.36-3.45 (m, 2H), 3.20 (dd, J=14.0, 3.6 Hz, 2H), 3.14 (d, J=8.4 Hz, 1H), 3.07-3.10 (m, 1H), 3.03 (s, 1H), 2.99 (s, 1H), 2.94 (s, 1H), 2.74-2.81 (m, 2H), 2.29-2.43 (m, 1H), 2.23-2.29 (m, 1H), 2.16-2.23 (m, 1H), 2.12 (s, 3H), 2.08 (d, J=10.0 Hz, 1H), 2.04 (d, J=5.2 Hz, 2H), 1.95-2.00 (m, 2H), 1.92 (d, J=6.8 Hz, 1H), 1.71-1.83 (m, 2H).

Example 29 Synthesis of Compound 34

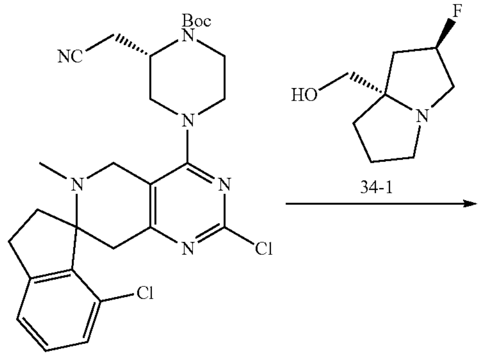

18-15

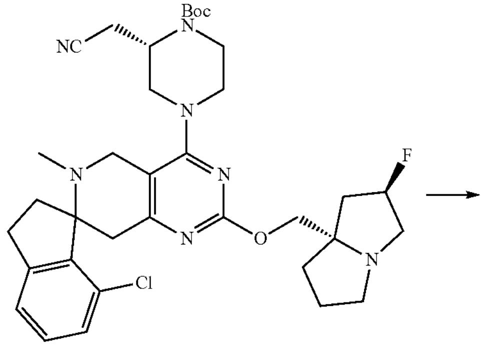

34-2

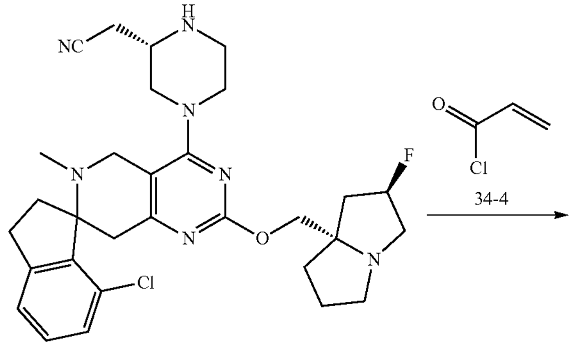

34-3

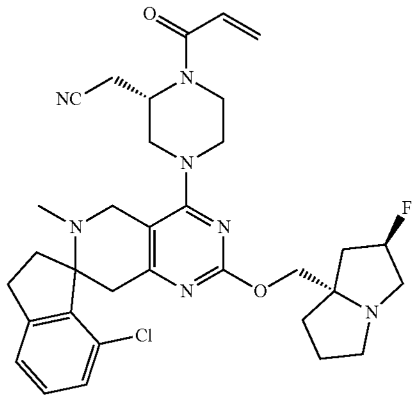

34

(1) To a solution of compound 18-15 (500 mg, 920 µmol) in dioxane (10.0 mL) was added compound 34-1 (220 mg, 1.38 mmol), potassium carbonate (382 mg, 2.76 mmol), dicyclohexyl(2',4',6'-triisopropyl-[1,1'-biphenyl]-2-yl)phosphine (176 mg, 369 mol) and bis (dibenzylidene acetone) palladium(169 mg, 185 µmol), and the reaction solution was stirred at 110° C. for 4 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 10:1) to obtain compound 34-2.

MS-ESI $[M+H]^+$, calculated: 666, found: 666.

(2) To a solution of compound 34-2 (485 g, 728 µmol) in dichloromethane (6.0 mL) was added trifluoroacetic acid (2.0 mL), and the reaction solution was stirred at 25° C. for 1 hour under nitrogen protection. Then the reaction solution was concentrated under reduced pressure to obtain crude trifluoroacetate of compound 34-3.

MS-ESI $[M+H]^+$, calculated: 566, found: 566.

(3) To a solution of trifluoroacetate of compound 34-3 (150 g, 221 µmol) in dichloromethane (3.0 mL) was added triethylamine (67.0 mg, 662 µmol) and compound 34-4 (39.9 mg, 441 µmol), and the reaction solution was stirred at −65° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm 3 µm, A: water (0.225% formic acid); B: acetonitrile, 7%-27%: 7 min) to obtain formate of compound 34.

MS-ESI $[M+H]^+$, calculated: 620, found: 620.

$^1H$ NMR (400 MHz, MeOD) δ 7.20-7.30 (m, 3H), 6.82 (d, J=11.6 Hz, 1H), 6.29 (d, J=16.8 Hz, 1H), 5.84 (d, J=10.4 Hz, 1H), 5.41-5.64 (m, 1H), 5.03 (s, 1H), 4.38-4.64 (m, 3H), 4.02-4.23 (m, 2H), 3.83-3.95 (m, 1H), 3.76-3.83 (m, 2H), 3.71-3.76 (m, 2H), 3.50-3.70 (m, 1H), 3.32-3.44 (m, 3H), 3.08-3.28 (m, 2H), 2.97-3.08 (m, 2H), 2.76-2.96 (m, 2H), 2.73 (d, J=18.0 Hz, 1H), 2.55-2.68 (m, 1H), 2.43-2.55 (m, 2H), 2.28-2.41 (m, 2H), 2.25 (d, J=2.4 Hz, 3H), 2.10-2.20 (m, 1H), 1.77-1.91 (m, 1H).

Example 30 Synthesis of Compound 35

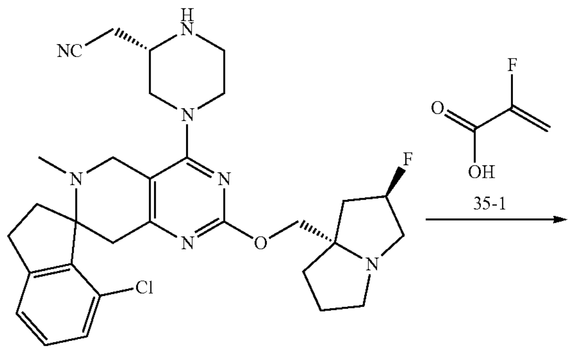

34-3

-continued

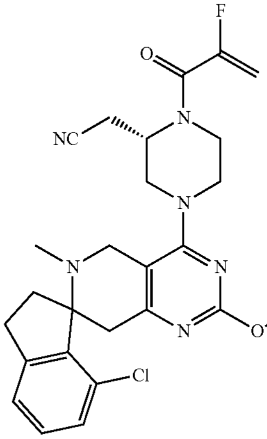

35

-continued

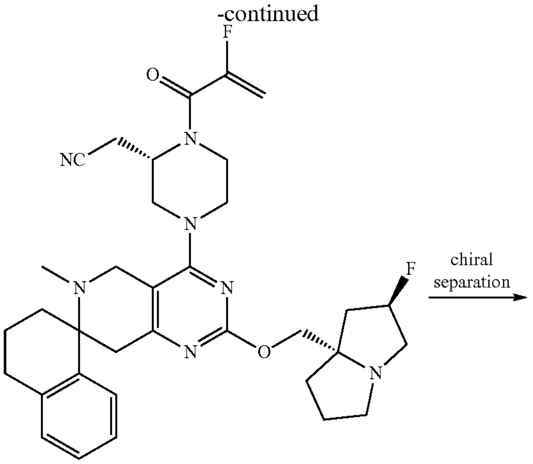

36-2

Compounds 36 and 37

To a solution of compound 35-1 (108 mg, 1.20 mmol) in ethyl acetate (10.0 mL) was added 4A molecular sieve (270 mg), triethylamine (121 mg, 1.20 mmol), trifluoroacetic acid of compound 34-3 (270 mg, 397 μmol) and propanephosphonic acid anhydride solution (1.02 g, 1.60 mmol, 50% ethyl acetate solution), and the reaction solution was stirred at 25° C. for 0.5 hours. After filtration, the filter cake was washed with ethyl acetate (10.0 mL×3), and the filtrate was washed with saturated NaCl aqueous solution (20.0 mL×2), dried over anhydrous sodium sulfate, filtered, and concentrated under reduced pressure. The crude product was separated by preparative high performance liquid chromatography (Phenomenex Gemini-NX C18, 75 mm×30 mm 3 μm, A: water (10 mmol/L ammonium bicarbonate); B: acetonitrile, 40%-70%: 10 minutes) to obtain compound 35.

MS-ESI $[M+H]^+$, calculated: 638, found: 638.

$^1$H NMR (400 MHz, MeOD) δ 7.23-7.30 (m, 3H), 5.28-5.45 (m, 2H), 5.13-5.25 (m, 1H), 3.90-3.98 (m, 2H), 3.83-3.90 (m, 2H), 3.77-3.83 (m, 1H), 3.60-3.77 (m, 1H), 3.50 (dd, J=14.8, 8.8 Hz, 1H), 3.18-3.23 (m, 1H), 3.13 (dd, J=18.4, 5.6 Hz, 2H), 3.05 (s, 3H), 2.93-3.01 (m, 4H), 2.77-2.84 (m, 1H), 2.53-2.71 (m, 2H), 2.35-2.43 (m, 1H), 2.28-2.34 (m, 1H), 2.12 (d, J=4.4 Hz, 3H), 2.06-2.09 (m, 1H), 1.99 (s, 1H), 1.94 (s, 1H), 1.77-1.83 (m, 1H), 1.66-1.76 (m, 3H).

Example 31 Synthesis of Compounds 36 and 37

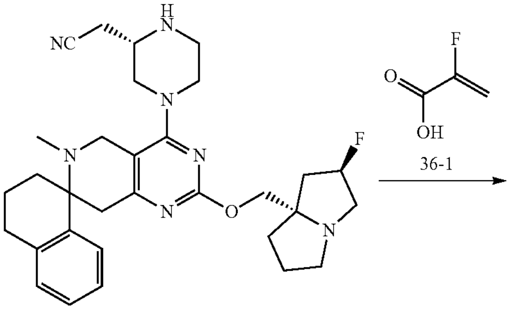

32-3

To a solution of compound 36-1 (1.02 g, 11.3 mmol) in ethyl acetate (20.0 mL) was added 4A molecular sieve (2.0 g), triethylamine (1.15 g, 11.3 mmol), hydrochloride of compound 32-3 (2.2 g, 3.78 mmol) and propanephosphonic acid anhydride solution (9.62 g, 15.1 mmol, 50% ethyl acetate solution), and the reaction solution was stirred at 25° C. for 0.5 hours. After filtration, the filter cake was washed with ethyl acetate (10.0 mL×3), and the filtrate was washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 16:1) to obtain compound 36-2.

(2) Compound 36-2 was separated by chiral supercritical fluid chromatography to obtain compounds 36 and 37.

Separation conditions: Chromatographic column model: Chiralpak OD-3; column specification: 50×4.6 mm I.D., 3 m; Injection volume: 4.0 μL; Mobile phase: A: Carbon dioxide, B: Ethanol (0.05% diethylamine), B %: 5%-40% gradient elution for 2.5 minutes, 40% fixed concentration elution for 0.5 minutes, 5% fixed concentration elution for 1 minute; Detection wavelength: 254 nm; column temperature: 35° C.

Compound 36: retention time: 1.567 minutes, 98.46% ee. MS-ESI $[M+H]^+$, calculated: 618, found: 618.

$^1$H NMR (400 MHz, MeOD) δ 7.51 (d, J=7.6 Hz, 1H), 7.19-7.25 (m, 1H), 7.15 (t, J=7.2 Hz, 1H), 7.07-7.12 (m, 1H), 5.37-5.46 (m, 1H), 5.30-5.36 (m, 1H), 5.25-5.30 (m, 1H), 4.86 (s, 1H), 4.61 (s, 1H), 4.25-4.32 (m, 1H), 4.22 (d, J=11.2 Hz, 1H), 4.11-4.19 (m, 2H), 4.10 (s, 1H), 3.77 (d, J=3.2 Hz, 2H), 3.51 (d, J=15.2 Hz, 1H), 3.39-3.49 (m, 2H), 3.33-3.38 (m, 1H), 3.13 (d, J=1.6 Hz, 1H), 3.05-3.12 (m, 2H), 3.00 (s, 2H), 2.90-2.95 (m, 1H), 2.73-2.80 (m, 2H), 2.31-2.45 (m, 1H), 2.30 (d, J=7.6 Hz, 1H), 2.18 (d, J=8.4 Hz, 1H), 2.12 (s, 3H), 2.07 (s, 1H), 2.04 (s, 1H), 2.00 (s, 1H), 1.97 (d, J=3.2 Hz, 2H), 1.75-1.85 (m, 2H).

Compound 37: retention time: 1.778 minutes, 99.36% ee. MS-ESI $[M+H]^+$, calculated: 618, found: 618.

$^1$H NMR (400 MHz, MeOD) δ 7.51 (d, J=7.2 Hz, 1H), 7.17-7.23 (m, 1H), 7.14 (td, J=7.2, 1.2 Hz, 1H), 7.04-7.10 (m, 1H), 5.34-5.41 (m, 1H), 5.29-5.34 (m, 1H), 5.18-5.28 (m, 1H), 4.27 (d, J=13.6 Hz, 1H), 4.10-4.25 (m, 2H), 4.01-4.10 (m, 1H), 3.80-4.01 (m, 1H), 3.74 (q, J=14.8 Hz, 2H), 3.32-3.62 (m, 1H), 3.25-3.29 (m, 1H), 3.24 (d, J=8.4 Hz, 1H), 3.19-3.22 (m, 2H), 3.17 (d, J=6.8 Hz, 2H), 3.08 (s,

1H), 3.01-3.06 (m, 1H), 2.98 (s, 1H), 2.87-2.98 (m, 1H), 2.69-2.79 (m, 2H), 2.20-2.47 (m, 1H), 2.14-2.20 (m, 1H), 2.11 (s, 3H), 2.09 (s, 1H), 1.99-2.07 (m, 1H), 1.98 (s, 1H), 1.95 (d, J=4.0 Hz, 2H), 1.87-1.93 (m, 1H), 1.80-1.87 (m, 1H), 1.57-1.80 (m, 2H).
Example 32 Synthesis of Compound 38
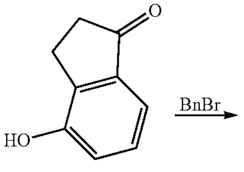
38-1
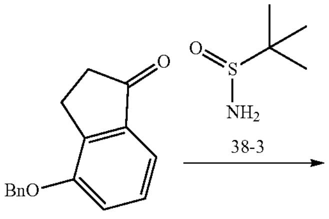
38-2
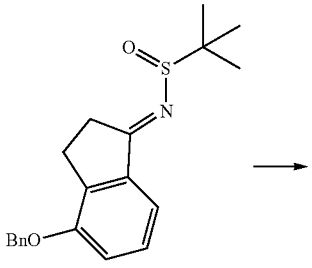
38-4
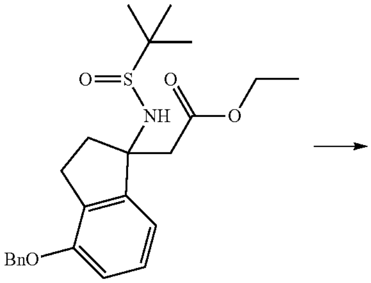
38-5
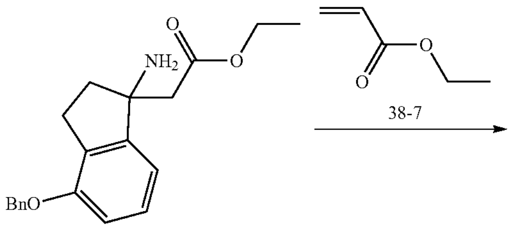
38-6
-continued
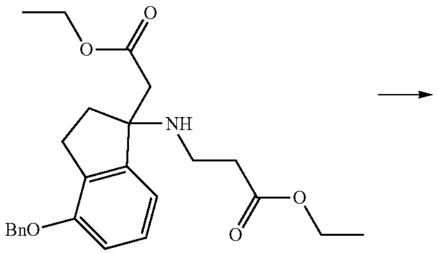
38-8
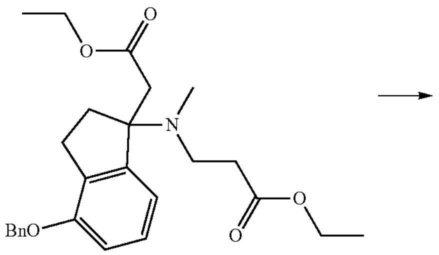
38-9
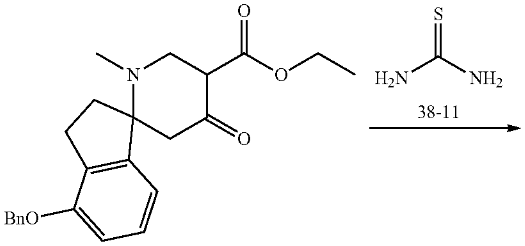
38-10
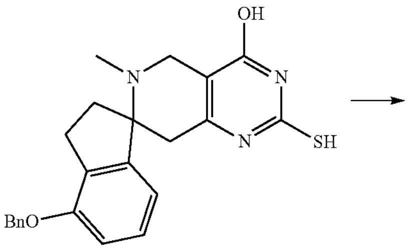
38-12
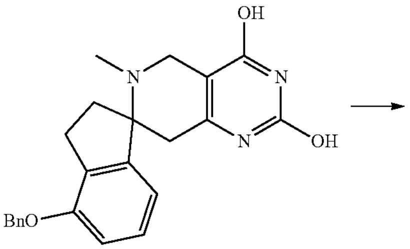
38-13
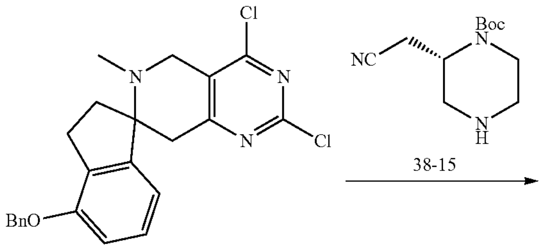
38-14

-continued

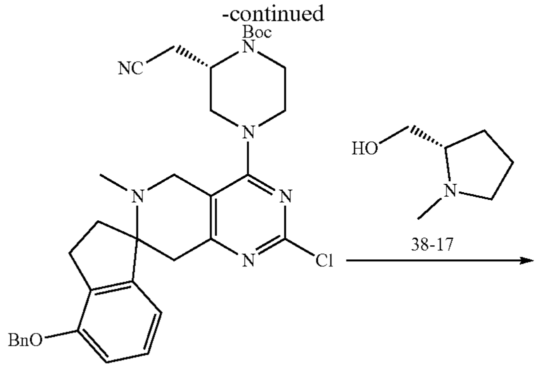

38-16

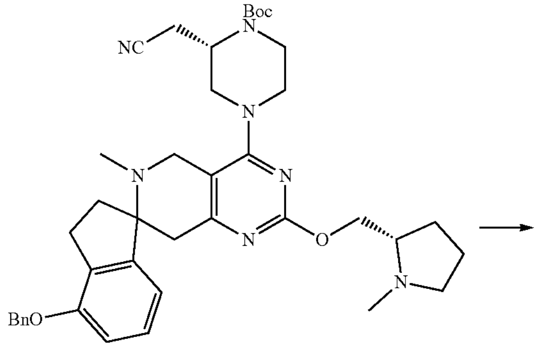

38-18

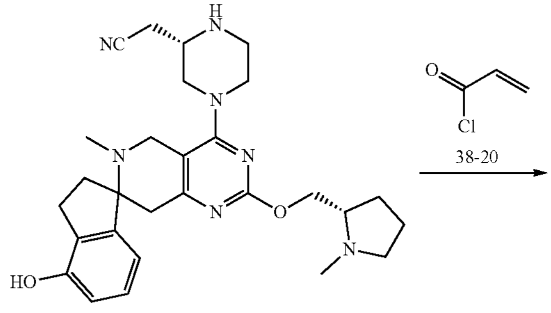

38-19

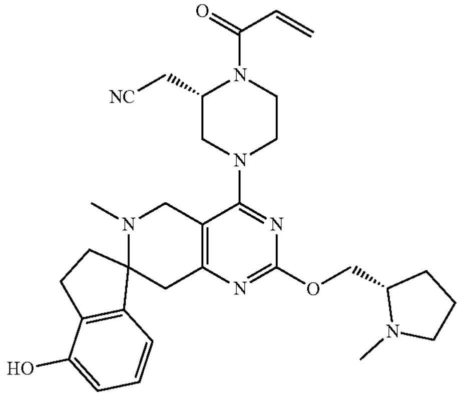

38

(1) To a solution of compound 38-1 (25.0 g, 168 mmol) in acetonitrile (250 mL) was added benzyl bromide (43.3 g, 253 mmol) and cesium carbonate (110 g, 338 mmol), and the reaction solution was stirred at 20° C. for 12 hours under nitrogen protection. Then the reaction solution was concentrated under reduced pressure, added with water (50.0 mL), and extracted with ethyl acetate (40.0 mL×2). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 3:1) to obtain compound 38-2.

MS-ESI $[M+H]^+$, calculated: 239, found: 239.

$^1H$ NMR (400 MHz, $CDCl_3$) δ 7.32-7.40 (m, 4H), 7.30-7.31 (m, 2H), 7.20-7.26 (m, 1H), 7.02-7.04 (d, J=8 Hz, 1H), 5.12 (s, 2H), 3.03-3.06 (m, 2H), 2.62-2.65 (m, 2H).

(2) To a solution of compound 38-2 (20.0 g, 83.9 mmol) in toluene (200 mL) was added compound 38-3 (13.2 g, 109 mmol), and tetraethyl titanate (38.3 g, 168 mmol), and then the reaction solution was stirred at 120° C. for 12 hours under nitrogen protection. Then the reaction solution was added with water (400 mL), and filtered. The filter cake was washed with ethyl acetate (400 mL×2). The combined organic phase was washed with saturated NaCl aqueous solution (500 mL), dried over anhydrous sodium sulfate, filtered, and concentrated under reduced pressure. The crude product was separated by silica gel column chromatography (petroleum ether/ethyl acetate=1:0 to 3:1) to obtain compound 38-4.

MS-ESI $[M+H]^+$, calculated: 342, found: 342.

$^1H$ NMR (400 MHz, $CDCl_3$) δ 7.26-7.44 (m, 7H), 6.99-7.01 (d, J=8 Hz, 1H), 5.15 (s, 2H), 3.42-3.50 (m, 1H), 3.07-3.14 (m, 3H), 1.32 (s, 9H).

(3) To a solution of ethyl acetate (13.7 g, 156 mmol) in tetrahydrofuran (50.0 mL) was added dropwise with lithium diisopropylamide (2 mol/L, 39.0 mL, tetrahydrofuran solution) at −78° C. under nitrogen protection, and the reaction solution was stirred at −78° C. for 1 hour. Then the reaction solution was added dropwise with a solution of compound 38-4 (13.3 g, 39.0 mmol) in tetrahydrofuran (500 mL), and continued stirring for 3 hours at −78° C. Then the reaction solution was quenched with saturated ammonium chloride aqueous solution (1000 mL), and extracted with ethyl acetate (1000 mL×1). The combined organic phase was washed with saturated ammonium chloride aqueous solution (1000 mL×1) and saturated NaCl aqueous solution (1000 mL), dried over anhydrous sodium sulfate, filtered, and concentrated under reduced pressure. The crude product was separated by silica gel column chromatography (petroleum ether/ethyl acetate=1:0 to 1:1) to obtain compound 38-5.

MS-ESI $[M+H]^+$, calculated: 430, found: 430.

(4) To a solution of compound 38-5 (6.80 g, 15.8 mmol) in ethanol (54.0 mL) was added hydrochloric acid in dioxane (4 mol/L, 18.0 mL), and the reaction solution was stirred at 25° C. for 0.5 hour under nitrogen protection. Then the reaction solution was concentrated under reduced pressure to obtain crude product of hydrochloride of compound 38-6.

MS-ESI $[M-NH_2+H]^+$, calculated: 309, found: 309.

(5) To a solution of hydrochloride of compound 38-6 (5.70 g, 15.8 mmol) in ethanol (40.0 mL) was added compound 38-7 (15.8 g, 158 mmol), copper oxide (250 mg, 3.15 mmol), and triethylamine (1.60 g, 15.7 mmol), and the reaction solution was reacted at 78° C. in a sealed tube for 12 hours under nitrogen protection. Then the reaction solution was added with water (200 mL), and extracted with ethyl acetate (100 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 1:1) to obtain compound 38-8.

MS-ESI $[M+H]^+$, calculated: 426, found: 426.

(6) To a solution of compound 38-8 (6.20 g, 14.6 mmol) in ethanol (60.0 mL) was added paraformaldehyde (2.20 g) and sodium cyanoborohydride (2.75 g, 43.7 mmol), and the reaction solution was reacted for 12 hours at 30° C. under nitrogen protection. Then the reaction solution was added with water (100 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 3:1) to obtain compound 38-9.

MS-ESI $[M+H]^+$, calculated: 440, found: 440.

$^1$H NMR (400 MHz, $CDCl_3$) δ 7.40-7.45 (m, 2H), 7.34-7.40 (m, 2H), 7.28-7.33 (m, 1H), 7.11-7.16 (t, 1H), 6.86-6.88 (d, J=7.2 Hz, 1H), 6.75-6.77 (d, J=8.0 Hz, 1H), 5.02-5.11 (m, 2H), 4.07-4.13 (m, 2H), 3.83-3.97 (m, 2H), 2.83-2.97 (m, 3H), 2.71-2.81 (m, 2H), 2.61-2.69 (m, 2H), 2.36-2.47 (m, 3H), 2.22-2.35 (m, 2H), 1.79-1.88 (m, 1H), 1.24 (m, 3H), 1.00-1.04 (t, 3H).

(7) To a solution of compound 38-9 (5.80 g, 13.2 mmol) in tetrahydrofuran (60.0 mL) was added potassium bis (trimethylsilyl) amide (1 mol/L, 39.6 mL, tetrahydrofuran solution) at −78° C., and the reaction solution was reacted at −78° C. for 1 hour under nitrogen protection. Then the reaction solution was added with saturated ammonium chloride aqueous solution (300 mL), and extracted with ethyl acetate (200 mL×2). The combined organic phase was washed with saturated NaCl aqueous solution (200 mL×2), dried over anhydrous sodium sulfate, filtered, and concentrated under reduced pressure. The crude product was separated by silica gel column chromatography (petroleum ether/ethyl acetate=1:0 to 3:1) to obtain compound 38-10.

MS-ESI $[M+H]^+$, calculated: 394, found: 394.

(8) To a solution of compound 38-10 (3.90 g, 9.91 mmol) in ethanol (40.0 mL) was added compound 38-11 (1.51 g, 11.8 mmol) and sodium ethoxide (2.02 g, 29.7 mmol), and the reaction solution was stirred at 80° C. for 12 hours under nitrogen protection. After concentrated under reduced pressure, the reaction solution was adjusted to pH 6 with hydrochloric acid (1 mol/L). The resulting solution was precipitated, and filtered. The filter cake was dried to obtain compound 38-12.

MS-ESI $[M+H]^+$, calculated: 406, found: 406.

(9) To a solution of intermediate 38-12 (3.50 g, 8.64 mmol) in water (40.0 mL) was added chloroacetic acid (7.34 g, 77.6 mmol), and the reaction solution was stirred at 100° C. for 12 hours under nitrogen protection. After the reaction solution was filtered, the filtrate was adjusted to pH 8 with saturated sodium bicarbonate aqueous solution to get precipitate. After filtration, the filter cake was dried to obtain compound 38-13.

MS-ESI $[M+H]^+$, calculated: 390, found: 390.

$^1$H NMR (400 MHz, DMSO-d6) δ 11.37 (s, 1H), 11.17 (s, 1H), 7.45-7.58 (m, 3H), 7.32-7.43 (m, 4H), 7.11 (br s, 1H), 5.17 (s, 2H), 4.05-4.17 (m, 1H), 3.80-3.96 (m, 1H), 3.24-3.29 (m, 1H), 2.88-3.03 (m, 2H), 2.61-2.74 (m, 1H), 2.54-2.60 (m, 1H), 2.43-2.48 (m, 3H), 1.96-2.17 (m, 1H).

(10) Compound 38-13 (1.00 g, 2.57 mmol) was dissolved in phosphorus oxychloride (16.5 g, 107 mmol), and the reaction solution was stirred at 80° C. for 12 hours under nitrogen protection. Then the reaction solution was concentrated under reduced pressure, and extracted with dichloromethane (100 mL×2). The organic phase was washed with saturated sodium bicarbonate aqueous solution (100 mL×2) and saturated NaCl aqueous solution (100 mL×2), dried over anhydrous sodium sulfate, filtered, and concentrated under reduced pressure to obtain compound 38-14.

MS-ESI $[M+H]^+$, calculated: 426, found: 426.

(11) To a solution of compound 38-14 (1.10 g, 2.58 mmol) in N-methylpyrrolidone (10.0 mL) was added potassium carbonate (1.07 g, 7.74 mmol) and compound 38-15 (697 mg, 3.10 mmol), and the reaction solution was stirred at 50° C. for 12 hours under nitrogen protection. Then the reaction solution was added with water (30.0 mL), and extracted with ethyl acetate (20.0 mL×2). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 1:1) to obtain compound 38-16.

MS-ESI $[M+H]^+$, calculated: 615, found: 615.

(12) To a solution of compound 38-16 (790 mg, 1.28 mmol) in dioxane (10.0 mL) was added compound 38-17 (445 mg, 3.85 mmol), cesium carbonate (1.26 g, 3.85 mmol) and (2-dicyclohexylphosphino-2',6'-diisopropoxy-1,1'-biphenyl) [2-(2'-amino-1,1'-biphenyl)]palladium(II) methanesulfonate (215 mg, 257 μmol), and the reaction solution was stirred at 110° C. for 6 hours under nitrogen protection. Then the reaction solution was added with water (30.0 mL), and extracted with ethyl acetate (40.0 mL×2). The combined organic phase was washed with saturated NaCl aqueous solution (40.0 mL×2), dried over anhydrous sodium sulfate, filtered, and concentrated under reduced pressure. The crude product was separated by silica gel column chromatography (dichloromethane/methanol=1:0 to 10:1) to obtain compound 38-18.

MS-ESI $[M+H]^+$, calculated: 694, found: 694.

(13) Compound 38-18 (200 g, 288 μmol) was added into trifluoroacetic acid (10.0 mL), and the reaction solution was stirred at 50° C. for 3 hours under nitrogen protection. Then the reaction solution was concentrated under reduced pressure to obtain the crude trifluoroacetate of compound 38-19.

MS-ESI $[M+H]^+$, calculated: 504, found: 504.

(14) To a solution of trifluoroacetate of compound 38-19 (70.0 mg, 139 μmol) in dichloromethane (1.0 mL) was added triethylamine (42.2 mg, 417 μmol) and compound 38-20 (15.1 mg, 167 μmol), and the reaction solution was stirred at −78° C. for 0.5 hours under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm×3 μm+YMC AQ, 100 mm×30 mm×10 μm, A: water (0.05% hydrochloric acid); B: methanol, 0%-40%: 20 min) to obtain hydrochloride of compound 38.

MS-ESI $[M+H]^+$, calculated: 558, found: 558.

$^1$H NMR (400 MHz, MeOD) δ 7.24-7.31 (m, 2H), 6.84 (br s, 2H), 6.25-6.37 (m, 1H), 5.82-5.92 (m, 1H), 5.01-5.19 (m, 2H), 4.77 (br s, 3H), 4.13 (br s, 2H), 3.99-4.06 (m, 1H), 3.85 (br d, J=6.8 Hz, 3H), 3.45-3.68 (m, 2H), 3.33-3.44 (m, 1H), 3.23-3.29 (m, 1H), 3.11-3.22 (m, 2H), 3.10 (d, J=1.4 Hz, 3H), 2.98-3.08 (m, 2H), 2.73-2.85 (m, 5H), 2.39-2.52 (m, 2H), 2.14-2.29 (m, 2H), 2.04-2.12 (m, 1H).

Example 33 Synthesis of Compound 39

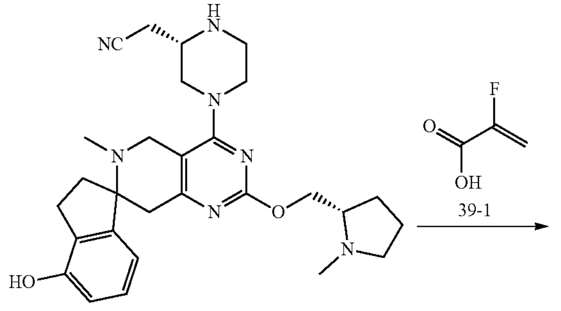

38-19

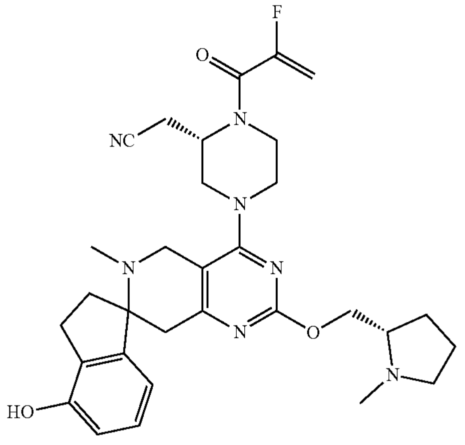

39

To a solution of trifluoroacetate of compound 38-19 (90.0 mg, 180 μmol) in dichloromethane (2.0 mL) was added triethylamine (18.1 mg, 180 μmol), compound 39-1 (113 mg, 1.25 mmol) and propanephosphonic acid anhydride solution (341 mg, 536 μmol, 50% ethyl acetate solution) at 0° C., and the reaction solution was stirred at 0° C. for 0.5 hours. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Phenomenex Luna C18, 100 mm×30 mm×3 μm, A: water (0.225% formic acid); B: acetonitrile, 0%-30%: 8 min) to obtain formate of compound 39.

MS-ESI $[M+H]^+$, calculated: 576, found: 576.

$^1H$ NMR (400 MHz, MeOD) δ 6.95-7.39 (m, 2H), 6.76-6.91 (m, 1H), 5.22-5.47 (m, 2H), 4.54-4.67 (m, 5H), 4.32-4.50 (m, 2H), 3.99-4.26 (m, 3H), 3.68-3.92 (m, 3H), 3.42-3.62 (m, 3H), 3.18-3.27 (m, 2H), 3.10-3.17 (m, 2H), 2.93-3.07 (m, 4H), 2.52-2.86 (m, 3H), 2.37 (br s, 1H), 2.10-2.27 (m, 3H), 1.94-2.08 (m, 1H).

Example 34 Synthesis of Compounds 40 and 41

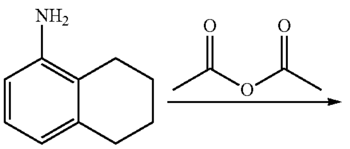

40-1

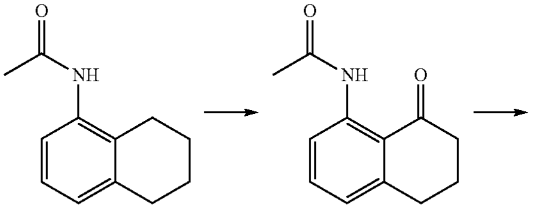

40-2 40-3

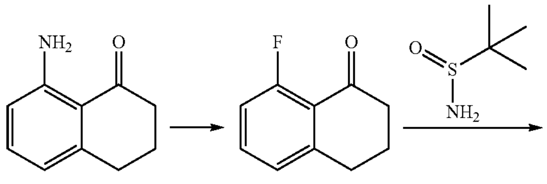

40-4 40-5

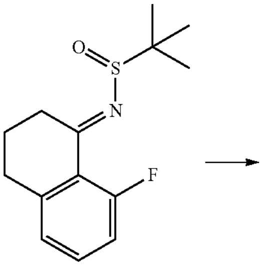

40-6

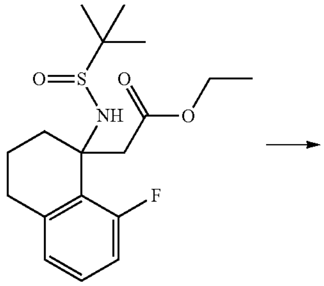

40-7

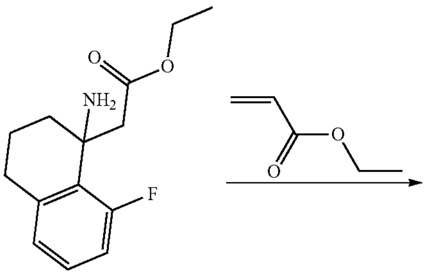

40-8

-continued
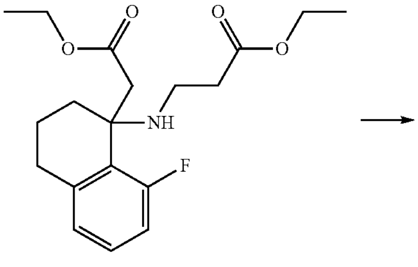
40-9
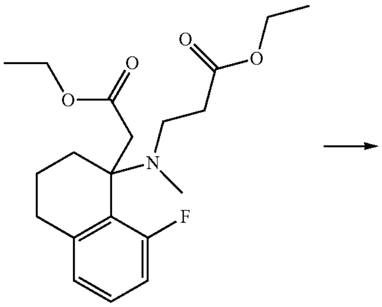
40-10
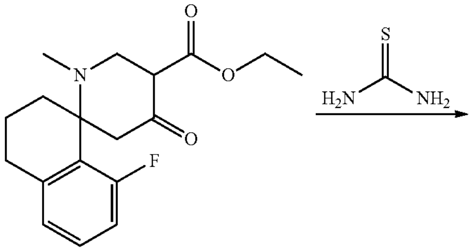
40-11
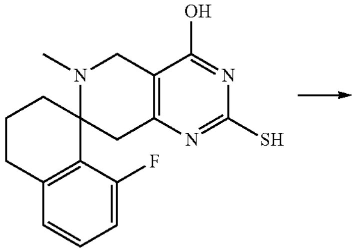
40-12
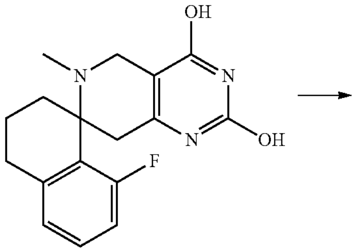
40-13
-continued
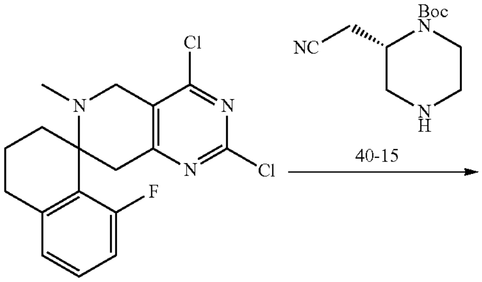
40-14
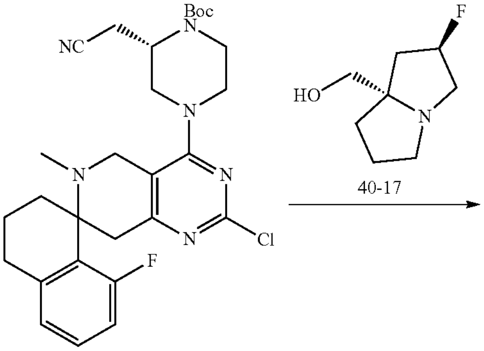
40-16
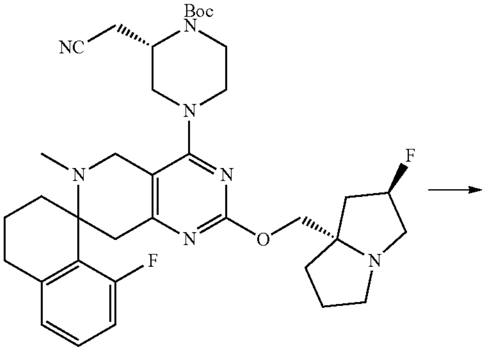
40-18
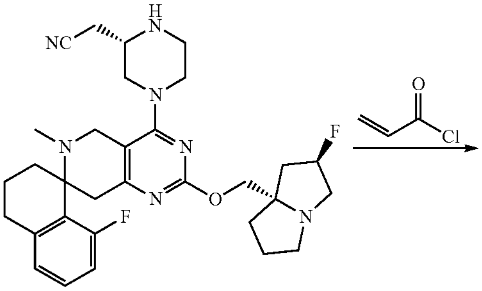
40-19

-continued

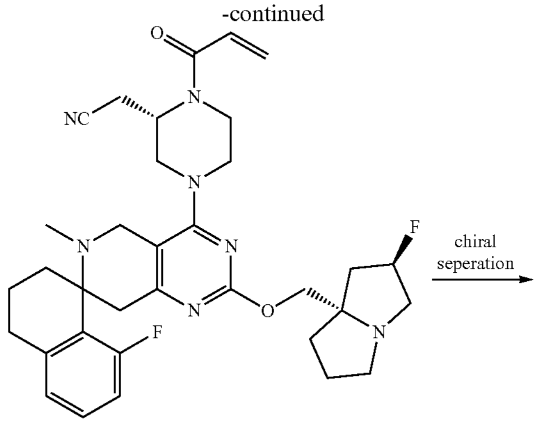

40-20

Compounds 40 and 41

(1) To a solution of compound 40-1 (100 g, 679 mmol) in ethanol (1.0 L) was added acetic anhydride (139 g, 1.36 μmol), and the reaction solution was stirred at 30° C. for 1 hour under nitrogen protection. Then the reaction solution was concentrated under reduced pressure to remove ethanol to obtain crude compound 40-2.

MS-ESI $[M+H]^+$, calculated: 190, found: 190.

(2) To a solution of compound 40-2 (101 g, 534 mmol) in acetone (1.0 L) was added magnesium sulfate (89.1 g, 740 mmol), water (300 mL) and potassium permanganate (253 g, 1.60 μmol), and the reaction solution was stirred at 25° C. for 3 hours under nitrogen protection. After filtration, the residue was added with water (600 mL) and extracted with dichloromethane (500 mL×1). The organic phase was washed with saturated NaCl aqueous solution (500 mL×1), dried over anhydrous sodium sulfate, filtered, concentrated under reduced pressure. The crude product was separated by silica gel column chromatography (petroleum ether/ethyl acetate=1:0 to 10:1) to obtain compound 40-3.

$^1$H NMR (400 MHz, $CDCl_3$) δ 8.60 (d, J=8.4 Hz, 1H), 7.45 (t, J=8.0 Hz, 1H), 6.94 (d, J=7.6, 0.8 Hz, 1H), 2.98 (t, J=6.0 Hz, 2H), 2.66-2.75 (m, 2H), 2.24 (s, 3H), 2.03-2.15 (m, 2H).

(3) To a solution of compound 40-3 (140 g, 689 mmol) in water (1.0 L) was added hydrochloric acid (12 mol/L, 459 mL), and the reaction solution was stirred at 110° C. for 3 hours under nitrogen protection. Then the reaction solution was concentrated under reduced pressure, added with sodium hydroxide aqueous solution (2 mol/L) to adjust pH to 8. After filtration, the filter cake was washed with water (100 mL×1) to obtain compound 40-4.

MS-ESI $[M+H]^+$, calculated: 162, found: 162.

(4) To a solution of compound 40-4 (90.0 g, 558 mmol) in dichloromethane (1.0 L) was added boron trifluoride diethyl etherate (119 g, 838 mmol), and the reaction solution was stirred at 0° C. for 20 minutes. Then the reaction solution was added with isoamyl nitrite (74.9 g, 726 mmol), and continued stirring for 40 minutes at 0° C. under nitrogen protection.

Methyl tert-butyl ether (200 mL) was added. After filtration, the filter cake was washed with methyl tert-butyl ether (200 mL), and dissolved in xylene (100 mL). The resulting solution was stirred at 120° C. for 30 minutes. Then the reaction solution was adjusted to pH 8 with the addition of sodium hydroxide aqueous solution (2 mol/L), and extracted with ethyl acetate (200 mL×3). The combined organic phase was washed with saturated NaCl aqueous solution (500 mL×1), dried over anhydrous sodium sulfate, filtered, and concentrated under reduced pressure. The crude product was separated by silica gel column chromatography (petroleum ether/ethyl acetate=1:0 to 10:1) to obtain compound 40-5.

MS-ESI $[M+H]^+$, calculated: 165, found: 165.

$^1$H NMR (400 MHz, $CDCl_3$) δ 7.42 (d, J=8.0, 5.2 Hz, 1H), 7.06 (d, J=7.6 Hz, 1H), 6.98 (d, J=11.2, 8.4 Hz, 1H), 2.98 (t, J=6.0 Hz, 2H), 2.64-2.69 (m, 2H), 2.09-2.17 (m, 2H).

(5) A solution of compound 40-5 (40.0 g, 244 mmol) in toluene (400 mL) was added with tert-butyl sulfinamide (35.4 g, 292 mmol), and tetraethyl titanate (111 g, 487 mmol), and then stirred at 100° C. for 3 hours under nitrogen protection. Then the reaction solution was added with water (200 mL), and filtered. The filter cake was washed with ethyl acetate (200 mL×3). The combined organic phase was washed with saturated NaCl aqueous solution (300 mL), dried over anhydrous sodium sulfate, filtered, and concentrated under reduced pressure. The crude product was separated by silica gel column chromatography (petroleum ether/ethyl acetate=1:0 to 5:1) to obtain compound 40-6.

MS-ESI $[M+H]^+$, calculated: 268, found: 268.

$^1$H NMR (400 MHz, $CDCl_3$) δ 7.32 (td, J=8.0, 5.2 Hz, 1H), 6.93-7.01 (m, 2H), 3.35 (d, J=17.6, 8.0, 6.0 Hz, 1H), 3.08 (d, J=5.6 Hz, 1H), 2.83-2.90 (m, 2H), 1.91-2.01 (m, 2H), 1.34 (s, 9H).

(6) To a solution of ethyl acetate (49.4 g, 561 mmol) in tetrahydrofuran (200 mL) was added dropwise with lithium diisopropylamide (2 mol/L, 112 mL, tetrahydrofuran solution) at −78° C. under nitrogen protection, and the reaction solution was stirred at −78° C. for 1 hour. Then the reaction solution was added dropwise with a solution of compound 40-6 (30.0 g, 112 mmol) in tetrahydrofuran (100 mL), and continued stirring for 2 hours at −78° C. Then the reaction solution was quenched with saturated ammonium chloride aqueous solution (200 mL), and extracted with ethyl acetate (200 mL×2). The combined organic phase was washed with saturated ammonium chloride aqueous solution (200 mL×1) and saturated NaCl aqueous solution (100 mL×3), dried over anhydrous sodium sulfate, filtered, and concentrated under reduced pressure. The crude product was separated by silica gel column chromatography (petroleum ether/ethyl acetate=1:0 to 3:1) to obtain compound 40-7.

MS-ESI $[M+H]^+$, calculated: 356, found: 356.

$^1$H NMR (400 MHz, $CDCl_3$) δ 7.25 (d, J=8.0, 5.6 Hz, 1H), 7.00 (d, J=7.6 Hz, 1H), 6.88 (d, J=12.4, 8.4 Hz, 1H), 4.01-4.13 (m, 2H), 3.03-3.21 (m, 2H), 2.88 (d, J=16.8, 4.8 Hz, 1H), 2.70-2.80 (m, 1H), 2.19-2.34 (m, 2H), 2.10 (m, J=13.6, Hz, 1H), 1.71-1.82 (m, 1H), 1.20 (s, 9H), 1.14 (t, J=7.2 Hz, 3H).

(7) To a solution of compound 40-7 (20.0 g, 56.3 mmol) in ethanol (100 mL) was added hydrochloric acid in dioxane (4 mol/L, 141 mL), and the reaction solution was stirred at 25° C. for 1 hour under nitrogen protection. Then the reaction solution was concentrated under reduced pressure to obtain crude product of hydrochloride of compound 40-8.

(8) To a solution of hydrochloride of compound 40-8 (18.0 g, 62.6 mmol) in ethanol (200 mL) was added ethyl acrylate (93.9 g, 188 mmol), copper oxide (995 mg, 12.5 mmol), and triethylamine (19.0 g, 188 mmol), and the reaction solution was reacted at 85° C. in a sealed tube for 10 hours under nitrogen protection. Then the reaction solution was added with water (100 mL), and extracted with ethyl acetate (100 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 2:1) to obtain compound 40-9.

MS-ESI $[M+H]^+$, calculated: 352, found: 352.

(9) To a solution of compound 40-9 (15.0 g, 42.7 mmol) in ethanol (200 mL) was added paraformaldehyde (5.50 g), acetic acid (2.56 g, 42.7 mmol) and sodium cyanoborohydride (8.05 g, 128 mmol), and the reaction solution was reacted for 12 hours at 30° C. under nitrogen protection. Then the reaction solution was added with water (100 mL), and extracted with ethyl acetate (100 mL). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 3:1) to obtain compound 40-10.

$^1$H NMR (400 MHz, $CDCl_3$) δ 7.11 (d, J=7.6, 5.2 Hz, 1H), 6.76-6.89 (m, 2H), 4.05-4.13 (m, 2H), 3.79-3.93 (m, 2H), 2.68-2.87 (m, 6H), 2.38 (m, J=14.8, 7.6 Hz, 2H), 2.23 (s, 3H), 2.08-2.18 (m, 2H), 1.69-1.87 (m, 2H), 1.18-1.29 (m, 3H), 0.97 (t, J=7.2 Hz, 3H).

(10) To a solution of compound 40-8 (10.0 g, 27.4 mmol) in tetrahydrofuran (100 mL) was added potassium bis (trimethylsilyl) amide (1 mol/L, 82.1 mL, tetrahydrofuran solution) at −78° C., and the reaction solution was reacted at 0° C. for 2 hours under nitrogen protection. Then the reaction solution was added with saturated ammonium chloride aqueous solution (300 mL), and extracted with ethyl acetate (300 mL). The combined organic phase was washed with saturated NaCl aqueous solution (300 mL), dried over anhydrous sodium sulfate, filtered, and concentrated under reduced pressure. The crude product was separated by silica gel column chromatography (petroleum ether/ethyl acetate=1:0 to 5:1) to obtain compound 40-11.

MS-ESI $[M+H]^+$, calculated: 320, found: 320.

(11) To a solution of compound 40-11 (8.00 g, 25.0 mmol) in ethanol (20.0 mL) was added with thiourea (3.81 g, 50.1 mmol) and sodium ethoxide (5.11 g, 75.2 mmol), and the reaction solution was stirred at 80° C. for 12 hours under nitrogen protection. After being concentrated under reduced pressure, the reaction solution was adjusted to pH 6 with hydrochloric acid (1 mol/L). The resulting solution was precipitated, and filtered. The filter cake was dried to obtain compound 40-12.

MS-ESI $[M+H]^+$, calculated: 332, found: 332.

(12) To a solution of intermediate 40-12 (9.00 g, 27.2 mmol) in water (60.0 mL) was added chloroacetic acid (18.0 g, 190 mmol), and the reaction solution was stirred at 100° C. for 12 hours under nitrogen protection. After the reaction solution was filtered, the filtrate was adjusted to pH 8 with saturated sodium bicarbonate aqueous solution to get precipitate. After filtration, the filter cake was dried to obtain compound 40-13.

MS-ESI $[M+H]^+$, calculated: 316, found: 316.

$^1$H NMR (400 MHz, MeOD) δ7.24 (m, J=7.6, 5.2 Hz, 1H), 6.89-7.01 (m, 2H), 3.58-3.66 (m, 1H), 3.08-3.26 (m, 2H), 2.60-2.84 (m, 3H), 2.11 (s, 3H), 1.89-2.02 (m, 2H), 1.61-1.81 (m, 2H).

(13) Compound 40-13 (8.00 g, 25.4 mmol) was dissolved in phosphorus oxychloride (15.6 g), and the reaction solution was stirred at 100° C. for 3 hours under nitrogen protection. Then the reaction solution was concentrated under reduced pressure, and extracted with dichloromethane (200 mL). The organic phase was washed with saturated sodium bicarbonate aqueous solution (200 mL×2) and saturated NaCl aqueous solution (200 mL×2), dried over anhydrous sodium sulfate, filtered, and concentrated under reduced pressure to obtain compound 40-14.

MS-ESI $[M+H]^+$, calculated: 352, found: 352.

(14) To a solution of compound 40-14 (600 mg, 17.0 mmol) in N-methylpyrrolidone (50.0 mL) was added potassium carbonate (7.06 g, 51.1 mmol) and compound 40-15 (4.99 g, 22.1 mmol), and the reaction solution was stirred at 50° C. for 3 hours under nitrogen protection. Then the reaction solution was added with ethyl acetate (200 mL), washed with saturated NaCl aqueous solution (200 mL×5), dried over anhydrous sodium sulfate, filtered, and concentrated under reduced pressure. The crude product was separated by silica gel column chromatography (petroleum ether/ethyl acetate=1:0 to 10:1) to give compound 40-16.

MS-ESI $[M+H]^+$, calculated: 541, found: 541.

(15) To a solution of compound 40-16 (1.00 g, 1.85 mmol) in dioxane (20.0 mL) was added compound 40-17 (442 mg, 2.78 mmol), cesium carbonate (1.81 g, 5.54 mmol) and (2-dicyclohexylphosphino-2',6'-diisopropoxy-1,1'-biphenyl) [2-(2'-amino-1,1'-biphenyl)] palladium(II) methanesulfonate (100 mg, 120 μmol), and the reaction solution was stirred at 110° C. for 3 hours under nitrogen protection. Then the reaction solution was added with ethyl acetate (50.0 mL), washed with saturated NaCl aqueous solution (50.0 mL×3), dried over anhydrous sodium sulfate, filtered, and concentrated under reduced pressure. The crude product was separated by silica gel column chromatography (dichloromethane/methanol=1:0 to 30:1) to obtain compound 40-18.

MS-ESI $[M+H]^+$, calculated: 664, found: 664.

$^1$H NMR (400 MHz, MeOD) δ 7.22 (td, J=7.6, 5.2 Hz, 1H), 6.98 (d, J=7.6 Hz, 1H), 6.91 (dd, J=12.4, 8.0 Hz, 1H), 5.13-5.43 (m, 1H), 4.60 (d, J=12.4 Hz, 2H), 4.04-4.23 (m, 3H), 3.84-4.04 (m, 2H), 3.56-3.77 (m, 2H), 3.40 (dd, J=13.6, 3.6 Hz, 1H), 3.22-3.29 (m, 2H), 3.10-3.22 (m, 3H), 2.94-3.05 (m, 3H), 2.71-2.86 (m, 3H), 2.22-2.36 (m, 1H), 2.13-2.18 (m, 3H), 2.04-2.13 (m, 2H), 1.94-2.02 (m, 3H), 1.83-1.93 (m, 2H), 1.56-1.82 (m, 2H), 1.51 (d, J=2.4 Hz, 9H).

(16) To a solution of compound 40-18 (910 g, 1.37 mmol) in dichloromethane (10.0 mL) was added hydrochloric acid in dioxane (4 mol/L, 5.0 mmol), and the reaction solution was stirred at 25° C. for 2 hours under nitrogen protection. Then the reaction solution was adjusted to pH 8 by saturated sodium bicarbonate aqueous solution and extracted with dichloromethane (20 mL×2). The organic phase was washed with saturated sodium bicarbonate aqueous solution (20 mL) and saturated NaCl aqueous solution (50 mL), dried over anhydrous sodium sulfate, filtered, and concentrated under reduced pressure to obtain compound 40-19.

MS-ESI $[M+H]^+$, calculated: 564, found: 564.

(17) To a solution compound 40-19 (672 g, 1.19 mmol) in dichloromethane (10.0 mL) was added triethylamine (362 mg, 3.58 mmol) and acryloyl chloride (216 mg, 2.39 mmol), and then the reaction solution was stirred at −65° C. for 0.5 hour under nitrogen protection. Then the reaction solution was added with dichloromethane (20.0 mL), washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 30:1) to obtain compound 40-20.

(18) Compound 40-20 was separated by chiral supercritical fluid chromatography to obtain compounds 40 and 41.

Separation conditions: Chromatographic column model: (S,S)-Whelk-0-1.8; Column specification: 50×4.6 mm I.D., 1.8 m; Injection volume: 10.0 μL; Mobile phase: A: carbon dioxide, B: ethanol (0.05% diethylamine), B %: 40% elution for 7 min; Detection wavelength: 254 nm; Column temperature: 35° C.

Compound 40: retention time 2.328 minutes, 100% ee.

MS-ESI $[M+H]^+$, calculated: 618, found: 618.

$^1H$ NMR (400 MHz, MeOD) δ 7.22 (m, J=7.6, 5.2 Hz, 1H), 6.98 (d, J=7.6 Hz, 1H), 6.91 (dd, J=12.4, 8.0 Hz, 1H), 6.28 (d, J=16.8 Hz, 1H), 5.83 (d, J=10.4 Hz, 1H), 5.18-5.37 (m, 1H), 5.03 (s, 1H), 4.70-4.85 (m, 2H), 4.10-4.32 (m, 3H), 3.90-4.10 (m, 2H), 3.65-3.80 (m, 2H), 3.38-3.51 (m, 1H), 3.18-3.28 (m, 3H), 3.08-3.18 (m, 2H), 2.95-3.02 (m, 2H), 2.89 (s, 2H), 2.67-2.84 (m, 2H), 2.16-2.41 (m, 2H), 2.16 (s, 3H), 2.03-2.13 (m, 2H), 1.94-2.03 (m, 3H), 1.85-1.93 (m, 2H), 1.68-1.79 (m, 1H).

Compound 41: retention time 1.677 minutes, 100% ee.

MS-ESI $[M+H]^+$, calculated: 618, found: 618.

$^1H$ NMR (400 MHz, MeOD) δ 7.22 (td, J=7.6, 5.2 Hz, 1H), 6.98 (d, J=7.6 Hz, 1H), 6.92 (dd, J=12.4, 8.0 Hz, 1H), 6.29 (d, J=16.8 Hz, 1H), 5.83 (d, J=10.4 Hz, 1H), 5.14-5.41 (m, 1H), 5.08 (s, 1H), 4.70-4.84 (m, 2H), 4.11-4.40 (m, 3H), 3.92-4.11 (m, 2H), 3.60-3.78 (m, 2H), 3.37-3.60 (m, 1H), 3.21-3.29 (m, 3H), 3.17-3.21 (m, 2H), 3.12-3.17 (m, 2H), 2.94-3.01 (m, 2H), 2.72-2.86 (m, 2H), 2.17-2.34 (m, 2H), 2.16 (s, 3H), 2.03-2.13 (m, 2H), 1.94-2.02 (m, 3H), 1.82-1.92 (m, 2H), 1.68-1.80 (m, 1H).

Example 35 Synthesis of Compounds 42 and 43

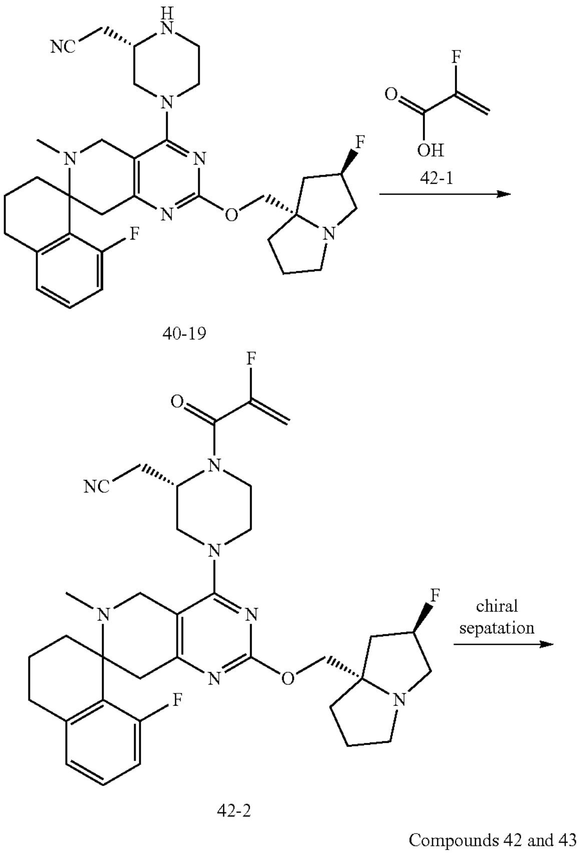

40-19

42-2

Compounds 42 and 43

To a solution of compound 40-19 (1.50 g, 2.66 mmol) in ethyl acetate (15.0 mL) was added triethylamine (809 mg, 7.99 mmol), compound 42-1 (719 mg, 7.98 mmol), 4A molecular sieve (1.50 g) and propanephosphonic acid anhydride solution (6.78 g, 10.6 mmol, 50% ethyl acetate solution), and the reaction solution was stirred at 25° C. for 0.5 hours. Then the reaction solution was added with ethyl acetate (50.0 mL), washed with saturated NaCl aqueous solution (50.0 mL×2), dried over anhydrous sodium sulfate, filtered, and concentrated under reduced pressure. The crude product was separated by silica gel column chromatography (dichloromethane/methanol=1:0 to 30:1) to obtain compound 42-2.

(2) Compound 42-2 was separated by chiral supercritical fluid chromatography to obtain compounds 42 and 43.

Separation conditions: Chromatographic column model: Chiralpak OX-3; column specification: 100×4.6 mm I.D., 3 m; Injection volume: 10.0 μL; Mobile phase: A: Carbon dioxide, B: Ethanol (0.05% diethylamine), B %: 40% fixed concentration elution for 4 min; detection wavelength: 254 nm; column temperature: 35° C.

Compound 42: retention time 1.385 minutes, 100% ee.

MS-ESI $[M+H]^+$, calculated: 636, found: 636.

$^1H$ NMR (400 MHz, MeOD) δ 7.22 (td, J=7.6, 5.2 Hz, 1H), 6.98 (d, J=7.6 Hz, 1H), 6.92 (dd, J=12.8, 8.0 Hz, 1H), 5.29-5.44 (m, 2H), 5.18-5.28 (m, 1H), 4.11-4.19 (m, 2H), 4.05-4.11 (m, 2H), 3.71-3.78 (m, 1H), 3.63-3.68 (m, 1H), 3.46 (d, J=13.2 Hz, 1H), 3.32-3.33 (m, 1H), 3.22-3.30 (m, 3H), 3.13-3.22 (m, 2H), 2.99-3.12 (m, 3H), 2.89-2.99 (m, 2H), 2.75-2.88 (m, 2H), 2.22-2.33 (m, 1H), 2.18 (s, 1H), 2.16 (s, 3H), 2.04-2.14 (m, 2H), 1.95-2.04 (m, 3H), 1.88-1.88 (m, 3H), 1.76-1.94 (m, 1H).

Compound 43: retention time 2.071 minutes, 100% ee.

MS-ESI $[M+H]^+$, calculated: 636, found: 636.

$^1H$ NMR (400 MHz, MeOD) δ 7.22 (td, J=7.6, 5.2 Hz, 1H), 6.98 (d, J=7.6 Hz, 1H), 6.91 (dd, J=12.8, 8.0 Hz, 1H), 5.29-5.43 (m, 2H), 5.26 (s, 1H), 4.27 (d, J=13.6 Hz, 1H), 4.18 (q, J=10.4 Hz, 2H), 3.99 (d, J=11.2 Hz, 1H), 3.71-3.79 (m, 1H), 3.59-3.68 (m, 1H), 3.38-3.56 (m, 1H), 3.36 (d, J=2.4 Hz, 1H), 3.27 (d, J=3.6 Hz, 3H), 3.21-3.27 (m, 2H), 3.05-3.20 (m, 3H), 2.85-3.05 (m, 2H), 2.65-2.84 (m, 2H), 2.26-2.40 (m, 1H), 2.19-2.26 (m, 1H), 2.16 (s, 3H), 2.04-2.15 (m, 2H), 1.96-2.04 (m, 3H), 1.77-1.96 (m, 3H), 1.65-1.77 (m, 1H).

Example 36 Synthesis of Compounds 44 and 45

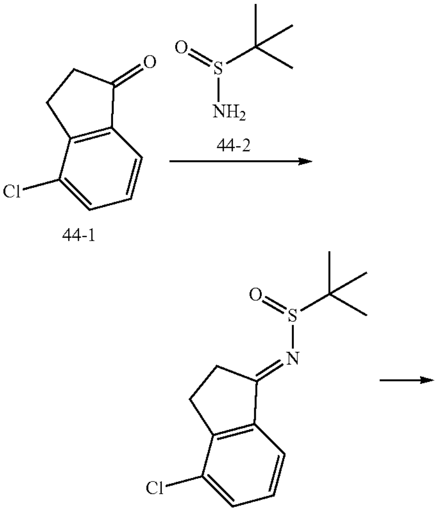

44-1

44-3

-continued
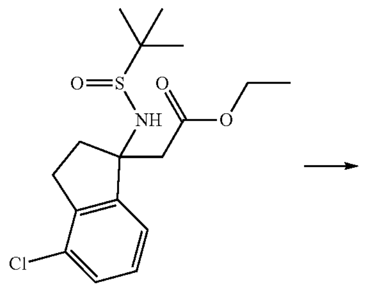
44-4
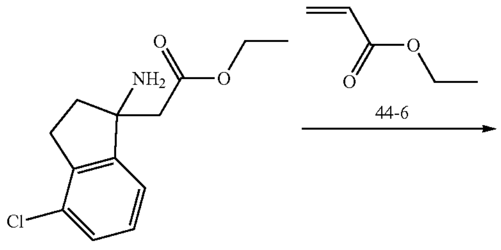
44-5
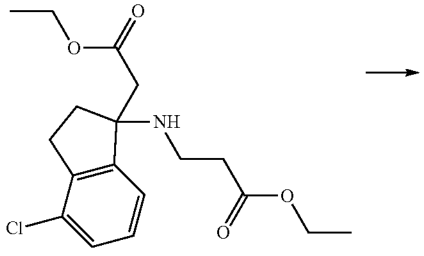
44-7
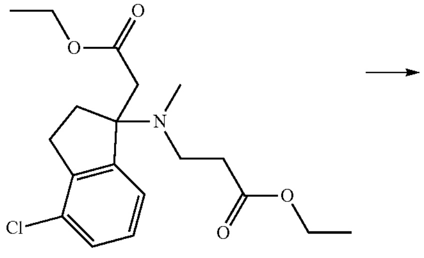
44-8
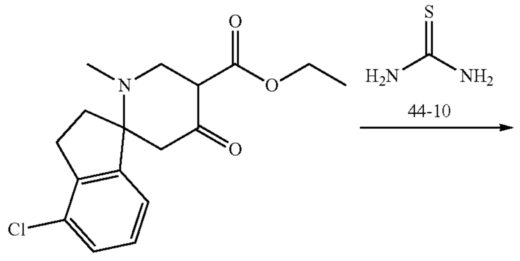
44-9
-continued
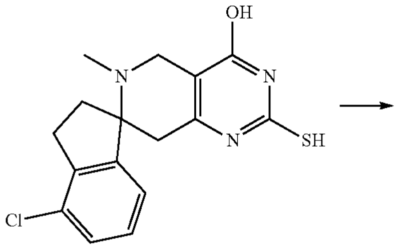
44-11
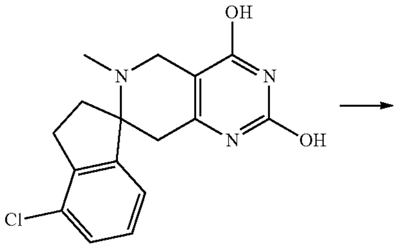
44-12
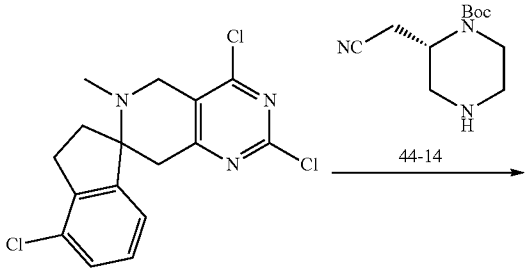
44-13
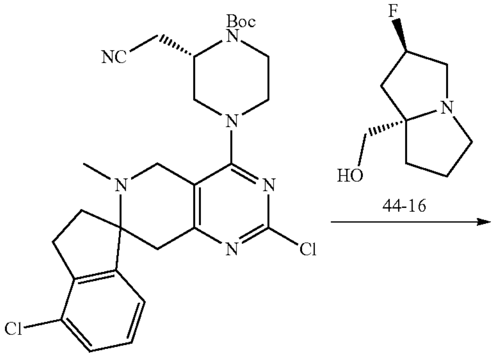
44-15
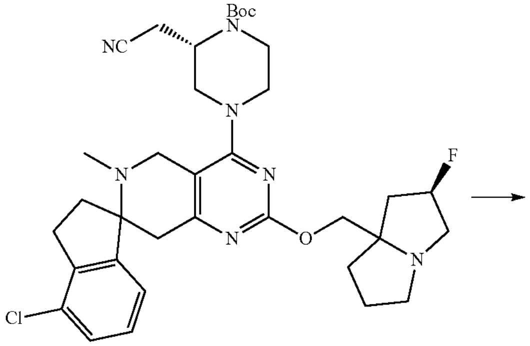
44-17

-continued

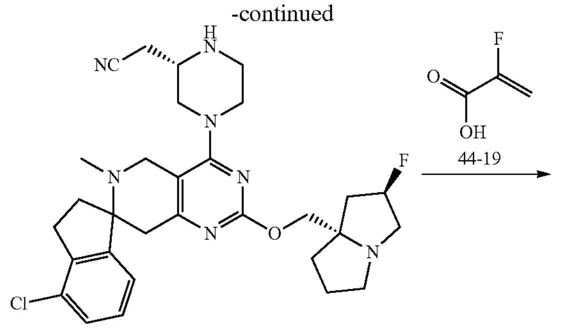

44-18

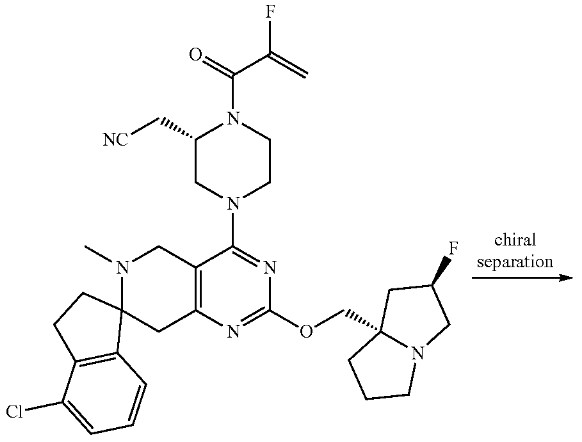

44-20

Compounds 44 and 45

(1) To a solution of compound 44-1 (5.00 g, 30.0 mmol) in toluene (50.0 mL) was added compound 44-2 (4.36 g, 36.0 mmol), tetraethyl titanate (13.7 g, 60.0 mmol), and the reaction solution was stirred at 110° C. for 12 hours under nitrogen protection. Then the reaction solution was added with water (150 mL), and filtered. The filter cake was washed with ethyl acetate (150 mL×2). The combined organic phase was washed with saturated NaCl aqueous solution (150 mL), dried over anhydrous sodium sulfate, filtered, and concentrated under reduced pressure. The crude product was separated by silica gel column chromatography (petroleum ether/ethyl acetate=1:0 to 10:1) to obtain compound 44-3.

MS-ESI $[M+H]^+$, calculated: 270, found: 270.

$^1H$ NMR (400 MHz, $CDCl_3$) δ 7.70 (d, J=7.6 Hz, 1H), 7.50 (d, J=8.0 Hz, 1H), 7.30 (t, J=7.6 Hz, 1H), 3.46-3.56 (m, 1H), 3.06-3.19 (m, 3H), 1.33 (s, 9H).

(2) To a solution of ethyl acetate (8.16 g, 92.6 mmol) in tetrahydrofuran (200 mL) was added dropwise with lithium diisopropylamide (2 mol/L, 18.5 mL, tetrahydrofuran solution) at −78° C. under nitrogen protection, and the reaction solution was stirred at −65° C. for 1 hour. Then the reaction solution was added dropwise with a solution of compound 44-3 (5.0 g, 18.5 mmol) in tetrahydrofuran (500 mL), and then continued stirring for 2 hours at −65° C. Then the reaction solution was quenched with saturated ammonium chloride aqueous solution (50.0 mL), and extracted with ethyl acetate (100 mL). The combined organic phase was washed with saturated ammonium chloride aqueous solution (100 mL×1) and saturated NaCl aqueous solution (100 mL), dried over anhydrous sodium sulfate, filtered, and concentrated under reduced pressure. The crude product was separated by silica gel column chromatography (petroleum ether/ethyl acetate=1:0 to 6:1) to obtain compound 44-4.

MS-ESI $[M+H]^+$, calculated: 358, found: 358.

(3) To a solution of compound 44-4 (2.30 g, 6.43 mmol) in ethanol (15.0 mL) was added hydrochloric acid in dioxane (4 mol/L, 10.0 mL), and the reaction solution was stirred at 25° C. for 1 hour under nitrogen protection. Then the reaction solution was concentrated under reduced pressure to obtain crude product of hydrochloride of compound 44-5.

(4) To a solution of hydrochloride of compound 44-5 (2.30 g, 9.06 mmol) in ethanol (20.0 mL) was added compound 44-6 (9.08 g, 90.6 mmol), copper oxide (144 mg, 1.81 mmol), triethylamine (2.75 g, 27.2 mmol), and the reaction solution was reacted at 85° C. in a sealed tube for 12 hours under nitrogen protection. Then the reaction solution was added with water (100 mL), and extracted with ethyl acetate (200 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 6:1) to obtain compound 44-7.

MS-ESI $[M+H]^+$, calculated: 354, found: 354.

$^1H$ NMR (400 MHz, $CDCl_3$) δ 7.19-7.23 (m, 1H), 7.12-7.19 (m, 2H), 4.06-4.16 (m, 4H), 2.95-3.06 (m, 1H), 2.81-2.93 (m, 1H), 2.67-2.79 (m, 2H), 2.59-2.67 (m, 1H), 2.48-2.55 (m, 1H), 2.42-2.48 (m, 2H), 2.34 (dt, J=13.6, 8.0 Hz, 1H), 2.19 (ddd, J=13.6, 8.8, 4.4 Hz, 1H), 1.25 (t, J=7.2 Hz, 3H), 1.20 (t, J=7.2 Hz, 3H).

(5) To a solution of compound 44-7 (2.00 g, 5.65 mmol) in ethanol (20.0 mL) was added paraformaldehyde (2.00 g) and sodium cyanoborohydride (1.07 g, 17.0 mmol), and the reaction solution was reacted for 10 hours at 25° C. under nitrogen protection. Then the reaction solution was added with water (100 mL), and extracted with ethyl acetate (100 mL). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 6:1) to obtain compound 44-8.

MS-ESI $[M+H]^+$, calculated: 368, found: 368.

$^1H$ NMR (400 MHz, $CDCl_3$) δ 7.18-7.24 (m, 1H), 7.12-7.17 (m, 2H), 4.11 (q, J=7.2 Hz, 2H), 3.82-3.98 (m, 2H), 2.83-3.02 (m, 3H), 2.71-2.81 (m, 1H), 2.56-2.68 (m, 2H), 2.23-2.48 (m, 4H), 2.17 (s, 3H), 1.25 (t, J=7.2 Hz, 3H), 1.02 (t, J=7.2 Hz, 3H).

(6) To a solution of compound 44-8 (1.50 g, 4.08 mmol) in tetrahydrofuran (15.0 mL) was added potassium bis(trimethylsilyl) amide (1 mol/L, 8.16 mL, tetrahydrofuran solution) at −78° C., and the reaction solution was reacted at −65° C. for 2 hours under nitrogen protection. Then the reaction solution was added with saturated ammonium chloride aqueous solution (50.0 mL), and extracted with ethyl acetate (50.0 mL). The combined organic phase was washed with saturated NaCl aqueous solution (50.0 mL), dried over anhydrous sodium sulfate, filtered, and concentrated under reduced pressure. The crude product was separated by silica gel column chromatography (petroleum ether/ethyl acetate=1:0 to 6:1) to obtain compound 44-9.

MS-ESI $[M+H]^+$, calculated: 322, found: 322.

(7) To a solution of compound 44-9 (1.08 g, 3.36 mmol) in ethanol (10.0 mL) was added compound 44-10 (510 mg, 6.71 mmol) and sodium ethoxide (685 mg, 10.1 mmol), and the reaction solution was stirred at 80° C. for 12 hours under nitrogen protection. After being concentrated under reduced pressure, the reaction solution was adjusted to pH 6 with hydrochloric acid (1 mol/L). The resulting solution was precipitated, and filtered. The filter cake was dried to obtain compound 44-11.

MS-ESI $[M+H]^+$, calculated: 334, found: 334.

$^1$H NMR (400 MHz, DMSO-d6) δ 12.42-12.50 (m, 1H), 12.31 (br d, J=2.0 Hz, 1H), 7.13-7.51 (m, 3H), 3.36-3.42 (m, 2H), 2.85-2.99 (m, 2H), 2.63-2.70 (m, 1H), 2.53 (br d, J=2.0 Hz, 1H), 2.29-2.37 (m, 1H), 2.16-2.28 (m, 1H), 1.88-2.15 (m, 3H).

(8) To a solution of intermediate 44-11 (848 mg, 2.54 mmol) in water (10.0 mL) was added chloroacetic acid (1.20 g, 12.7 mmol), and the reaction solution was stirred at 100° C. for 16 hours under nitrogen protection. After the reaction solution was filtered, the filtrate was adjusted to pH 8 with saturated sodium bicarbonate aqueous solution to get precipitate. After filtration, the filter cake was dried to obtain compound 44-12.

MS-ESI $[M+H]^+$, calculated: 318, found: 318.

$^1$H NMR (400 MHz, DMSO-d6) δ 11.03 (br s, 1H), 10.78 (br s, 1H), 7.28 (s, 2H), 7.15-7.20 (m, 1H), 2.75-3.25 (m, 4H), 2.31-2.40 (m, 2H), 2.20 (dt, J=13.6, 8.0 Hz, 1H), 1.96 (s, 3H), 1.69 (ddd, J=13.6, 8.8, 4.8 Hz, 1H).

(9) Compound 44-12 (236 mg, 743 μmol) was dissolved in phosphorus oxychloride (13.3 g, 86.7 mmol), and the reaction solution was stirred at 80° C. for 6 hours under nitrogen protection. Then the reaction solution was concentrated under reduced pressure, and extracted with dichloromethane (10.0 mL). The organic phase was washed with saturated sodium bicarbonate aqueous solution (10.0 mL×2) and saturated NaCl aqueous solution (10.0 mL×2), dried over anhydrous sodium sulfate, filtered, and concentrated under reduced pressure to obtain compound 44-13.

MS-ESI $[M+H]^+$, calculated: 354, found: 354.

(10) To a solution of compound 44-13 (600 mg, 1.69 mmol) in N-methylpyrrolidone (10.0 mL) was added potassium carbonate (701 mg, 5.08 mmol) and compound 44-14 (419 mg, 1.86 mmol), and the reaction solution was stirred at 50° C. for 10 hours under nitrogen protection. Then the reaction solution was added with ethyl acetate (30.0 mL), washed with saturated NaCl aqueous solution (30.0 mL×5), dried over anhydrous sodium sulfate, filtered, and concentrated under reduced pressure. The crude product was separated by silica gel column chromatography (petroleum ether/ethyl acetate=1:0 to 3:1) to give compound 44-15.

MS-ESI $[M+H]^+$, calculated: 543, found: 543.

(11) To a solution of compound 44-15 (200 mg, 367 μmol) in dioxane (5.00 mL) was added compound 44-16 (175 mg, 1.10 mmol), potassium carbonate (127 mg, 1.10 mmol), tris(dibenzylidene acetone)dipalladium (67.4 mg, 73.6 μmol) and 2-dicyclohexylphosphine-2', 6'-diisopropoxy-1, 1'-biphenyl (68.6 mg, 147 μmol), and the reaction solution was stirred at 110° C. for 4 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by silica gel column chromatography (dichloromethane/methanol=1:0 to 3:1) to obtain compound 44-17.

MS-ESI $[M+H]^+$, calculated: 666, found: 666.

(12) To a solution of compound 44-17 (74.0 g, 111 μmol) in dichloromethane (3.0 mL) was added trifluoroacetic acid (2.85 g, 24.9 mmol), and the reaction solution was stirred at 25° C. for 1 hour under nitrogen protection. Then the reaction solution was extracted with ethyl acetate (50 mL×2) and the organic phase was washed by saturated sodium bicarbonate aqueous solution (50 mL) and saturated NaCl aqueous solution (50 mL), dried over anhydrous sodium sulfate, filtered, and concentrated under reduced pressure to obtain crude compound 44-18.

MS-ESI $[M+H]^+$, calculated: 566, found: 566.

(13) To a solution of compound 44-18 (65.0 mg, 114 μmol) in ethyl acetate (3.0 mL) was added triethylamine (34.8 mg, 344 μmol), compound 44-19 (31.0 mg, 344 μmol), 4A molecular sieve (40.0 mg) and propanephosphonic acid anhydride solution (219 mg, 344 μmol, 50% ethyl acetate solution) at 0° C., and the reaction solution was stirred at 25° C. for 1 hour. Then the reaction solution was added with dichloromethane (10.0 mL), washed with saturated NaCl aqueous solution (10.0 mL×2), dried over anhydrous sodium sulfate, filtered, and concentrated under reduced pressure. The crude product was separated by preparative high performance liquid chromatography (Phenomenex Luna C18, 75 mm×30 mm×3 μm, A: water (10 mmol/L ammonium bicarbonate); B: acetonitrile, 41%-61%: 11 min) to obtain compound 44-20.

(14) Compound 44-20 was separated by chiral supercritical fluid chromatography to obtain compounds 44 and 45.

Separation conditions: Chromatographic column model: Chiralpak IC-3; column specification: 50×4.6 mm I.D., 3 m; Injection volume: 8.0 μL; Mobile phase: A: Carbon dioxide, B: Ethanol (0.05% diethylamine), B %: 40% fixed concentration elution for 4 min; detection wavelength: 254 nm; column temperature: 35° C.

Compound 44: retention time: 1.342 minutes, 98.64% ee.

MS-ESI $[M+H]^+$, calculated: 638, found: 638.

$^1$H NMR (400 MHz, MeOD) δ 7.24-7.32 (m, 2H), 7.16 (dd, J=7.2, 1.2 Hz, 1H), 5.32-5.40 (m, 1H), 5.23-5.31 (m, 1H), 4.09-4.31 (m, 4H), 4.00 (br d, J=12.4 Hz, 1H), 3.71 (s, 2H), 3.27 (br s, 2H), 3.20-3.23 (m, 1H), 2.90-3.16 (m, 8H), 2.39-2.50 (m, 1H), 2.16-2.25 (m, 5H), 2.08-2.15 (m, 1H), 1.96-2.04 (m, 2H), 1.91 (ddd, J=13.6, 8.8, 4.4 Hz, 2H), 1.25-1.36 (m, 4H).

Compound 45: retention time: 1.807 minutes, 97.24% ee.

MS-ESI $[M+H]^+$, calculated: 638, found: 638.

$^1$H NMR (400 MHz, MeOD) δ 7.24-7.32 (m, 2H), 7.16 (dd, J=7.2, 1.2 Hz, 1H), 5.32-5.40 (m, 1H), 5.23-5.31 (m, 1H), 4.09-4.31 (m, 4H), 4.00 (br d, J=12.4 Hz, 1H), 3.71 (s, 2H), 3.27 (br s, 2H), 3.20-3.23 (m, 1H), 2.90-3.16 (m, 8H), 2.39-2.50 (m, 1H), 2.16-2.25 (m, 5H), 2.08-2.15 (m, 1H), 1.96-2.04 (m, 2H), 1.91 (ddd, J=13.6, 8.8, 4.4 Hz, 2H), 1.25-1.36 (m, 4H).

Example 37 Synthesis of Compounds 46 and 47

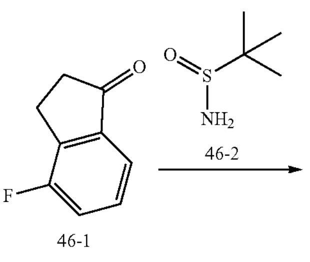

46-1

-continued
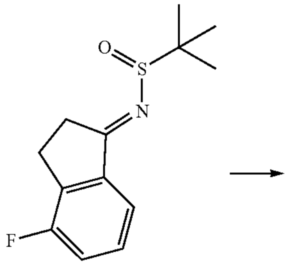
46-3
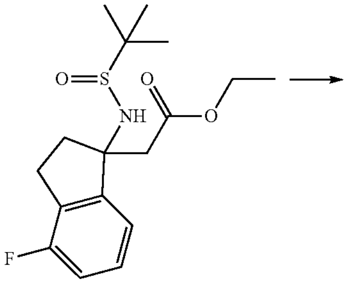
46-4
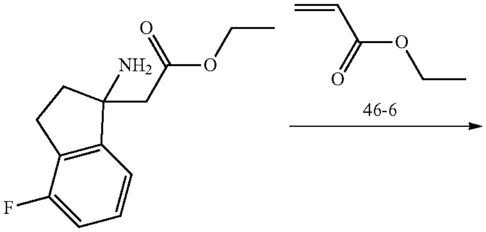
46-5
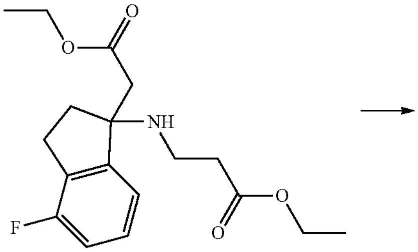
46-7
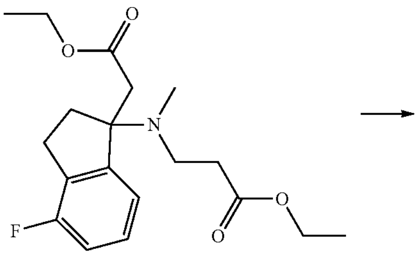
46-8
-continued
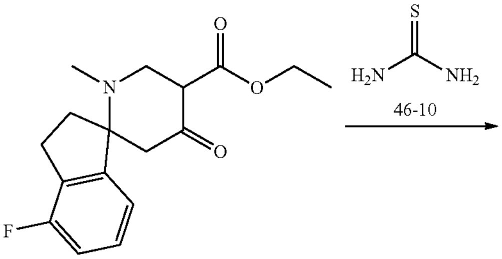
46-9
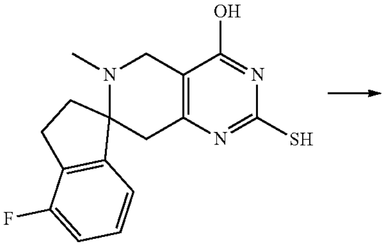
46-11
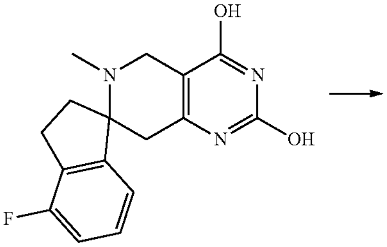
46-12
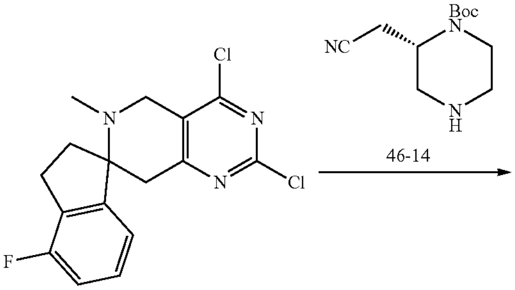
46-13
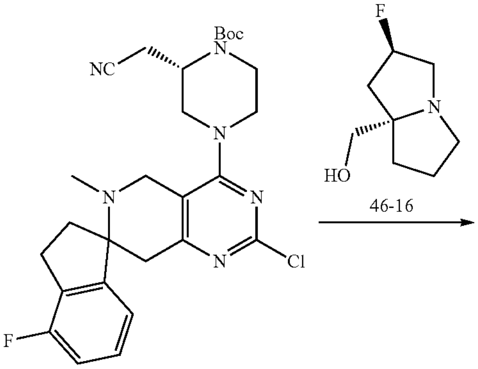
46-15

-continued

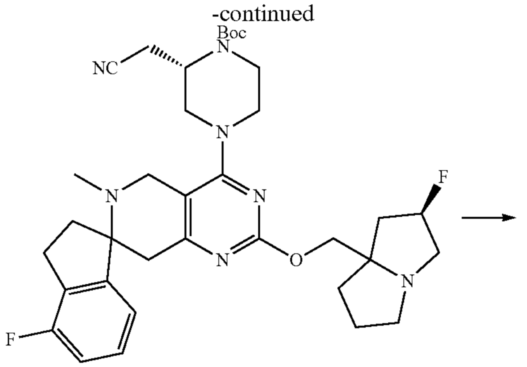

46-17

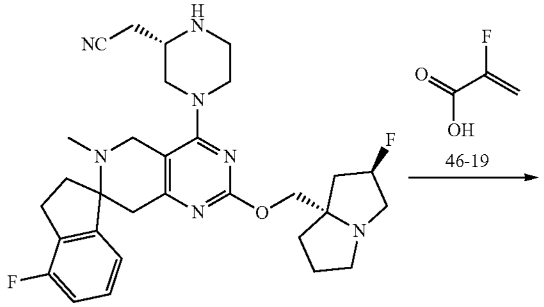

46-18

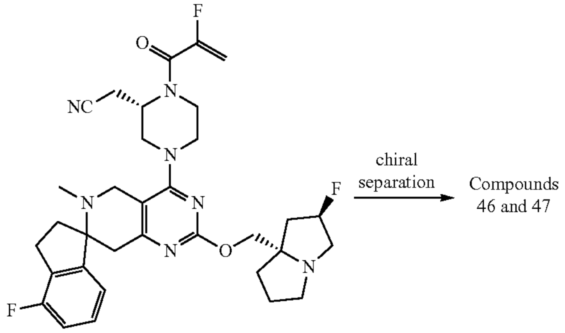

46-20

(1) To a solution of compound 46-1 (21.0 g, 140 mmol) in toluene (300 mL) was added compound 46-2 (20.3 g, 168 mmol), tetraethyl titanate (63.8 g, 280 mmol), and the reaction solution was stirred at 110° C. for 2 hours under nitrogen protection. Then the reaction solution was added with water (200 mL), and filtered. The filter cake was washed with ethyl acetate (500 mL×3). The combined organic phase was washed with saturated NaCl aqueous solution (150 mL), dried over anhydrous sodium sulfate, filtered, and concentrated under reduced pressure. The crude product was separated by silica gel column chromatography (petroleum ether/ethyl acetate=1:0 to 2:1) to obtain compound 46-3.

MS-ESI $[M+H]^+$, calculated: 254, found: 254.

$^1H$ NMR (400 MHz, $CDCl_3$) δ 7.59 (d, J=8.0 Hz, 1H), 7.28-7.34 (m, 1H), 7.13-7.20 (m, 1H), 3.44-3.55 (m, 1H), 3.10-3.20 (m, 3H), 1.32 (s, 9H).

(2) To a solution of ethyl acetate (27.0 g, 306 mmol) in tetrahydrofuran (200 mL) was added dropwise with lithium diisopropylamide (2 mol/L, 61.2 mL, tetrahydrofuran solution) at −78° C. under nitrogen protection, and the reaction solution was stirred at −78° C. for 1 hour. Then the reaction solution was added dropwise with a solution of compound 46-3 (15.5 g, 61.2 mmol) in tetrahydrofuran (200 mL), and continued stirring for 2 hours at −78° C. Then the reaction solution was quenched with saturated ammonium chloride aqueous solution (200 mL), and extracted with ethyl acetate (100 mL×3). The combined organic phase was washed with saturated ammonium chloride aqueous solution (200 mL×1) and saturated NaCl aqueous solution (100 mL×3), dried over anhydrous sodium sulfate, filtered, and concentrated under reduced pressure. The crude product was separated by silica gel column chromatography (petroleum ether/ethyl acetate=1:0 to 2:1) to obtain compound 46-4.

MS-ESI $[M+H]^+$, calculated: 342, found: 342.

$^1H$ NMR (400 MHz, $CDCl_3$) δ 7.16-7.24 (m, 1H), 6.91-7.02 (m, 2H), 4.12-4.22 (m, 2H), 3.13-3.24 (m, 1H), 2.83-2.97 (m, 2H), 2.67-2.80 (m, 2H), 2.30-2.41 (m, 1H), 1.25 (t, J=8.0 Hz, 3H), 1.19 (s, 9H).

(3) To a solution of compound 46-4 (4.50 g, 13.2 mmol) in ethanol (30.0 mL) was added hydrochloric acid in dioxane (4 mol/L, 10.0 mL), and the reaction solution was stirred at 25° C. for 1 hour under nitrogen protection. Then the reaction solution was concentrated under reduced pressure to obtain crude product of hydrochloride of compound 46-5.

(4) To a solution of hydrochloride of compound 46-5 (6.32 g, 13.2 mmol) in ethanol (40.0 mL) was added compound 46-6 (13.8 g, 138 mmol), copper oxide (209 mg, 2.63 mmol), and triethylamine (2.66 g, 26.3 mmol), and the reaction solution was reacted at 80° C. in a sealed tube for 12 hours under nitrogen protection. Then the reaction solution was added with water (100 mL), and extracted with ethyl acetate (150 mL×2). The combined organic phase was washed with saturated NaCl aqueous solution (100 mL×2), dried over anhydrous sodium sulfate, filtered, and concentrated under reduced pressure. The crude product was separated by silica gel column chromatography (petroleum ether/ethyl acetate=1:0 to 2:1) to obtain compound 46-7.

MS-ESI $[M+H]^+$, calculated: 338, found: 338.

$^1HNMR$ (400 MHz, $CDCl_3$) δ 7.14-7.21 (m, 1H), 6.98-7.07 (m, 1H), 6.90 (t, J=8.0 Hz, 1H), 4.07-4.15 (m, 4H), 2.94-3.06 (m, 1H), 2.84-2.92 (m, 1H), 2.61-2.79 (m, 3H), 2.49-2.56 (m, 1H), 2.40-2.47 (m, 2H), 2.30-2.39 (m, 1H), 2.16-2.25 (m, 1H), 1.22-1.26 (m, 3H), 1.20 (t, J=8.0 Hz, 3H).

(5) To a solution of compound 46-7 (4.10 g, 12.2 mmol) in ethanol (50.0 mL) was added paraformaldehyde (3.65 g), sodium cyanoborohydride (2.29 g, 36.5 mmol), and acetic acid (1.46 g, 24.3 mmol), and the reaction solution was reacted for 15 hours at 35° C. under nitrogen protection. Then the reaction solution was added with water (30.0 mL), and extracted with ethyl acetate (100 mL). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 2:1) to obtain compound 46-8.

MS-ESI $[M+H]^+$, calculated: 352, found: 352.

$^1H$ NMR (400 MHz, $CDCl_3$) δ 7.12-7.19 (m, 1H), 7.02 (d, J=8.0 Hz, 1H), 6.89 (t, J=8.0 Hz, 1H), 4.05-4.15 (m, 2H), 3.84-3.96 (m, 2H), 2.84-2.98 (m, 3H), 2.72-2.81 (m, 1H), 2.56-2.68 (m, 2H), 2.28-2.47 (m, 4H), 2.16 (s, 3H), 1.20-1.27 (m, 3H), 0.99-1.05 (m, 3H).

(6) To a solution of compound 46-8 (3.40 g, 9.68 mmol) in tetrahydrofuran (50.0 mL) was added potassium bis(trimethylsilyl) amide (1 mol/L, 29.0 mL, tetrahydrofuran solution) at −78° C., and the reaction solution was reacted at −78° C. for 2 hours under nitrogen protection. Then the reaction solution was added with saturated ammonium chloride aqueous solution (50.0 mL), and extracted with dichloromethane (50.0 mL). The combined organic phase was washed with saturated NaCl aqueous solution (50.0 mL), dried over anhydrous sodium sulfate, filtered, and concentrated under reduced pressure. The crude product was separated by silica gel column chromatography (petroleum ether/ethyl acetate=1:0 to 2:1) to obtain compound 46-9.

MS-ESI $[M+H]^+$, calculated: 306, found: 306.

$^1$H NMR (400 MHz, $CDCl_3$) δ 7.19-7.26 (m, 1H), 7.02-7.14 (m, 1H), 6.88-7.01 (m, 1H), 4.21-4.32 (m, 2H), 3.47-3.57 (m, 1H), 3.13-3.33 (m, 2H), 2.88-3.06 (m, 2H), 2.61-2.73 (m, 1H), 2.34-2.44 (m, 1H), 2.22-2.33 (m, 1H), 2.06-2.13 (m, 3H), 1.77-1.89 (m, 1H), 1.30-1.34 (m, 3H).

(7) To a solution of compound 46-9 (2.50 g, 8.19 mmol) in ethanol (50.0 mL) was added compound 46-10 (1.25 g, 16.4 mmol) and sodium ethoxide (1.67 g, 24.6 mmol), and the reaction solution was stirred at 80° C. for 15 hours under nitrogen protection. After being concentrated under reduced pressure, the reaction solution was adjusted to pH 6 with hydrochloric acid (1 mol/L). The resulting solution was precipitated, and filtered. The filter cake was dried to obtain compound 46-11.

MS-ESI $[M+H]^+$, calculated: 318, found: 318.

$^1$H NMR (400 MHz, DMSO-d6) δ 7.28-7.35 (m, 1H), 7.03-7.12 (m, 2H), 3.41-3.51 (m, 1H), 3.06 (d, J=16.0 Hz, 1H), 2.82-2.99 (m, 2H), 2.59-2.69 (m, 1H), 2.51-2.53 (m, 1H), 2.16-2.27 (m, 1H), 1.98 (s, 3H), 1.68-1.76 (m, 1H).

(8) To a solution of intermediate 46-11 (2.20 g, 6.93 mmol) in water (50.0 mL) was added chloroacetic acid (3.30 g, 34.9 mmol), and the reaction solution was stirred at 100° C. for 15 hours under nitrogen protection. After the reaction solution was filtered, the filtrate was adjusted to pH 8 with saturated sodium bicarbonate aqueous solution to get precipitate. After filtration, the filter cake was dried to obtain compound 46-12.

MS-ESI $[M+H]^+$, calculated: 302, found: 302.

$^1$H NMR (400 MHz, DMSO-d6) δ 11.02 (s, 1H), 10.78 (s, 1H), 7.27-7.35 (m, 1H), 7.02-7.12 (m, 2H), 3.43 (s, 1H), 2.99-3.06 (m, 1H), 2.82-2.96 (m, 2H), 2.54-2.63 (m, 1H), 2.33-2.43 (m, 1H), 2.17-2.27 (m, 1H), 1.97 (s, 3H), 1.65-1.77 (m, 1H).

(9) Compound 46-12 (400 mg, 1.33 mmol) was dissolved in phosphorus oxychloride (10.0 mL), and the reaction solution was stirred at 80° C. for 12 hours under nitrogen protection. Then the reaction solution was concentrated under reduced pressure, and extracted with dichloromethane (20.0 mL). The organic phase was washed with saturated sodium bicarbonate aqueous solution (20.0 mL×2) and saturated NaCl aqueous solution (20.0 mL×2), dried over anhydrous sodium sulfate, filtered, and concentrated under reduced pressure to obtain compound 46-13.

MS-ESI $[M+H]^+$, calculated: 338, found: 338.

(10) To a solution of compound 46-13 (600 mg, 1.31 mmol) in N-methylpyrrolidone (20.0 mL) was added potassium carbonate (701 mg, 3.94 mmol) and compound 46-14 (444 mg, 1.97 mmol), and the reaction solution was stirred at 50° C. for 5 hours under nitrogen protection. Then the reaction solution was added with ethyl acetate (50.0 mL), washed with saturated NaCl aqueous solution (30.0 mL×5), dried over anhydrous sodium sulfate, filtered, and concentrated under reduced pressure. The crude product was separated by silica gel column chromatography (dichloromethane/methanol=1:0 to 10:1) to obtain compound 46-15.

MS-ESI $[M+H]^+$, calculated: 527, found: 527.

$^1$H NMR (400 MHz, $CDCl_3$) δ 7.20-7.26 (m, 1H), 6.93-7.07 (m, 2H), 3.96-4.07 (d, J=12.0 Hz, 2H), 3.59-3.85 (m, 2H), 3.38-3.52 (m, 1H), 3.21-3.31 (m, 1H), 2.94-3.12 (m, 6H), 2.61-2.74 (m, 2H), 2.30-2.43 (m, 1H), 2.18-2.28 (m, 3H), 1.82-1.94 (m, 2H), 1.50 (s, 9H).

(11) To a solution of compound 46-15 (500 mg, 949 μmol) in dioxane (15.0 mL) was added compound 46-16 (227 mg, 1.42 mmol), cesium carbonate (927 mg, 2.85 mmol) and (2-dicyclohexylphosphino-2',6'-diisopropoxy-1,1'-biphenyl) [2-(2'-amino-1,1'-biphenyl)] palladium(II) methanesulfonate (159 mg, 190 μmol), and the reaction solution was stirred at 110° C. for 4 hours under nitrogen protection. Then the reaction solution was added with ethyl acetate (50.0 mL), washed with saturated NaCl aqueous solution (50.0 mL×2), dried over anhydrous sodium sulfate, filtered, and concentrated under reduced pressure. The crude product was separated by silica gel column chromatography (dichloromethane/methanol=1:0 to 10:1) to obtain compound 46-17.

MS-ESI $[M+H]^+$, calculated: 650, found: 650.

$^1$H NMR (400 MHz, $CDCl_3$) δ 7.18-7.25 (m, 1H), 6.90-7.03 (m, 2H), 4.13-4.18 (m, 1H), 3.91-4.08 (m, 2H), 3.73-3.89 (m, 1H), 3.62-3.72 (m, 1H), 3.55 (br d, J=12.0 Hz, 1H), 3.13-3.48 (m, 4H), 2.86-3.11 (m, 6H), 2.57-2.78 (m, 2H), 2.28-2.43 (m, 2H), 2.12-2.27 (m, 5H), 1.59-2.02 (m, 8H), 1.42-1.57 (m, 9H).

(12) To a solution of compound 46-17 (300 g, 462 μmol) in dichloromethane (5.0 mL) was added trifluoroacetic acid (1.54 g, 13.5 mmol), and the reaction solution was stirred at 25° C. for 2 hours under nitrogen protection. Then the reaction solution was extracted with ethyl acetate (50 mL×2) and the organic phase was washed by saturated sodium bicarbonate aqueous solution (50 mL) and saturated NaCl aqueous solution (50 mL), dried over anhydrous sodium sulfate, filtered, and concentrated under reduced pressure to obtain crude compound 46-18.

MS-ESI $[M+H]^+$, calculated: 550, found: 550.

(13) To a solution of compound 46-18 (150 mg, 273 μmol) in ethyl acetate (3.0 mL) was added triethylamine (82.8 mg, 819 μmol), compound 46-19 (73.7 mg, 819 μmol), 4A molecular sieve (150 mg) and propanephosphonic acid anhydride solution (521 mg, 819 μmol, 50% ethyl acetate solution) at 0° C., and the reaction solution was stirred at 25° C. for 1 hour. Then the reaction solution was added with dichloromethane (10.0 mL), washed with saturated NaCl aqueous solution (10.0 mL×2), dried over anhydrous sodium sulfate, filtered, and concentrated under reduced pressure. The crude product was separated by silica gel column chromatography (dichloromethane/methanol=1:0 to 10:1) to obtain compound 46-20.

(14) Compound 46-20 was separated by chiral supercritical fluid chromatography to obtain compounds 46 and 47.

Separation conditions: Chromatographic column model: Chiralpak OX-3; column specification: 10×4.6 mm I.D., 3 m; Injection volume: 8.0 μL; Mobile phase: A: carbon dioxide, B: ethanol (0.05% diethylamine), B %: 5%-40% gradient elution for 4 minutes, 40% fixed concentration elution for 1 minute, 10% fixed concentration elution for 1 minute; Detection wavelength: 254 nm; Column temperature: 35° C.

Compound 46: retention time 3.680 minutes, 100% ee.

MS-ESI $[M+H]^+$, calculated: 622, found: 622.

$^1$H NMR (400 MHz, MeOD) δ 7.27-7.34 (m, 1H), 6.98-7.09 (m, 1H), 6.98-7.03 (m, 1H), 5.25-5.45 (m, 3H), 4.89-5.01 (m, 1H), 4.26-4.40 (m, 2H), 4.04-4.23 (m, 3H), 3.69-3.82 (m, 2H), 3.44-3.62 (m, 4H), 3.08-3.29 (m, 3H), 3.03-3.08 (m, 1H), 2.90-3.02 (m, 5H), 2.33-2.53 (m, 3H), 2.23 (s, 4H), 2.10-2.17 (m, 2H), 1.98-2.06 (m, 1H), 1.86-2.06 (m, 1H).

Compound 47: retention time: 4.052 minutes, 98.44% ee.

MS-ESI $[M+H]^+$, calculated: 622, found: 622.
$^1H$ NMR (400 MHz, MeOD) δ 7.24-7.33 (m, 1H), 6.95-7.08 (m, 2H), 5.19-5.43 (m, 3H), 4.25 (d, J=12.0 Hz, 1H), 4.03-4.22 (m, 3H), 3.96-4.03 (m, 1H), 3.71 (s, 2H), 3.18-3.28 (m, 4H), 3.09-3.17 (m, 2H), 2.96-3.08 (m, 3H), 2.93 (d, J=4.0 Hz, 2H), 2.42-2.52 (m, 1H), 2.27-2.39 (m, 1H), 2.16-2.27 (m, 4H), 2.05-2.15 (m, 1H), 1.84-2.03 (m, 4H), 1.29 (s, 3H).
Example 38 Synthesis of Compounds 48 and 49
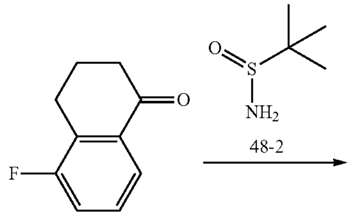
48-1
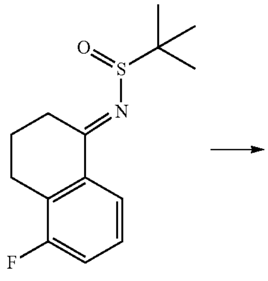
48-3
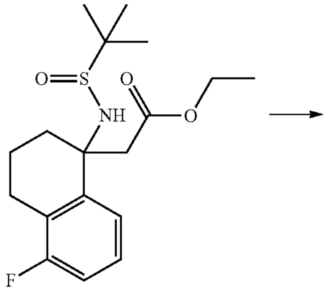
48-4
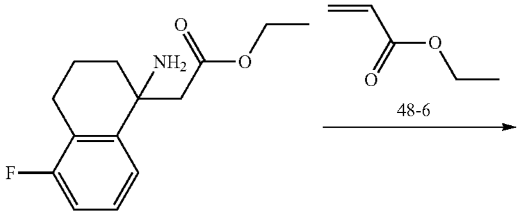
48-5
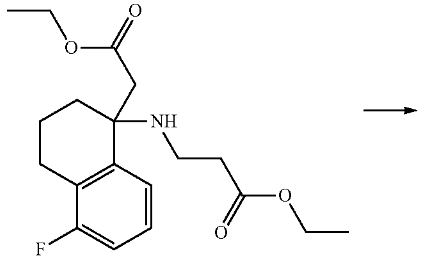
48-7
-continued
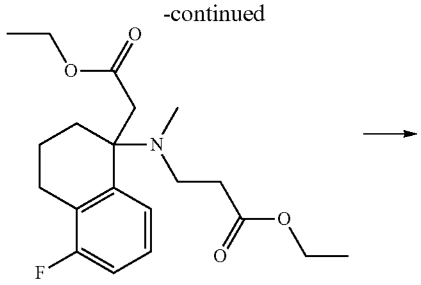
48-8
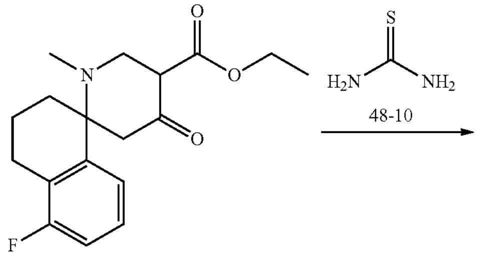
48-9
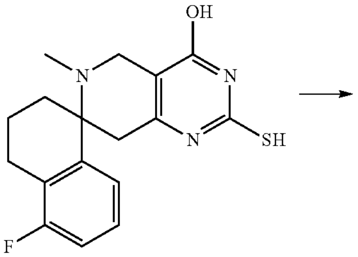
48-11
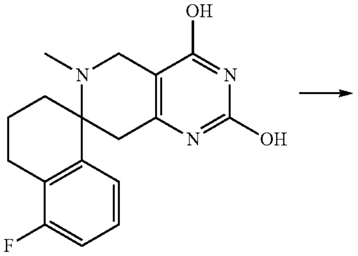
48-12
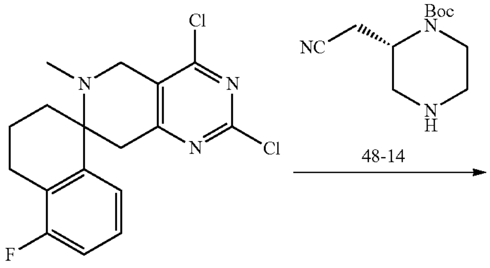
48-13

-continued

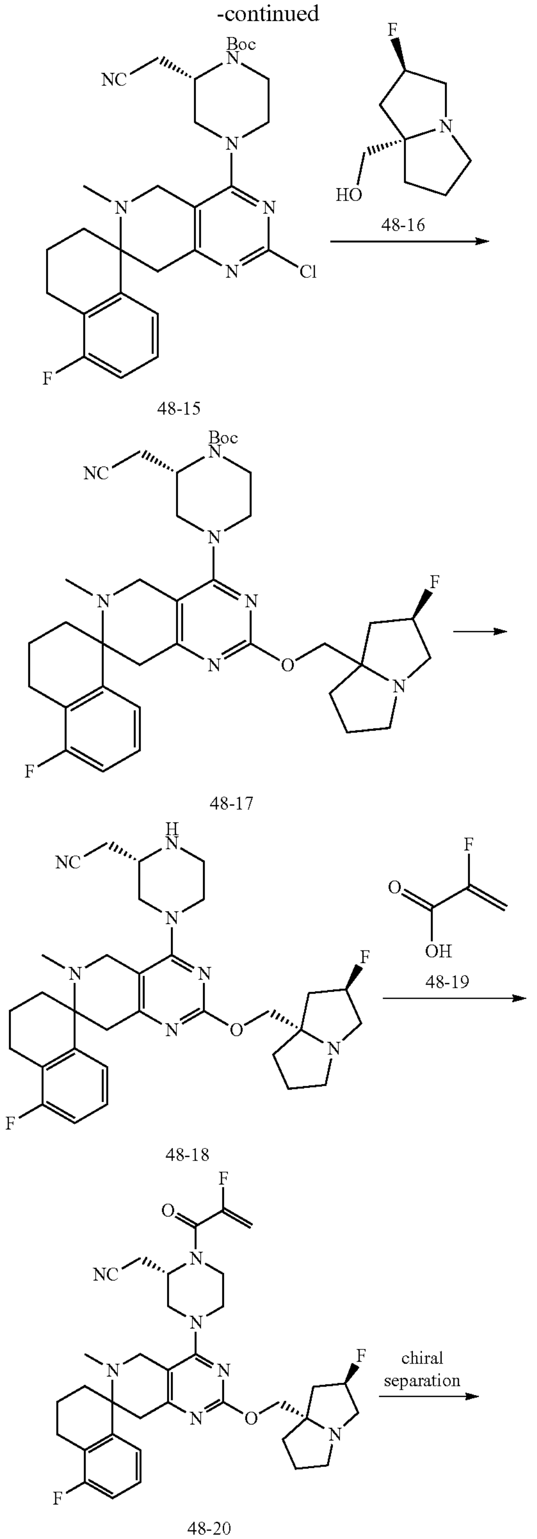

48-15

48-16

48-17

48-18

48-19

48-20

Compound 48 and 49

(1) To a solution of compound 48-1 (5.00 g, 30.4 mmol) in toluene (150 mL) was added compound 48-2 (3.69 g, 30.4 mmol), tetraethyl titanate (13.8 g, 60.9 mmol), and the reaction solution was stirred at 120° C. for 10 hours under nitrogen protection. Then the reaction solution was added with water (300 mL), and filtered. The filter cake was washed with ethyl acetate (300 mL×3). The combined organic phase was washed with saturated NaCl aqueous solution (300 mL), dried over anhydrous sodium sulfate, filtered, and concentrated under reduced pressure. The crude product was separated by silica gel column chromatography (petroleum ether/ethyl acetate=1:0 to 0:1) to obtain compound 48-3.

MS-ESI $[M+H]^+$, calculated: 268, found: 268.

$^1$H NMR (400 MHz, $CDCl_3$) δ 7.95 (d, J=7.64 Hz, 1H), 7.18-7.24 (m, 1H), 7.11-7.17 (m, 1H), 3.22-3.32 (m, 1H), 3.03-3.11 (m, 1H), 2.77-2.95 (m, 2H), 1.91-2.10 (m, 2H) 1.32 (s, 9H).

(2) To a solution of ethyl acetate (8.57 g, 97.2 mmol) in tetrahydrofuran (50 mL) was added dropwise with lithium diisopropylamide (2 mol/L, 19.4 mL, tetrahydrofuran solution) at −78° C. under nitrogen protection, and the reaction solution was stirred at −78° C. for 1 hour. Then the reaction solution was added dropwise with a solution of compound 48-3 (15.5 g, 61.2 mmol) in tetrahydrofuran (200 mL), and continued stirring for 2 hours at −78° C. Then the reaction solution was quenched with saturated ammonium chloride aqueous solution (200 mL), and extracted with ethyl acetate (100 mL×3). The combined organic phase was washed with saturated ammonium chloride aqueous solution (200 mL×1) and saturated NaCl aqueous solution (100 mL×3), dried over anhydrous sodium sulfate, filtered, and concentrated under reduced pressure. The crude product was separated by silica gel column chromatography (petroleum ether/ethyl acetate=1:0 to 0:1) to obtain compound 48-4.

MS-ESI $[M+H]^+$, calculated: 356, found: 356.

$^1$H NMR (400 MHz, $CDCl_3$) δ 7.08-7.20 (m, 2H), 6.92 (d, J=9.2, 1.6 Hz, 1H), 5.17 (s, 1H), 4.13-4.21 (m, 2H), 2.81-2.88 (m, 2H), 2.68-2.80 (m, 2H), 2.39-2.49 (m, 1H), 2.11-2.18 (m, 1H), 2.04-2.10 (m, 1H), 1.74-1.86 (m, 1H), 1.25-1.28 (m, 3H), 1.22-1.24 (m, 9H).

(3) To a solution of compound 48-4 (3.70 g, 10.4 mmol) in ethanol (30.0 mL) was added hydrochloric acid in dioxane (4 mol/L, 10.0 mL), and the reaction solution was stirred at 25° C. for 1 hour under nitrogen protection. Then the reaction solution was concentrated under reduced pressure to obtain crude product of hydrochloride of compound 48-5.

(4) To a solution of hydrochloride of compound 48-5 (2.60 g, 10.3 mmol) in ethanol (40.0 mL) was added compound 48-6 (10.3 g, 103 mmol), copper oxide (164 mg, 2.07 mmol), and triethylamine (3.14 g, 31.0 mmol), and the reaction solution was reacted at 85° C. in a sealed tube for 12 hours under nitrogen protection. Then the reaction solution was added with water (50.0 mL), and extracted with ethyl acetate (50.0 mL×2). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 0:1) to obtain compound 48-7.

MS-ESI $[M+H]^+$, calculated: 352, found: 352.

$^1$H NMR (400 MHz, $CDCl_3$) δ 7.36 (s, 1H), 7.14 (q, 1H), 6.81-6.94 (m, 1H), 4.06-4.19 (m, 4H), 2.72-2.86 (m, 3H), 2.57-2.69 (m, 2H), 2.43 (s, 3H), 2.02-2.11 (m, 1H), 1.94 (d, J=4.8 Hz, 2H), 1.84 (d, J=10.8, 5.6 Hz, 1H) 1.25 (m, 3H), 1.21 (t, J=7.2 Hz, 3H).

(5) To a solution of compound 48-7 (1.90 g, 5.41 mmol) in ethanol (30.0 mL) was added paraformaldehyde (1.62 g) and sodium cyanoborohydride (1.02 g, 16.2 mmol), and the reaction solution was reacted for 16 hours at 30° C. under nitrogen protection. Then the reaction solution was added with water (100 mL), and extracted with ethyl acetate (100 mL). The combined organic phase was washed with saturated NaCl aqueous solution (50.0 mL×2), dried over anhydrous sodium sulfate, filtered, and concentrated under reduced pressure. The crude product was separated by silica gel column chromatography (petroleum ether/ethyl acetate=1:0 to 0:1) to obtain compound 48-8.

MS-ESI $[M+H]^+$, calculated: 366, found: 366.

$^1$H NMR (400 MHz, $CDCl_3$) δ 7.31 (d, J=8.0 Hz, 1H), 7.05-7.12 (m, 1H), 6.81-6.88 (m, 1H), 4.09 (q, J=7.2 Hz, 2H), 3.81-3.92 (m, 2H), 2.69-2.81 (m, 4H), 2.54-2.68 (m, 2H), 2.31-2.48 (m, 2H), 2.21 (s, 3H), 2.04-2.13 (m, 2H), 1.81 (q, J=6.4 Hz, 2H), 1.23 (t, J=7.2 Hz, 3H), 1.01 (t, J=7.2 Hz, 3H).

(6) To a solution of compound 48-8 (1.70 g, 4.65 mmol) in tetrahydrofuran (30.0 mL) was added potassium bis (trimethylsilyl) amide (1 mol/L, 9.30 mL, tetrahydrofuran solution) at −78° C., and the reaction solution was reacted at −78° C. for 2 hours under nitrogen protection. Then the reaction solution was added with saturated ammonium chloride aqueous solution (50.0 mL), and extracted with ethyl acetate (50.0 mL). The combined organic phase was washed with saturated NaCl aqueous solution (50.0 mL), dried over anhydrous sodium sulfate, filtered, and concentrated under reduced pressure. The crude product was separated by silica gel column chromatography (petroleum ether/ethyl acetate=1:0 to 0:1) to obtain compound 48-9.

MS-ESI $[M+H]^+$, calculated: 320, found: 320.

$^1$H NMR (400 MHz, $CDCl_3$) δ 7.26-7.56 (m, 1H), 7.13-7.24 (m, 1H), 6.81-7.01 (m, 1H), 4.08-4.36 (m, 2H), 3.42-3.61 (m, 1H), 3.09-3.21 (m, 1H), 2.86-2.96 (m, 1H), 2.49-2.77 (m, 2H), 2.26-2.48 (m, 1H), 2.01 (s, 3H), 1.61-1.81 (m, 3H), 1.59 (s, 2H), 1.28-1.35 (m, 3H).

(7) To a solution of compound 48-9 (1.20 g, 3.76 mmol) in ethanol (20.0 mL) was added compound 48-10 (572 mg, 7.51 mmol) and sodium ethoxide (767 mg, 11.2 mmol), and the reaction solution was stirred at 80° C. for 15 hours under nitrogen protection. After being concentrated under reduced pressure, the reaction solution was adjusted to pH 6 with hydrochloric acid (1 mol/L). The resulting solution was precipitated, and filtered. The filter cake was dried to obtain compound 48-11.

MS-ESI $[M+H]^+$, calculated: 332, found: 332.

(8) To a solution of intermediate 48-11 (1.10 g, 3.25 mmol) in water (30.0 mL) was added chloroacetic acid (1.25 g, 13.2 mmol), and the reaction solution was stirred at 100° C. for 12 hours under nitrogen protection. After the reaction solution was filtered, the filtrate was adjusted to pH 8 with saturated sodium bicarbonate aqueous solution to get precipitate. After filtration, the filter cake was dried to obtain compound 48-12.

MS-ESI $[M+H]^+$, calculated: 316, found: 316.

$^1$H NMR (400 MHz, DMSO-d6) δ 11.03 (s, 1H), 10.75 (s, 1H), 7.38 (d, J=7.6 Hz, 1H), 7.20-7.32 (m, 1H), 7.04 (t, J=8.4 Hz, 1H), 3.52 (d, J=14.8 Hz, 1H), 3.05 (d, J=14.0 Hz, 1H), 2.81 (d, J=16.4 Hz, 1H), 2.52-2.59 (m, 2H), 2.40-2.48 (m, 1H), 1.94 (s, 4H), 1.70-1.80 (m, 1H), 1.47-1.61 (m, 2H).

(9) Compound 48-12 (200 mg, 634 μmol) was dissolved in phosphorus oxychloride (2.0 mL), and the reaction solution was stirred at 80° C. for 12 hours under nitrogen protection. Then the reaction solution was concentrated under reduced pressure, and extracted with dichloromethane (20.0 mL). The organic phase was washed with saturated sodium bicarbonate aqueous solution (20.0 mL×2) and saturated NaCl aqueous solution (20.0 mL×2), dried over anhydrous sodium sulfate, filtered, and concentrated under reduced pressure to obtain compound 48-13.

MS-ESI $[M+H]^+$, calculated: 352, found: 352.

(10) To a solution of compound 48-13 (150 mg, 425 μmol) in N-methylpyrrolidone (5.0 mL) was added potassium carbonate (176 mg, 1.28 mmol) and compound 48-14 (115 mg, 551 mol), and the reaction solution was stirred at 50° C. for 5 hours under nitrogen protection. Then the reaction solution was added with ethyl acetate (50.0 mL), washed with saturated NaCl aqueous solution (30.0 mL×5), dried over anhydrous sodium sulfate, filtered, and concentrated under reduced pressure. The crude product was separated by silica gel column chromatography (petroleum ether/ethyl acetate=1:0 to 0:1) to give compound 48-15.

MS-ESI $[M+H]^+$, calculated: 541, found: 541.

$^1$H NMR (400 MHz, $CDCl_3$) δ 7.35 (s, 1H), 7.20 (s, 1H), 6.83-7.01 (m, 1H), 4.57 (s, 1H), 4.00 (s, 2H), 3.82 (d, J=11.2 Hz, 1H), 3.72 (dd, J=6.0, 3.2 Hz, 1H), 3.30-3.66 (m, 2H), 3.08-3.29 (m, 3H), 2.80-3.07 (m, 3H), 2.65 (d, J=6.8 Hz, 2H), 2.42-2.52 (m, 1H), 2.12 (s, 2H), 2.02 (s, 1H), 1.19-1.94 (m, 1H), 1.64-1.78 (m, 2H), 1.50 (d, J=2.0 Hz, 9H).

(11) To a solution of compound 48-15 (440 mg, 813 μmol) in dioxane (10.0 mL) was added compound 48-16 (388 mg, 2.44 mmol), cesium carbonate (794 mg, 2.44 mmol) and (2-dicyclohexylphosphino-2',6'-diisopropoxy-1,1'-biphenyl) [2-(2'-amino-1,1'-biphenyl)] palladium(II) methanesulfonate (136 mg, 162 μmol), and the reaction solution was stirred at 110° C. for 4 hours under nitrogen protection. Then the reaction solution was added with ethyl acetate (50.0 mL), washed with saturated NaCl aqueous solution (50.0 mL×2), dried over anhydrous sodium sulfate, filtered, and concentrated under reduced pressure. The crude product was separated by silica gel column chromatography (dichloromethane/methanol=1:0 to 10:1) to obtain compound 48-17.

MS-ESI $[M+H]^+$, calculated: 664, found: 664.

(12) To a solution of compound 48-17 (270 g, 406 μmol) in dichloromethane (5.0 mL) was added hydrochloric acid in dioxane (4 mol/L, 36.7 μmol), and the reaction solution was stirred at 25° C. for 2 hours under nitrogen protection. Then the reaction solution was adjusted to pH 8 by saturated sodium bicarbonate aqueous solution and extracted with dichloromethane (20 mL×2). The organic phase was washed with saturated sodium bicarbonate aqueous solution (20 mL) and saturated NaCl aqueous solution (50 mL), dried over anhydrous sodium sulfate, filtered, and concentrated under reduced pressure. The crude product was separated by silica gel column chromatography (dichloromethane/methanol=1:0 to 10:1) to obtain compound 48-18.

MS-ESI $[M+H]^+$, calculated: 564, found: 564.

(13) To a solution of compound 48-18 (200 mg, 354 μmol) in ethyl acetate (1.0 mL) was added triethylamine (17.9 mg, 177 μmol), compound 48-19 (35.9 mg, 354 μmol), 4A molecular sieve (100 mg) and propanephosphonic acid anhydride solution (677 mg, 819 μmol, 50% ethyl acetate solution) at 0° C., and the reaction solution was stirred at 25° C. for 1 hour. Then the reaction solution was added with dichloromethane (10.0 mL), washed with saturated NaCl aqueous solution (10.0 mL×2), dried over anhydrous sodium sulfate, filtered, and concentrated under reduced pressure. The crude product was separated by silica gel column chromatography (dichloromethane/methanol=1:0 to 10:1) to obtain compound 48-20.

(14) Compound 48-20 was separated by chiral supercritical fluid chromatography to obtain compounds 48 and 49.

Separation conditions: Chromatographic column model: Chiralpak OD-3; column specification: 50×4.6 mm I.D., 3 m; Injection volume: 8.0 μL; Mobile phase: A: carbon dioxide, B: ethanol (0.05% diethylamine), B %: 5%-40% gradient elution for 2.5 minutes, 40% fixed concentration elution for 0.5 minutes, 5% fixed concentration elution for 1 minute; Detection wavelength: 254 nm; Column temperature: 35° C.

Compound 48: retention time: 1.743 minutes, 98.58% ee.

MS-ESI $[M+H]^+$, calculated: 636, found: 636.

$^1H$ NMR (400 MHz, MeOD) δ7.37 (d, J=8.0 Hz, 1H), 7.20-7.27 (m, 1H), 6.94 (t, J=8.8 Hz, 1H), 5.24-5.42 (m, 3H), 4.38-4.63 (m, 1H), 4.20-4.25 (m, 1H), 4.08-4.19 (m, 3H), 3.77 (s, 2H), 3.46-3.60 (m, 1H), 3.35 (d, J=2.8 Hz, 1H), 3.28 (s, 1H), 3.04-3.14 (m, 3H), 2.89-3.02 (m, 4H), 2.43-2.55 (m, 1H), 2.27-2.39 (m, 1H), 2.15-2.26 (m, 2H), 2.12 (s, 3H), 1.97-2.08 (m, 4H), 1.85-1.97 (m, 2H), 1.70-1.84 (m, 2H), 1.28-1.53 (m, 2H).

Compound 49: retention time: 1.937 minutes, 98.18% ee.

MS-ESI $[M+H]^+$, calculated: 636, found: 636.

$^1H$ NMR (400 MHz, MeOD) δ 7.61 (d, J=8.0 Hz, 1H), 7.39-7.46 (m, 1H), 7.16 (t, J=8.4 Hz, 1H), 5.63 (t, J=3.6 Hz, 0.5H), 5.50 (d, J=3.2 Hz, 0.5H), 5.30-5.43 (m, 2H), 4.62 (s, 1H), 4.53-4.59 (m, 3H), 3.94-4.03 (m, 2H), 3.83-3.93 (m, 3H), 3.41-3.49 (m, 4H), 3.38 (s, 1H), 3.10-3.28 (m, 2H), 2.87-3.10 (m, 3H), 2.57-2.64 (m, 4H), 2.51-2.57 (m, 1H), 2.40 (d, J=8.4 Hz, 1H), 2.25-2.37 (m, 3H), 2.13-2.24 (m, 4H), 1.81-1.91 (m, 1H), 1.28-1.51 (m, 1H).

Example 39 Synthesis of Compounds 50 and 51

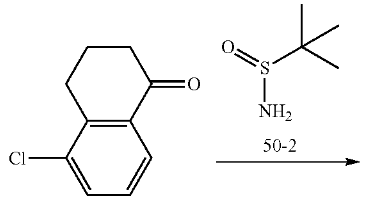

50-1

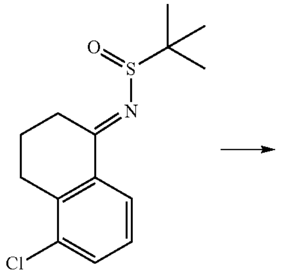

50-3

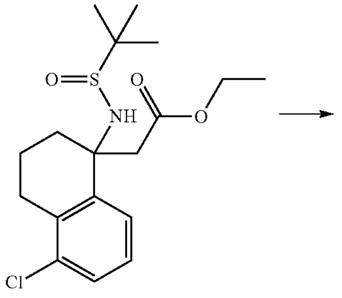

50-4

-continued

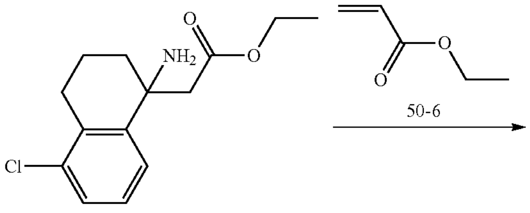

50-5

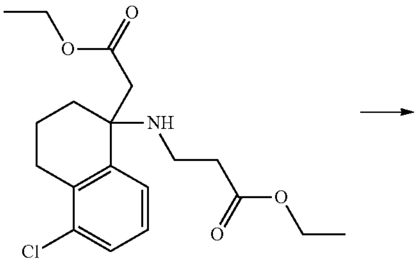

50-7

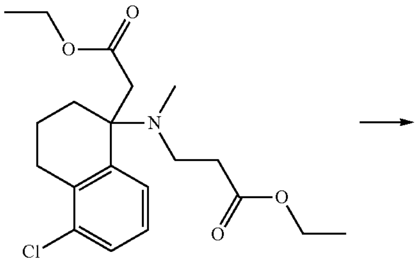

50-8

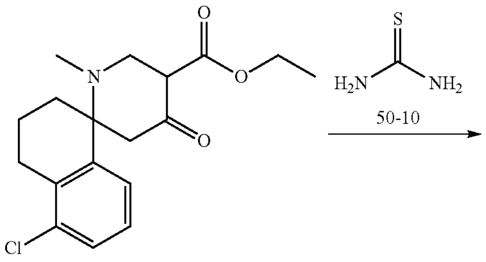

50-9

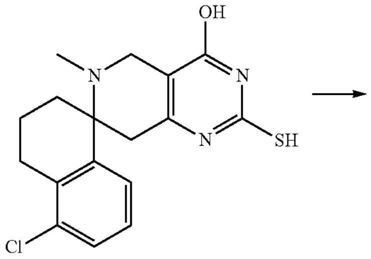

50-11

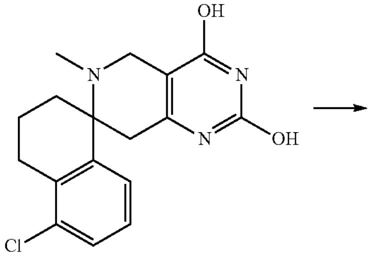

50-12

-continued

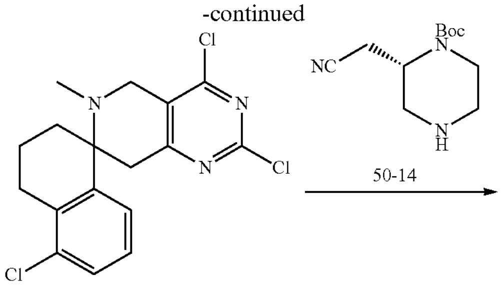

50-13

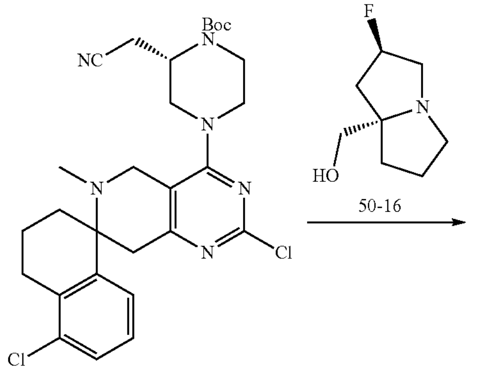

50-15

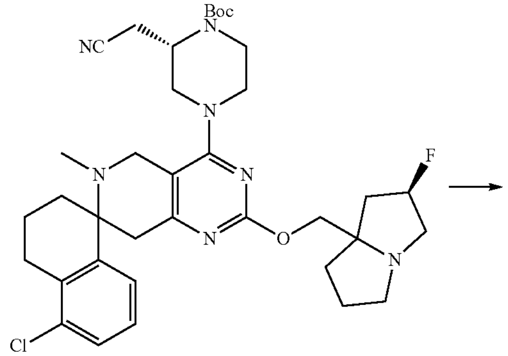

50-17

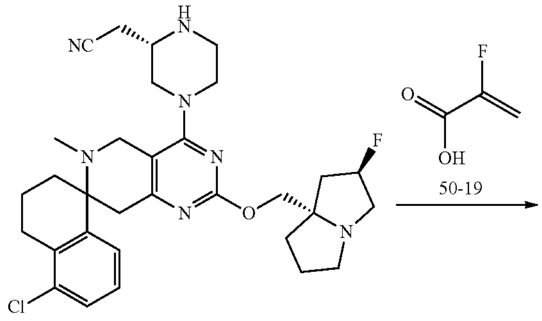

50-18

-continued

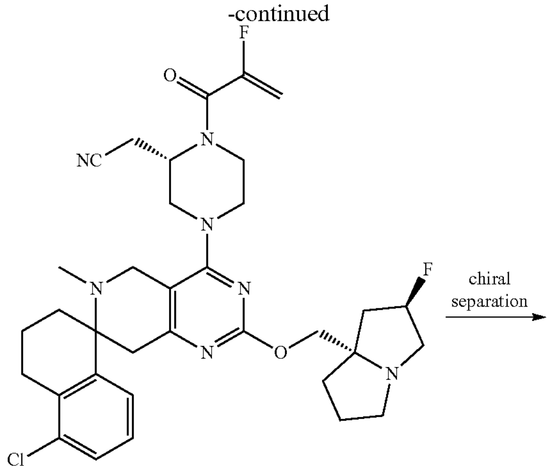

50-20

Compounds 50 and 51

(1) To a solution of compound 50-1 (20.0 g, 111 mmol) in toluene (240 mL) was added compound 50-2 (16.1 g, 133 mmol), tetraethyl titanate (50.5 g, 221 mmol), and the reaction solution was stirred at 110° C. for 13 hours under nitrogen protection. Then the reaction solution was added with water (200 mL), and filtered. The filter cake was washed with ethyl acetate (100 mL×3). The combined organic phase was washed with saturated NaCl aqueous solution (100 mL), dried over anhydrous sodium sulfate, filtered, and concentrated under reduced pressure. The crude product was separated by silica gel column chromatography (petroleum ether/ethyl acetate=1:0 to 5:1) to obtain compound 50-3.

MS-ESI $[M+H]^+$, calculated: 284, found: 284.

$^1H$ NMR (400 MHz, $CDCl_3$) δ 8.07-8.14 (m, 1H), 7.49 (dd, J=7.6, 1.2 Hz, 1H), 7.21 (t, J=8.0 Hz, 1H), 3.03-3.33 (m, 2H), 2.86-3.02 (m, 2H), 2.05-2.13 (m, 1H), 1.96-2.04 (m, 1H), 1.33 (s, 9H).

(2) To a solution of ethyl acetate (26.9 g, 305 mmol) in tetrahydrofuran (320 mL) was added dropwise with lithium diisopropylamide (2 mol/L, 60.9 mL, tetrahydrofuran solution) at −78° C. under nitrogen protection, and the reaction solution was stirred at −78° C. for 1 hour. Then the reaction solution was added dropwise with a solution of compound 50-3 (15.5 g, 61.2 mmol) in tetrahydrofuran (200 mL), and continued stirring for 3 hours at −78° C. Then the reaction solution was quenched with saturated ammonium chloride aqueous solution (200 mL), and extracted with ethyl acetate (100 mL×3). The combined organic phase was washed with saturated ammonium chloride aqueous solution (200 mL×1) and saturated NaCl aqueous solution (100 mL×3), dried over anhydrous sodium sulfate, filtered, and concentrated under reduced pressure. The crude product was separated by silica gel column chromatography (petroleum ether/ethyl acetate=1:0 to 3:1) to obtain compound 50-4.

MS-ESI $[M+H]^+$, calculated: 372, found: 372.

$^1H$ NMR (400 MHz, $CDCl_3$) δ 7.31 (dd, J=17.2, 8.0 Hz, 2H), 7.09-7.16 (m, 1H), 4.11-4.19 (m, 2H), 2.75-2.90 (m, 4H), 2.41-2.49 (m, 1H), 2.06-2.18 (m, 2H), 1.78-1.89 (m, 1H), 1.25-1.28 (m, 3H), 1.24 (s, 9H).

(3) To a solution of compound 50-4 (17.1 g, 46.0 mmol) in ethanol (80.0 mL) was added hydrochloric acid in dioxane (4 mol/L, 38.9 mL), and the reaction solution was stirred at 25° C. for 1 hour under nitrogen protection. Then the reaction solution was concentrated under reduced pressure to obtain crude product of hydrochloride of compound 50-5.

(4) To a solution of hydrochloride of compound 50-5 (4.60 g, 15.1 mmol) in ethanol (30.0 mL) was added compound 50-6 (15.1 g, 151 mmol), copper oxide (241 mg, 3.02 mmol), and triethylamine (1.53 g, 15.1 mmol), and the reaction solution was reacted at 85° C. in a sealed tube for 12 hours under nitrogen protection. Then the reaction solution was added with water (90.0 mL), and extracted with ethyl acetate (40.0 mL×3). The combined organic phase was washed with saturated NaCl aqueous solution (30.0 mL×1), dried over anhydrous sodium sulfate, filtered, and concentrated under reduced pressure. The crude product was separated by silica gel column chromatography (petroleum ether/ethyl acetate=1:0 to 3:1) to obtain compound 50-7.

MS-ESI $[M+H]^+$, calculated: 368, found: 368.

(5) To a solution of compound 50-7 (2.30 g, 6.25 mmol) in ethanol (20.0 mL) was added paraformaldehyde (1.88 g) and sodium cyanoborohydride (1.18 g, 18.8 mmol), and the reaction solution was reacted for 25 hours at 25° C. under nitrogen protection. Then the reaction solution was added with water (30.0 mL), and extracted with ethyl acetate (15.0 mL×3). The combined organic phase was washed with saturated NaCl aqueous solution (15.0 mL×2), dried over anhydrous sodium sulfate, filtered, and concentrated under reduced pressure. The crude product was separated by silica gel column chromatography (petroleum ether/ethyl acetate=1:0 to 3:1) to obtain compound 50-8.

MS-ESI $[M+H]^+$, calculated: 382, found: 382.

$^1$H NMR (400 MHz, $CDCl_3$) δ 7.48 (d, J=8.0 Hz, 1H), 7.20-7.24 (m, 1H), 7.05-7.11 (m, 1H), 4.10 (q, J=7.2 Hz, 2H), 3.79-3.96 (m, 2H), 2.70-2.86 (m, 5H), 2.54-2.65 (m, 1H), 2.31-2.50 (m, 2H), 2.22 (s, 3H), 1.99-2.16 (m, 2H), 1.84 (quin, J=6.4 Hz, 2H), 1.24 (t, J=7.2 Hz, 3H), 1.01 (t, J=7.2 Hz, 3H).

(6) To a solution of compound 50-8 (1.70 g, 4.45 mmol) in tetrahydrofuran (35.0 mL) was added potassium bis(trimethylsilyl) amide (1 mol/L, 13.4 mL, tetrahydrofuran solution) at −78° C., and the reaction solution was reacted at −78° C. for 2 hours under nitrogen protection. Then the reaction solution was added with saturated ammonium chloride aqueous solution (15.0 mL), and extracted with ethyl acetate (50.0 mL). The combined organic phase was washed with saturated NaCl aqueous solution (50.0 mL), dried over anhydrous sodium sulfate, filtered, and concentrated under reduced pressure. The crude product was separated by silica gel column chromatography (petroleum ether/ethyl acetate=1:0 to 0:1) to obtain compound 50-9.

MS-ESI $[M+H]^+$, calculated: 336, found: 336.

$^1$H NMR (400 MHz, $CDCl_3$) δ 7.47-7.59 (m, 1H), 7.23-7.26 (m, 1H), 7.11-7.22 (m, 1H), 4.20-4.34 (m, 2H), 3.46-3.64 (m, 1H), 2.93-3.32 (m, 3H), 2.44-2.73 (m, 3H), 2.01 (d, J=14.4 Hz, 4H), 1.66-1.84 (m, 3H), 1.33 (t, J=7.2 Hz, 3H).

(7) To a solution of compound 50-9 (1.29 g, 3.84 mmol) in ethanol (25.0 mL) was added compound 50-10 (585 mg, 7.68 mmol) and sodium ethoxide (784 mg, 11.5 mmol), and the reaction solution was stirred at 80° C. for 15 hours under nitrogen protection. After being concentrated under reduced pressure, the reaction solution was adjusted to pH 6 with hydrochloric acid (1 mol/L). The resulting solution was precipitated, and filtered. The filter cake was dried to obtain compound 50-11.

MS-ESI $[M+H]^+$, calculated: 348, found: 348.

$^1$H NMR (400 MHz, $CDCl_3$) δ 7.54 (dd, J=7.6, 1.2 Hz, 1H), 7.28-7.33 (m, 1H), 7.20-7.27 (m, 1H), 7.04-7.19 (m, 1H), 3.53 (d, J=16.4 Hz, 2H), 3.02 (d, J=16.4 Hz, 1H), 2.88 (d, J=17.6 Hz, 1H), 2.52-2.64 (m, 2H), 1.91-1.96 (m, 1H), 1.89 (s, 3H), 1.47-1.73 (m, 3H).

(8) To a solution of intermediate 50-11 (1.18 g, 3.39 mmol) in water (75.0 mL) was added chloroacetic acid (3.21 g, 33.9 mmol), and the reaction solution was stirred at 110° C. for 12 hours under nitrogen protection. After the reaction solution was filtered, the filtrate was adjusted to pH 8 with saturated sodium bicarbonate aqueous solution to get precipitate. After filtration, the filter cake was dried to obtain compound 50-12.

MS-ESI $[M+H]^+$, calculated: 332, found: 332.

(9) Compound 50-12 (1.20 g, 3.62 mmol) was dissolved in phosphorus oxychloride (10.0 mL), and the reaction solution was stirred at 80° C. for 12 hours under nitrogen protection. Then the reaction solution was concentrated under reduced pressure, and extracted with dichloromethane (20.0 mL). The organic phase was washed with saturated sodium bicarbonate aqueous solution (20.0 mL×2) and saturated NaCl aqueous solution (20.0 mL×2), dried over anhydrous sodium sulfate, filtered, and concentrated under reduced pressure to obtain compound 50-13.

MS-ESI $[M+H]^+$, calculated: 368, found: 368.

(10) To a solution of compound 50-13 (520 mg, 1.41 mmol) in N-methylpyrrolidone (5.0 mL) was added potassium carbonate (585 mg, 4.23 mmol) and compound 50-14 (381 mg, 1.69 mmol), and the reaction solution was stirred at 50° C. for 4 hours under nitrogen protection. Then the reaction solution was added with ethyl acetate (50.0 mL), washed with saturated NaCl aqueous solution (30.0 mL×5), dried over anhydrous sodium sulfate, filtered, and concentrated under reduced pressure. The crude product was separated by silica gel column chromatography (petroleum ether/ethyl acetate=1:0 to 4:1) to obtain compound 50-15.

MS-ESI $[M+H]^+$, calculated: 557, found: 557.

$^1$H NMR (400 MHz, $CDCl_3$) δ 7.42-7.56 (m, 1H), 7.29-7.42 (m, 1H), 7.11-7.24 (m, 1H), 4.50-4.68 (m, 1H), 3.92-4.09 (m, 2H), 3.56 (s, 3H), 3.28-3.54 (m, 1H), 2.96-3.26 (m, 5H), 2.44-2.79 (m, 3H), 2.06-2.19 (m, 3H), 1.62-1.99 (m, 4H), 1.51 (d, J=2.4 Hz, 9H).

(11) To a solution of compound 50-15 (230 mg, 412 μmol) in dioxane (5.00 mL) was added compound 50-16 (197 mg, 1.24 mmol), potassium carbonate (171 mg, 1.24 mmol), tris(dibenzylidene acetone)dipalladium (75.6 mg, 82.5 μmol) and 2-dicyclohexylphosphine-2',6'-diisopropoxy-1,1'-biphenyl (77.0 mg, 165 μmol), and the reaction solution was stirred at 90° C. for 5 hours under nitrogen protection. Then the reaction solution was added with ethyl acetate (20.0 mL), washed with saturated NaCl aqueous solution (20.0 mL×2), dried over anhydrous sodium sulfate, filtered, and concentrated under reduced pressure. The crude product was separated by preparative high performance liquid chromatography (Xtimate C18, 150 mm×40 mm 10 μm, A: water (0.225% formic acid); B: acetonitrile, 20%-50%: 10 min) to obtain formate of compound 50-17.

MS-ESI $[M+H]^+$, calculated: 680, found: 680.

(12) To a solution of formate of compound 50-17 (80 g, 118 μmol) in dichloromethane (1.0 mL) was added trifluoroacetic acid (1.0 mL), and the reaction solution was stirred at 25° C. for 1 hour under nitrogen protection. Then the reaction solution was concentrated under reduced pressure to remove trifluoroacetic acid, then adjusted to pH 8 by saturated sodium bicarbonate aqueous solution and extracted with dichloromethane (20 mL×2). The organic phase was washed with saturated sodium bicarbonate aqueous solution (20 mL) and saturated NaCl aqueous solution (50 mL), dried over anhydrous sodium sulfate, filtered, and concentrated under reduced pressure to obtain compound 50-18.

MS-ESI $[M+H]^+$, calculated: 580, found: 580.

(13) To a solution of compound 50-18 (55.0 mg, 94.8 μmol) in ethyl acetate (1.0 mL) was added triethylamine (57.6 mg, 79.2 μmol), compound 50-19 (25.6 mg, 284 μmol), 4A molecular sieve (100 mg) and propanephosphonic acid anhydride solution (181 mg, 284 μmol, 50% ethyl acetate solution) at 0° C., and the reaction solution was stirred at 25° C. for 1 hour. Then the reaction solution was added with ethyl acetate (10.0 mL), washed with saturated NaCl aqueous solution (10.0 mL×2), dried over anhydrous sodium sulfate, filtered, and concentrated under reduced pressure. The crude product was separated by preparative high performance liquid chromatography (Phenomenex C18, 75 mm×30 mm 3 μm, A: water (10 mmol/L ammonium bicarbonate); B: acetonitrile, 38%-78%: 28 min) to obtain compound 50-20.

(14) Compound 50-20 was separated by chiral supercritical fluid chromatography to obtain compounds 50 and 51.

Separation conditions: Chromatographic column model: Chiralpak OD-3; column specification: 50×4.6 mm I.D., 3 m; Injection volume: 8.0 μL; Mobile phase: A: Carbon dioxide, B: Ethanol (0.05% diethylamine), B %: 5%-40% gradient elution for 2.5 minutes, 40% fixed concentration elution for 0.5 minutes, 5% fixed concentration elution for 1 minute; Detection wavelength: 254 nm; Column temperature: 35° C.

Compound 50: retention time: 1.657 minutes, 99.30% ee.

MS-ESI $[M+H]^+$, calculated: 652, found: 652.

$^1$H NMR (400 MHz, MeOD) δ 7.53 (d, J=7.6 Hz, 1H), 7.26-7.32 (m, 1H), 7.17-7.25 (m, 1H), 5.11-5.48 (m, 3H), 4.30 (d, J=13.6 Hz, 1H), 4.10-4.22 (m, 2H), 4.00 (d, J=11.2 Hz, 1H), 3.70-3.82 (m, 2H), 3.61 (q, J=7.2 Hz, 1H), 2.90-3.31 (m, 11H), 2.55 (ddd, J=17.2, 12.0, 5.2 Hz, 1H), 2.06-2.39 (m, 6H), 1.84-2.06 (m, 5H), 1.77 (d, J=11.2 Hz, 2H), 1.15-1.33 (m, 2H).

Compound 51: retention time: 1.810 minutes, 100% ee.

MS-ESI $[M+H]^+$, calculated: 652, found: 652.

$^1$H NMR (400 MHz, MeOD) δ 7.53 (d, J=7.6 Hz, 1H), 7.26-7.32 (m, 1H), 7.17-7.25 (m, 1H), 5.11-5.48 (m, 3H), 4.30 (d, J=13.6 Hz, 1H), 4.10-4.22 (m, 2H), 4.00 (d, J=11.2 Hz, 1H), 3.70-3.82 (m, 2H), 3.61 (q, J=7.2 Hz, 1H), 2.90-3.31 (m, 11H), 2.55 (ddd, J=17.2, 12.0, 5.2 Hz, 1H), 2.06-2.39 (m, 6H), 1.84-2.06 (m, 5H), 1.77 (d, J=11.2 Hz, 2H), 1.15-1.33 (m, 2H).

Test Example 1

Inhibitory effect of compounds on the proliferation of NCI-11358 cells

1. Experimental principle: NCI-H358 cell is human non-small cell lung cancer cell line expressing KRAS G12C. The compounds of the present invention inhibit the proliferation of NCI-H358 cells by covalently binding to KRAS G12C.
2. Test materials: NCI-H358 cells were purchased from ATCC; CellTiter-GloR was purchased from Promega (item: G7571); RPMI-1640 was purchased from ATCC (item: 30-2001): fetal bovine serum (FBS) was purchased from EXCELL (item: FND500); Penicillin-streptomycin was purchased from Gibco (item: 15140-122); 0.25% trypsin-ethylenediaminetetraacetic acid digestive juice (Trypsin-EDTA) was purchased from Gibco (item: 25200-072); dimethyl sulfoxide (DMSO) was purchased from Sigma (item: D2650); 96-well plate was purchased from Corning (item: 3610); Incubator was purchased from Thermo (model: 3111); Inverted microscope was purchased from Nikon (item: TS-100); Automatic cell counter was purchased from Life technologies (model: Countess II); Enzyme plate reader was purchased from PerkinElmer (model: Envision); The data processing software was GraphPad Prism 5.0.
3. Test method:

Cells in logarithmic growth phase were resuspended in growth medium (RPMI-1640+10% FBS) and diluted to target density (2000 cells/mL). The above cell suspension was inoculated into 96-well plates at 100 μL per well; incubated overnight in a 37° C., 5% $CO_2$ incubator. Medium was used as background control.

The test compound was dissolved in DMSO to prepare a stock solution at a concentration of 10 mmol/L. The stock solution was first diluted to 2 mmol/L with DMSO, and then diluted in 3-fold gradient for a total of 10 concentrations. 3 μL of each concentration of the above solution was taken and diluted with 197 μL of growth medium. Cells were then inoculated at 50 μL/well in the 96-well plate. The cells to which the test compound was added were incubated in a 37° C., 5% $CO_2$ incubator for 72 hours. The 96-well plate was equilibrated at room temperature, and 40 μL CellTiter-Glo reagent was added to each well. Then, the plate was mixed on the vortex for 2 minutes, incubated at room temperature for 60 minutes. The luminescence value was read on an EnVision microplate reader, and the $IC_{50}$ of the compound was calculated using the GraphPad Prism 5.0 software.

The test results were shown in Table 1 (the number of each compound as indicated in the examples), wherein A represents $IC_{50}$<100 nM, B represents 100 nM<$IC_{50}$<1 μM, and C represents 1 μM<$IC_{50}$<10 μM.

TABLE 1

| Compound | NCI-H358 $IC_{50}$(nM) |
|---|---|
| 1 | C |
| Formate of 3 | A |
| Formate of 4 | C |
| 5 | B |
| 6 | A |
| 7 | B |
| 8 | B |
| Formate of 10 | B |
| Formate of 11 | C |
| Formate of 12 | C |
| 14 | C |
| Formate of 15 | B |
| Formate of 17 | B |
| Formate of 18 | A |
| Formate of 19 | B |
| Formate of 20 | A |
| Formate of 21 | B |
| Formate of 22 | B |
| Hydrochloride of 23 | C |
| Formate of 24 | B |
| Formate of 25 | C |
| 26 | A |
| 28 | A |
| 32 | A |
| 33 | A |
| Formate of 34 | A |
| 35 | A |
| 36 | A |
| 37 | B |
| 40 | A |
| 41 | B |
| 42 | A |
| 43 | B |
| 44 | A |

TABLE 1-continued

| Compound | NCI-H358 $IC_{50}$(nM) |
|---|---|
| 45 | B |
| 46 | A |
| 47 | C |
| 48 | A |
| 49 | C |
| 50 | A |
| 51 | C |

It can be seen from the test data in Table 1 that the compounds of formula I of the present invention shows a better inhibitory effect on the growth of NCI-1H358 cells and has the potential to be prepared as drugs for the treatment and prevention of cancer.

Test Example 2

Determination of Pharmacokinetic Properties of the Compound in Rats

1. Test purpose: to determine the pharmacokinetic characteristics of some of the example compound of the present invention in SD rats after single intravenous injection(IV) and oral administration(PO) by LC-MS/MS method.
2. Test material: the test drug is self-made from the example compounds of the present invention; the positive compound AMG-510 and MRTX-849 were purchased from Chengdu Zhihui Zhongxin Biopharmaceutical Co., Ltd.; SD male rats were obtained from the Laboratory Animal Management Department of Shanghai Family Planning Research Institute. Animal production license number (SCXK (Shanghai) 2018-0006).

3. Test method:

Preparation of 0.5% methyl cellulose: 5 g of methyl cellulose were weighed and dissolved in 1000 mL of purified water.

Preparation of oral formulation: A required amount of test compound was weighed and dissolved in 0.5% methyl cellulose solution to obtain a suspension or solution of 0.5 mg/mL.

Preparation of intravenous injection formulation: A required amount of test compound was weighed, and dissolved in 0.5 mL of dimethyl sulfoxide to prepare a solution of 4 mg/mL. 0.25 mL of the above solution was added into 0.5 mL of polyethylene glycol 15 hydroxystearate (solutol) and 4.25 mL of normal saline to obtain a solution of 0.2 mg/mL.

Administration: SD male rats were orally administered (PO) after fasting overnight, and the single intravenous injection (IV) group did not need fasting. The dosage and volume administered were shown in the table below Feeding, 4 hours after administration

| Route of administration | Number of animal | Dosage (mg/kg) | Concentration of administration (mg/mL) | Volume of administration (mL/kg) |
|---|---|---|---|---|
| IV | 3 | 1 | 0.2 | 5 |
| PO | 3 | 5 | 0.5 | 10 |

Sample Collection: blood is collected through jugular vein or other suitable vein, and 0.2 mL of blood was collected at each time point. Samples were placed into tubes containing ethylenediaminetetraacetic acid dipotassium salt and kept on ice before centrifugation. Within 1 hour after blood collection, the blood samples were centrifuged at 2-8° C. and 6800 g for 6 minutes and stored at −80° C. The time point for blood collection was 0.083, 0.25, 0.5, 1, 2, 4, 8 and 24 hours after intravenous administration, and 0.25, 0.5, 1, 2, 4, 6, 8 and 24 hours after oral administration. The test results were shown in Table 2.

TABLE 2

| | Intravenous injection, 1 mg/kg | | | | | Oral gavage, 5 mg/kg | | | |
|---|---|---|---|---|---|---|---|---|---|
| Compound | $t_{1/2}$ h | $C_{max}$ ng/mL | $AUC_{(0-\infty)}$ h*ng/mL | Vz L/kg | CL mL/min/kg | $t_{1/2}$ h | $C_{max}$ ng/mL | $AUC_{(0-\infty)}$ h*ng/mL | F % |
| AMG510 | 0.36 | 762.12 | 318.99 | 1.57 | 50.73 | 1.81 | 1258.08 | 584.27 | 35.41 |
| MRTX849 | 3.16 | 136.78 | 347.91 | 13.14 | 48.14 | 2.80 | 23.31 | 237.61 | 13.66 |
| 26 | 1.55 | 379.11 | 246.53 | 9.30 | 68.35 | 1.00 | 162.55 | 384.60 | 30.99 |
| 28 | 1.82 | 547.05 | 725.88 | 3.63 | 23.20 | 1.34 | 801.74 | 2854.83 | 78.41 |

The data in Table 2 showed that some of the example compounds of the present invention have excellent pharmacokinetic property in rats, even better than that of the positive compound.

Test Example 3

Whole Blood Stability Assay of Compounds

1. Test purpose: to determine the whole blood stability of the compounds by monitoring the clearance rate of the parent compound after incubation of some of the example compounds of the invention with dog and rat whole blood.
2. Test materials: the test drug is self-made from the example compounds of the present invention; the positive compound AMG-510 and MRTX-849 were purchased from Chengdu Zhihui Zhongxin Biopharmaceutical Co., Ltd.
3. Test method:

Solution preparation: A required amount of test compound was weighed, and dissolved in dimethyl sulfoxide to prepare a stock solution of 4 mg/mL. Then, the stock solution of the test compound was diluted to 1 mmol/L and 0.2 mmol/L with 70% acetonitrile aqueous solution, respectively, as working solution.

The working solution was added to the whole blood. The concentration of each test compound was 5 μmol/L. 90 μL was taken and then mixed evenly with 90 μL of water. Then 600 μL of acetonitrile termination solution containing propranolol as internal standard was added. Incubated at 37° C. in a water bath and shook gently. At 30, 60, 120 and 240 minutes, 90 μL of each mixture was placed on a clean 96-well plate prefilled with 90 μL of water, mixed well, and then 600 μL of acetonitrile termination solution containing propranolol as internal standard was added and centrifuged at 5000 g for 15 min. 80 μL of the supernatant was taken and placed in a 96-well plate preloaded with 160 μL of ultrapure water, then analyzed by LC-MS/MS.

The test results were shown in Table 3.

TABLE 3

| Compound | Half-Life in Whole Blood of Rat (min) | Half-Life in Whole Blood of Dog (min) |
|---|---|---|
| AMG510 | 111.3 | 87.5 |
| MRTX849 | 783.9 | 369.0 |
| 28 | 258.9 | 380.4 |

The above data showed that the compounds of some examples of the present invention have excellent whole blood stability.

Test Example 4

NCI-H358 pERK Inhibitory Activity

1. Test purpose: to detect the inhibitory effect of the test compound on the phosphorylation level of ERK in NCI-H358 cells.
2. Test materials: the test drug was self-made from the example compounds of the present invention; the positive compound AMG-510 was purchased from Chengdu Zhihui Zhongxin Biomedical Co., Ltd.; the NCI-H358 cells were purchased from Wuhan Procell Life Science&Technology Co., Ltd.; the 96-well cell culture plate was purchased from Corning; the incubator was purchased from Thermo Fisher Scientific; the PRMI1640 culture medium was purchased from Biological Industries; dimethyl sulfoxide was purchased from Sinopharm Chemical Reagent Co., Ltd.; pipettes was purchased from Thermo Fwasher Scientific; 384 microplate was purchased from Greiner; phospho-ERK (Thr202/Tyr204) kit was purchased from Cwasbio; the multi-label analyzer was purchased from PerkinElmer.
3. Test method:

NCI-H358 cells suspension was seeded at 80 μL per well in a clear 96-well cell culture plate, with 10000 cells each well. The cell culture plate was placed in an incubator and incubated overnight at 37° C. under 5% $CO_2$. After incubation, the cell supernatant was discarded, 80 μL of PRMI1640 medium containing 0.02% serum was added to each well, and the cell culture plate was placed in an incubator and incubated overnight at 37° C., under 5% $CO_2$. The test compound was diluted with 100% DMSO to 4 mmol/L as the first concentration, and then diluted 5-fold to the 8th concentration using a pipette. 2 μL of compound or DMSO (as negative control) was taken and added with 158 μL of cell culture medium. After mixing evenly, 20 μL of the compound solution was taken and added to corresponding cell plate well. The cell wells of the blank group were incubated without any compound and DMSO, and the cell plates were placed in the incubator at 37° C. with 5% $CO_2$ and incubated for 1 hour. At the end of incubation, the cell supernatant was discarded, and 50 μL of 1× cell lysate was added to each well. The cell plate was incubated and shook at room temperature for 30 minutes. Phosphorylated ERK1/2 Eu cryptate antibody and phosphorylated ERK1/2 d2 antibody were diluted 20-fold using assay buffer. 16 μL cell lysate supernatant was taken from each well and added into a new 384 white microplate followed by the addition of 2 μL phosphorylated ERK1/2 Eu cryptate antibody dilution and 2 μL phosphorylated ERK1/2 d2 antibody dilution, and then incubated at room temperature for 4 hours. After incubation, the signals at 615 nm and 665 nm were read using a multi-label analyzer. The percent inhibition was calculated according to the following formula: Ratio=(signal 665 nm/signal 615 nm)×10000; the percent inhibition=(ratio of test compound-ratio of negative control)/(ratio of blank-ratio of negative control)×100%.

The test results were shown in Table 4.

TABLE 4

| Compound | NCI-H358 pERK $IC_{50}$(nM) |
|---|---|
| AMG510 | 88.33 |
| MRTX849 | 67.61 |
| 26 | 2.98 |
| 28 | 42.73 |

The above data showed that the compounds of some examples of the present invention have good inhibitory activity on NCI-H358 ERK phosphorylation.

Test Example 5

Cell Selectivity Test

1. Test purpose: to detect the proliferation inhibition of the test compounds on NCI-H23, NCI-H2122, HCC827, Mia paca2, A549 and SW837 cell lines.
2. Experimental materials: the test drug was made by the example compounds of the present invention; the positive compounds AMG-510 and MRTX849 were purchased from Chengdu Zhihui Zhongxin Biomedical Co., Ltd.; NCI-H23, NCI-H2122, HCC827, Mia paca2, A549 and SW837 cell lines were purchased from ATCC; CellTiter-Glo were purchased from Promega (Art. No. G7571); DMEM culture medium was purchased from ATCC (Art. No. 30-2002); RPMI-1640 culture medium was purchased from ATCC (Art. No. 30-2001); F-12K culture medium was purchased from ATCC (Art. No. 30-2004); Leibovitz's L-15 culture medium was purchased from ATCC (item: 30-2008); Fetal bovine serum (FBS) was purchased from EXCELL (Art. No. FND500); Penicillin-streptomycin was purchased from Gibco (Art. No. 15140-122); 0.25% trypsin-ethylenediaminetetraacetic acid digestive juice (Trypsin-EDTA) was purchased from Gibco (Art. No. 25200-072); dimethyl sulfoxide (DMSO) was purchased from Sigma (Art. No. D2650); 96-well cell plate was purchased from Corning (Art. No. 3610); incubator was purchased from NuAire (model number: NU-5700E); Biosafety cabinet was purchased from AuAire (model number: NU-543-600S); Inverted microscope was purchased from Nikon (Art. No. TS-100); Automated cell counter was purchased from Life technologies (model number: Countess II); Microplate reader was purchased from PerkinElmer (model number: Envision); the data processing software was GraphPad Prism 5.0.

3. Experimental Methods:

The cells in logarithmic growth phase were re-suspended in growth medium (the growth medium for NCI-H23, NCI-H2122 and HCC827 was RPMI-1640+10% FBS; the growth medium for Mia paca2 was DMEM+10% FBS+2.5% horse serum; the growth medium for A549 was F-12K+10% FBS; the growth medium for SW837 was Leibovitz's L-15+10% FBS), and diluted to target density (800 cells/well, 1500 cells/well, 3000 cells/well, 2000 cells/well, 1000 cells/well, and 2000 cells/well for NCI-H23, NCI-H2122, HCC827, Mia paca2, A549, and SW837 cells, respectively). The above cell suspension was inoculated into 96-well plates at 100 μL per well; incubated overnight in a 37° C., 5% $CO_2$ incubator. Medium was used as background control; DMSO was used as negative control.

The test compound was dissolved in DMSO to prepare a stock solution with a concentration of 10 mmol/L. The stock solution was first diluted to 2 mmol/L with DMSO, and then diluted in 5-fold gradient for a total of 8 concentrations. 3 μL of each concentration of the above solutions were taken and diluted with 197 μL of growth medium. 50 μL/well was then added to the cell-seeded 96-well plate. The cells to which the test compound was added were incubated in a 37° C., 5% $CO_2$ incubator for 72 hours. The 96-well plate was equilibrated at room temperature, and 40 μL CellTiter-Glo reagent was added to each well. Then, the plate was mixed on the vortex for 2 minutes, incubated at room temperature for 60 minutes. The luminescence values were read on an EnVision microplate reader, and the $IC_{50}$ of the compounds were calculated using the GraphPad Prism 5.0 software.

The test results were shown in Table 5.

TABLE 5

| Cell line | $IC_{50}$ (nM) | | |
|---|---|---|---|
| (KRAS mutation) | AMG510 | MRTX849 | 28 |
| NCI-H23 (G12C) | 7.55 | 27.28 | 3.89 |
| NCI-H2122 (G12C) | 27.02 | 40.27 | 20.30 |
| Mia paca2(G12C) | 15.67 | 45.15 | 8.61 |
| SW837(G12C) | 284.90 | 16.65 | 7.29 |

TABLE 5-continued

| Cell line | $IC_{50}$ (nM) | | |
|---|---|---|---|
| (KRAS mutation) | AMG510 | MRTX849 | 28 |
| A549(G12S) | >10000 | 3498 | >10000 |
| HCC827(wt) | >10000 | 2495 | >10000 |

The above data showed that some of the example compounds of the present invention have good selectivity for KRAS G12C mutant cell lines.

Test Example 6

Pharmacokinetics Study in Mice

1. Test purpose: to determine the pharmacokinetic characteristics of some of the example compounds of the present invention in ICR male mice after single intravenous injection (IV) and oral administration (PO) by LC-MS/MS method.
2. Test materials: the test drugs are self-made from the example compound of the present invention, the positive compound AMG-510 is purchased from Chengdu Zhihui Zhongxin Biopharmaceutical Co., Ltd., and the ICR male mice are from Shanghai Sippe-Bk Lab Animal Co., Ltd. (Sino-British SIPPR Lab Animal Ltd, Shanghai).
3. Test method:

Preparation of 0.5% methyl cellulose: 5 g of methyl cellulose were weighed and dissolved in 1000 mL of purified water.

Preparation of oral formulation: a required amount of the test compound was weighed and dissolved in 0.5% methyl cellulose solution to obtain a suspension or solution of 0.5 mg/mL.

Preparation of intravenous injection formulation: a required amount of test compound was weighed, and dissolved in 0.5 mL of dimethyl sulfoxide to prepare a solution of 4 mg/mL. 0.06 mL of the above solution was taken, and 0.12 mL of polyethylene glycol 15 hydroxystearate (solutol) and 1.02 mL of normal saline were added thereto to obtain a solution of 0.2 mg/mL.

Administration: ICR male mice were orally administered (PO) after overnight fasting, and the single intravenous (IV) group did not need fasting. The dosage and volume administered were shown in the table below. Feeding 4 hours after administration.

| route of administration | Number of animal | Dosage (mg/kg) | Concentration of administration (mg/mL) | Volume of administration (mL/kg) |
|---|---|---|---|---|
| IV | 3 | 1 | 0.2 | 5 |
| PO | 3 | 5 | 0.5 | 10 |

Sample Collection: blood was collected via the jugular vein or other suitable vein, and 0.03 mL blood was collected at each time point. Samples were placed into tubes containing ethylenediaminetetraacetic acid dipotassium salt and kept on ice before centrifugation. Within 1 hour after blood collection, the blood samples were centrifuged at 2-8° C. and 6800 g for 6 minutes and stored at −80° C. The time points for blood collection were 0.083, 0.25, 0.5, 1, 2, 4, 8 and 24 hours after intravenous and oral administration.

The test results were shown in Table 6.

TABLE 6

| | Intravenous injection, 1 mg/kg | | | | | Oral gavage, 5 mg/kg | | | |
|---|---|---|---|---|---|---|---|---|---|
| Compound | $t_{1/2}$ h | $C_{max}$ ng/mL | $AUC_{(0-\infty)}$ h*ng/mL | Vz L/kg | CL mL/min/kg | $t_{1/2}$ h | $C_{max}$ ng/mL | $AUC_{(0-\infty)}$ h*ng/mL | F % |
| AMG510 | 0.22 | 622.56 | 226.81 | 1.42 | 74.67 | 0.36 | 7.25 | 6.12 | 0.33 |
| 28 | 1.59 | 575.45 | 623.02 | 3.71 | 26.92 | 1.42 | 1444.02 | 2678.57 | 86.09 |

The data in Table 6 showed that some of the example compounds of the present invention have excellent pharmacokinetic properties in mice, even better than the positive compound.

Test Example 7

Pharmacokinetic Study in Dogs

1. The test purpose: to determine the pharmacokinetic characteristics of some of the example compounds of the present invention in beagle dogs after single intravenous injection(IV) and oral administration(PO) by LC-MS/MS method.
2. Test materials: the test drug was self-made from the example compounds of the present invention; Beagle dogs were obtained from Medicilon Colony: 999M-004.
3. Test method:

Preparation of 0.5% methyl cellulose: 5 g of methyl cellulose were weighed and dissolved in 1000 mL of purified water.

Preparation of oral formulation: a required amount of test compound was weighed and dissolved in 0.5% methyl cellulose solution to obtain a suspension or solution of 1 mg/mL.

Preparation of intravenous injection formulation: an appropriate amount of the test compound was weighed, and dissolved in dimethyl sulfoxide to prepare a solution of 10 mg/mL. 3 mL of the above solution was taken, and 6 mL of polyethylene glycol 15 hydroxystearate (solutol) and 51 mL of normal saline were added thereto to obtain a solution of 0.5 mg/mL.

Administration: Beagle dogs were orally (PO) administered after overnight fasting, and the single intravenous (IV) group did not need fasting. The dosage and volume administered were shown in the table below. Feeding 4 hours after administration.

| route of administration | Number of animal | Dosage (mg/kg) | Concentration of administration (mg/mL) | Volume of administration (mL/kg) |
|---|---|---|---|---|
| IV | 3 | 1 | 0.5 | 2 |
| PO | 3 | 5 | 1 | 5 |

Sample Collection: blood was collected via the jugular vein or other suitable vein, and 1 mL blood was collected at each time point. Samples were placed into tubes containing ethylenediaminetetraacetic acid dipotassium salt and kept on ice before centrifugation. Within 1 hour after blood collection, blood samples were centrifuged at 2-8° C. and 2200 g for 10 minutes and stored at −80° C. The time point for blood collection was 0.083, 0.25, 0.5, 1, 2, 4, 8 and 24 hours after intravenous administration, and 0.25, 0.5, 1, 2, 4, 6, 8 and 24 hours after oral administration, respectively. The test results were shown in Table 7.

TABLE 7

| | Intravenous injection, 1 mg/kg | | | | | Oral gavage, 5 mg/kg | | | |
|---|---|---|---|---|---|---|---|---|---|
| Compound | $t_{1/2}$ h | $C_{max}$ ng/mL | $AUC_{(0-\infty)}$ h*ng/mL | Vz L/kg | CL mL/min/kg | $t_{1/2}$ h | $C_{max}$ ng/mL | $AUC_{(0-\infty)}$ h*ng/mL | F % |
| 28 | 1.79 | 575.49 | 928.81 | 2.72 | 18.37 | 5.88 | 191.42 | 1511.42 | 32.30 |

The data in Table 7 showed that some of the example compounds of the present invention have excellent pharmacokinetic properties in dogs.

Test Example 8

Brain Tissue Distribution Test

1. Test purpose: to determine the ability of some of the example compounds of the present invention to cross the blood-brain barrier after a single oral administration (PO) by LC-MS/MS.
2. Test materials: the test drugs were self-made from the example compounds of the present invention, the positive compounds AMG-510 and MRTX849 were purchased from Chengdu Zhihui Zhongxin Biopharmaceutical Co., Ltd., and SD rats were obtained from Sino-British SIPPR Lab Animal Ltd, Shanghai.
3. Test method:

5 g of methyl cellulose was weighed and dissolved in 1000 mL of purified water to obtain 0.5% methyl cellulose. A required amount of the test compound was weighed and dissolved in 0.5% methylcellulose solution to obtain a suspension of 2 mg/mL.

Administration: SD rats were orally administered (PO) after overnight fasting. The dosage and volume administered were shown in the table below. Feeding 4 hours after administration.

| route of administration | Number of animal | Dosage (mg/kg) | Concentration of administration (mg/mL) | Volume of administration (mL/kg) |
|---|---|---|---|---|
| PO | 6 | 20 | 2 | 10 |

Sample Collection: 0.5 mL of blood was collected at each time point via the jugular vein. Samples were placed into tubes containing ethylenediamine tetraacetic acid dipotassium salt ($K_2EDTA$) and kept on ice before centrifugation. Within 1 hour after blood collection, blood samples were centrifuged at 2-8° C. and 6800 g for 6 minutes and stored at −80° C. After the rats were euthanized by carbon dioxide inhalation, the brains of the rats were collected, quickly frozen on dry ice, and stored at −80° C. before bioanalysis. The time points for blood collection were 0.5 and 2 hours after oral administration. The test results were shown in Table 8.

TABLE 8

| Compound | Brain concentration 0.5 hours after administration (ng/g) | Brain concentration 2 hours after administration (ng/g) |
|---|---|---|
| AMG510 | Below detection limit | Below detection limit |
| MRTX849 | 8.00 | 69.79 |
| 28 | 133.97 | 92.81 |

The data in Table 8 showed that some of the example compounds of the present invention have excellent brain exposure.

Test Example 9

CYP Inhibition Test

1. Test purpose: to evaluate the inhibitory ability of some of the example compounds of the present invention against CYP1A2, 2B6, 2C8, 2C9, 2C19, 2D6 and 3A4 via human liver microsomes.

2. Test materials: the test drug was self-made from the example compounds of the present invention, the positive compounds AMG-510 and MRTX849 were purchased from Chengdu Zhihui Zhongxin Biopharmaceutical Co., Ltd., and the human liver microsomes were purchased from Xenotech.
3. Test method:

Solution Preparation:

1. K/Mg buffer: the components were 0.1 mol/L potassium phosphate and 5 mmol/L magnesium chloride with pH 7.4±0.1, preheated.
2. Solution of the test compound: the test compound was dissolved in dimethyl sulfoxide to prepare a stock solution of 10 mmol/L. 8 μL of 10 mmol/L stock solution was transferred to a 96-well plate containing 12 μL of acetonitrile as the highest concentration point, at 3-fold dilution, for 8 concentrations.
3. NADPH solution: 66.7 mg of NADPH was dissolved in 10 mL of 0.1 mol/L K/Mg buffer to obtain 8 mmol/L NADPH solution with pH 7.4.
4. Human liver microsomal stock solution: human liver microsomes were dissolved in 0.1 mol/L K/Mg buffer to obtain 20 mg/mL stock solution.
5. Human liver microsomal working solution: 10 μL of 20 mg/mL human liver microsomal stock solution was taken and added into 990 μL of 0.1 mol/L K/Mg buffer to prepare 0.2 mg/mL human liver microsomal solution.
6. Substrate solution:

CYP 1A2 substrate solution (120 μM): 8 μL of 30 mmol/L phenacetin stock solution was taken and diluted with 1992 μL K/Mg buffer;

CYP 2B6 substrate solution (280 μM): 40 μL of 14 mmol/L bupropion stock solution was taken and diluted with 1960 μL K/Mg buffer;

CYP 2C8 substrate solution (40 μM, containing 1.6 mg/ml human liver microsomes); 8 μL of 10 mmol/L paclitaxel stock solution was taken and added into 160 μL human liver microsomal stock solution and 1832 μL of K/Mg buffer;

CYP 2C9 substrate solution (40 μM): 8 μL of 10 mmol/L diclofenac stock solution was taken and diluted with 1992 μL of K/Mg buffer;

CYP 2C19 substrate solution (140 μM, containing 1.6 mg/ml HLM); 40 μL of 7 mmol/L mephenytoin stock solution was taken and added into 160 μL of human liver microsomal stock solution and 1800 μL of K/Mg buffer;

CYP 2D6 substrate solution (20 μM); 8 μL of 5 mmol/L dextromethorphan stock solution was taken and diluted with 1992 μL K/Mg buffer;

CYP 3A4M substrate solution (20 μM); 8 μL of 5 mmol/L midazolam stock solution was taken and diluted with 1992 μL K/Mg buffer;

CYP 3A4T substrate solution (320 μM); 40 μL of 16 mmol/L testosterone stock solution was taken and diluted with 1960 μL K/Mg buffer.

Incubation and Detection:

600 μL of 0.2 mg/mL human liver microsomal solution and 3 μL of stepwise diluted test compound solution were added to the 96-well plate. 30 μL of the above solution was added on the 96-well plate followed by the addition of 15 μL of the corresponding substrate solution. The 96-well plate and the NADPH solution were pre-incubated at 37° C. for 5 minutes, and 15 μL of NADPH solution was added to the 96-well plate to start the reaction. The assay plate was incubated at 37° C. for 5 minutes for 3A4, 10 minutes for 1A2, 2B6 and 2C9, 20 minutes for 2C8 and 2D6, and 45 minutes for 2C19. Then the reaction was terminated by 180 μL of acetonitrile containing internal standard substance. After quenching, the plate was shook for 10 minutes (600 rpm/min) and then centrifuged at 6000 rpm for 15 minutes. 80 μL of supernatant was taken from each well and transferred to a 96-well sample plate containing 120 μL of ultrapure water for LC-MS/MS analysis.

The test results were shown in Table 10.

TABLE 10

| CYP | $IC_{50}$(μM) | | |
|---|---|---|---|
| | AMG510 | MRTX849 | 28 |
| 1A2 | >10 | >10 | >10 |
| 2B6 | >10 | 3.93 | >10 |
| 2C19 | >10 | >10 | >10 |
| 2C8 | >10 | >10 | >10 |
| 2C9 | >10 | 1.35 | >10 |
| 2D6 | >10 | 9.72 | >10 |
| 3 A4-M | 5.07 | 6.83 | >10 |
| 3 A4-T | >10 | >10 | >10 |

The data in Table 10 showed that some of the example compounds of the present invention have no inhibitory activity on each subtype of CYP enzyme, and there was no risk of drug-drug interactions.

Test Example 10

Plasma Protein Binding Assay

1. Test purpose: to evaluate the protein binding rate of the test compound in human, dog, monkey, rat and mouse plasma by equilibrium dialysis;
2. Experimental materials: the test drug was self-made from the example compound of the present invention; the positive compounds AMG-510 and MRTX849 were purchased from Chengdu Zhihui Zhongxin Biopharmaceutical Co., Ltd.
3. Experimental methods:

0.1 mol/L sodium phosphate and 0.15 mol/L sodium chloride buffer with pH 7.4±0.1 was preheated;

Preparation of plasma containing test substance: the test compound was dissolved in DMSO to prepare a 10 mmol/l stock solution. 5 μL of stock solution was taken and diluted with 95 μL of acetonitrile to obtain solution A (0.5 mmol/L). 8 μL of solution A was taken and diluted with 192 μL of 0.1 mol/L sodium phosphate buffer to obtain solution B (0.02 mmol/L). 570 μL of plasma was added into a 96-well plate followed by the addition of 30 μL of solution B. The final concentration was 1 μmol/L with 0.01% DMSO.

Preparation of TO plasma samples (in triplicate): 25 μL of plasma containing test substance was taken and added into a 96-well plate, followed by the addition of 25 μL of buffer and 200 μL of acetonitrile solution containing internal standard (the internal standard of MRTX849 and compound 28 is tolbutamide; the internal standard of AMG510 is verapamil). The plate was shook at 600 rpm for 10 minutes, covered and stored in a freezer (−20° C.).

T5 sample preparation (in triplicate): the dialysis device was added with 100 μL of buffer on its receiver side and 100 μL of plasma containing the test compound on its doner side. And the dialysis device was then shook at 37° C. and 120 rpm for 5 hours. At the end of culture, 25 μL of plasma containing the test substance was taken from the plasma side and then added to a 96-well plate, followed by the addition of 25 μL of buffer and 200 μL of acetonitrile solution containing internal standard. 25 μL of buffer was taken from the buffer side and then added to a 96-well plate, followed by the addition of 25 μL of blank plasma and 200 μL of acetonitrile solution containing internal standard. All samples were rotated at 600 rpm for 10 minutes and then centrifuged at 6000 rpm. 100 μL of supernatant was taken from each well and transferred to a 96-well sample plate pre-loaded with 100 μL of ultrapure water for LC-MS/MS analysis. The specific test results were shown in Table 11.

TABLE 11

| species | Plasma protein binding rate (%) | | |
|---|---|---|---|
| | AMG510 | MRTX849 | 28 |
| Mice | 90.9 | 99.6 | 97.5 |
| Rat | 85.9 | 99.0 | 95.5 |
| Dog | 92.1 | 98.8 | 67.5 |
| Monkey | 98.3 | 98.7 | 71.7 |
| Human | 92.5 | 98.2 | 61.8 |

Test Example 11 hERG Experiment

1. Test purpose: to test the inhibition of hERG current on HEK293 cells stably transfected with hERG potassium channel by manual membrane clamp;
2. Experimental materials: the positive compounds AMG-510 and MRTX849 were purchased from Chengdu Zhihui Zhongxin Biopharmaceutical Co., Ltd.; HEK293 cells were from the Academy of Military Medical Sciences. Manual membrane clamp system amplifier was purchased from Molecular Devices (Model No. MultiClamp700B); Manual membrane clamp system digital-to-analog converter was purchased from Molecular Devices (Model No. Axon Digidata1550B); Rapid perfusion system was purchased from ALA Scientific Ins. (Model No. ALA-VM8); Micro-manipulator was purchased from Sutter Instrument Co (model No. MP-225); Inverted microscope was purchased from Nikon (model No. Ti2-U); Micropipette Puller was purchased from NARISHIGE (model number PC-10).
3. Experimental methods:

Preparation of Electrophysiological Solution:

Extracellular fluid: N-2-hydroxyethylpiperazine-N'-2-ethanesulfonic acid 10 mmol/L, sodium chloride 145 mmol/L, potassium chloride 4 mmol/L, calcium chloride 2 mmol/L, magnesium chloride 1 mmol/L, glucose 10 mmol/L, the pH was adjusted to 7.3~7.4 with sodium hydroxide; the osmotic pressure was adjusted to 290-310 mOsm; stored at 4° C. after filtration.

Electrode internal fluid (mM): potassium chloride 120 mmol/L, potassium hydroxide 31.25 mmol/L, calcium chloride 5.374 mmol/L, magnesium chloride 1.75 mmol/L, ethylene glycol bis (β-aminoethyl ether)-N,N,N',N'-tetraacetic acid 10 mmol/L, N-2-hydroxyethylpiperazine-N'-2-ethanesulfonic acid 10 mmol/L, adenosine triphosphate disodium salt 4 mmol/L, the pH was adjusted to 7.2-7.3 with potassium hydroxide; the osmotic pressure was adjusted to 290-310 mOsm; after filtration, it was divided and stored at −20° C.

Cell Preparation:

After the HEK-293-hERG cells were subcultured to a suitable state, the cells were washed with phosphate buffer salt, digested and separated with Tryple solution. The cells were resuspended with culture medium and stored in a centrifuge tube, the supernatant was discarded after centrifugation, then the cells were resuspended with extracellular liquid for later use, and stored at 2-8° C. Prior to membrane clamp recording, the cells were added dropwise to culture dish to ensure that the cells had a certain density and were individually separated.

Electrophysiological Experiments:

The whole-cell membrane clamp technique was applied to record hERG currents. The cell suspension was added into small Petri dishes and placed on an inverted microscope stage. After cells were adhered, they were perfused with extracellular fluid at a recommended flow rate of 1-2 mL/min. The glass microelectrode was drawn in two steps by a micropipette puller, and its resistance value in water was 2-5 MΩ after filling with electrode internal fluid.

After the whole-cell recording mode was established, the clamp potential was maintained at −80 mV. The hERG tail current was elicited by applying a depolarizing voltage to +60 mV for 850 ms and then repolarizing to −50 mV for 1275 ms. Such a set of pulse was repeated every 15 seconds throughout the experiment. After the current was stabilized, the drug was continuously extracellularly perfused from low concentration to high concentration (0.3, 1, 3, 10 and 30 μmol/L). The perfusion started from low concentration and continued until the drug effect was stable, and then proceeded to the next concentration.

Data Collection and Analysis:

Stimulus release and signal acquisition were performed on PatchMaster software. The signal was amplified by a diaphragm clamp amplifier. Further data analysis and curve fitting were performed using FitMaster, EXCEL, Graphpad Prism or SPSS 21.0. Data was expressed as mean and standard deviation. The $IC_{50}$ value was obtained by fitting the Hill equation (if applicable). If the maximum inhibition rate of all concentrations of the test substance was less than 50%, the $IC_{50}$ value was not calculated.

Test Results: The $IC_{50}$ of AMG 510, MRTX849 and compound 28 were >30 μM, 0.99 μM and >30 μM, respectively.

Test Example 12

In Vivo Efficacy Test on NCI-11358

1. Test purpose: to evaluate the in vivo efficacy of the test substance in the female BALB/c nude mouse model of subcutaneous transplantation of NCI-H358 tumor.
2. Experimental materials: the test drug was self-made compound of the example of the present invention; the positive compounds AMG-510 and MRTX849 were purchased from Chengdu Zhihui Zhongxin Biopharmaceutical Co., Ltd.; BALB/c nude mice were purchased from Shanghai Lingchang Biotechnology Co., Ltd;
3. Experimental methods:

BALB/c nude mice, female, 6-8 weeks old, weight 18-22 g. NCI-H358 tumor cells were resuspended in phosphate buffer to prepare a 0.1 mL (containing $5\times10^6$ cells) cell suspension, then subcutaneously inoculated on the right nape of each mouse ($5\times10^6$ cells/mouse) (+50% Matrigel). The mice were randomly grouped and administered intragastrically when the mean volume of tumor reached approximately 150-200 $mm^3$, and the dosing frequency was once a day. The tumor diameter was measured twice a week with vernier calipers. The tumor volume was calculated by formula: $V=0.5\ a\times b^2$, a and b represented the long diameter and short diameter of the tumor, respectively.

The results were shown in FIG. 1, and the results showed that compound 28 of the present invention exhibited equivalent therapeutic effect to that of the positive control drug MRTX849 in the animal model of subcutaneous transplantation of NCI-H358 tumors, and was superior to that of the positive control drug AMG 510.

Test Example 13

Pharmacodynamic Experiment of NCI-H1373-Luc Lung Cancer Brain Metastasis Model

1. Test purpose: to evaluate the in vivo efficacy of the test substance in the BALB/c nude mouse NCI-H1373-luc intracranial inoculation model.
2. Experimental materials: the test drug was self-made compound of the present invention; the positive compound MRTX849 was purchased from Chengdu Zhihui Zhongxin Biopharmaceutical Co., Ltd.; BALB/c nude mice (female, 6-8 weeks old, weight 18-22 g) were purchased from Beijing Weitong Lihua Experimental Animal Technology Co., Ltd.
3. Experimental methods:

NCI-H1373-luc cells were cultured in vitro with a culture medium supplemented by 10% fetal bovine serum, at 37° C., 5% $CO_2$. The cells were routinely passaged 2 times a week. When cells were maintained in the exponential growth phase, cells were harvested, counted, and seeded. BALB/c nude mice were anesthetized, fixed on a brain stereotaxic instrument, and the skin of the brain was sterilized. A sagittal incision of about 2 mm was made at the parietal bone and occipital bone to expose the skull. The skull was perforated 2 mm to the right of the bregma and 1 mm to the anterior coronal suture with a 25G sharp needle. The cell suspension was extracted with a syringe, and the needle was inserted vertically into the previous perforation to a depth of 3 mm. The cell suspension (3 μL, containing $3\times10^5$ NCI-H1373-luc cells and 20% Matrigel, for 3 min) was injected slowly. After injection, the syringe was retained for 1 minute, and then withdrawn slowly to reduce the backflow of cell fluid. The perforation was sealed with adhesive, the scalp was reset, and the incision was sutured. The animals should be observed until fully awakened after the operation. When the fluorescence value of the tumor reached about 3E+08, the mice were randomly grouped and administered intragastrically, and the dosing frequency was once a day. Imaging was performed with IVIS once a week.

Figure 2:
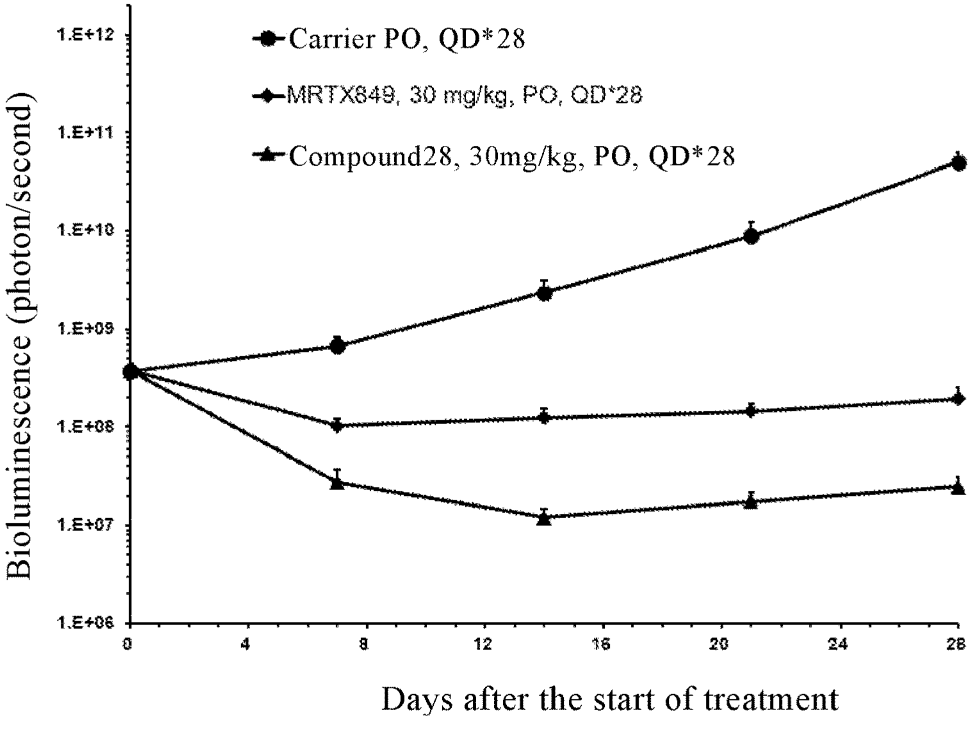
FIG. 2 shows the in vivo efficacy results of the test substances in the BALB/c nude mouse NCI-H1373-luc intracranial inoculation model.

The results were shown in FIG. 2, and the results showed that the therapeutic effect of compound 28 of the present invention was better than that of positive control drug MRTX849 in the BALB/c nude mouse NCI-H1373-luc intracranial inoculation animal model.

The applicant declares that the present invention illustrates the spirocyclic compound, the pharmaceutical composition thereof and the use thereof through the above examples, but the present invention is not limited to the above-described examples, that is, it does not mean that the present invention must rely on the above-described examples to be implemented. Those skilled in the art should understand that any improvement of the present invention, equivalent replacement of each raw material of the product of the present invention, addition of auxiliary components, selection of specific methods, etc., all fall within the scope of protection and disclosure of the present invention.

The invention claimed is:

1. A compound of formula I, or a pharmaceutically acceptable salt thereof, enantiomer, diastereomer, tautomer, cis-trans isomer, or deuterated compound thereof,

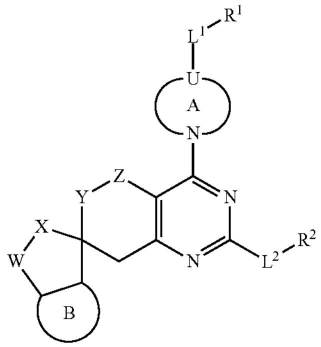

I wherein, the moiety represented by

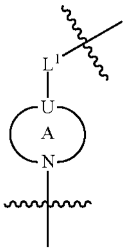

is selected from the group consisting of:

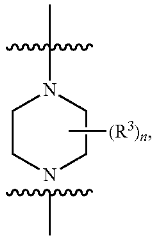

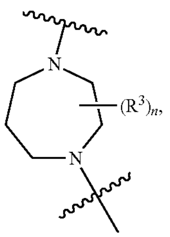

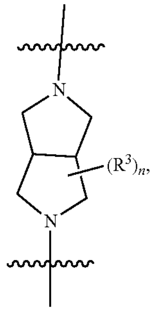

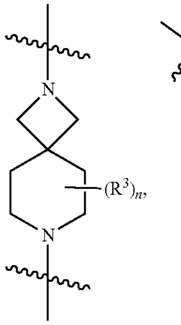

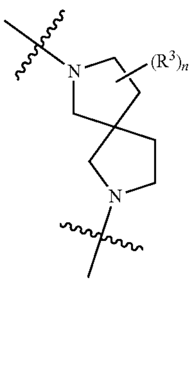

,

-continued

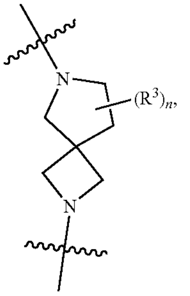

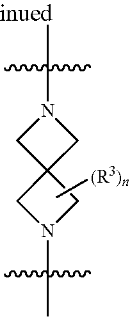

, and

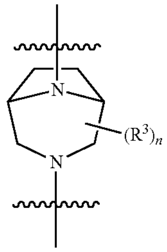

;

n represents the number of $R^3$, and n is 0, 1, 2 or 3;

each $R^3$ is independently oxo, $C_{1-3}$ alkyl, $C_{2-4}$ alkenyl, $C_{2-4}$ alkynyl, cyano, —C(O)$OR^4$, —$CON(R^4)_2$, or —$N(R^4)_2$, wherein the $C_{1-3}$ alkyl is optionally substituted by cyano, halogen, —$OR^4$, or —$N(R^4)_2$;

each $R^4$ is independently hydrogen or $C_{1-3}$ alkyl;

U is N or CH;

$L^1$ is absent or $NR^N$, and when U is N, $L^1$ is absent, and when U is CH, $L^1$ is $NR^N$;

$R^N$ is hydrogen or $C_{1-3}$ alkyl;

$R^1$ is

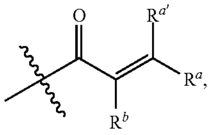

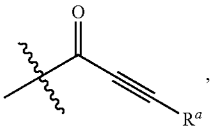

,

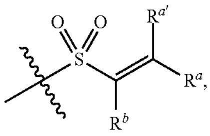

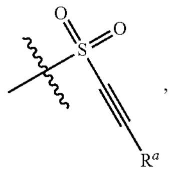

,

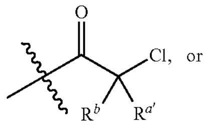

or

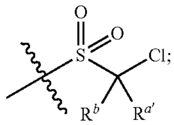

wherein, $R^a$ is hydrogen, halogen, optionally substituted $C_{1-3}$ alkyl, —$N(R^5)_2$, optionally substituted 4-6 membered saturated heterocyclyl, $C_{1-3}$ alkoxy, $C_{1-3}$ alkylthio or acetyl, wherein the substituent for optionally substituted described in $R^a$ is selected from the group consisting of: methyl, ethyl, —$N(R^5)_2$, halogen, $C_{1-3}$ alkoxy, and 4-6 membered saturated heterocyclyl;

each $R^5$ is independently hydrogen or $C_{1-3}$ alkyl;

$R^{a'}$ and $R^b$ are independently hydrogen, halogen or $C_{1-3}$ alkyl;

$L^2$ is absent, —O—, —S—, —$NR^6$—, —SO—, —$SO_2$— or —CO—, wherein, $R^6$ is hydrogen or $C_{1-4}$ alkyl;

$R^2$ is optionally substituted $C_{1-4}$ alkyl; wherein the substituent for optionally substituted described in $R^2$ is selected from the group consisting of optionally substituted 3-8 membered saturated carbocyclyl, and optionally substituted 4-8 membered saturated heterocyclyl; the substituent for optionally substituted is selected from the group consisting of halogen, $C_{1-3}$ alkyl, $C_{1-3}$ haloalkyl, hydroxy, cyano, oxo, and $C_{1-3}$ alkoxy;

W is —($CR^8R^9$)—, —$NR^{10}$—, O or S, wherein $R^8$, $R^9$ and $R^{10}$ are independently hydrogen or $C_{1-3}$ alkyl;

X is —$(CR^{11}R^{12})_m$— or —(C═O)—, wherein each $R^{11}$ is independently hydrogen or $C_{1-3}$ alkyl, and each $R^{12}$ is independently hydrogen or $C_{1-3}$ alkyl;

m=1, 2 or 3;

B is a 6-10 membered aryl or a 5-8 membered heteroaryl, wherein the 6-10 membered aryl or the 5-8 membered heteroaryl is optionally substituted by one or more $R^{13}$;

each $R^{13}$ is independently halogen, hydroxy, amino, $C_{1-3}$ alkylamino, $(C_{1-3}\ alkyl)_2$amino, $C_{1-3}$ alkyl, $C_{1-6}$ haloalkyl, $C_{3-6}$ carbocyclyl, $C_{1-3}$ alkoxy, or $C_{1-3}$ haloalkoxy;

Y is —$NR^{14}$—, wherein $R^{14}$ is hydrogen, $C_{1-6}$ alkyl, $C_{1-6}$ haloalkyl or $C_{3-6}$ carbocyclyl; and Z is —($CR^{15}R^{16}$)—, wherein $R^{15}$ and $R^{16}$ are each independently hydrogen or $C_{1-3}$ alkyl.

2. The compound of Formula I according to claim 1, or the pharmaceutically acceptable salt thereof, enantiomer, diastereomer, tautomer, cis-trans isomer, or deuterated compound, wherein $R^2$ is optionally substituted $C_{1-4}$ alkyl, wherein the substituent for optionally substituted described in the $R^2$ is selected from the group consisting of: optionally substituted 3-8 membered saturated carbocyclyl and optionally substituted 4-8 membered saturated heterocyclyl;

$L^2$ is absent, —O—, —S—, or —$NR^6$—, wherein $R^6$ is hydrogen or $C_{1-4}$ alkyl;

$R^a$ is hydrogen, fluorine, optionally substituted $C_{1-3}$ alkyl, optionally substituted 4-6 membered saturated heterocyclyl or acetyl;

wherein the substituents for optionally substituted described in $R^a$ are selected from the group consisting of methyl, ethyl, —$N(R^5)_2$, halogen, $C_{1-3}$ alkoxy and 4-6 membered saturated heterocyclyl;

each $R^5$ is independently hydrogen or $C_{1-3}$ alkyl;

$R^{a'}$ and $R^b$ are independently hydrogen, fluorine or $C_{1-3}$ alkyl;

W is —($CR^8R^9$)— or —$NR^{10}$—, wherein $R^8$, $R^9$ and $R^{10}$ are independently hydrogen or $C_{1-3}$ alkyl;

X is —$(CR^{11}R^{12})_m$—; wherein each $R^{11}$ is independently hydrogen or $C_{1-3}$ alkyl, and each $R^{12}$ is independently hydrogen or $C_{1-3}$ alkyl; m is 1, 2 or 3.

3. The compound of Formula I according to claim 1, or the pharmaceutically acceptable salt thereof, enantiomer, diastereomer, tautomer, cis-trans isomer, or deuterated compound, wherein the moiety represented by

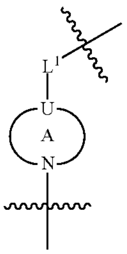

is selected from the group consisting of:

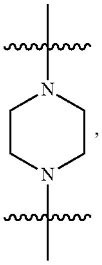,
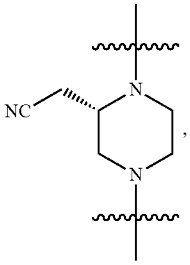,
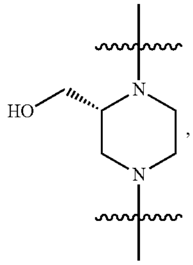,
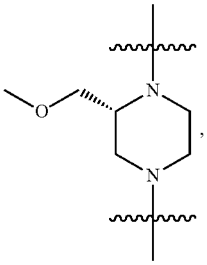,
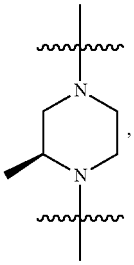, and
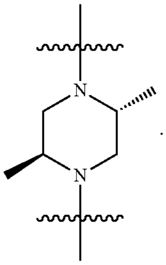.

4. The compound of Formula I according to claim 1, or the pharmaceutically acceptable salt thereof, enantiomer, diastereomer, tautomer, cis-trans isomer, or deuterated compound thereof, wherein $R^1$ is

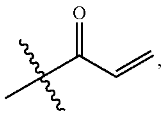,
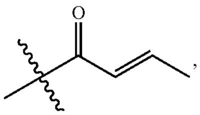,
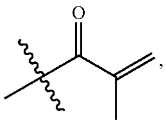,
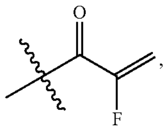,
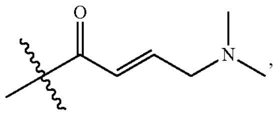,
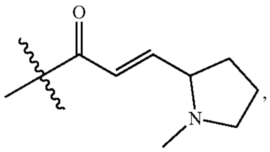,
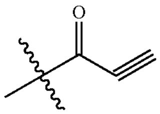,
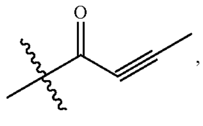,
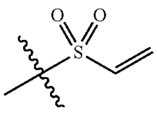, -continued

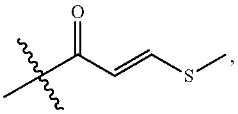, 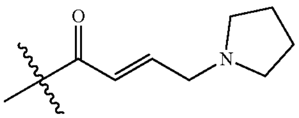,

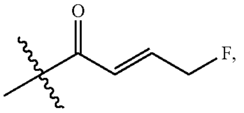 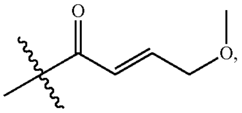

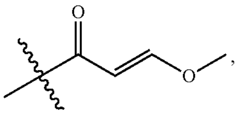, 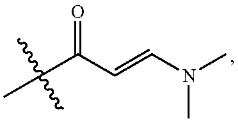,

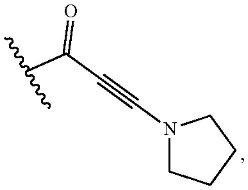, 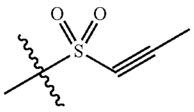,

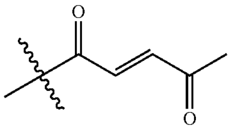, 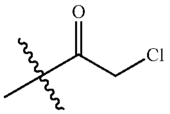 or

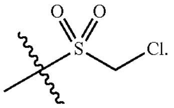

5. The compound of Formula I according to claim 1, or the pharmaceutically acceptable salt thereof, enantiomers, diastereomer, tautomer, cis-trans isomer, or deuterated compound, wherein $R^2$ is

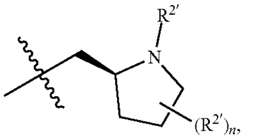 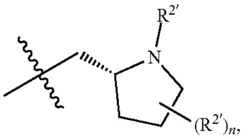

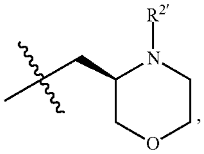, 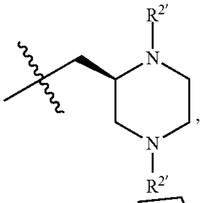,

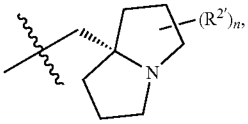 or 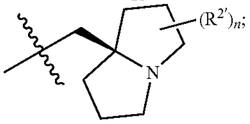;

wherein n represents the number of $R^{2'}$, and selected from: 0, 1, 2 and 3; each $R^{2'}$ is independently halogen, $C_{1-3}$ alkyl, $C_{1-3}$ haloalkyl, hydroxy, cyano, oxo, and $C_{1-3}$ alkoxy.

6. The compound according to claim 1, or the pharmaceutically acceptable salt thereof, enantiomer, diastereomer, tautomer, cis-trans isomer, or deuterated compound, wherein The spiro ring represented by

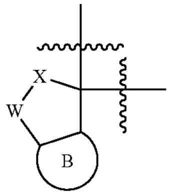

is selected from the group consisting of:

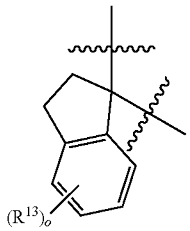, 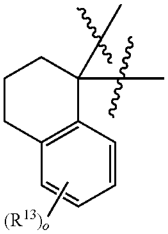,

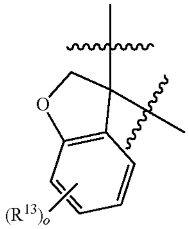, 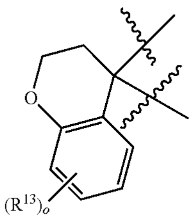,

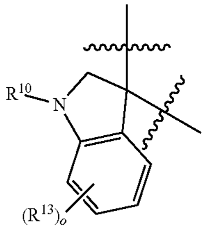, 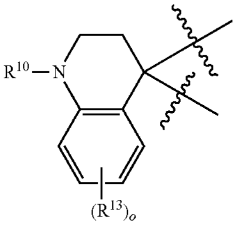,

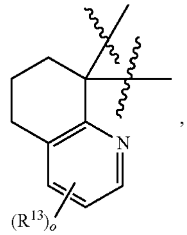, 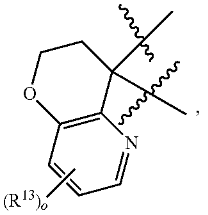,

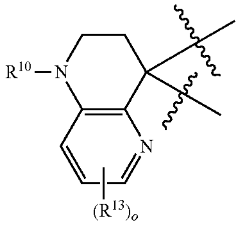, 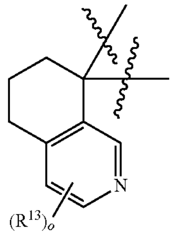,

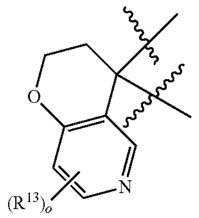, 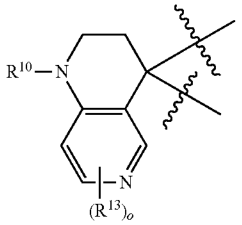,

-continued
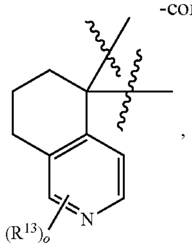, 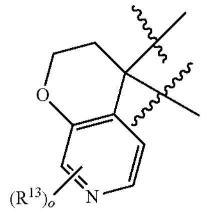,
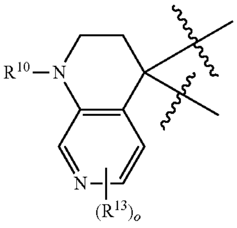, 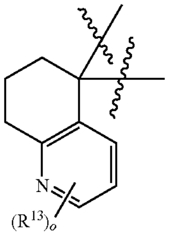,
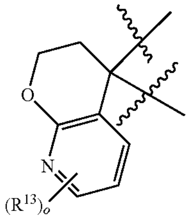, 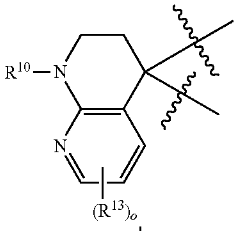,
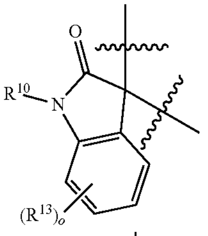, 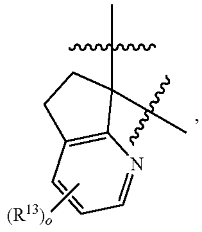,
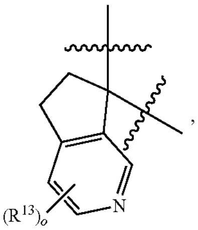, 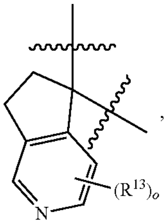,
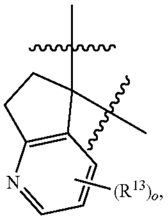, 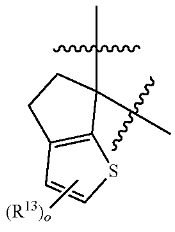, 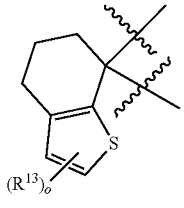,
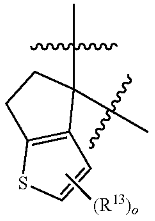, and 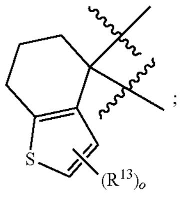;
$R^{10}$ is independently hydrogen or $C_{1-3}$ alkyl;
o represents the number of $R^{13}$, which is 0, 1, 2 or 3;
each $R^{13}$ is independently selected from the group consisting of halogen, $C_{1-6}$ alkyl, $C_{1-6}$ haloalkyl, $C_{3-6}$ carbocyclyl, $C_{1-3}$ alkoxy, and $C_{1-3}$ haloalkoxy.
7. A compound selected from the group consisting of:
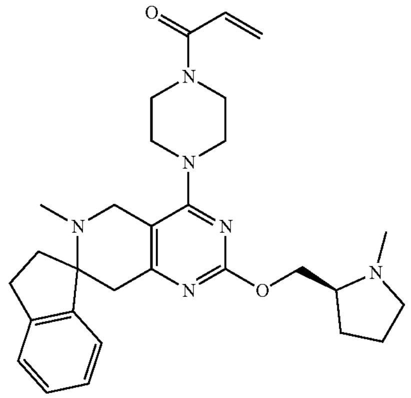
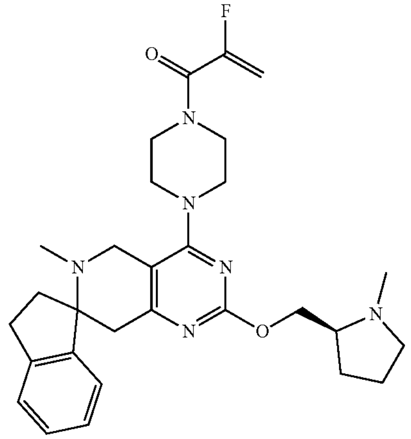
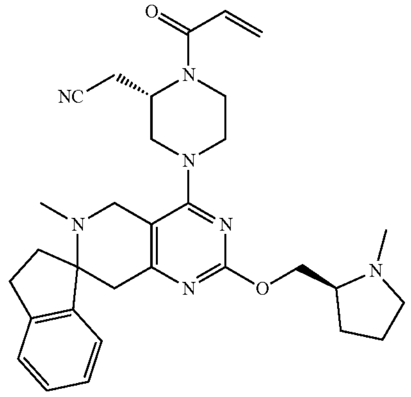
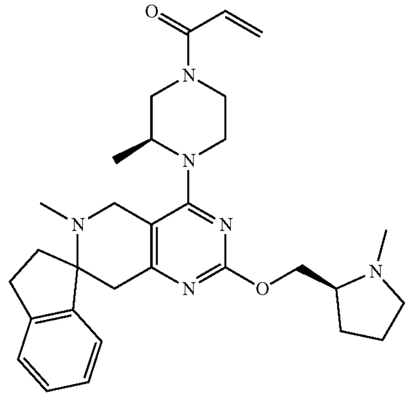

-continued
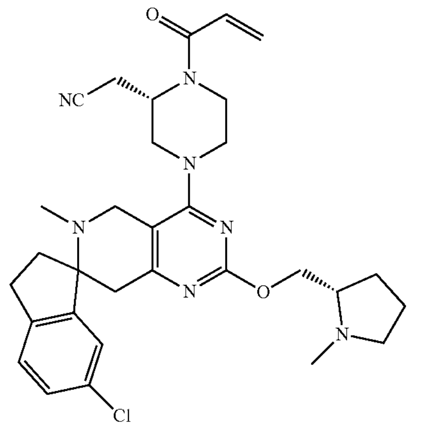
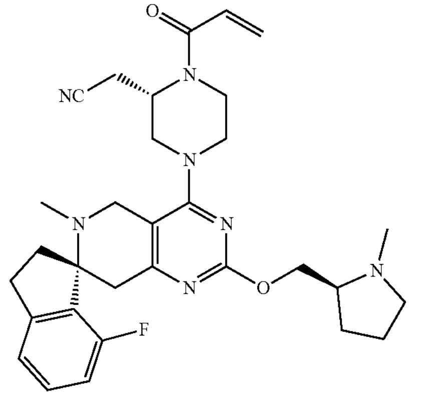
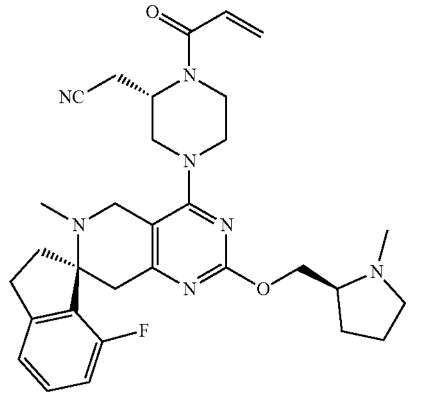
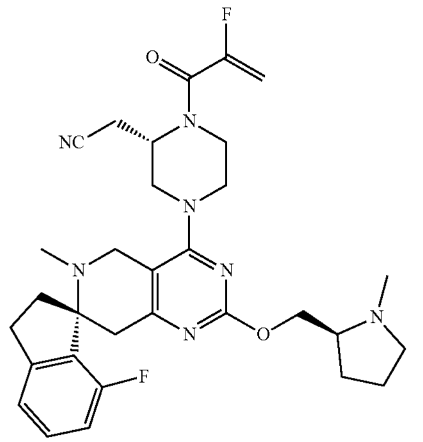
-continued
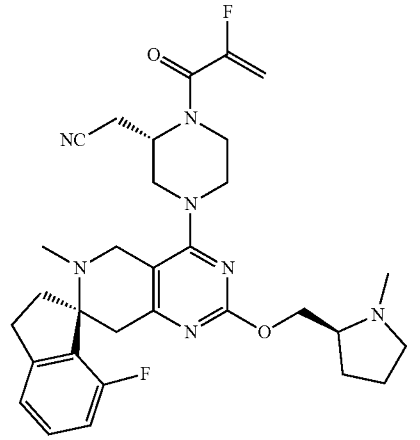
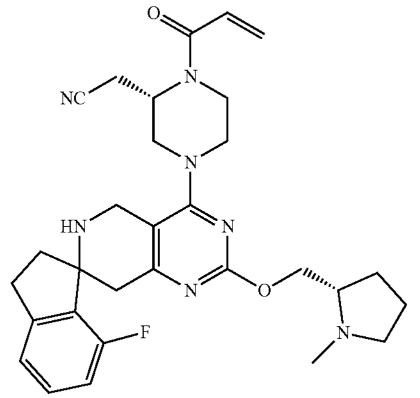
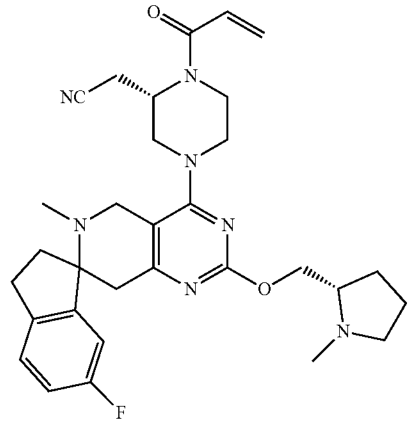
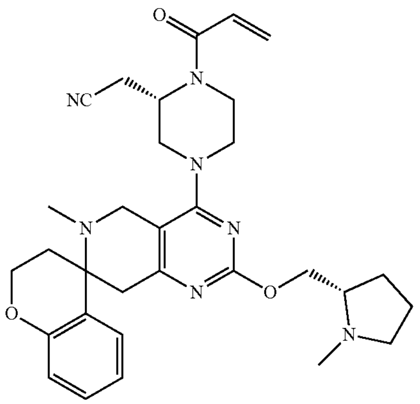

-continued
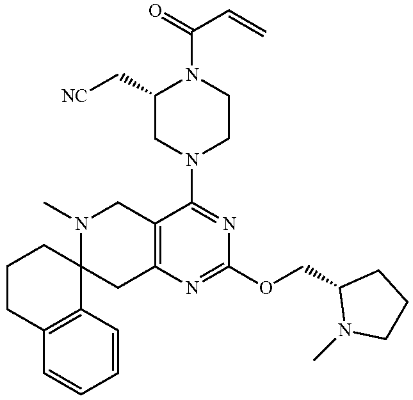
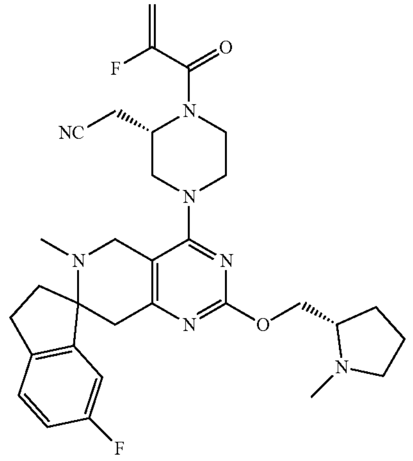
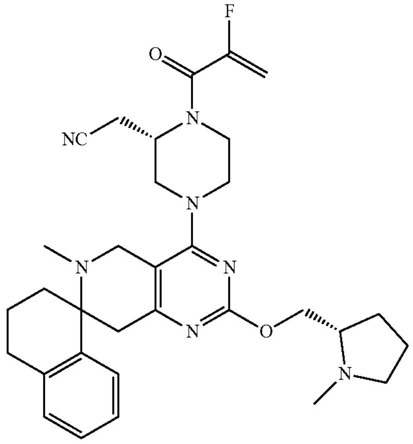
-continued
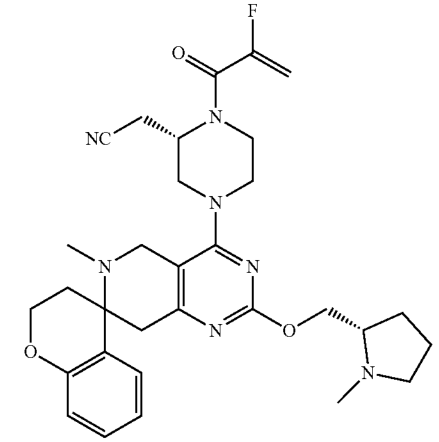
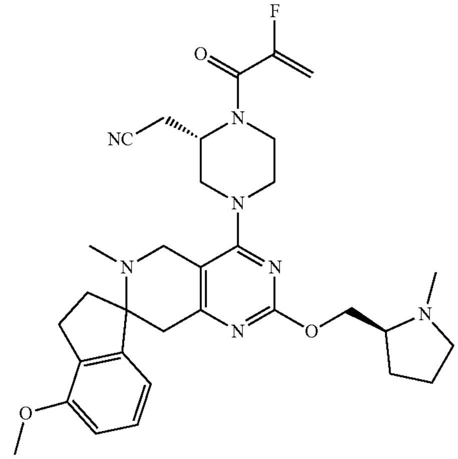
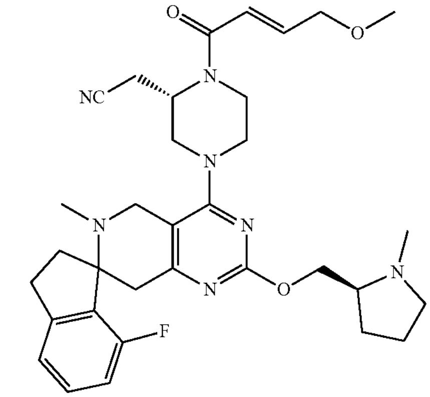
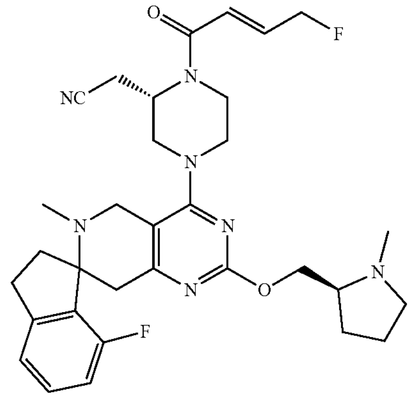

-continued
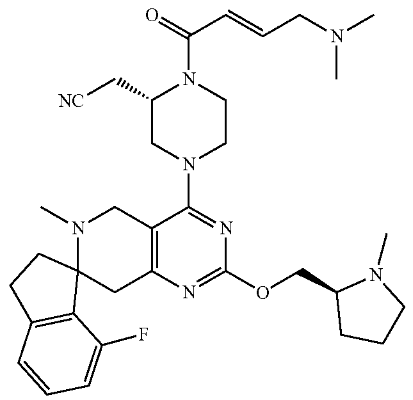
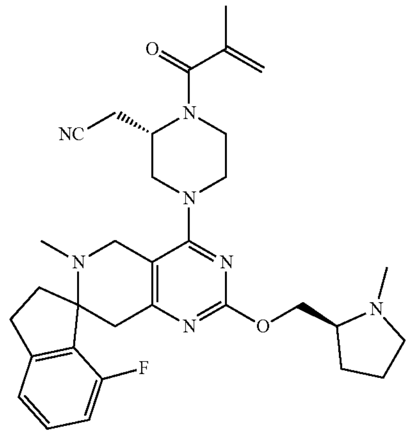
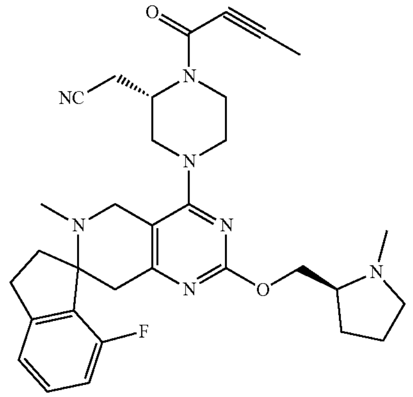
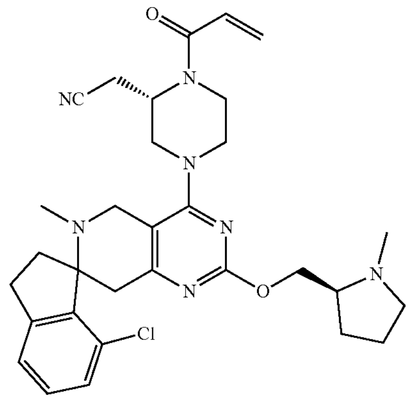
-continued
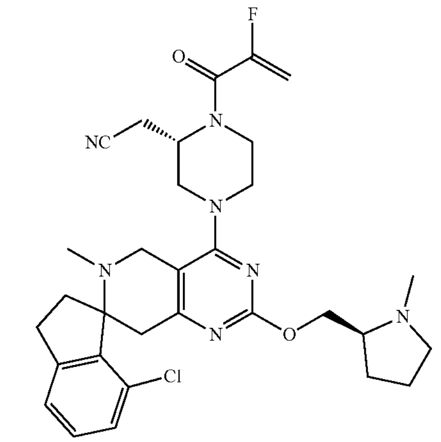
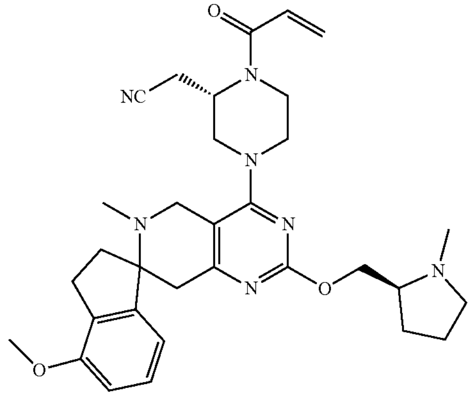
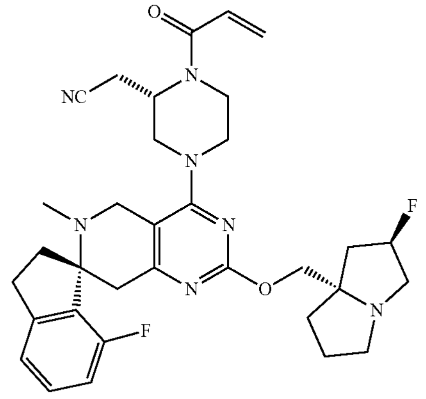
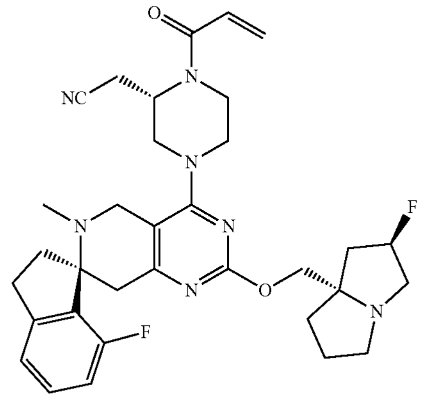

-continued
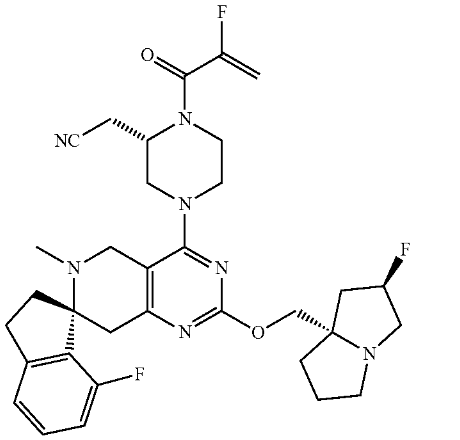
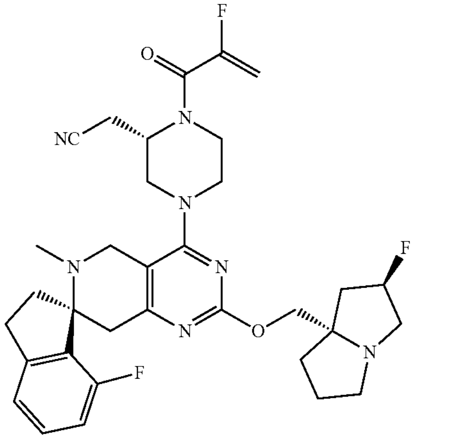
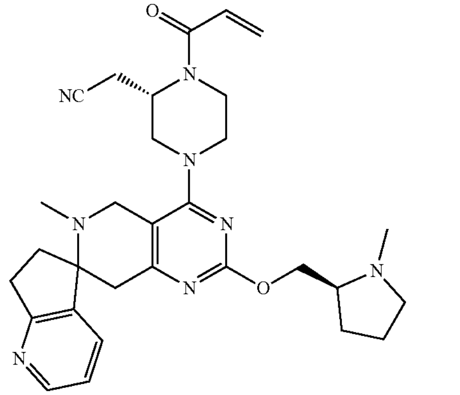
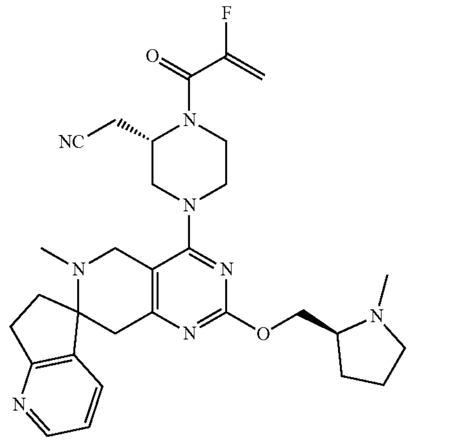
-continued
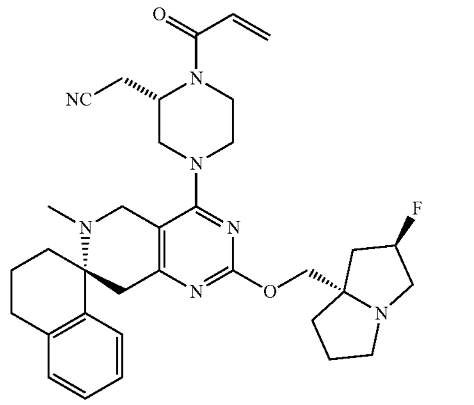
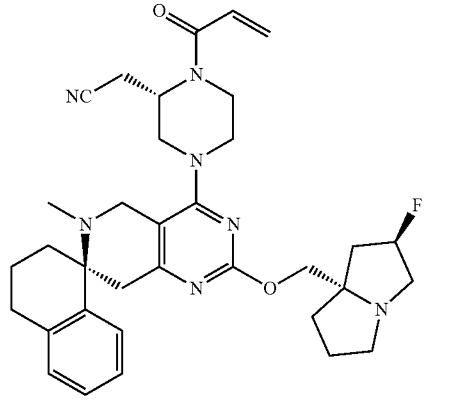
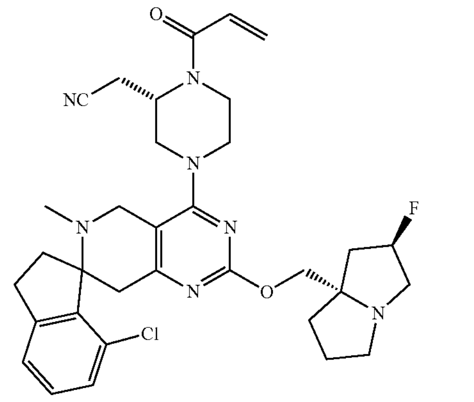
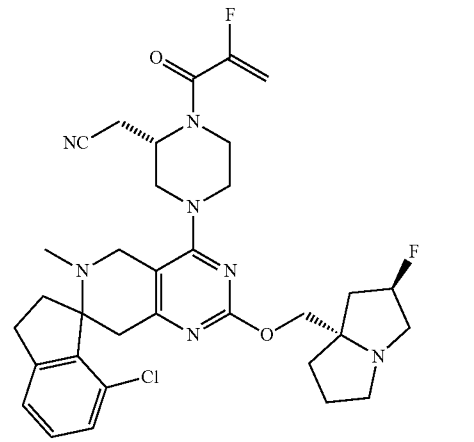

-continued
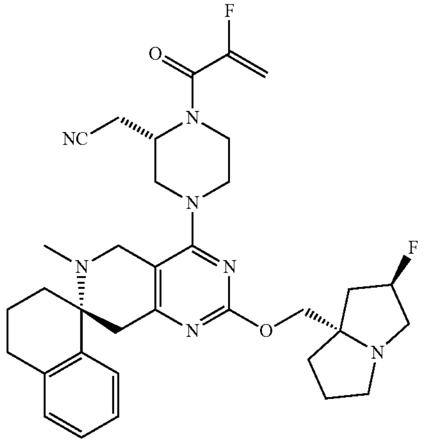
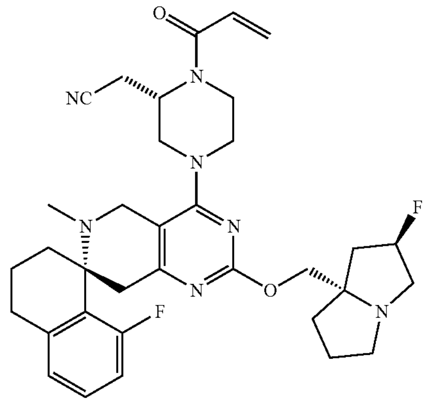
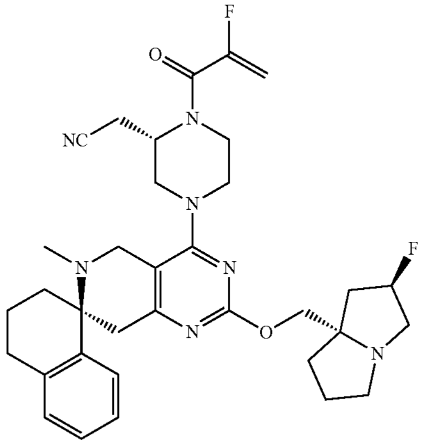
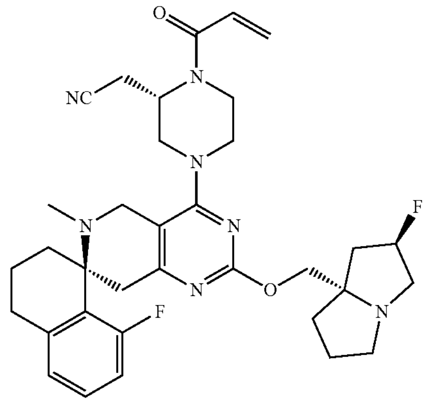
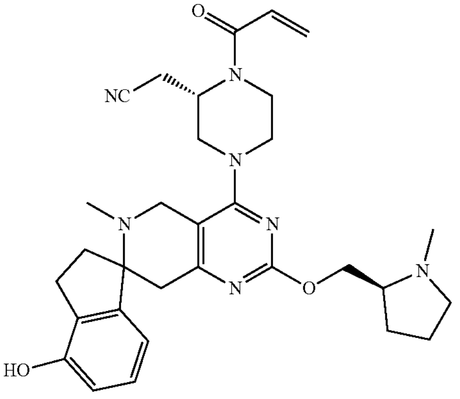
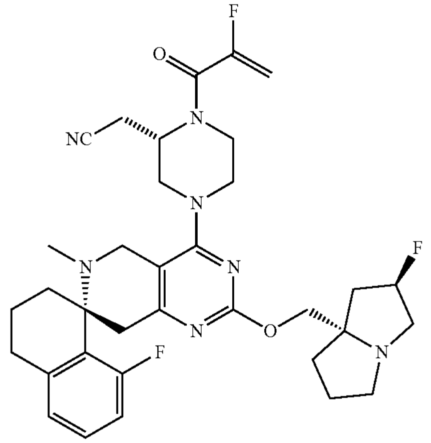
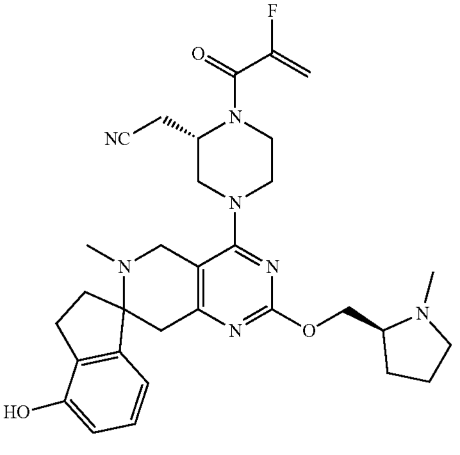
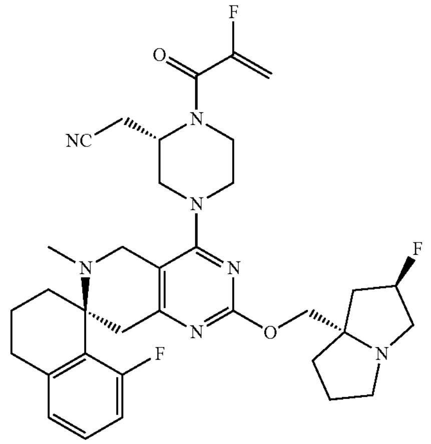

-continued
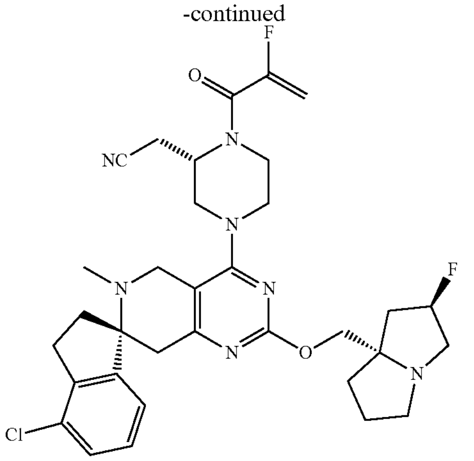
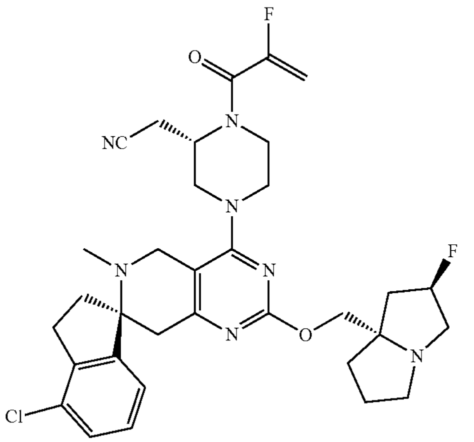
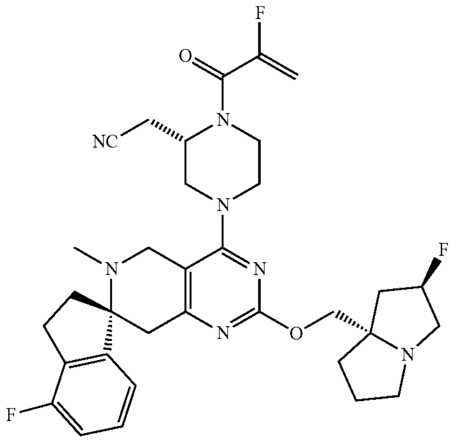
-continued
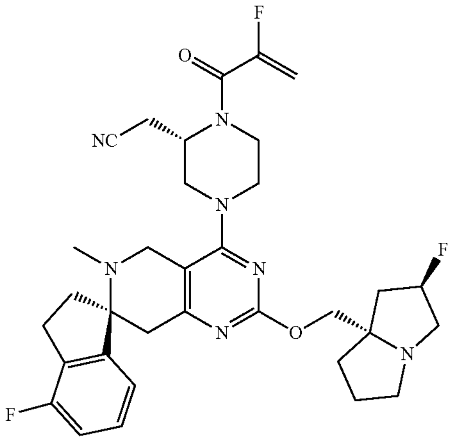
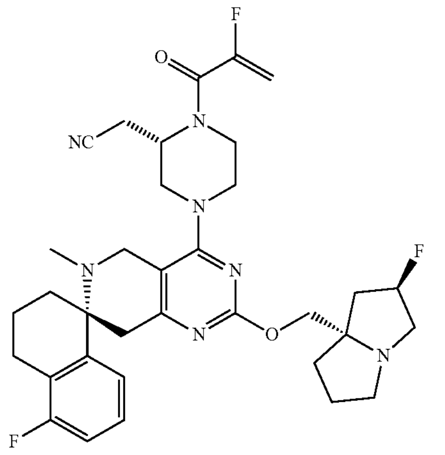
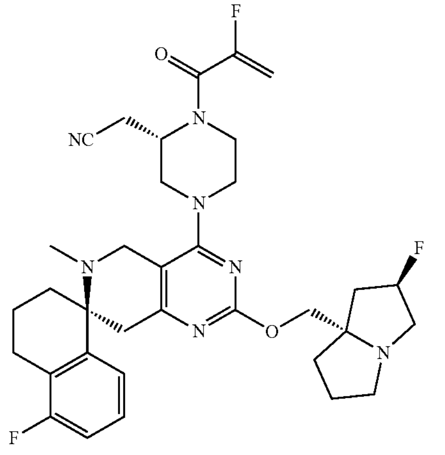

-continued

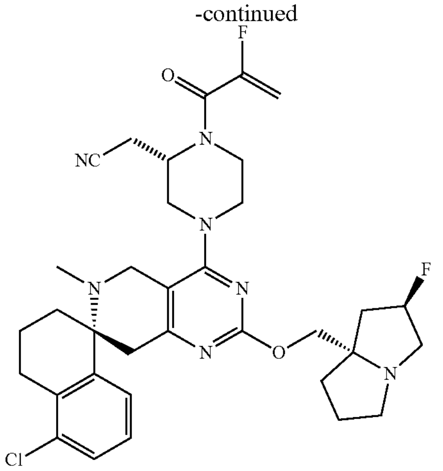

and

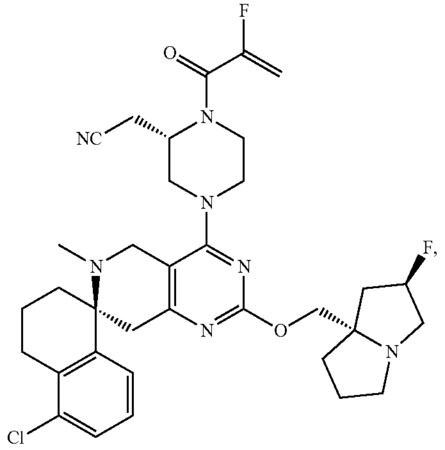

or a pharmaceutically acceptable salt thereof, enantiomer, diastereomer, tautomer, cis-trans isomer, or deuterated compound thereof.

8. A pharmaceutical composition, comprising:

(1) a therapeutically effective amount of one or more of the compounds according to claim 1, or the pharmaceutically acceptable salt thereof, enantiomer, diastereomer, tautomer, cis-trans isomer, and deuterated compound thereof as active ingredients; and (2) optionally, pharmaceutically acceptable excipients.

9. A method of treating cancer mediated by KRAS G12C mutation in a subject in need thereof, the method comprising administering to the subject the compound according to claim 1, or the pharmaceutically acceptable salt thereof, enantiomer, diastereomer, tautomer, cis-trans isomer, or deuterated compound thereof.

10. The method according to claim 9, wherein, the cancer is selected from the group consisting of lung cancer, pancreatic cancer, colorectal cancer, leukemia, Ewing's sarcoma, breast cancer, prostate cancer, T-cell lymphoma, B-cell lymphoma, malignant rhabdomyoma, synovial sarcoma, endometrioma, gastric cancer, liver cancer, renal cancer, melanoma, ovarian cancer, brain glioma, cholangiocarcinoma, nasopharyngeal carcinoma, cervical cancer, head and neck cancer, esophageal cancer, thyroid cancer and bladder cancer, in particular, selected from non-small cell lung cancer, pancreatic cancer, and colorectal cancer.

11. A method of treating cancer mediated by KRAS G12C mutation in a subject in need thereof, the method comprising administering to the subject the pharmaceutical composition according to claim 8.

12. The method according to claim 11, wherein, the cancer is selected from the group consisting of lung cancer, pancreatic cancer, colorectal cancer, leukemia, Ewing's sarcoma, breast cancer, prostate cancer, T-cell lymphoma, B-cell lymphoma, malignant rhabdomyoma, synovial sarcoma, endometrioma, gastric cancer, liver cancer, renal cancer, melanoma, ovarian cancer, brain glioma, cholangiocarcinoma, nasopharyngeal carcinoma, cervical cancer, head and neck cancer, esophageal cancer, thyroid cancer and bladder cancer, in particular, selected from non-small cell lung cancer, pancreatic cancer, and colorectal cancer.

13. The compound of Formula I according to claim 1, or the pharmaceutically acceptable salt thereof, enantiomer, diastereomer, tautomer, cis-trans isomer, or deuterated compound, wherein $R^1$ is

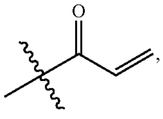,
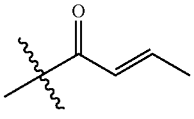,
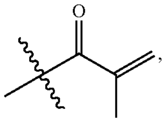,
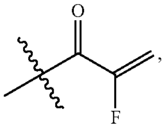,
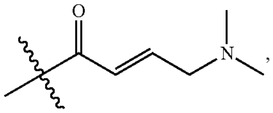,
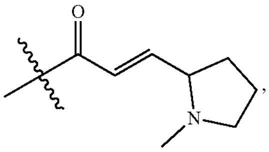,
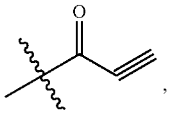,
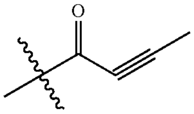,
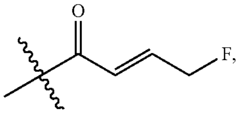,
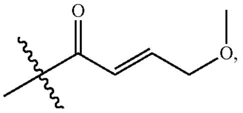,
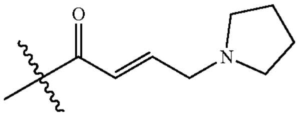
or
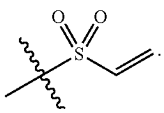.

* * * * *